US010647998B2

(12) United States Patent
Wilson et al.

(10) Patent No.: US 10,647,998 B2
(45) **Date of Patent: *May 12, 2020**

(54) TISSUE PREFERENTIAL CODON MODIFIED EXPRESSION CASSETTES, VECTORS CONTAINING SAME, AND USES THEREOF

(71) Applicant: The Trustees of the University of Pennsylvania, Philadelphia, PA (US)

(72) Inventors: James M. Wilson, Philadelphia, PA (US); Anna Tretiakova, Philadelphia, PA (US)

(73) Assignee: The Trustees of the University of Pennsylvania, Philadelphia, PA (US)

( * ) Notice: Subject to any disclaimer, the term of this patent is extended or adjusted under 35 U.S.C. 154(b) by 0 days.

This patent is subject to a terminal disclaimer.

(21) Appl. No.: 15/627,805

(22) Filed: Jun. 20, 2017

(65) Prior Publication Data

US 2017/0292132 A1 Oct. 12, 2017

Related U.S. Application Data

(63) Continuation of application No. 14/787,622, filed as application No. PCT/US2014/035880 on Apr. 29, 2014, now Pat. No. 9,719,106.

(60) Provisional application No. 61/817,110, filed on Apr. 29, 2013.

(51) Int. Cl.

*C12N 15/85* (2006.01)
*A61K 48/00* (2006.01)
*C12N 15/86* (2006.01)

(52) U.S. Cl.

CPC .......... *C12N 15/85* (2013.01); *A61K 48/0058* (2013.01); *C12N 15/86* (2013.01); *C12N 2750/14143* (2013.01); *C12N 2800/22* (2013.01); *C12N 2830/008* (2013.01)

(58) Field of Classification Search

None

See application file for complete search history.

(56) References Cited

U.S. PATENT DOCUMENTS

| | | | |
|---|---|---|---|
| 4,757,006 | A | 7/1988 | Toole, Jr. et al. |
| 4,886,876 | A | 12/1989 | Zimmerman et al. |
| 5,004,803 | A | 4/1991 | Kaufman et al. |
| 5,045,455 | A | 9/1991 | Kuo et al. |
| 5,112,950 | A | 5/1992 | Meulien et al. |
| 5,149,637 | A | 9/1992 | Scandella et al. |
| 5,171,844 | A | 12/1992 | van Ooyen et al. |
| 5,422,260 | A | 6/1995 | Kaufman et al. |
| 5,451,521 | A | 9/1995 | Kaufman et al. |
| 5,478,745 | A | 12/1995 | Samulski et al. |
| 5,563,045 | A | 10/1996 | Pittman et al. |
| 5,587,310 | A | 12/1996 | Kane et al. |
| 5,595,886 | A | 1/1997 | Chapman et al. |
| 5,633,150 | A | 5/1997 | Wood et al. |
| 5,661,008 | A | 8/1997 | Almstedt et al. |
| 5,668,108 | A | 9/1997 | Capon et al. |
| 5,681,746 | A | 10/1997 | Bodner et al. |
| 5,693,499 | A | 12/1997 | Yonemura et al. |
| 5,786,464 | A | 7/1998 | Seed |
| 5,789,203 | A | 8/1998 | Chapman et al. |
| 5,830,462 | A | 11/1998 | Crabtree et al. |
| 5,834,266 | A | 11/1998 | Crabtree et al. |
| 5,869,337 | A | 2/1999 | Crabtree et al. |
| 5,871,753 | A | 2/1999 | Crabtree et al. |
| 6,011,018 | A | 1/2000 | Crabtree et al. |
| 6,015,709 | A | 1/2000 | Natesan |
| 6,043,082 | A | 3/2000 | Crabtree et al. |
| 6,046,047 | A | 4/2000 | Crabtree et al. |
| 6,063,625 | A | 5/2000 | Crabtree et al. |
| 6,114,148 | A | 9/2000 | Seed et al. |
| 6,117,680 | A | 9/2000 | Natesan et al. |
| 6,127,521 | A | 10/2000 | Berlin et al. |
| 6,133,456 | A | 10/2000 | Holt et al. |
| 6,140,120 | A | 10/2000 | Crabtree et al. |
| 6,150,137 | A | 11/2000 | Berlin et al. |
| 6,150,527 | A | 11/2000 | Holt et al. |
| 6,165,787 | A | 12/2000 | Crabtree et al. |
| 6,187,757 | B1 | 2/2001 | Clackson et al. |
| 6,200,560 | B1 | 3/2001 | Cuoto et al. |

(Continued)

FOREIGN PATENT DOCUMENTS

| | | |
|---|---|---|
| EP | 0162067 | 10/1984 |
| EP | 0182448 | 5/1986 |

(Continued)

OTHER PUBLICATIONS

Seto et al "Gene replacement therapies for Duchenne muscular dystrophy" (Curr gene ther; Jun. 2012 vol. 12, No. 3: pp. 139-151 (Year: 2012).*

Wu, J. et al., Optimization of Self-Complementary AAV Vectors for Liver-Directed Expression Results in Sustained Correction of Hemophilia B at Low Vector Dose, Molecular Therapy, vol. 16(2):280-289, Dec. 2007.

Attanasio, R. et al., NCBI GenBank Accession No. AY544578.1: Cercocebus Torquatus Atys Immunoglobulin Gamma-3 Heavy Chain Constant Region (IGHG3) Gene, Nov. 2006.

Kueppers, R. et al., NCBI GenBank Accession No. X73164: *H. sapiens* 3L31VH1.1 Gene for Ig Heavy Chain Variable Region Subgroup I, Feb. 1994.

Amara, A versatile synthetic dimerizer for the regulation of protein-protein interactions, PNAS, vol. 94(20):10618-10623, Sep. 1997.

(Continued)

*Primary Examiner* — Catherine S Hibbert

(74) *Attorney, Agent, or Firm* — Howson & Howson LLP; Cathy Kodroff

(57) ABSTRACT

Described herein are synonymously altered gene sequences which express protein in differing levels within secretory as compared to non-secretory target tissue. An expression cassette comprising an open reading frame (ORF) for a protein under the control of regulatory sequences which direct expression of the product in cell, which ORF has been modified to preferentially increase expression levels in a selected tissue, wherein the modified ORF is characterized by a triplet frequency of any one of Tables 3-12, 16 or 17.

22 Claims, 71 Drawing Sheets

Specification includes a Sequence Listing.

(56) References Cited

U.S. PATENT DOCUMENTS

| | | | | |
|---|---|---|---|---|
| 6,221,349 | B1 | 4/2001 | Cuoto et al. | |
| 6,258,603 | B1 | 7/2001 | Carlson et al. | |
| 6,258,823 | B1 | 7/2001 | Holt et al. | |
| 6,326,166 | B1 | 12/2001 | Pomerantz et al. | |
| 6,464,974 | B1 | 10/2002 | Berlin et al. | |
| 6,476,200 | B1 | 11/2002 | Sabatini et al. | |
| 6,479,653 | B1 | 11/2002 | Natesan et al. | |
| 6,492,106 | B1 | 12/2002 | Sabatini et al. | |
| 6,506,379 | B1 | 1/2003 | Clackson et al. | |
| 6,509,152 | B1 | 1/2003 | Berlin et al. | |
| 6,649,595 | B2 | 11/2003 | Clackson et al. | |
| 6,693,189 | B2 | 2/2004 | Holt et al. | |
| 6,972,193 | B1 | 12/2005 | Crabtree et al. | |
| 6,984,635 | B1 | 1/2006 | Schreiber et al. | |
| 7,008,780 | B2 | 3/2006 | Pomerantz et al. | |
| 7,045,315 | B2 | 5/2006 | Evans et al. | |
| 7,067,526 | B1 | 6/2006 | Yang et al. | |
| 7,091,038 | B2 | 8/2006 | Palli et al. | |
| 7,109,317 | B1 | 9/2006 | Clemons et al. | |
| 7,196,192 | B2 | 3/2007 | Yang et al. | |
| 7,282,199 | B2 | 10/2007 | Gao et al. | |
| 7,485,441 | B2 | 2/2009 | Pomerantz et al. | |
| 7,790,449 | B2 | 9/2010 | Gao et al. | |
| 7,906,111 | B2 | 3/2011 | Wilson et al. | |
| 9,719,106 | B2 * | 8/2017 | Wilson .................. | C12N 15/85 |
| 2001/0049144 | A1 | 12/2001 | Rivera et al. | |
| 2002/0110861 | A1 | 8/2002 | Dhadialla et al. | |
| 2002/0173474 | A1 | 11/2002 | Schreiber et al. | |
| 2004/0033600 | A1 | 2/2004 | Palli et al. | |
| 2004/0096942 | A1 | 5/2004 | Kapitskaya et al. | |
| 2004/0209323 | A1 | 10/2004 | Kincaid et al. | |
| 2005/0266457 | A1 | 12/2005 | Palli et al. | |
| 2006/0014711 | A1 | 1/2006 | Evans et al. | |
| 2006/0100416 | A1 | 5/2006 | Palli et al. | |
| 2007/0036760 | A1 | 2/2007 | Wilson et al. | |
| 2007/0161086 | A1 | 7/2007 | Palli et al. | |
| 2009/0100535 | A1 | 4/2009 | Pomerantz et al. | |
| 2009/0197338 | A1 | 8/2009 | Vandenberghe et al. | |
| 2013/0023033 | A1 | 1/2013 | Wilson et al. | |
| 2014/0031418 | A1 | 1/2014 | Wilson et al. | |
| 2017/0043035 | A1 | 2/2017 | Wilson et al. | |
| 2017/0081392 | A1 | 3/2017 | Wilson et al. | |
| 2018/0155412 | A1 | 6/2018 | Limberis et al. | |

FOREIGN PATENT DOCUMENTS

| | | |
|---|---|---|
| EP | 0232112 | 8/1987 |
| EP | 0270618 | 12/1987 |
| EP | 0160457 | 1/1991 |
| EP | 0500731 | 3/1995 |
| EP | 0670332 | 9/1995 |
| EP | 0533862 | 10/1999 |
| EP | 0786474 | 2/2003 |
| EP | 0672138 | 5/2003 |
| EP | 0874057 | 7/2004 |
| EP | 0506757 | 10/2005 |
| EP | 0795021 | 2/2006 |
| EP | 1310571 | 2/2006 |
| WO | WO-1987/007144 | 12/1987 |
| WO | WO-1991/007490 | 5/1991 |
| WO | WO-1991/009122 | 6/1991 |
| WO | WO-1992/016557 | 10/1992 |
| WO | WO-1994/011503 | 5/1994 |
| WO | WO-1994/018347 | 8/1994 |
| WO | WO-1995/033052 | 12/1995 |
| WO | WO-1996/006097 | 2/1996 |
| WO | WO-1996/020951 | 7/1996 |
| WO | WO-1996/021035 | 7/1996 |
| WO | WO-1996/041865 | 12/1996 |
| WO | WO-1997/003195 | 1/1997 |
| WO | WO-1997/031898 | 9/1997 |
| WO | WO-1998/002441 | 1/1998 |
| WO | WO-1999/036553 | 7/1999 |
| WO | WO-1999/041258 | 8/1999 |
| WO | WO-2001/070816 | 9/2001 |
| WO | WO-2002/029075 | 4/2002 |
| WO | WO-2002/066613 | 8/2002 |
| WO | WO-2002/066614 | 8/2002 |
| WO | WO-2002/066615 | 8/2002 |
| WO | WO-2003/042397 | 5/2003 |
| WO | WO-2007/014162 | 2/2007 |
| WO | WO-2009/130208 | 10/2009 |
| WO | WO-2013/049493 | 4/2013 |
| WO | WO-2017/040528 | 3/2017 |
| WO | WO-2017/106244 | 6/2017 |
| WO | WO-2017/106326 | 6/2017 |
| WO | WO-2018/057916 | 3/2018 |

OTHER PUBLICATIONS

Ariad Pharmaceuticals, Inc., Argent™ Regulated Heterodimerization Kit Version 2.0, pp. 1-15, retrieved on Jan. 14, 2016 from http://www.ariad.com/pdf/Reg_Heterodimerization.pdf, Sep. 9, 2002.

Ariad Pharmaceuticals, Inc., Argent™ Regulated Transcription Plasmid Kit Version 2.0, pp. 1-20, retrieved on Jan. 14, 2016 from http://www.ariad.com/pdf/Reg_Tx-Plasmid.pdf, Sep. 9, 2002.

Ariad Pharmaceuticals, Inc., Argent™ Regulated Transcription Retrovirus Kit Version 2.0, pp. 1-25, retrieved on Jan. 14, 2016 from http://www.ariad.com/pdf/Reg_Tx-Retrovirus.pdf, Sep. 9, 2002.

Ch'Ng et al., Antisense RNA complementary to 3' coding and noncoding sequences of creatine kinase is a potent inhibitor of translation in vivo, PNAS, vol. 86(11):10006-10010, Dec. 1989.

Deuschle et al., Tetracycline-reversible silencing of eukaryotic promotors, Molecular Cell Biology, vol. 15(4):1907-1914, Apr. 1995.

Fisher et al., Transduction with recombinant adeno-associated virus for gene therapy is limited by leading-strand synthesis, Journal of Virology, vol. 70(1):520-532, Jan. 1996.

Gossen et al., Tight control of gene expression in mammalian cells by tetracycline-responsive promoters, PNAS, vol. 89(12):5547-5551, Jun. 1992.

Hynes et al., Hormone-responsive expression of an endogenous proviral gene of mouse mammary tumor virus after molecular cloning and gene transfer into cultured cells, PNAS, vol. 78(4):2038-2040, Apr. 1981.

Lind et al., Novel Forms of B-Domain-Deleted Recombinant Factor VIII Molecules : Construction and Biochemical Characterization, European Journal of Biochemistry, vol. 232(1):19-27, May 12, 1995 (received Feb. 24, 1995).

Nam et al., Structure of Adeno-Associated Virus Serotype 8, a Gene Therapy Vector, Journal of Virology, vol. 81(22):12260-12271, Nov. 2007.

Plotkin et al., Tissue-specific codon usage and the expression of human genes, PNAS, vol. 101(34):12588-12591, Aug. 16, 2004.

Roscilli et al., Long-Term and Tight Control of Gene Expression in Mouse Skeletal Muscle by a New Hybrid Human Transcription Factor, Molecular Therapy, vol. 6(5):653-663, Nov. 2002.

Sambrook et al., Molecular Cloning: A Laboratory Manual, Cole Spring Harbor Press:Col Spring Harbor, NY, pp. 16.5-16.6, Jan. 1989.

Scharfmann et al., Long-term in vivo expression of retrovirus-mediated gene transfer in mouse fibroblasts implants, PNAS, vol. 88(11):4626-4630, Jun. 1991.

Schillinger et al., Regulatable atrial natriuretic peptide gene therapy for hypertension, PNAS, vol. 102(39):13789-13794, Sep. 2005.

Searle et al., Building a metal-responsive promoter with synthetic regulatory elements, Molecular and Cellular Biology, vol. 5(6):1480-1489, Jun. 1985.

Semon et al., No Evidence for Tissue-Specific Adaptation of Synonymous Codon Usage in Humans, Molecular Biology and Evolution, vol. 23(3):523-529, Mar. 2006 (Accepted Nov. 2, 2005).

Thomson et al., A comprehensive comparison of multiple sequence alignments, Nucleic Acids Research, vol. 27(13):2682-2690, Jul. 1999.

Urrutia, KRAB-containing zinc-finger repressor proteins, Genome Biology, vol. 4(10):231-238, Sep. 2003.

Wang et al., A regulatory system for use in gene transfer, PNAS, vol. 91(17):8180-8184, Aug. 1994.

(56) References Cited

OTHER PUBLICATIONS

Brinster et al., Regulation of metallothionein—thymidine kinase fusion plasmids injected into mouse eggs, Nature, vol. 296(5852):39-42, Mar. 1982.
Buning et al., Recent developments in adeno-associated virus vector technology, The Journal of Gene Medicine, vol. 10(7):717-733, Jul. 2008.
Gossen et al., Transcriptional activation by tetracyclines in mammalian cells, Science, vol. 268(5218):1766-1769, Jun. 1995.
Israel et al., Highly inducible expression from vectors containing multiple GRE's in CHO cells overexpressing the glucocorticoid receptor, Nucleic Acids Research, vol. 17(12):2589-2604, Mar. 1989.
Klock et al., Oestrogen and glucocorticoid responsive elements are closely related but distinct, Nature, vol. 329(6141):734-736, Oct. 1987.
Lee et al., Glucocorticoids regulate expression of dihydrofolate reductase cDNA in mouse mammary tumour virus chimaeric plasmids, Nature, vol. 294:228-232, Nov. 1981.
Mayo et al., The mouse metallothionein-I gene is transcriptionally regulated by cadmium following transfection into humans or mouse cells, Cell, vol. 29(1):99-108, May 1982.
Seto, et al. "Gene replacement therapies for duchenne muscular dystrophy using adeno-associated viral vectors." Current gene therapy 12.3 (2012): 139-151.
International Search Report and Written Opinion issued on parent International Application No. PCT/US2014/035880, dated Jan. 7, 2015.
Maria P. Limberis, Anna P. Tretiakova, James M. Wilson, Michael Naso, Joost Kolkman, Robert Friesen, and Qiang Wang. U.S. Appl. No. 15/906,887, filed Feb. 27, 2018.
Requirement for Restriction/Election issued in U.S. Appl. No. 14/787,622, dated Jul. 21, 2016.
Response to the Jul. 21, 2016 Requirement for Restriction/Election issued in Parent U.S. Appl. No. 14/787,622, filed Nov. 21, 2016.
Limberis, U.S. Appl. No. 15/906,887, filed Feb. 27, 2018.
Foster et al. Codon and mRNA sequence optimization of microdystrophin transgenes improves expression and physiological outcome in dystrophic mdx mice following AAV2/8 gene transfer. Mol Ther 2008; 16: 1825-32 and Supplementary Material, Figure S1 and S2. Epub Sep. 2, 2008.

* cited by examiner

FIG. 1A

```
         SEQ ID NO:
ORF35    3    ATGTATAGGATGCAACTGTTGTCGTGCATTGCTCTGAGCCTCGCCTTAGTGACCAATAGC
ORF42    30   ATGTACCGGATGCAGCTACTGTCGTGTATCGCTCTTTCGTTAGCATTAGTCACAAACTCG
ORF39    2    ATGTATAGGATGCAGTTACTCTCATGCATTGCTCTCTCACTGGCACTTGTAACCAATTCT
ORFIAU   10   ATGTACCGAATGCAACTGCTGTCCTGCATCGCCCTGTCCCTGGCACTGGTCACCAACAGC
ORFIAM   11   ATGTACCGAATGCAACTGCTGTCCTGCATCGCCCTGTCCCTGGCACTGGTCACCAACAGC
BASE     12   ATGTACAGGATGCAACTCCTGTCTTGCATTGCACTAAGTCTTGCACTTGTCACAAACAGT
ORF1     9    ATGTACCGTATGCAGCTCCTATCGTGCATTGCCTTGTCGTTGGCCTTAGTTACAAACAGT
ORF40    1    ATGTACCGTATGCAGCTTCTCTCATGTATAGCCCTGAGTTTAGCCCTAGTTACAAATAGC
ORF11    7    ATGTACCGCATGCAATTACTCTCCTGTATCGCTCTGTCTCTGGCTCTGGTGACAAACAGC
ORF30    4    ATGTATCGTATGCAACTTCTCAGCTGCATTGCACTTAGTCTCGCTCTGGTTACAAACAGT
ORF28    5    ATGTACAGAATGCAGCTTCTGTCTTGCATTGCACTTTCTCTGGCCTTAGTGACTAACTCT
ORF26    6    ATGTACCGGATGCAGTTACTTTCGTGCATCGCCCTGTCACTCGCCCTTGTGACTAATAGC
ORF2     8    ATGTATCGGATGCAGCTTCTCTCCTGCATTGCCTTAAGTCTCGCCCTTGTAACAAATAGT
              *****  * *****  *  *    ** ** **  *     * **  * ** ** **

ORF35         CAAGTACAACTCCTCCAGTCTGGAGCAGCTGTTACCAAGCCAGGCGCTTCGGTTAGGGTT
ORF42         CAAGTCCAGCTGCTGCAGTCAGGGGCTGCAGTGACAAAGCCCGGAGCATCAGTTCGCGTT
ORF39         CAAGTGCAGCTTCTCCAGTCTGGCGCTGCCGTCACCAAGCCAGGAGCCAGCGTTCGAGTT
ORFIAU        CAGGTCCAGCTGCTGCAGAGCGGAGCAGCAGTCACAAAACCAGGAGCCAGCGTCAGAGTC
ORFIAM        CAGGTCCAGCTGCTGCAGAGCGGCGCCGCCGTGACAAAGCCAGGAGCCAGCGTGCGGGTC
BASE          CAGGTCCAATTGTTACAGTCTGGGGCAGCGGTGACGAAGCCCGGGGCCTCAGTGAGAGTC
ORF1          CAGGTGCAGCTTTTGCAGTCCGGGGCTGCAGTGACCAAACCCGGCGCATCTGTGAGGGTG
ORF40         CAGGTGCAGCTGCTACAGAGCGGGGCTGCGGTCACAAAGCCTGGGGCCAGCGTTCGCGTG
ORF11         CAGGTCCAGCTGCTGCAGAGTGGCGCCGCAGTGACTAAGCCTGGCGCTAGTGTGAGAGTC
ORF30         CAAGTTCAGCTGCTTCAGTCCGGCGCTGCCGTGACCAAGCCTGGAGCTTCGGTCAGAGTG
ORF28         CAAGTGCAGCTCCTTCAGAGCGGCGCAGCTGTGACAAAGCCTGGGGCCAGCGTTAGAGTG
ORF26         CAGGTACAGCTACTGCAGAGCGGTGCTGCTGTGACTAAGCCAGGGGCCTCTGTGCGGGTG
ORF2          CAGGTTCAGCTTTTACAGAGTGGCGCCGCAGTCACCAAACCCGGAGCATCCGTGCGAGTC
              ** ** **  *  * ***   ** ** ** ** ** ** ** ** **    **  * **

ORF35         TCATGCGAAGCAAGTGGCTATAACATCCGGGACTATTTCATCCATTGGTGGAGACAAGCC
ORF42         TCATGTGAGGCCAGTGGCTACAACATACGGGACTATTTCATCCACTGGTGGAGACAGGCA
ORF39         TCATGCGAAGCTTCTGGGTACAATATCAGAGATTACTTCATTCACTGGTGGCGCCAGGCT
ORFIAU        AGCTGCGAGGCCAGCGGGTACAACATTCGGGACTACTTCATCCACTGGTGGCGGCAGGCA
ORFIAM        AGCTGCGAGGCCTCCGGCTACAACATTCGGGATTACTTCATCCACTGGTGGCGGCAGGCC
BASE          TCCTGCGAGGCTTCTGGATACAACATTCGTGACTACTTTATTCATTGGTGGCGACAGGCC
ORF1          TCATGCGAAGCCTCGGGGTACAACATTCGGGACTACTTTATCCACTGGTGGAGGCAGGCC
ORF40         TCCTGTGAGGCTTCCGGGTACAATATCCGCGATTACTTTATCCACTGGTGGCGTCAAGCT
ORF11         AGTTGCGAAGCAAGCGGCTACAACATTCGCGATTACTTTATCCATTGGTGGAGGCAGGCT
ORF30         TCATGTGAAGCCAGCGGGTATAACATTAGAGACTATTTCATTCACTGGTGGAGACAGGCC
ORF28         TCGTGTGAGGCATCCGGCTATAACATCAGAGACTATTTCATTCATTGGTGGCGCCAAGCG
ORF26         TCTTGCGAGGCGTCGGGATACAATATCCGGGACTACTTTATCCACTGGTGGAGACAGGCA
ORF2          TCCTGCGAAGCCAGTGGGTACAACATTAGGGACTATTTCATCCATTGGTGGAGGCAGGCA
                 ** ** **    ** ** ** **  * ** ** ** ** ** ****** * ** **

ORF35         CCCGGACAAGGGCTGCAATGGGTCGGCTGGATTAACCCAAAGACCGGCCAACCCAACAAC
ORF42         CCAGGCCAGGGATTACAGTGGGTTGGCTGGATCAACCCGAAAACAGGCCAGCCCAATAAC
ORF39         CCCGGGCAGGGGCTCCAGTGGGTGGATGGATTAACCCCAAGACGGGACAGCCCAACAAT
ORFIAU        CCAGGGCAGGGGCTGCAGTGGGTGGGCTGGATCAACCCTAAAACCGGACAACCCAACAAC
ORFIAM        CCAGGCCAGGGACTGCAGTGGGTGGGCTGGATCAACCCAAAGACAGGCCAGCCAAACAAC
BASE          CCAGGACAGGGCCTTCAGTGGGTGGGATGGATCAATCCTAAGACAGGTCAGCCAAACAAT
ORF1          CCAGGGCAGGGATTACAGTGGGTGGGGTGGATCAACCCGAAAACAGGGCAGCCTAACAAC
ORF40         CCGGGTCAGGGGTTACAGTGGGTCGGTTGGATCAATCCAAAAACAGGACAGCCCAACAAT
ORF11         CCCGGTCAGGGCTTGCAATGGGTCGGCTGGATTAACCCCAAAACCGGGCAGCCCAATAAC
ORF30         CCTGGACAGGGGCTTCAGTGGGTCGGCTGGATTAACCCTAAAACCGGCCAGCCCAACAAT
ORF28         CCCGGTCAGGGACTTCAGTGGGTGGGCTGGATCAATCCAAAGACAGGGCAGCCTAACAAT
ORF26         CCGGGTCAGGGACTTCAGTGGGTGGGCTGGATCAATCCCAAAACAGGCCAGCCCAACAAT
ORF2          CCCGGCCAAGGACTTCAGTGGGTTGGGTGGATCAATCCTAAGACGGGACAGCCCAATAAC
              ** ** ** **  * ** ***** ** ***** ** ** ** ** ** ** ** ** **
```

FIG. 1B

```
ORF35     CCCCGGCAGTTTCAAGGGAGGGTGAGCCTGACCCGCCATGCAAGCTGGGACTTCGACACT
ORF42     CCGCGACAGTTTCAGGGCCGTGTCAGTCTCACCCGCCACGCATCTTGGGATTTCGATACG
ORF39     CCCAGGCAGTTCCAGGGGCGTGTTAGCCTGACAAGACATGCCTCATGGGACTTTGATACA
ORFIAU    CCACGACAGTTTCAGGGCAGAGTGAGCCTGACCAGACACGCCAGCTGGGACTTTGACACC
ORFIAM    CCTCGGCAGTTCCAGGGACGGGTGAGCCTGACCCGGCACGCCAGCTGGGATTTCGATACA
BASE      CCTCGTCAATTTCAGGGTAGAGTCAGTCTGACTCGACACGCGTCGTGGGACTTTGACACA
ORF1      CCCCGACAGTTCCAGGGGCGCGTCTCGTTGACGAGGCACGCGAGTTGGGATTTCGACACA
ORF40     CCTCGCCAGTTTCAGGGGCGTGTCAGCCTTACACGTCACGCCAGTTGGGATTTTGACACA
ORF11     CCTCGACAATTTCAGGGACGCGTTAGTTTAACGAGGCATGCGTCATGGGATTTTGACACA
ORF30     CCAAGACAGTTTCAGGGCCGGGTGTCCCTTACCCGACATGCCAGCTGGGATTTCGATACA
ORF28     CCAAGACAGTTTCAGGGCCGGGTGTCCTTGACTCGGCATGCGAGCTGGGATTTTGATACG
ORF26     CCCCGGCAGTTCCAGGGTCGCGTCTCTCTGACTAGGCACGCCTCCTGGGATTTCGACACC
ORF2      CCGAGACAGTTTCAGGGGCGCGTCTCTCTTACTCGCCATGCTTCTTGGGATTTTGACACC
          **  * ** ** ** **  * **     * **  * ** **    ***** ** ** **

ORF35     TTTTCCTTCTACATGGATCTGAAAGCTCTGAGGTCCGACGACACCGCCGTGTACTTCTGT
ORF42     TTTTCCTTCTACATGGATCTGAAGGCACTGCGCAGCGACGATACCGCAGTTTACTTCTGC
ORF39     TTCAGTTTCTATATGGACTTGAAAGCTCTGAGAAGTGATGATACCGCTGTTTACTTTTGC
ORFIAU    TTTTCCTTCTATATGGATCTGAAAGCACTGCGATCCGACGATACCGCCGTGTACTTTTGC
ORFIAM    TTCTCCTTCTACATGGATCTGAAAGCCCTGCGGTCCGACGATACAGCCGTGTACTTCTGC
BASE      TTTTCCTTTTACATGGACCTGAAGGCACTAAGATCGGACGACACGGCCGTTTATTTCTGT
ORF1      TTCAGCTTCTACATGGACCTCAAGGCGCTGAGAAGTGACGACACAGCCGTCTACTTCTGC
ORF40     TTCAGCTTTTACATGGACCTGAAGGCCCTGCGAAGCGACGACACAGCCGTGTACTTTTGC
ORF11     TTTTCGTTCTATATGGATCTGAAGGCTCTGCGGTCTGATGACACCGCTGTGTACTTTTGT
ORF30     TTTTCGTTCTATATGGACCTTAAGGCTTTGAGATCTGATGATACAGCTGTGTATTTCTGT
ORF28     TTCTCCTTTTACATGGACCTGAAGGCCCTAAGGTCTGACGACACCGCTGTGTATTTCTGC
ORF26     TTCTCGTTCTATATGGACCTCAAGGCTCTTCGGTCCGACGACACCGCCGTGTACTTTTGC
ORF2      TTTTCTTTCTACATGGACCTCAAAGCCCTTCGCAGCGACGATACCGCTGTGTATTTCTGT
          **    ** ** *****  * ** **  *  *    ** ** ** ** ** ** ** **

ORF35     GCTCGGCAGAGGAGCGACTATTGGGACTTTGACGTTTGGGGCTCTGGCACCCAAGTTACA
ORF42     GCAAGGCAGCGTAGCGATTACTGGGACTTCGATGTCTGGGGGTCAGGCACACAAGTAACG
ORF39     GCTCGGCAGCGATCAGACTATTGGGATTTCGATGTGTGGGGATCAGGCACCCAAGTGACG
ORFIAU    GCACGACAGCGGTCCGATTACTGGGACTTCGACGTCTGGGGCAGCGGGACACAAGTCACA
ORFIAM    GCCCGGCAGCGGTCCGATTACTGGGACTTCGATGTGTGGGGAAGCGGCACACAAGTCACC
BASE      GCGCGACAGCGCAGCGACTATTGGGATTTCGACGTCTGGGGCAGTGGAACCCAGGTCACT
ORF1      GCGAGGCAGAGATCGGACTATTGGGACTTCGACGTGTGGGGTTCGGGAACGCAAGTGACC
ORF40     GCCAGACAGCGGAGCGACTACTGGGACTTTGATGTGTGGGGGAGCGGTACACAAGTGACA
ORF11     GCCAGGCAACGGTCCGACTATTGGGACTTTGATGTGTGGGGGTCGGGTACGCAAGTAACG
ORF30     GCACGACAGCGGTCTGATTACTGGGATTTTGACGTGTGGGGGTCCGGCACACAAGTCACA
ORF28     GCCAGGCAGAGATCAGACTATTGGGACTTTGATGTGTGGGGCTCTGGTACTCAAGTGACA
ORF26     GCACGCCAGAGATCCGACTACTGGGACTTTGACGTTTGGGGGTCCGGAACTCAAGTGACA
ORF2      GCCAGGCAGCGCTCTGACTACTGGGACTTTGATGTTTGGGGATCTGGTACGCAAGTCACA
          **  * **  *    ** ** ***** ** ** ** *****    ** ** ** ** **

ORF35     GTTTCCTCGGCTTCCACAAAGGGCCCCTCGGTATTTCCCTTGGCCCCCTCGTCTAAGTCC
ORF42     GTTTCATCCGCTTCCACAAAAGGGCCATCAGTGTTTCCCCTGGCACCCTCCTCAAAATCT
ORF39     GTGTCAAGCGCTTCAACAAAAGGACCCTCAGTGTTCCCTCTCGCCCCTTCATCTAAATCA
ORFIAU    GTGTCCAGCGCCTCCACCAAGGGACCAAGCGTGTTTCCACTGGCACCATCCAGCAAGAGC
ORFIAM    GTCAGCAGCGCCAGCACCAAGGGCCCTTCCGTGTTCCCACTGGCCCCTTCCAGCAAGTCC
BASE      GTCTCGTCAGCGTCGACCAAGGGGCCCTCGGTCTTCCCCCTGGCACCCTCCTCCAAGAGC
ORF1      GTGTCCTCAGCGTCCACGAAAGGGCCATCAGTGTTCCCTCTGGCGCCATCCTCGAAGTCT
ORF40     GTCTCCAGCGCGTCCACCAAAGGACCCAGCGTGTTTCCTCTGGCCCCATCTTCCAAGTCA
ORF11     GTGTCCAGCGCTTCCACAAAAGGCCCAAGCGTGTTTCCCCTCGCTCCATCTTCTAAGTCT
ORF30     GTGTCCAGTGCATCCACAAAAGGACCTTCAGTCTTTCCTCTCGCCCCGTCCAGCAAGTCA
ORF28     GTGAGCAGTGCGTCTACAAAGGGCCCATCAGTCTTTCCTCTGGCCCCTTCCAGCAAGTCT
ORF26     GTTAGTTCTGCGTCTACCAAGGGTCCCTCAGTGTTCCCTCTGGCCCCCTCTAGTAAGTCA
ORF2      GTCTCTAGTGCAAGTACCAAAGGCCCCAGTGTGTTTCCCCTCGCTCCGTCTAGCAAGTCT
          **       **    ** ** ** **    ** ** **  * ** ** **    **
```

FIG. 1C

```
ORF35     ACCAGCGGAGGAACTGCTGCTTTAGGCTGCCTTGTTAAGGACTACTTCCCCGAGCCCGTG
ORF42     ACCAGCGGAGGCACCGCAGCTCTCGGCTGTCTGGTTAAAGACTACTTTCCCGAACCCGTC
ORF39     ACAAGCGGTGGCACCGCTGCCTTGGGATGTCTCGTTAAGGACTACTTTCCCGAGCCCGTC
ORFIAU    ACATCCGGAGGCACCGCAGCACTGGGCTGCCTGGTCAAGGATTACTTCCCTGAACCAGTC
ORFIAM    ACCTCCGGAGGCACAGCCGCCCTGGGCTGCCTGGTGAAAGATTACTTCCCTGAGCCCGTG
BASE      ACCTCTGGGGGCACAGCGGCCCTGGGCTGCCTGGTCAAGGACTACTTCCCCGAACCGGTG
ORF1      ACGTCAGGCGGGACGGCTGCTCTGGGATGCCTGGTGAAAGACTACTTTCCCGAGCCGGTG
ORF40     ACATCCGGCGGAACTGCGGCCCTAGGGTGCCTGGTGAAAGACTACTTTCCTGAGCCCGTA
ORF11     ACAAGCGGCGGCACCGCTGCTCTGGGCTGTCTGGTGAAAGATTACTTTCCAGAGCCGGTC
ORF30     ACCAGCGGGGGTACAGCGGCTTTGGGGTGCCTTGTCAAGGACTACTTTCCTGAACCCGTG
ORF28     ACGTCCGGCGGGACTGCCGCCCTCGGATGCTTAGTGAAGGACTATTTCCCTGAGCCCGTG
ORF26     ACCTCTGGTGGTACCGCGGCCTTAGGCTGTCTGGTGAAAGATTACTTTCCCGAACCCGTG
ORF2      ACCTCTGGCGGTACTGCAGCCCTTGGATGTCTGGTCAAAGACTACTTTCCAGAGCCGGTG
          **     ** ** ** ** **  * ** **  * ** ** ** ** ** ** ** ** **

ORF35     ACTGTCTCGTGGAACTCAGGCGCGCTCACTAGCGGGGTTCATACCTTTCCCGCTGTGTTG
ORF42     ACCGTTTCTTGGAATTCTGGGGCTCTAACCTCAGGCGTGCACACGTTCCCCGCCGTTCTG
ORF39     ACAGTGAGTTGGAATTCTGGCGCTCTTACTAGCGGGGTGCATACTTTCCCCGCTGTACTG
ORFIAU    ACCGTCAGCTGGAACTCCGGAGCCCTGACAAGCGGCGTGCACACCTTCCCTGCCGTGCTG
ORFIAM    ACCGTGAGCTGGAACTCCGGAGCCCTGACCAGCGGAGTGCACACCTTCCCTGCCGTGCTG
BASE      ACGGTGTCGTGGAACTCAGGCGCCCTGACCAGCGGCGTGCACACCTTCCCGGCTGTCCTA
ORF1      ACTGTCTCGTGGAATTCAGGCGCGTTGACATCCGGTGTTCACACGTTCCCCGCTGTGTTG
ORF40     ACTGTGAGCTGGAACTCCGGGGCTCTGACATCCGGGGTTCATACATTCCCTGCAGTACTT
ORF11     ACTGTGTCCTGGAATAGCGGCGCTCTGACTTCTGGTGTTCATACCTTTCCCGCTGTCCTG
ORF30     ACTGTGTCATGGAACTCGGGTGCCCTGACATCGGGGGTCCACACTTTTCCCGCTGTGCTC
ORF28     ACCGTGAGCTGGAATAGCGGCGCTCTGACGTCTGGCGTGCACACATTCCCTGCTGTGCTG
ORF26     ACCGTGTCTTGGAATAGCGGTGCTCTCACGAGTGGGGTGCATACGTTTCCTGCCGTCCTG
ORF2      ACAGTGAGTTGGAATTCGGGTGCTCTAACATCTGGCGTGCACACTTTTCCGGCTGTGCTG
          ** **    *****    ** **  * **    ** ** ** ** ** ** ** **  *

ORF35     CAGAGCAGTGGCTTGTATAGCCTGTCTAGCGTCGTGACCGTTCCCAGCAGCAGCCTCGGG
ORF42     CAGAGCAGCGGCCTGTACTCCTTATCAAGTGTAGTAACTGTTCC-ATCATCAAGCTTGGG
ORF39     CAGTCCAGCGGCCTGTATTCATTGTCATCAGTGGTTACAGTACC-CTCATCGAGTCTGGG
ORFIAU    CAGTCCAGCGGCCTGTATTCCCTGAGCTCCGTGGTGACCGTGCC-CAGCTCCAGCCTGGG
ORFIAM    CAGTCCAGCGGACTGTACAGCCTGTCCTCCGTGGTGACAGTGCC-CAGCTCCAGCCTGGG
BASE      CAGTCCTCAGGACTCTACTCCCTCAGCAGCGTGGTGACCGTGCC-CTCCAGCAGCTTGGG
ORF1      CAGAGCAGCGGACTGTACTCTCTGAGCAGTGTGGTGACAGTGCC-CTCCTCATCGCTGGG
ORF40     CAGTCCTCCGGCCTGTATAGCTTATCTAGCGTAGTAACAGTGCC-CTCCTCTTCCTTGGG
ORF11     CAAAGCAGCGGCCTGTACAGCCTGAGCTCCGTGGTGACCGTACC-CTCCTCCAGCTTGGG
ORF30     CAGTCCTCGGGGCTATACTCCCTTAGCTCGGTGGTTACAGTCCC-ATCCTCATCATTAGG
ORF28     CAGAGCAGTGGCCTTTACTCCCTTAGTAGCGTGGTGACAGTGCC-CTCTAGTTCTCTAGG
ORF26     CAATCAAGTGGACTTTACAGCTTGTCAAGTGTCGTGACGGTGCC-GTCCAGCTCACTAGG
ORF2      CAGTCCAGTGGACTTTACTCTCTGAGCAGTGTGGTTACTGTGCC-CTCTAGTTCTCTTGG
          **         **  * **      *        ** ** ** ** **             **

ORF35     -ACCCAGACGTACATTTGTAACGTTAATCATAAGCCTTCAAACACCAAAGTCGATAAGAA
ORF42     CACCCAGACCTACATCTGCAATGTTAATCACAAACCTTCCAACACTAAGGTGGACAAGAA
ORF39     CACGCAGACCTACATCTGCAACGTCAACCATAAACCCTCTAACACCAAAGTCGATAAGAA
ORFIAU    CACCCAGACCTACATTTGCAATGTCAACCATAAACCAAGCAATACCAAAGTCGACAAGAA
ORFIAM    CACCCAGACCTACATTTGCAACGTCAACCATAAGCCAAGCAACACAAAGGTGGATAAGAA
BASE      CACCCAGACCTACATCTGCAACGTGAATCACAAGCCCAGCAACACCAAGGTGGACAAGAA
ORF1      GACGCAGACGTACATCTGCAACGTGAACCACAAGCCGAGCAACACGAAGGTGGACAAGAA
ORF40     GACACAGACCTACATTTGCAATGTGAATCATAAGCCCTCCAACACAAAGGTGGATAAGAA
ORF11     CACACAGACATACATATGCAATGTGAACCACAAGCCTAGTAATACCAAGGTTGATAAGAA
ORF30     GACACAGACATACATCTGTAATGTGAACCACAAGCCTTCAAATACTAAGGTTGATAAGAA
ORF28     CACCCAGACATACATTTGTAATGTAAATCACAAACCTAGCAACACAAAGGTGGACAAGAA
ORF26     TACCCAGACCTACATCTGCAATGTGAATCATAAGCCTTCGAATACCAAGGTGGATAAGAA
ORF2      GACGCAGACCTACATCTGCAATGTGAATCATAAGCCATCTAATACAAAGGTGGATAAGAA
           ** ***** ***** ** ** ** ** ** ** **    ** ** ** ** ** *****
```

FIG. 1D

```
ORF35     GGTGGAACCCAAGAGTTGTGACAAAACCCACACCTGCCCGCCCTGTCCCGCACCCGAGCT
ORF42     GGTTGAGCCAAAAAGTTGTGATAAGACCCACACATGTCCTCCGTGTCCCGCTCCTGAGCT
ORF39     AGTAGAACCCAAATCTTGCGACAAAACACATACATGCCCACCATGTCCCGCTCCAGAGTT
ORFIAU    AGTCGAGCCCAAAAGCTGCGACAAAACCCACACATGCCCTCCATGCCCTGCCCCAGAGCT
ORFIAM    AGTGGAGCCAAAAAGCTGTGACAAGACACACACCTGTCCTCCCTGCCCCGCCCCCGAGCT
BASE      AGTTGAGCCCAAATCTTGTGACAAAACTCACACATGCCCACCGTGCCCAGCACCTGAACT
ORF1      GGTCGAGCCGAAGTCTTGTGATAAGACTCACACATGTCCCCCATGCCCCGCTCCAGAGCT
ORF40     GGTGGAGCCGAAATCCTGCGACAAAACGCACACTTGCCCTCCTTGTCCAGCCCCCGAGCT
ORF11     GGTAGAACCTAAGAGTTGTGACAAGACCCATACTTGTCCACCGTGTCCTGCACCAGAACT
ORF30     AGTTGAACCCAAGTCTTGCGATAAGACACACACATGTCCCCCTTGTCCTGCACCAGAGCT
ORF28     GGTGGAACCTAAGAGTTGTGATAAGACCCATACATGTCCCCCATGCCCAGCCCCAGAGCT
ORF26     GGTGGAGCCCAAGTCATGCGACAAGACCCATACCTGTCCTCCCTGCCCCGCACCTGAGCT
ORF2      GGTGGAACCAAAGTCATGCGACAAAACCCACACGTGCCCACCATGTCCAGCTCCGGAGTT
           ** ** ** **    ** ** ** ** ** ** ** ** ** ** ** ** ** **  *

ORF35     GTTAGGTGGTCCTTCTGTCTTTCTGTTTCCTCCCAAGCCAAAGGACACCCTTATGATATC
ORF42     GCTAGGTGGCCCCAGTGTGTTCCTCTTTCCCCCTAAACCCAAAGACACACTGATGATCTC
ORF39     GTTGGGTGGACCCTCCGTGTTTCTGTTCCCTCCCAAACCCAAAGATACACTCATGATTTC
ORFIAU    GCTGGGGGGACCCTCCGTCTTTCTGTTTCCCCCTAAACCAAAAGACACCCTGATGATCAG
ORFIAM    GCTGGGCGGACCAAGCGTGTTCCTGTTCCCTCCTAAGCCCAAGGACACACTGATGATCAG
BASE      CCTGGGGGGACCGTCAGTCTTCCTCTTCCCCCCAAAACCCAAGGACACCCTCATGATCTC
ORF1      GCTGGGTGGCCCTAGCGTGTTTCTGTTCCCACCGAAGCCAAAGGACACCTTGATGATCAG
ORF40     GCTAGGGGGACCCTCCGTTTTTCTGTTTCCACCAAAACCCAAGGACACCCTTATGATTTC
ORF11     GCTCGGGGGACCCAGCGTCTTTCTGTTTCCGCCAAAACCTAAGGATACTCTAATGATTTC
ORF30     GCTTGGCGGGCCTTCAGTTTTTCTTTTTCCTCCAAAACCTAAGGATACACTTATGATCTC
ORF28     TCTTGGCGGTCCATCAGTTTTCTTGTTTCCTCCAAAACCTAAGGACACTCTGATGATTTC
ORF26     GTTGGGCGGTCCATCCGTGTTTCTGTTTCCCCCTAAGCCCAAGGACACCCTGATGATATC
ORF2      ACTGGGCGGACCCTCTGTCTTTCTGTTTCCGCCCAAGCCGAAGGATACACTGATGATATC
            * ** ** **    ** **  * ** ** ** ** ** ** ** **  * *****

ORF35     GAGGACCCCTGAAGTAACCTGCGTCGTAGTTGACGTTTCCCACGAAGATCCCGAGGTCAA
ORF42     AAGGACCCCTGAAGTTACATGCGTTGTTGTTGATGTTTCCCACGAAGATCCAGAAGTTAA
ORF39     GCGGACCCCCGAGGTGACTTGCGTCGTCGTGGATGTGTCCCACGAGGACCCCGAGGTCAA
ORFIAU    CAGAACCCCCGAAGTCACATGCGTGGTGGTCGACGTCAGCCACGAGGACCCTGAGGTCAA
ORFIAM    CCGGACCCCAGAGGTCACATGTGTGGTGGTGGATGTGAGCCACGAGGACCCTGAGGTGAA
BASE      CCGGACCCCTGAGGTCACATGCGTGGTGGTGGACGTGAGCCACGAAGACCCTGAGGTCAA
ORF1      CAGGACCCCGGAAGTGACCTGCGTTGTGGTCGACGTGTCACATGAGGACCCCGAAGTGAA
ORF40     ACGCACACCGGAGGTAACCTGTGTTGTGGTAGACGTGTCGCATGAAGATCCAGAGGTCAA
ORF11     CCGTACCCCCGAAGTCACTTGCGTGGTCGTGGACGTGTCACATGAGGACCCCGAGGTAAA
ORF30     AAGGACACCAGAAGTCACATGCGTCGTGGTGGATGTGTCCCATGAGGACCCCGAGGTCAA
ORF28     GAGAACACCGGAAGTCACTTGTGTGGTCGTGGATGTGTCACACGAGGACCCTGAGGTCAA
ORF26     TCGCACCCCAGAGGTGACCTGCGTAGTGGTCGACGTCAGTCACGAGGACCCAGAAGTGAA
ORF2      TCGTACCCCAGAGGTGACATGCGTGGTTGTCGATGTGTCCCATGAGGACCCCGAGGTGAA
            * ** ** ** ** ** ** ** ** ** ** **    ** ** ** ** ** ** **

ORF35     GTTCAACTGGTATGTCGACGGGGTTGAAGTGCACAACGCAAAAACAAAGCCTCGTGAGGA
ORF42     GTTCAACTGGTATGTTGATGGCGTTGAAGTTCACAACGCAAAAACTAAACCGCGTGAAGA
ORF39     ATTCAACTGGTATGTTGATGGAGTGGAGGTTCATAACGCCAAGACCAAACCCAGAGAGGA
ORFIAU    GTTCAATTGGTACGTCGACGGGGTCGAGGTCCACAATGCCAAGACCAAGCCCAGAGAGGA
ORFIAM    GTTCAACTGGTACGTGGATGGAGTCGAAGTGCACAACGCCAAAACCAAGCCTCGGGAGGA
BASE      GTTCAACTGGTACGTGGACGGCGTGGAGGTGCATAATGCCAAGACAAAGCCGCGGGAGGA
ORF1      GTTTAACTGGTACGTGGACGGGGTGGAGGTGCATAACGCAAAGACTAAGCCCCGGGAGGA
ORF40     GTTTAACTGGTATGTTGATGGAGTGGAGGTCCATAACGCAAAGACAAAACCCAGAGAGGA
ORF11     GTTTAACTGGTATGTGGACGGCGTGGAGGTTCATAACGCCAAGACTAAGCCCCGGGAGGA
ORF30     GTTTAACTGGTATGTGGATGGGGTCGAAGTGCACAACGCCAAAACAAAGCCACGCGAAGA
ORF28     GTTCAATTGGTATGTGGACGGCGTGGAGGTACATAACGCCAAAACGAAGCCTCGTGAGGA
ORF26     GTTTAACTGGTACGTGGACGGCGTAGAAGTGCATAATGCCAAAACCAAGCCCCGGGAAGA
ORF2      GTTTAACTGGTATGTGGACGGCGTGGAAGTCCATAATGCTAAGACTAAACCAAGGGAAGA
           ** ** ***** ** ** ** ** ** ** ** ** ** ** ** ** **  * ** **
```

FIG. 1E

```
ORF35     ACAATACAACTCAACGTATAGGGTTGTCTCCGTTCTTACCGTTCTGCACCAAGACTGGTT
ORF42     ACAGTATAACTCTACATACCGTGTGGTTTCAGTTCTTACAGTCCTGCATCAGGATTGGCT
ORF39     GCAGTACAACAGTACGTACAGAGTTGTGTCTGTTCTCACTGTTCTACACCAGGACTGGCT
ORFIAU    ACAGTATAACAGCACCTACCGGGTCGTGTCCGTGCTGACAGTGCTGCATCAGGACTGGCT
ORFIAM    GCAGTACAACAGCACCTACCGGGTGGTGAGCGTGCTGACCGTGCTGCATCAGGACTGGCT
BASE      GCAGTACAACAGCACGTACCGTGTGGTCAGCGTCCTCACCGTCCTGCACCAGGACTGGCT
ORF1      GCAATACAATTCCACCTACCGGGTCGTGTCGGTGCTGACTGTGCTGCACCAGGACTGGCT
ORF40     GCAGTACAATAGTACTTACCGTGTGGTTTCTGTACTGACAGTATTACATCAGGACTGGTT
ORF11     ACAGTATAACAGTACGTATCGAGTCGTAAGCGTGCTGACTGTTCTGCACCAAGACTGGTT
ORF30     GCAATACAATTCGACTTACAGAGTCGTGAGTGTACTGACCGTGCTGCACCAGGATTGGCT
ORF28     GCAGTACAACTCCACCTATCGAGTGGTCAGCGTCCTTACCGTGTTACACCAGGACTGGCT
ORF26     ACAGTACAATTCCACCTACCGTGTGGTGTCTGTTTTGACCGTGCTCCACCAGGATTGGCT
ORF2      ACAGTACAATTCCACGTACCGCGTCGTTAGCGTCTTGACCGTGCTCCATCAGGACTGGCT
           ** ** **    ** **  * ** **    **  * ** **  * ** ** ** *** *

ORF35     GAACGGGAAGGAGTACAAATGCAAAGTATCGAACAAAGCCCTGCCCGCACCCATTGAGAA
ORF42     TAACGGGAAAGAATACAAATGTAAAGTATCCAACAAAGCACTTCCCGCACCCATTGAGAA
ORF39     TAACGGAAAGGAGTATAAGTGTAAAGTGTCCAACAAGGCACTCCCTGCTCCCATTGAAAA
ORFIAU    GAACGGAAAGGAGTACAAGTGCAAGGTGTCCAACAAGGCCCTGCCCGCACCAATTGAAAA
ORFIAM    GAATGGAAAGGAATACAAGTGTAAAGTGTCCAACAAAGCCCTGCCAGCCCCCATCGAAAA
BASE      GAATGGCAAGGAGTACAAGTGCAAGGTCTCCAACAAAGCCCTCCCAGCCCCCATCGAGAA
ORF1      GAACGGGAAGGAGTACAAGTGCAAGGTGTCGAATAAGGCCCTGCCAGCACCTATCGAAAA
ORF40     GAACGGGAAAGAGTACAAATGTAAAGTTAGTAACAAAGCCCTTCCTGCACCTATAGAAAA
ORF11     GAATGGGAAGGAGTATAAGTGTAAGGTCAGCAACAAGGCTCTTCCCGCTCCTATCGAAAA
ORF30     GAACGGCAAAGAGTACAAATGCAAAGTGAGCAACAAAGCTCTACCAGCTCCCATAGAAAA
ORF28     TAACGGAAAGGAGTATAAGTGTAAGGTATCCAACAAAGCCCTGCCTGCACCTATTGAGAA
ORF26     GAATGGCAAGGAATACAAGTGCAAGGTGTCTAACAAGGCTCTCCCTGCACCCATTGAGAA
ORF2      CAACGGAAAGGAGTATAAGTGTAAGGTCAGTAACAAGGCTCTTCCGGCTCCAATTGAGAA
           ** ** ** ** ** ** ** ** **    ** ** ** ** ** ** ** ** ** **

ORF35     AACCATTTCGAAGGCCAAAGGCCAACCCCGGGAACCCCAAGTGTATACCCTCCCACCTTC
ORF42     AACGATTTCAAAAGCAAAGGGACAGCCCAGGGAACCCCAAGTTTACACGCTGCCGCCATC
ORF39     GACAATCTCAAAAGCTAAGGGCCAGCCCAGAGAACCGCAAGTGTACACGCTACCGCCTAG
ORFIAU    GACAATCAGCAAGGCCAAGGGGCAGCCCCGAGAGCCCCAAGTCTATACCCTGCCCCCTTC
ORFIAM    GACAATTTCCAAAGCCAAGGGACAGCCACGGGAGCCACAAGTGTACACCCTGCCCCCAAG
BASE      AACCATCTCCAAAGCCAAAGGGCAGCCCCGAGAACCACAGGTGTACACCCTGCCCCCATC
ORF1      GACGATATCTAAGGCAAAGGGGCAGCCGCGGGAGCCCCAAGTATACACACTGCCTCCGTC
ORF40     GACCATATCCAAAGCCAAAGGCCAGCCCAGAGAGCCCCAAGTTTACACGCTACCGCCAAG
ORF11     GACCATTTCAAAAGCCAAGGGACAGCCGCGGGAGCCTCAAGTGTATACCCTGCCGCCAAG
ORF30     GACAATCTCTAAAGCTAAGGGGCAGCCGCGGGAGCCCCAAGTCTATACCCTACCTCCTTC
ORF28     AACTATATCTAAAGCCAAGGGCCAGCCGCGAGAGCCTCAAGTTTACACACTTCCTCCTTC
ORF26     AACCATTTCCAAGGCCAAGGGTCAGCCCCGAGAACCCCAAGTGTACACCTTACCGCCCTC
ORF2      AACAATTAGTAAGGCTAAGGGGCAGCCTCGCGAACCTCAAGTCTACACCCTACCACCGTC
           ** **    ** ** ** ** ** **  * ** ** ** ** ** **  * ** **

ORF35     CAGAGATGAACTGACCAAGAATCAGGTGTCGCTGACCTGCCTGGTGAAGGGCTTCTACCC
ORF42     TCGTGATGAGCTGACCAAGAATCAGGTATCTTTGACGTGCCTGGTCAAAGGTTTCTACCC
ORF39     TCGAGATGAGCTGACCAAGAACCAGGTGTCCTTGACTTGCCTCGTTAAAGGGTTCTATCC
ORFIAU    CCGAGATGAACTGACCAAGAACCAAGTCAGCCTGACATGCCTGGTGAAGGGATTCTACCC
ORFIAM    CCGGGATGAGCTGACAAAGAATCAGGTCAGCCTGACATGTCTGGTCAAGGGCTTCTACCC
BASE      CCGGGATGAGCTGACCAAGAACCAGGTCAGCCTGACCTGCCTGGTCAAAGGCTTCTATCC
ORF1      CAGGGATGAGTTGACCAAGAACCAGGTGTCTCTGACCTGCCTGGTTAAGGGCTTCTACCC
ORF40     CCGAGACGAGCTGACTAAGAATCAGGTGTCCCTGACTTGTCTAGTCAAGGGCTTTTACCC
ORF11     TAGAGACGAGCTCACCAAGAACCAGGTTTCACTGACATGTCTGGTAAAGGGCTTCTATCC
ORF30     CCGCGACGAACTCACAAAGAACCAGGTTAGCCTTACATGTCTCGTAAAGGGGTTCTATCC
ORF28     GAGAGACGAGCTCACCAAGAATCAGGTGTCACTTACCTGCCTTGTGAAAGGCTTTTACCC
ORF26     CCGCGACGAACTGACCAAAAACCAGGTGTCCCTTACCTGCCTGGTGAAGGGATTCTACCC
ORF2      TCGCGACGAACTCACTAAGAATCAGGTGTCGCTCACCTGCCTCGTCAAAGGTTTCTATCC
            * ** **  * ** ** ** ** **     * ** ** ** ** ** ** ** ** **
```

FIG. 1F

```
ORF35     CTCTGATATTGCCGTGGAATGGGAAAGCAATGGCCAACCCGAAAACAATTACAAGACCAC
ORF42     TTCGGACATCGCGGTTGAGTGGGAGTCAAACGGCCAGCCAGAAAACAATTACAAAACCAC
ORF39     CTCGGATATAGCTGTCGAGTGGGAGTCAAATGGGCAACCCGAGAATAACTACAAGACCAC
ORFIAU    TTCCGATATCGCCGTCGAGTGGGAATCCAACGGCCAACCCGAGAATAACTACAAAACAAC
ORFIAM    AAGCGATATCGCCGTGGAGTGGGAGTCCAATGGCCAGCCCGAAAACAACTACAAGACCAC
BASE      CAGCGACATCGCCGTGGAGTGGGAGAGCAATGGGCAGCCGGAGAACAACTACAAGACCAC
ORF1      ATCCGACATAGCAGTGGAGTGGGAGAGCAACGGCCAGCCGGAGAACAACTATAAGACCAC
ORF40     CAGCGATATTGCTGTGGAGTGGGAGAGCAATGGCCAGCCCGAGAATAACTACAAAACAAC
ORF11     ATCCGACATTGCCGTAGAATGGGAGAGTAACGGCCAGCCAGAGAATAACTATAAGACCAC
ORF30     TTCGGATATCGCTGTCGAATGGGAGTCTAACGGGCAGCCTGAAAACAACTACAAAACAAC
ORF28     TAGTGATATCGCGGTGGAATGGGAGAGCAATGGGCAGCCTGAGAACAACTATAAGACAAC
ORF26     GAGTGACATCGCTGTGGAATGGGAAAGCAACGGCCAGCCTGAAAACAATTACAAGACTAC
ORF2      CTCTGACATCGCAGTAGAATGGGAATCCAATGGCCAGCCGGAGAACAATTACAAGACCAC
              ** ** ** ** ** *****    ** ** ** ** ** ** ** ** ** ** **

ORF35     TCCCCCGGTTTTAGACTCAGACGGCTCATTCTTTCTGTATTCAAAGTTGACTGTTGACAA
ORF42     TCCTCCTGTCTTGGACAGCGATGGGTCATTCTTTCTTTACTCAAAACTCACTGTTGACAA
ORF39     ACCCCCTGTGCTGGATTCAGACGGTAGCTTCTTTCTATACTCCAAACTGACGGTTGACAA
ORFIAU    CCCACCCGTGCTGGACAGCGACGGGTCCTTCTTTCTGTATAGCAAGCTGACCGTGGACAA
ORFIAM    CCCACCAGTGCTGGACTCCGATGGCTCCTTCTTCCTGTACTCCAAGCTGACCGTGGACAA
BASE      GCCTCCCGTGCTGGACTCCGACGGCTCCTTCTTCCTCTACAGCAAGCTCACCGTGGACAA
ORF1      ACCCCCGGTGCTGGACAGCGACGGCTCGTTCTTCCTGTACAGTAAGTTGACCGTCGACAA
ORF40     ACCCCCGGTCCTTGACTCCGATGGGAGTTTCTTTCTGTACAGCAAATTGACAGTAGACAA
ORF11     GCCCCCTGTGTTGGACTCCGACGGGTCATTCTTTCTGTATAGCAAGCTGACAGTTGACAA
ORF30     TCCCCCTGTGCTTGATAGCGACGGTAGTTTCTTTCTGTACAGCAAACTTACAGTCGATAA
ORF28     CCCTCCCGTACTGGACAGCGATGGCAGCTTCTTTCTCTATTCTAAGCTGACCGTCGATAA
ORF26     CCCACCAGTACTCGATTCAGACGGAAGCTTTTTCCTTTACAGCAAGCTCACTGTGGACAA
ORF2      CCCGCCAGTGCTAGACTCAGACGGGAGTTTCTTCTTATACTCTAAGCTTACCGTAGATAA
           ** ** **  * **    ** **    ** **  * **    **  * ** ** ** **

ORF35     GTCCAGATGGCAGCAAGGGAACGTTTTCTCCTGTAGTGTTATGCATGAAGCCCTGCATAA
ORF42     GTCTCGATGGCAGCAAGGCAACGTCTTTAGTTGCTCTGTGATGCATGAAGCCCTCCACAA
ORF39     ATCCCGTTGGCAGCAGGGGAACGTTTTCTCATGCTCAGTTATGCATGAAGCACTGCATAA
ORFIAU    ATCCCGATGGCAGCAAGGAAACGTGTTCAGCTGCAGCGTGATGCATGAGGCCCTGCACAA
ORFIAM    AAGCCGGTGGCAGCAGGGAAACGTGTTCAGCTGTAGCGTGATGCACGAAGCCCTGCACAA
BASE      GAGCAGGTGGCAGCAGGGGAACGTCTTCTCATGCTCCGTGATGCATGAGGCTCTGCACAA
ORF1      GAGCCGGTGGCAGCAGGGGAATGTGTTCTCATGCAGCGTGATGCACGAAGCCCTGCACAA
ORF40     GAGCAGATGGCAGCAGGGGAATGTGTTTAGCTGCAGCGTGATGCATGAGGCTCTCCATAA
ORF11     GTCACGGTGGCAACAGGGCAACGTGTTTTCATGTTCCGTGATGCACGAAGCTCTGCATAA
ORF30     GAGTAGATGGCAACAGGGGAATGTGTTTTCTTGTTCCGTGATGCACGAGGCACTGCACAA
ORF28     GAGTCGGTGGCAGCAGGGTAACGTGTTCTCTTGTTCTGTGATGCATGAGGCATTGCACAA
ORF26     GTCTCGATGGCAGCAGGGCAATGTGTTCTCATGCTCTGTGATGCATGAGGCATTGCATAA
ORF2      GTCCCGGTGGCAGCAGGGCAATGTGTTTTCCTGTTCAGTGATGCATGAAGCGCTGCATAA
               * ***** ** ** ** ** **    **    ** ***** ** **  * ** **

ORF35     TCATTACACCCAGAAGTCGTTGAGCCTATCTCCCGGTAGGAAAAGGCGGGCTCCTGTGAA
ORF42     TCACTATACACAGAAAAGTCTATCACTCTCACCTGGCAGAAAACGGAGGGCACCCGTGAA
ORF39     CCACTATACGCAGAAATCATTATCACTTAGTCCCGGACGGAAAAGGCGCGCTCCCGTGAA
ORFIAU    CCACTATACCCAGAAAAGCCTGAGCCTGAGCCCAGGCCGGAAGCGGAGAGCCCCAGTCAA
ORFIAM    CCACTACACCCAGAAAAGCCTGAGCCTGAGCCCAGGCCGGAAGCGGCGGGCCCCAGTGAA
BASE      CCACTACACGCAGAAGAGCCTCTCCCTGTCTCCCGGCCGAAAGCGGAGAGCCCCCGTGAA
ORF1      TCACTACACCCAGAAGTCACTGTCGCTGAGCCCTGGCCGGAAAAGGAGGGCCCCAGTCAA
ORF40     TCATTACACGCAGAAATCCCTGAGCTTGTCTCCCGGGCGTAAACGACGCGCACCCGTGAA
ORF11     CCACTATACCCAGAAGTCCCTGTCTCTGAGCCCAGGGAGGAAGAGGCGCGCACCAGTGAA
ORF30     TCACTACACACAGAAGAGTCTCAGCTTATCTCCTGGAAGGAAGAGACGAGCTCCCGTCAA
ORF28     TCATTACACGCAGAAGAGTCTGTCCCTTTCTCCTGGCCGTAAAAGGCGAGCTCCTGTGAA
ORF26     CCACTATACACAGAAGTCATTATCACTCTCCCCCGGCAGAAAACGCAGGGCTCCTGTGAA
ORF2      TCACTATACACAAAAGTCACTTTCTCTGAGTCCCGGTCGGAAGAGAAGAGCTCCTGTTAA
           ** ** ** ** **     *     *    ** **  * **  *  * ** ** ** **
```

FIG. 1G

```
ORF35      GCAAACTCTGAACTTTGACTTGCTGAAGCTCGCCGGTGACGTAGAATCAAACCCTGGACC
ORF42      GCAGACACTCAATTTCGACTTACTGAAACTGGCTGGGGATGTCGAATCTAATCCAGGCCC
ORF39      ACAGACCCTCAACTTTGACTTACTGAAGCTCGCCGGAGACGTCGAGTCAAATCCTGGTCC
ORFIAU     ACAGACCCTGAACTTCGATCTGCTGAAACTGGCAGGCGACGTGGAGTCCAACCCAGGGCC
ORFIAM     ACAGACCCTGAATTTCGATCTGCTGAAGCTGGCCGGAGATGTGGAAAGCAACCCCGGACC
BASE       GCAGACCCTGAACTTCGACCTGCTGAAGCTGGCCGGCGACGTGGAAAGCAACCCTGGCCC
ORF1       ACAGACTCTGAACTTCGACCTGCTGAAGCTCGCGGGGGACGTGGAGAGTAATCCCGGGCC
ORF40      ACAGACATTGAATTTCGACTTGCTGAAGTTAGCCGGGGACGTCGAGAGTAATCCAGGCCC
ORF11      ACAGACCTTGAATTTCGACCTGCTGAAGCTGGCTGGCGATGTTGAATCCAACCCAGGCCC
ORF30      ACAGACGCTAAACTTTGACCTGTTAAAGCTTGCCGGCGATGTCGAATCCAATCCAGGGCC
ORF28      GCAGACTCTTAACTTTGACTTGCTCAAGCTCGCTGGCGATGTGGAGTCCAATCCTGGGCC
ORF26      GCAGACTCTTAACTTTGACCTGCTGAAACTTGCTGGTGACGTGGAATCAAACCCCGGTCC
ORF2       ACAGACACTGAATTTCGATTTGCTCAAACTCGCTGGAGACGTAGAAAGCAATCCTGGTCC
            ** **  * ** ** **  *  * **  * ** ** ** ** **    ** ** ** **

ORF35      CATGTACAGAATGCAGCTGTTGTCCTGTATTGCACTGAGTCTGGCTCTCGTGACCAATTC
ORF42      TATGTACCGCATGCAACTACTGTCATGTATTGCCCTTTCATTAGCTCTCGTAACAAATTC
ORF39      GATGTATAGAATGCAGCTGCTTTCTTGCATTGCATTGAGTCTCGCCCTGGTCACCAACAG
ORFIAU     AATGTATAGAATGCAGCTGCTGAGCTGCATTGCCCTGAGCCTGGCCCTGGTGACCAATTC
ORFIAM     CATGTACCGGATGCAGCTGCTGAGCTGTATCGCCCTGAGCCTGGCCCTGGTGACCAATTC
BASE       TATGGGATGGTCATG--TATCATCCTTTTTCTAGTAGCAACTGCAACCGGTGTACA-TTC
ORF1       AATGTATCGCATGCAGTTGCTGTCGTGCATCGCCCTGTCTCTGGCGCTGGTCACCAATTC
ORF40      TATGTACAGAATGCAGCTCCTGTCCTGCATAGCTCTCAGCCTGGCCCTTGTGACAAATTC
ORF11      CATGTATAGAATGCAGCTGCTGTCTTGTATCGCCTTGAGCCTGGCCTTGGTCACAAATTC
ORF30      TATGTACCGGATGCAGCTACTTAGTTGCATAGCTCTTAGCCTTGCTCTCGTGACTAACAG
ORF28      CATGTACCGAATGCAACTTCTTAGCTGCATAGCACTTTCCCTTGCACTTGTGACGAATTC
ORF26      AATGTACAGAATGCAGCTTTTGTCATGCATTGCTCTCAGCCTAGCTCTAGTGACCAATTC
ORF2       TATGTACCGAATGCAGCTTTTGTCTTGCATCGCTCTGAGCCTTGCGCTTGTTACGAATAG
            ***    *        *       *   *           *       **    *

ORF35      AGACATCCAGATGACCCAATCACCCTCCAGCCTTTCCGCCTCGGTTGGAGACACCGTAAC
ORF42      TGATATCCAGATGACCCAGTCCCCCTCATCTCTGTCAGCATCGGTTGGCGATACCGTTAC
ORF39      TGATATCCAGATGACCCAGAGTCCTTCATCTCTCTCAGCTTCAGTGGGAGACACGGTCAC
ORFIAU     CGATATCCAGATGACCCAGAGCCCCTCCTCCCTGAGCGCATCCGTCGGAGACACCGTGAC
ORFIAM     CGATATTCAGATGACACAGAGCCCCAGCTCCCTGAGCGCCAGCGTGGGCGATACCGTCAC
BASE       TGACATCCAGATGACCCAGTCTCCATCCTCCCTGTCTGCATCTGTAGGAGATACCGTCAC
ORF1       TGATATTCAGATGACGCAGAGCCCTAGCAGCCTCTCTGCAAGCGTGGGGGACACGGTGAC
ORF40      TGATATACAGATGACGCAGTCGCCCTCAAGCCTCAGTGCCTCCGTGGGGGATACTGTTAC
ORF11      GGATATCCAGATGACGCAATCCCCCTCCTCCCTCAGCGCTTCAGTAGGTGACACAGTAAC
ORF30      CGACATCCAGATGACGCAGTCACCTTCCTCCCTGTCAGCCTCAGTCGGCGATACCGTAAC
ORF28      TGACATCCAGATGACCCAGAGTCCCTCCTCTTTGAGTGCAAGTGTGGGCGACACCGTGAC
ORF26      AGATATTCAGATGACTCAGAGTCCAAGTAGTCTAAGCGCCTCAGTCGGCGATACAGTGAC
ORF2       CGACATACAGATGACACAGTCTCCGAGTTCTCTTAGTGCTAGTGTGGGCGATACAGTCAC
            ** ** ******** **    **        *    **    ** ** ** ** ** **

ORF35      AATTACTTGTCAGGCTAACGGTTACCTTAACTGGTATCAGCAGCGCCGAGGGAAAGCTCC
ORF42      TATTACGTGCCAGGCAAATGGCTACTTGAACTGGTACCAACAACGGCGCGGTAAAGCACC
ORF39      GATAACCTGCCAGGCTAACGGCTATCTCAATTGGTACCAGCAGCGCAGGGGTAAAGCTCC
ORFIAU     AATCACATGCCAGGCAAACGGCTATCTGAACTGGTATCAGCAGCGGAGAGGGAAGGCACC
ORFIAM     CATCACATGCCAGGCCAACGGATACCTGAACTGGTACCAGCAGCGGCGGGGAAAGGCCCC
BASE       TATCACTTGCCAGGCAAACGGCTACTTAAATTGGTATCAACAGAGGCGAGGGAAAGCCCC
ORF1       GATTACATGCCAGGCTAACGGATATCTGAACTGGTACCAACAGCGGAGGGGGAAGGCCCC
ORF40      AATCACATGTCAGGCCAATGGCTATCTAAACTGGTATCAGCAGCGGAGGGGAAAGGCACC
ORF11      AATTACATGTCAGGCCAATGGGTACCTCAATTGGTATCAGCAGCGAAGGGGCAAAGCTCC
ORF30      TATAACATGTCAGGCGAATGGGTATCTGAATTGGTATCAGCAGCGACGTGGGAAAGCTCC
ORF28      CATCACTTGTCAGGCCAATGGCTATCTCAACTGGTATCAGCAGCGGAGAGGGAAGGCACC
ORF26      GATCACCTGTCAGGCAAACGGATACTTGAATTGGTACCAGCAGAGGAGGGGGAAGGCTCC
ORF2       TATAACATGCCAGGCTAATGGTTACCTGAACTGGTACCAACAACGCCGCGGTAAAGCCCC
            ** ** ** ***** ** ** **  * ** ***** ** **  *  * ** ** ** **
```

FIG. 1H

```
ORF35     CAAGCTACTCATATACGACGGCTCTAAGCTGGAACGCGGCGTTCCTTCACGGTTTAGTGG
ORF42     CAAACTATTGATATACGATGGCTCAAAGTTGGAAAGAGGCGTGCCTTCAAGATTCTCCGG
ORF39     CAAACTGCTGATCTATGATGGTTCAAAACTGGAGCGCGGCGTACCCTCACGGTTTTCCGG
ORFIAU    TAAGCTGCTGATCTACGACGGAAGCAAGCTGGAACGAGGCGTCCCCAGCCGGTTCAGCGG
ORFIAM    AAAGCTGCTGATCTACGATGGAAGCAAGCTGGAGCGGGGAGTGCCCAGCCGGTTCAGCGG
BASE      AAAACTCCTGATCTACGATGGGTCCAAATTGGAAAGAGGGGTCCCATCAAGGTTCAGTGG
ORF1      GAAGCTGCTCATCTACGACGGGTCCAAATTGGAGCGAGGAGTACCGTCCCGGTTCTCGGG
ORF40     CAAGTTACTGATATACGACGGCTCCAAGTTGGAGCGCGGGGTCCCCAGCAGGTTTTCCGG
ORF11     TAAGTTGCTGATCTATGACGGCTCTAAGTTGGAACGCGGCGTTCCGAGTAGGTTTAGTGG
ORF30     TAAGTTGCTTATCTATGATGGGTCTAAGCTTGAGAGAGGGGTGCCAAGTAGATTTTCTGG
ORF28     TAAGCTACTCATCTATGACGGCAGTAAACTGGAGAGAGGCGTTCCAAGCAGATTCTCCGG
ORF26     GAAGCTTCTGATCTATGACGGCAGTAAGCTTGAACGCGGTGTGCCTAGCCGCTTCTCCGG
ORF2      CAAACTGCTCATCTATGATGGGTCAAAACTTGAACGCGGCGTCCCGAGCCGCTTTAGTGG
           **  *  * ** ** ** **    **  * **  * ** ** **     * **    **

ORF35     CCGGAGGTGGGGCCAGGAATACAACCTGACCATTAACAACCTGCAGCCCGAAGATATTGC
ORF42     CAGACGCTGGGGCCAGGAGTACAACCTAACTATCAACAACCTTCAGCCAGAGGATATTGC
ORF39     ACGACGATGGGGCCAGGAGTACAATCTGACTATCAACAACCTGCAGCCCGAGGACATAGC
ORFIAU    GAGAAGATGGGGGCAGGAATACAACCTGACAATCAACAATCTGCAGCCCGAGGACATTGC
ORFIAM    ACGGCGGTGGGGCCAGGAATACAACCTGACCATCAACAATCTGCAGCCAGAGGACATCGC
BASE      AAGAAGATGGGGGCAAGAATATAATCTGACCATCAACAATCTGCAGCCCGAAGACATTGC
ORF1      GCGGAGATGGGGGCAGGAATACAACCTAACCATAAACAACCTACAGCCCGAGGACATCGC
ORF40     CAGGAGATGGGGGCAGGAGTACAACCTGACCATAAACAATCTCCAGCCTGAGGATATTGC
ORF11     CCGGAGATGGGGACAAGAGTATAACCTGACGATCAACAACTTGCAACCCGAGGACATTGC
ORF30     ACGAAGGTGGGGGCAGGAGTATAACTTGACCATCAATAACCTTCAGCCTGAAGATATCGC
ORF28     TCGCCGATGGGGCCAGGAATACAATCTTACCATCAATAACCTGCAGCCCGAGGACATTGC
ORF26     TCGCCGCTGGGGTCAGGAGTACAACTTAACCATAAACAACCTCCAGCCTGAGGACATAGC
ORF2      CCGCCGTTGGGGGCAGGAATACAATCTTACCATCAACAATCTACAGCCCGAAGATATTGC
            *  * ***** ** ** ** **  * ** ** ** **  * ** ** ** ** ** **

ORF35     CACCTATTTCTGTCAGGTGTATGAATTTGTTGTTCCCGGGACCCGACTGGACTTGAAGCG
ORF42     AACCTACTTCTGTCAGGTGTATGAGTTTGTGGTGCCCGGCACGCGTCTGGATTTGAAGAG
ORF39     GACGTATTTCTGCCAGGTATATGAGTTTGTCGTCCCTGGGACCCGGCTGGACCTGAAAAG
ORFIAU    AACCTACTTCTGCCAGGTGTACGAGTTTGTCGTCCCAGGGACACGACTGGATCTGAAGCG
ORFIAM    CACCTACTTCTGCCAGGTCTACGAGTTCGTGGTGCCTGGAACCCGGCTGGATCTGAAGCG
BASE      AACATATTTTTGTCAAGTGTATGAGTTTGTCGTCCCTGGGACCAGACTGGATTTGAAACG
ORF1      CACTTACTTCTGCCAGGTGTACGAGTTCGTGGTGCCCGGCACCAGGCTGGACCTGAAGCG
ORF40     CACATACTTTTGCCAGGTATACGAGTTTGTTGTGCCTGGCACACGGCTCGATCTGAAAAG
ORF11     TACCTATTTCTGTCAGGTGTATGAATTTGTAGTACCAGGCACCCGGCTAGATCTGAAACG
ORF30     CACATACTTTTGCCAGGTATATGAGTTTGTTGTGCCCGGGACGAGACTTGATCTCAAACG
ORF28     CACCTATTTCTGTCAGGTGTATGAGTTCGTGGTGCCCGGAACGAGACTCGATCTCAAGAG
ORF26     AACCTATTTCTGTCAGGTGTATGAGTTTGTTGTGCCCGGTACAAGGCTAGACCTCAAGCG
ORF2      TACTTACTTTTGCCAGGTTTACGAATTTGTCGTCCCGGGAACGCGCCTTGATCTTAAGCG
           ** ** ** ** ** ** ** ** ** ** ** ** ** **  * ** **  * **  *

ORF35     GACCGTTGCGGCACCCAGCGTCTTTATCTTTCCCCCATCGGATGAACAACTGAAATCCGG
ORF42     AACAGTCGCGGCACCCTCAGTGTTTATCTTCCCTCCCAGTGATGAGCAGCTGAAATCAGG
ORF39     GACGGTCGCTGCACCCTCAGTATTCATATTCCCACCCTCCGATGAGCAGTTGAAAAGCGG
ORFIAU    GACAGTGGCCGCACCCAGCGTGTTTATCTTCCCTCCCTCCGACGAACAGCTGAAGTCCGG
ORFIAM    GACAGTGGCCGCCCCCTCCGTGTTCATCTTCCCCCCTAGCGACGAGCAGCTGAAATCCGG
BASE      TACGGTGGCTGCACCATCTGTCTTCATCTTCCCGCCATCTGATGAGCAGTTGAAATCTGG
ORF1      GACCGTGGCCGCACCTAGTGTGTTCATCTTCCCACCGTCCGATGAGCAGTTGAAGAGCGG
ORF40     GACCGTGGCTGCCCCAAGCGTGTTCATTTTCCCTCCCAGCGACGAACAGCTTAAGTCTGG
ORF11     GACAGTAGCTGCCCCCAGCGTGTTCATATTCCCTCCATCTGACGAACAGCTTAAGTCGGG
ORF30     AACGGTGGCTGCTCCTTCTGTGTTTATCTTTCCTCCTTCTGATGAGCAGCTCAAGAGCGG
ORF28     AACTGTGGCTGCCCCCAGCGTGTTCATTTTCCCTCCTTCCGACGAGCAGCTTAAGAGTGG
ORF26     AACCGTGGCCGCTCCATCCGTCTTTATCTTTCCTCCTAGCGACGAGCAGCTGAAGTCCGG
ORF2      GACTGTCGCCGCTCCGAGTGTGTTTATCTTTCCTCCATCAGACGAACAGCTTAAGTCAGG
           ** ** ** ** **    ** ** ** ** ** **    ** ** **  * **    **
```

FIG. 1I

```
ORF35        CACCGCCTCAGTTGTTTGCCTGCTGAACAACTTCTATCCGCGGGAAGCGAAGGTCCAGTG
ORF42        CACCGCCTCAGTGGTATGCCTGTTGAACAACTTCTACCCCCGTGAGGCAAAAGTTCAGTG
ORF39        AACAGCGTCAGTCGTGTGCCTCCTCAATAACTTCTACCCCCGGGAAGCCAAAGTTCAGTG
ORFIAU       CACCGCATCCGTGGTGTGCCTGCTGAACAATTTCTATCCCAGAGAGGCCAAAGTCCAGTG
ORFIAM       AACAGCCAGCGTGGTCTGTCTGCTGAACAACTTCTACCCTCGGGAGGCCAAAGTGCAGTG
BASE         AACTGCCTCTGTTGTGTGCCTGCTGAATAACTTCTACCCCAGAGAAGCCAAAGTGCAGTG
ORF1         GACAGCGAGCGTGGTGTGCCTGCTGAACAACTTCTATCCGCGCGAGGCCAAAGTACAGTG
ORF40        GACTGCGTCCGTCGTATGTTTGCTGAACAACTTCTATCCCCGTGAAGCCAAAGTGCAGTG
ORF11        CACCGCAAGCGTGGTGTGCCTGTTGAATAACTTCTATCCGAGAGAGGCTAAGGTGCAGTG
ORF30        AACAGCATCCGTTGTCTGTCTGCTCAACAACTTTTACCCTAGGGAAGCTAAGGTGCAGTG
ORF28        CACCGCTTCAGTGGTGTGTTTACTAAACAATTTCTACCCTCGAGAGGCGAAGGTGCAGTG
ORF26        CACCGCTTCAGTGGTCTGCCTCCTCAACAATTTCTACCCCAGGGAAGCCAAGGTGCAGTG
ORF2         CACCGCTTCTGTGGTGTGCTTGCTGAATAACTTCTATCCCCGGGAAGCCAAGGTTCAGTG
              ** **    ** ** **  *  * ** ** ** ** **  * ** ** ** ** *****

ORF35        GAAAGTTGACAACGCCCTGCAGTCAGGTAACTCGCAAGAATCTGTCACCGAACAGGACAG
ORF42        GAAGGTGGATAATGCCTTACAGTCAGGCAACTCACAAGAGAGCGTCACTGAGCAGGATTC
ORF39        GAAAGTTGACAATGCACTTCAGTCTGGAAATAGTCAGGAGAGCGTGACTGAGCAGGATTC
ORFIAU       GAAGGTGGACAATGCACTGCAGTCCGGAAATAGCCAAGAAAGCGTCACCGAGCAGGACTC
ORFIAM       GAAGGTCGATAACGCCCTGCAGTCCGGAAACAGCCAGGAGTCCGTGACCGAGCAGGATTC
BASE         GAAGGTGGACAACGCCCTGCAGAGCGGAAACAGCCAGGAAAGCGTGACAGAGCAGGATTC
ORF1         GAAGGTAGATAACGCCCTCCAGTCCGGAAACAGCCAGGAGTCCGTGACCGAGCAGGACTC
ORF40        GAAAGTGGACAATGCACTGCAGTCCGGGAACTCCCAAGAGAGCGTCACAGAGCAGGACTC
ORF11        GAAGGTCGACAACGCCCTACAGTCTGGCAATTCTCAAGAAAGCGTTACCGAACAGGATAG
ORF30        GAAGGTTGACAATGCTTTACAGAGCGGAAATAGCCAGGAGTCCGTCACAGAACAGGATAG
ORF28        GAAGGTGGATAATGCCCTTCAGTCAGGCAATTCTCAAGAAAGTGTGACCGAGCAGGATAG
ORF26        GAAAGTGGACAATGCACTGCAGAGTGGAAATTCTCAAGAGTCTGTGACCGAGCAGGACTC
ORF2         GAAGGTCGACAATGCTCTTCAGTCTGGTAATAGCCAGGAGTCAGTGACAGAACAGGACTC
             *** ** ** ** **  * ***   ** **    ** **    ** ** ** *****

ORF35        CAAGGACTCGACCTATAGTCTCAGCTCCACCCTAACGCTGTCCAAAGCCGATTATGAGAA
ORF42        AAAAGATTCAACATACAGTCTTAGCTCAACCCTGACCCTCTCTAAAGCGGATTACGAAAA
ORF39        AAAAGATTCTACGTATTCCCTGAGCTCAACGCTCACACTGTCTAAAGCTGATTATGAGAA
ORFIAU       CAAGGACTCCACATACTCCCTGAGCAGCACACTGACCCTGAGCAAGGCAGACTACGAGAA
ORFIAM       CAAGGATAGCACCTACAGCCTGAGCTCCACCCTGACACTGTCCAAGGCCGATTACGAGAA
BASE         CAAGGATTCCACATACAGCCTGAGCAGCACACTGACACTGTCCAAGGCCGACTACGAGAA
ORF1         AAAGGATTCCACATACTCCCTTTCCTCAACACTGACGCTGAGTAAGGCGGATTACGAGAA
ORF40        CAAAGACTCGACCTACTCTCTAAGCTCCACACTGACACTCAGCAAGGCTGACTATGAGAA
ORF11        CAAGGACAGCACGTATAGCTTGTCCTCCACACTGACGCTTTCCAAGGCAGACTATGAAAA
ORF30        CAAGGATAGCACATATAGCTTGAGCTCCACTCTGACACTCAGTAAGGCTGATTATGAGAA
ORF28        TAAGGACTCTACATACTCACTCTCCTCAACCCTGACACTCAGTAAGGCCGACTATGAGAA
ORF26        AAAAGACTCTACCTACAGCCTGAGTTCAACCCTTACCCTGTCAAAGGCCGATTACGAAAA
ORF2         CAAGGACAGTACCTACTCTCTATCCAGTACACTGACCCTGAGCAAAGCTGACTACGAAAA
              ** **    ** **     *       ** ** ** **    ** ** ** ** ** **

ORF35        GCACAAAGTCTATGCTTGTGAGGTTACGCACCAAGGGCTAAGCAGTCCCGTTACAAAGTC
ORF42        ACACAAAGTTTATGCCTGCGAAGTCACGCACCAGGGTCTGAGTAGCCCTGTTACTAAAAG
ORF39        ACATAAGGTTTATGCCTGCGAGGTAACGCATCAGGGTCTATCATCGCCCGTCACGAAAAG
ORFIAU       GCACAAGGTCTACGCCTGCGAAGTCACCCACCAGGGACTGTCCTCCCCTGTGACCAAATC
ORFIAM       ACACAAGGTGTACGCCTGCGAAGTGACCCATCAGGGACTGAGCAGCCCAGTGACCAAGAG
BASE         GCACAAGGTGTACGCCTGCGAAGTGACACACCAGGGACTGTCCTCCCCTGTGACAAAGAG
ORF1         GCACAAGGTGTATGCGTGTGAGGTGACTCACCAGGGGCTGTCCTCACCCGTGACGAAATC
ORF40        GCACAAAGTTTACGCCTGTGAAGTGACTCATCAGGGGCTCAGCTCCCCCGTGACAAAAAG
ORF11        ACATAAGGTGTACGCGTGTGAGGTGACTCATCAGGGCCTGTCCAGCCCGGTTACAAAGTC
ORF30        GCATAAGGTATATGCCTGTGAAGTCACACATCAAGGCCTTTCATCCCCTGTTACTAAGTC
ORF28        GCACAAGGTGTACGCGTGCGAAGTCACGCATCAGGGCCTATCTAGCCCCGTCACAAAGTC
ORF26        GCATAAGGTGTATGCTTGCGAGGTGACCCACCAGGGCCTGTCGAGCCCCGTGACCAAGAG
ORF2         GCACAAAGTCTATGCTTGTGAAGTAACGCATCAAGGCCTTAGCTCTCCTGTTACCAAGAG
              ** ** ** ** ** ** ** ** ** ** ** ** **       ** ** ** **
```

FIG. 1J

```
ORF35        CTTTAACCGGGGAGAGTGT
ORF42        TTTCAACCGAGGCGAATGT
ORF39        CTTTAACAGAGGGGAGTGT
ORFIAU       CTTCAATAGAGGAGAGTGC
ORFIAM       CTTCAATCGGGGAGAATGC
BASE         CTTCAACAGAGGAGAATGC
ORF1         GTTTAACCGGGGCGAGTGT
ORF40        CTTTAACCGGGGAGAATGT
ORF11        CTTTAACAGGGGCGAATGC
ORF30        TTTCAACAGAGGGGAATGC
ORF28        ATTCAATAGGGGCGAGTGC
ORF26        CTTTAACCGTGGAGAATGC
ORF2         CTTCAATAGGGGTGAATGC
              ** **  * ** ** **
```

PLASMID SEQUENCES
FIG. 5A

SEQ ID NO: 13

```
pRN007 {CMV.SDA.VRC01L.IgG1B12L.BGH.VRC8551]
LOCUS       pRN007\{CMV.SDA.        5102 bp    DNA     circular
FEATURES             Location/Qualifiers
     misc_feature    1380..1384
                     /vntifkey="21"
                     /label=KOZAK
     misc_feature    1385..2077
                     /vntifkey="21"
                     /label=VRC01L\{VRC01VL-B12CL}
BASE COUNT     1284 a      1318 c      1235 g      1265 t
ORIGIN
        1 tcgcgcgttt cggtgatgac ggtgaaaacc tctgacacat gcagctcccg gagacggtca
       61 cagcttgtct gtaagcggat gccgggagca gacaagcccg tcagggcgcg tcagcgggtg
      121 ttggcgggtg tcggggctgg cttaactatg cggcatcaga gcagattgta ctgagagtgc
      181 accatatgcg gtgtgaaata ccgcacagat gcgtaaggag aaaataccgc atcagattgg
      241 ctattggcca ttgcatacgt tgtatccata tcataatatg tacatttata ttggctcatg
      301 tccaacatta ccgccatgtt gacattgatt attgactagt tattaatagt aatcaattac
      361 ggggtcatta gttcatagcc catatatgga gttccgcgtt acataactta cggtaaatgg
      421 cccgcctggc tgaccgccca acgacccccg cccattgacg tcaataatga cgtatgttcc
      481 catagtaacg ccaataggga ctttccattg acgtcaatgg gtggagtatt tacggtaaac
      541 tgcccacttg gcagtacatc aagtgtatca tatgccaagt acgcccccta ttgacgtcaa
      601 tgacggtaaa tggcccgcct ggcattatgc ccagtacatg accttatggg actttcctac
      661 ttggcagtac atctacgtat tagtcatcgc tattaccatg gtgatgcggt tttggcagta
      721 catcaatggg cgtggatagc ggtttgactc acggggattt ccaagtctcc accccattga
      781 cgtcaatggg agtttgtttt ggcaccaaaa tcaacgggac tttccaaaat gtcgtaacaa
      841 ctccgcccca ttgacgcaaa tgggcggtag gcgtgtacgg tgggaggtct atataagcag
      901 agctcgttta gtgaaccgtc agatcgcctg gagacgccat ccacgctgtt ttgacctcca
      961 tagaagacac cgggaccgat ccagcctcca tcggctcgca tctctccttc acgcgcccgc
     1021 cgccctacct gaggccgcca tccacgccgg ttgagtcgcg ttctgccgcc tcccgcctgt
     1081 ggtgcctcct gaactgcgtc cgccgtctag gtaagtttaa agctcaggtc gagaccgggc
     1141 ctttgtccgg cgctcccttg gagcctacct agactcagcc ggctctccac gctttgcctg
     1201 accctgcttg ctcaactcta gttaacggtg gagggcagtg tagtctgagc agtactcgtt
     1261 gctgccgcgc gcgccaccag acataatagc tgacagacta acagactgtt cctttccatg
     1321 ggtcttttct gcagtcaccg tcgtcgacac gtgtgatcag atatcgcggc cgctctagac
     1381 caccatggga tggtcatgta tcatcctttt tctagtagca actgcaaccg gtgtacattc
     1441 agaaattgtg ttgacacagt ctccaggcac cctgtctttg tctccagggg aaacagccat
     1501 catctcttgt cggaccagtc agtatggttc cttagcctgg tatcaacaga ggcccggcca
     1561 ggcccccagg ctcgtcatct attcgggctc tactcgggcc gctggcatcc cagacaggtt
     1621 cagcggcagt cggtgggggc cagactacaa tctcaccatc agcaacctgg agtcgggaga
     1681 ttttggtgtt tattattgcc agcagtatga atttttggc caggggacca aggtccaggt
     1741 cgacattaaa cgtacggtgg ctgcaccatc tgtcttcatc ttcccgccat ctgatgagca
     1801 gttgaaatct ggaactgcct ctgttgtgtg cctgctgaat aacttctacc ccagagaagc
     1861 caaagtgcag tggaaggtgg acaacgccct gcagagcgga aacagccagg aaagcgtgac
     1921 agagcaggat tccaaggatt ccacatacag cctgagcagc acactgacac tgtccaaggc
     1981 cgactacgag aagcacaagg tgtacgcctg cgaagtgaca caccagggac tgtcctcccc
     2041 tgtgacaaag agcttcaaca gaggagaatg ctgataggat ccagatctgc tgtgccttct
     2101 agttgccagc catctgttgt ttgcccctcc cccgtgcctt ccttgaccct ggaaggtgcc
     2161 actcccactg tcctttccta ataaaatgag gaaattgcat cgcattgtct gagtaggtgt
     2221 cattctattc tggggggtgg ggtggggcag gacagcaagg gggaggattg ggaagacaat
     2281 agcaggcatg ctggggatgc ggtgggctct atgggtaccc aggtgctgaa gaattgaccc
     2341 ggttcctcct gggccagaaa gaagcaggca catccccttc tctgtgacac accctgtcca
     2401 cgcccctggt tcttagttcc agccccactc ataggacact catagctcag gagggctccg
     2461 ccttcaatcc cacccgctaa agtacttgga gcggtctctc cctccctcat cagcccacca
     2521 aaccaaacct agcctccaag agtgggaaga aattaaagca agataggcta ttaagtgcag
```

PLASMID SEQUENCES
FIG. 5B

```
2581 agggagagaa aatgcctcca acatgtgagg aagtaatgag agaaatcata gaattttaag
2641 gccatgattt aaggccatca tggccttaat cttccgcttc ctcgctcact gactcgctgc
2701 gctcggtcgt tcggctgcgg cgagcggtat cagctcactc aaaggcggta atacggttat
2761 ccacagaatc aggggataac gcaggaaaga acatgtgagc aaaaggccag caaaaggcca
2821 ggaaccgtaa aaaggccgcg ttgctggcgt ttttccatag gctccgcccc cctgacgagc
2881 atcacaaaaa tcgacgctca agtcagaggt ggcgaaaccc gacaggacta taaagatacc
2941 aggcgtttcc ccctggaagc tccctcgtgc gctctcctgt tccgaccctg ccgcttaccg
3001 gatacctgtc cgcctttctc ccttcgggaa gcgtggcgct ttctcatagc tcacgctgta
3061 ggtatctcag ttcggtgtag gtcgttcgct ccaagctggg ctgtgtgcac gaaccccccg
3121 ttcagcccga ccgctgcgcc ttatccggta actatcgtct tgagtccaac ccggtaagac
3181 acgacttatc gccactggca gcagccactg gtaacaggat tagcagagcg aggtatgtag
3241 gcggtgctac agagttcttg aagtggtggc ctaactacgg ctacactaga agaacagtat
3301 ttggtatctg cgctctgctg aagccagtta ccttcggaaa aagagttggt agctcttgat
3361 ccggcaaaca aaccaccgct ggtagcggtg gtttttttgt ttgcaagcag cagattacgc
3421 gcagaaaaaa aggatctcaa gaagatcctt tgatcttttc tacggggtct gacgctcagt
3481 ggaacgaaaa ctcacgttaa gggattttgg tcatgagatt atcaaaaagg atcttcacct
3541 agatcctttt aaattaaaaa tgaagtttta aatcaatcta aagtatatat gagtaaactt
3601 ggtctgacag ttaccaatgc ttaatcagtg aggcacctat ctcagcgatc tgtctatttc
3661 gttcatccat agttgcctga ctcggggggg gggggcgctg aggtctgcct cgtgaagaag
3721 gtgttgctga ctcataccag gcctgaatcg ccccatcatc cagccagaaa gtgagggagc
3781 cacggttgat gagagctttg ttgtaggtgg accagttggt gattttgaac ttttgctttg
3841 ccacggaacg gtctgcgttg tcgggaagat gcgtgatctg atccttcaac tcagcaaaag
3901 ttcgatttat tcaacaaagc cgccgtcccg tcaagtcagc gtaatgctct gccagtgtta
3961 caaccaatta accaattctg attagaaaaa ctcatcgagc atcaaatgaa actgcaattt
4021 attcatatca ggattatcaa taccatattt ttgaaaaagc cgtttctgta atgaaggaga
4081 aaactcaccg aggcagttcc ataggatggc aagatcctgg tatcggtctg cgattccgac
4141 tcgtccaaca tcaatacaac ctattaattt cccctcgtca aaaataaggt tatcaagtga
4201 gaaatcacca tgagtgacga ctgaatccgg tgagaatggc aaaagcttat gcatttcttt
4261 ccagacttgt tcaacaggcc agccattacg ctcgtcatca aaatcactcg catcaaccaa
4321 accgttattc attcgtgatt gcgcctgagc gagacgaaat acgcgatcgc tgttaaaagg
4381 acaattacaa acaggaatcg aatgcaaccg gcgcaggaac actgccagcg catcaacaat
4441 attttcacct gaatcaggat attcttctaa tacctggaat gctgttttcc cggggatcgc
4501 agtggtgagt aaccatgcat catcaggagt acggataaaa tgcttgatgg tcggaagagg
4561 cataaattcc gtcagccagt ttagtctgac catctcatct gtaacatcat tggcaacgct
4621 acctttgcca tgtttcagaa acaactctgg cgcatcgggc ttcccataca atcgatagat
4681 tgtcgcacct gattgcccga cattatcgcg agcccattta tacccatata aatcagcatc
4741 catgttggaa tttaatcgcg gcctcgagca agacgtttcc cgttgaatat ggctcataac
4801 acccttgta ttactgttta tgtaagcaga cagttttatt gttcatgatg atatattttt
4861 atcttgtgca atgtaacatc agagattttg agacacaacg tggctttccc cccccccca
4921 ttattgaagc atttatcagg gttattgtct catgagcgga tacatatttg aatgtattta
4981 gaaaaataaa caaatagggg ttccgcgcac atttccccga aaagtgccac ctgacgtcta
5041 agaaaccatt attatcatga cattaaccta taaaaatagg cgtatcacga ggccctttcg
5101 tc
//
```

PLASMID SEQUENCES
FIG. 5C

SEQ ID NO:14

```
pN117 3bnc117 MAB IRES assembly plasmid
LOCUS       3bnc117\MAB\IRES        6684 bp    DNA     circular
FEATURES             Location/Qualifiers
     misc_feature    2028..2716
                     /vntifkey="21"
                     /label=HCH23
     misc_feature    1305..1364
                     /vntifkey="21"
                     /label=IL2\signal\peptide
     misc_feature    1365..1750
                     /vntifkey="21"
                     /label=VH\IgG1
     misc_feature    3111..3415
                     /vntifkey="21"
                     /label=CL
     repeat_region   1..130
                     /vntifkey="34"
                     /label=ITR
     repeat_region   complement(3734..3863)
                     /vntifkey="34"
                     /label=ITR
     intron          1047..1179
                     /vntifkey="15"
                     /label=Promega\chimeric\intron
     polyA_signal    3438..3669
                     /vntifkey="25"
                     /label=SV40\late\polyadenylation\signal
     promoter        191..932
                     /vntifkey="29"
                     /label=human\CMV\I.E.\enhancer\&\promoter
     CDS             4626..5483
                     /vntifkey="4"
                     /label=Amp-R
     misc_feature    5657..6245
                     /vntifkey="21"
                     /label=COL\E1\Origin
     rep_origin      complement(4040..4495)
                     /vntifkey="33"
                     /label=f1\ori
     misc_feature    2798..3095
                     /vntifkey="21"
                     /label=3bnc117\light
     misc_feature    1752..2027
                     /vntifkey="21"
                     /label=CH1
     misc_feature    2724..2729
                     /vntifkey="21"
                     /label=STOP
     misc_feature    1248..1295
                     /vntifkey="21"
                     /label=c-myc\miniIRES\cloned\into\Nhe\site
     misc_feature    2738..2797
                     /vntifkey="21"
                     /label=IL2\signal\peptide
```

PLASMID SEQUENCES

FIG. 5D

```
     misc_feature    1300..1308
                     /vntifkey="21"
                     /label=Kozak
     misc_feature    897..901
                     /vntifkey="21"
                     /label=TATA\box
     misc_feature    1236..1325
                     /vntifkey="21"
                     /label=forwrad\primer\1
     misc_feature    2699..2756
                     /vntifkey="21"
                     /label=reverse\primer\1
     misc_feature    2745..2824
                     /vntifkey="21"
                     /label=forward\primer\2-
\remember\to\add\AgeI\site\and\6\bp\extra\on\5'\end
     misc_feature    3083..3106
                     /vntifkey="21"
                     /label=reverse\primer\2
BASE COUNT     1673 a     1745 c     1665 g     1601 t
ORIGIN
        1 ctgcgcgctc gctcgctcac tgaggccgcc cgggcaaagc ccgggcgtcg ggcgaccttt
       61 ggtcgcccgg cctcagtgag cgagcgagcg cgcagagagg gagtggccaa ctccatcact
      121 aggggttcct tgtagttaat gattaacccg ccatgctact tatctacgta gccatgctct
      181 aggaagatct tcaatattgg ccattagcca tattattcat tggttatata gcataaatca
      241 atattggcta ttggccattg catacgttgt atctatatca taatatgtac atttatattg
      301 gctcatgtcc aatatgaccg ccatgttggc attgattatt gactagttat taatagtaat
      361 caattacggg gtcattagtt catagcccat atatggagtt ccgcgttaca taacttacgg
      421 taaatggccc gcctggctga ccgcccaacg acccccgccc attgacgtca ataatgacgt
      481 atgttcccat agtaacgcca atagggactt tccattgacg tcaatgggtg gagtatttac
      541 ggtaaactgc ccacttggca gtacatcaag tgtatcatat gccaagtccg ccccctattg
      601 acgtcaatga cggtaaatgg cccgcctggc attatgccca gtacatgacc ttacgggact
      661 ttcctacttg gcagtacatc tacgtattag tcatcgctat taccatggtg atgcggtttt
      721 ggcagtacac caatgggcgt ggatagcggt ttgactcacg gggatttcca agtctccacc
      781 ccattgacgt caatgggagt ttgttttggc accaaaatca acgggacttt ccaaaatgtc
      841 gtaataaccc cgccccgttg acgcaaatgg gcggtaggcg tgtacggtgg gaggtctata
      901 taagcagagc tcgtttagtg aaccgtcaga tcactagaag ctttattgcg gtagtttatc
      961 acagttaaat tgctaacgca gtcagtgctt ctgacacaac agtctcgaac ttaagctgca
     1021 gaagttggtc gtgaggcact gggcaggtaa gtatcaaggt tacaagacag gtttaaggag
     1081 accaatagaa actgggcttg tcgagacaga gaagactctt gcgtttctga taggcaccta
     1141 ttggtcttac tgacatccac tttgcctttc tctccacagg tgtccactcc cagttcaatt
     1201 acagctctta aggctagagt acttaatacg actcactata ggctagcggg gactttgcac
     1261 tggaacttac aacacccgag caaggacgcg actctagacc caccatgtac aggatgcaac
     1321 tcctgtcttg cattgcacta agtcttgcac ttgtcacaaa cagtcaggtc caattgttac
     1381 agtctggggc agcggtgacg aagcccgggg cctcagtgag agtctcctgc gaggcttctg
     1441 gatacaacat tcgtgactac tttattcatt ggtggcgaca ggccccagga cagggccttc
     1501 agtgggtggg atggatcaat cctaagacag gtcagccaaa caatcctcgt caatttcagg
     1561 gtagagtcag tctgactcga cacgcgtcgt gggactttga cacatttcc ttttacatgg
     1621 acctgaaggc actaagatcg gacgacacgg ccgtttattt ctgtgcgcga cagcgcagcg
     1681 actattggga tttcgacgtc tggggcagtg gaacccaggt cactgtctcg tcagcgtcga
     1741 ccaagggccc ctcggtcttc cccctggcac cctcctccaa gagcacctct gggggcacag
     1801 cggccctggg ctgcctggtc aaggactact tccccgaacc ggtgacggtg tcgtggaact
     1861 caggcgccct gaccagcggc gtgcacacct tcccggctgt cctacagtcc tcaggactct
     1921 actccctcag cagcgtggtg accgtgccct ccagcagctt gggcacccag acctacatct
```

PLASMID SEQUENCES
FIG. 5E

```
1981 gcaacgtgaa tcacaagccc agcaacacca aggtggacaa gaaagttgag cccaaatctt
2041 gtgacaaaac tcacacatgc ccaccgtgcc cagcacctga actcctgggg ggaccgtcag
2101 tcttcctctt ccccccaaaa cccaaggaca ccctcatgat ctcccggacc cctgaggtca
2161 catgcgtggt ggtggacgtg agccacgaag accctgaggt caagttcaac tggtacgtgg
2221 acggcgtgga ggtgcataat gccaagacaa agccgcggga ggagcagtac aacagcacgt
2281 accgtgtggt cagcgtcctc accgtcctgc accaggactg gctgaatggc aaggagtaca
2341 agtgcaaggt ctccaacaaa gccctcccag cccccatcga gaaaaccatc tccaaagcca
2401 aagggcagcc ccgagaacca caggtgtaca ccctgccccc atcccgggat gagctgacca
2461 agaaccaggt cagcctgacc tgcctggtca aaggcttcta tcccagcgac atcgccgtgg
2521 agtgggagag caatgggcag ccggagaaca actacaagac cacgcctccc gtgctggact
2581 ccgacggctc cttcttcctc tacagcaagc tcaccgtgga caagagcagg tggcagcagg
2641 ggaacgtctt ctcatgctcc gtgatgcatg aggctctgca caaccactac acgcagaaga
2701 gcctctccct gtctcccggc aagtgataag gccggccatg taccgcatgc aactcctgtc
2761 ttgcattgca ctaagtcttg cacttgtcac aaacagtgat atccagatga cccagtctcc
2821 atcctccctg tctgcatctg taggagatac cgtcactatc acttgccagg caaacggcta
2881 cttaaattgg tatcaacaga ggcgagggaa agccccaaaa ctcctgatct acgatgggtc
2941 caaattggaa agaggggtcc catcaaggtt cagtggaaga agatgggggc aagaatataa
3001 tctgaccatc aacaatctgc agcccgaaga cattgcaaca tatttttgtc aagtgtatga
3061 gtttgtcgtc cctgggacca gactggattt gaaacgtacg gtggctgcac catctgtctt
3121 catcttcccg ccatctgatg agcagttgaa atctggaact gcctctgttg tgtgcctgct
3181 gaataacttc tatcccagag aggccaaagt gcagtggaag gtggacaacg ccctgcagag
3241 cggaaacagc caggaaagcg tgacagagca ggattccaag gattccacat acagcctgag
3301 cagcacactg acactgtcca aggccgacta cgagaagcac aaggtgtacg cctgcgaagt
3361 gacacaccag ggactgtcct cccctgtgac aaagagcttc aacagaggag aatgctgatg
3421 aaagcttgcg gccgcttcga gcagacatga taagatacat tgatgagttt ggacaaacca
3481 caactagaat gcagtgaaaa aaatgcttta tttgtgaaat ttgtgatgct attgctttat
3541 ttgtaaccat tataagctgc aataaacaag ttaacaacaa caattgcatt cattttatgt
3601 ttcaggttca gggggagatg tgggaggttt tttaaagcaa gtaaaacctc tacaaatgtg
3661 gtaaaatcga taaggatctt cctagagcat ggctacgtag ataagtagca tggcgggtta
3721 atcattaact acaaggaacc cctagtgatg gagttggcca ctccctctct gcgcgctcgc
3781 tcgctcactg aggccgggcg accaaaggtc gcccgacgcc cgggctttgc ccgggcggcc
3841 tcagtgagcg agcgagcgcg cagccttaat taacctaatt cactggccgt cgttttacaa
3901 cgtcgtgact gggaaaaccc tggcgttacc caacttaatc gccttgcagc acatccccct
3961 ttcgccagct ggcgtaatag cgaagaggcc cgcaccgatc gcccttccca acagttgcgc
4021 agcctgaatg gcgaatggga cgcgccctgt agcggcgcat taagcgcggc gggtgtggtg
4081 gttacgcgca gcgtgaccgc tacacttgcc agcgccctag cgcccgctcc tttcgctttc
4141 ttcccttcct ttctcgccac gttcgccggc tttccccgtc aagctctaaa tcgggggctc
4201 cctttagggt tccgatttag tgctttacgg cacctcgacc ccaaaaaact tgattagggt
4261 gatggttcac gtagtgggcc atcgccctga tagacggttt ttcgcccttt gacgttggag
4321 tccacgttct ttaatagtgg actcttgttc caaactggaa caacactcaa ccctatctcg
4381 gtctattctt ttgatttata agggattttg ccgatttcgg cctattggtt aaaaaatgag
4441 ctgatttaac aaaaatttaa cgcgaatttt aacaaaatat taacgcttac aatttaggtg
4501 gcacttttcg gggaaatgtg cgcggaaccc ctatttgttt atttttctaa atacattcaa
4561 atatgtatcc gctcatgaga caataaccct gataaatgct tcaataatat tgaaaaagga
4621 agagtatgag tattcaacat ttccgtgtcg cccttattcc cttttttgcg gcattttgcc
4681 ttcctgtttt tgctcaccca gaaacgctgg tgaaagtaaa agatgctgaa gatcagttgg
4741 gtgcacgagt gggttacatc gaactggatc tcaacagcgg taagatcctt gagagttttc
4801 gccccgaaga acgttttcca atgatgagca cttttaaagt tctgctatgt ggcgcggtat
4861 tatcccgtat tgacgccggg caagagcaac tcggtcgccg catacactat tctcagaatg
4921 acttggttga gtactcacca gtcacagaaa agcatcttac ggatggcatg acagtaagag
4981 aattatgcag tgctgccata accatgagtg ataacactgc ggccaactta cttctgacaa
5041 cgatcggagg accgaaggag ctaaccgctt ttttgcacaa catgggggat catgtaactc
5101 gccttgatcg ttgggaaccg gagctgaatg aagccatacc aaacgacgag cgtgacacca
5161 cgatgcctgt agcaatggca acaacgttgc gcaaactatt aactggcgaa ctacttactc
```

PLASMID SEQUENCES
FIG. 5F

```
5221 tagcttcccg gcaacaatta atagactgga tggaggcgga taaagttgca ggaccacttc
5281 tgcgctcggc ccttccggct ggctggttta ttgctgataa atctggagcc ggtgagcgtg
5341 ggtctcgcgg tatcattgca gcactggggc cagatggtaa gccctcccgt atcgtagtta
5401 tctacacgac ggggagtcag gcaactatgg atgaacgaaa tagacagatc gctgagatag
5461 gtgcctcact gattaagcat tggtaactgt cagaccaagt ttactcatat atactttaga
5521 ttgatttaaa acttcatttt taatttaaaa ggatctaggt gaagatcctt tttgataatc
5581 tcatgaccaa aatcccttaa cgtgagtttt cgttccactg agcgtcagac cccgtagaaa
5641 agatcaaagg atcttcttga gatccttttt ttctgcgcgt aatctgctgc ttgcaaacaa
5701 aaaaaccacc gctaccagcg gtggtttgtt tgccggatca agagctacca actctttttc
5761 cgaaggtaac tggcttcagc agagcgcaga taccaaatac tgttcttcta gtgtagccgt
5821 agttaggcca ccacttcaag aactctgtag caccgcctac atacctcgct ctgctaatcc
5881 tgttaccagt ggctgctgcc agtggcgata agtcgtgtct taccgggttg gactcaagac
5941 gatagttacc ggataaggcg cagcggtcgg gctgaacggg gggttcgtgc acacagccca
6001 gcttggagcg aacgacctac accgaactga gatacctaca gcgtgagcta tgagaaagcg
6061 ccacgcttcc cgaagggaga aaggcggaca ggtatccggt aagcggcagg gtcggaacag
6121 gagagcgcac gagggagctt ccagggggaa acgcctggta tctttatagt cctgtcgggt
6181 ttcgccacct ctgacttgag cgtcgatttt tgtgatgctc gtcagggggg cggagcctat
6241 ggaaaaacgc cagcaacgcg gcctttttac ggttcctggc cttttgctgg ccttttgctc
6301 acatgttctt tcctgcgtta tcccctgatt ctgtggataa ccgtattacc gcctttgagt
6361 gagctgatac cgctcgccgc agccgaacga ccgagcgcag cgagtcagtg agcgaggaag
6421 cggaagagcg cccaatacgc aaaccgcctc tccccgcgcg ttggccgatt cattaatgca
6481 gctggcacga caggtttccc gactggaaag cgggcagtga gcgcaacgca attaatgtga
6541 gttagctcac tcattaggca ccccaggctt tacactttat gcttccggct cgtatgttgt
6601 gtggaattgt gagcggataa caatttcaca caggaaacag ctatgaccat gattacgcca
6661 gatttaatta aggccttaat tagg
//
```

PLASMID SEQUENCES
FIG. 5G

SEQ ID NO: 18

```
pN232 3bnc117 MAB
LOCUS       pN232\3bnc117\MA        6703 bp    DNA     circular
FEATURES             Location/Qualifiers
     misc_feature    2678..2687
                     /vntifkey="21"
                     /label=furin\site
     misc_feature    2688..2759
                     /vntifkey="21"
                     /label=F2A\linker
     misc_feature    1983..1988
                     /vntifkey="21"
                     /label=need\a\site\here,\but\could\not\get\one\for\PG9-
\ended\up\SOWing...
     misc_feature    1983..2671
                     /vntifkey="21"
                     /label=HCH23
     misc_feature    2724..2783
                     /vntifkey="21"
                     /label=forward\primer\for\VL\for\MAB
     misc_feature    complement(2649..2741)
                     /vntifkey="21"
                     /label=reverse\primer\for\CHHCH23
     misc_feature    1325..1343
                     /vntifkey="21"
                     /label=from\bg102f
     misc_feature    1260..1319
                     /vntifkey="21"
                     /label=IL2\signal\peptide
     misc_feature    1320..1705
                     /vntifkey="21"
                     /label=VH\IgG1
     misc_feature    3123..3128
                     /vntifkey="21"
                     /label=introduce\NarI\here\via\PCR
     misc_feature    3130..3434
                     /vntifkey="21"
                     /label=CL
     repeat_region   1..130
                     /vntifkey="34"
                     /label=ITR
     repeat_region   complement(3753..3882)
                     /vntifkey="34"
                     /label=ITR
     intron          1047..1179
                     /vntifkey="15"
                     /label=Promega\chimeric\intron
     polyA_signal    3457..3688
                     /vntifkey="25"
                     /label=SV40\late\polyadenylation\signal
     promoter        191..932
                     /vntifkey="29"
                     /label=human\CMV\I.E.\enhancer\&\promoter
     CDS             4645..5502
                     /vntifkey="4"
```

PLASMID SEQUENCES
FIG. 5H

```
                     /label=Amp-R
     misc_feature    5676..6264
                     /vntifkey="21"
                     /label=COL\E1\Origin
     rep_origin      complement(4059..4514)
                     /vntifkey="33"
                     /label=f1\ori
     primer          1243..1271
                     /vntifkey="27"
                     /label=BG118F
     primer          complement(2439..2474)
                     /vntifkey="27"
                     /label=BG123R
     primer          complement(2439..2474)
                     /vntifkey="27"
                     /label=BG128R
     misc_feature    2803..3114
                     /vntifkey="21"
                     /label=3bnc117\light
     misc_feature    1707..1982
                     /vntifkey="21"
                     /label=CH1
BASE COUNT     1673 a     1751 c     1675 g     1604 t
ORIGIN
        1 ctgcgcgctc gctcgctcac tgaggccgcc cgggcaaagc ccgggcgtcg ggcgaccttt
       61 ggtcgcccgg cctcagtgag cgagcgagcg cgcagagagg gagtggccaa ctccatcact
      121 aggggttcct tgtagttaat gattaacccg ccatgctact tatctacgta gccatgctct
      181 aggaagatct tcaatattgg ccattagcca tattattcat tggttatata gcataaatca
      241 atattggcta ttggccattg catacgttgt atctatatca taatatgtac atttatattg
      301 gctcatgtcc aatatgaccg ccatgttggc attgattatt gactagttat taatagtaat
      361 caattacggg gtcattagtt catagcccat atatggagtt ccgcgttaca taacttacgg
      421 taaatggccc gcctggctga ccgcccaacg acccccgccc attgacgtca ataatgacgt
      481 atgttcccat agtaacgcca atagggactt tccattgacg tcaatgggtg gagtatttac
      541 ggtaaactgc ccacttggca gtacatcaag tgtatcatat gccaagtccg ccccctattg
      601 acgtcaatga cggtaaatgg cccgcctggc attatgccca gtacatgacc ttacgggact
      661 ttcctacttg gcagtacatc tacgtattag tcatcgctat taccatggtg atgcggtttt
      721 ggcagtacac caatgggcgt ggatagcggt ttgactcacg gggatttcca agtctccacc
      781 ccattgacgt caatgggagt ttgttttggc accaaaatca acgggacttt ccaaaatgtc
      841 gtaataaccc cgccccgttg acgcaaatgg gcggtaggcg tgtacggtgg gaggtctata
      901 taagcagagc tcgtttagtg aaccgtcaga tcactagaag ctttattgcg gtagtttatc
      961 acagttaaat tgctaacgca gtcagtgctt ctgacacaac agtctcgaac ttaagctgca
     1021 gaagttggtc gtgaggcact gggcaggtaa gtatcaaggt tacaagacag gtttaaggag
     1081 accaatagaa actgggcttg tcgagacaga gaagactctt gcgtttctga taggcaccta
     1141 ttggtcttac tgacatccac tttgcctttc tctccacagg tgtccactcc cagttcaatt
     1201 acagctctta aggctagagt acttaatacg actcactata ggctagcatc gatgccacca
     1261 tgtacaggat gcaactcctg tcttgcattg cactaagtct tgcacttgtc acaaacagtc
     1321 aggtccaatt gttacagtct ggggcagcgg tgacgaagcc cggggcctca gtgagagtct
     1381 cctgcgaggc ttctggatac aacattcgtg actactttat tcattggtgg cgacaggccc
     1441 caggacaggg ccttcagtgg gtgggatgga tcaatcctaa gacaggtcag ccaaacaatc
     1501 ctcgtcaatt tcagggtaga gtcagtctga ctcgacacgc gtcgtgggac tttgacacat
     1561 tttcctttta catggacctg aaggcactaa gatcggacga cacggccgtt tatttctgtg
     1621 cgcgacagcg cagcgactat tgggatttcg acgtctgggg cagtggaacc caggtcactg
     1681 tctcgtcagc gtcgaccaag ggccctcgg tcttccccct ggcaccctcc tccaagagca
     1741 cctctggggg cacagcggcc ctgggctgcc tggtcaagga ctacttcccc gaaccggtga
```

PLASMID SEQUENCES
FIG. 5I

```
1801 cggtgtcgtg gaactcaggc gccctgacca gcggcgtgca caccttcccg gctgtcctac
1861 agtcctcagg actctactcc ctcagcagcg tggtgaccgt gccctccagc agcttgggca
1921 cccagaccta catctgcaac gtgaatcaca agcccagcaa caccaaggtg gacaagaaag
1981 ttgagcccaa atcttgtgac aaaactcaca catgcccacc gtgcccagca cctgaactcc
2041 tggggggacc gtcagtcttc ctcttccccc caaaacccaa ggacaccctc atgatctccc
2101 ggacccctga ggtcacatgc gtggtggtgg acgtgagcca cgaagaccct gaggtcaagt
2161 tcaactggta cgtggacggc gtggaggtgc ataatgccaa gacaaagccg cgggaggagc
2221 agtacaacag cacgtaccgt gtggtcagcg tcctcaccgt cctgcaccag gactggctga
2281 atggcaagga gtacaagtgc aaggtctcca acaaagccct cccagccccc atcgagaaaa
2341 ccatctccaa agccaaaggg cagccccgag aaccacaggt gtacaccctg cccccatccc
2401 gggatgagct gaccaagaac caggtcagcc tgacctgcct ggtcaaaggc ttctatccca
2461 gcgacatcgc cgtggagtgg gagagcaatg ggcagccgga gaacaactac aagaccacgc
2521 ctcccgtgct ggactccgac ggctccttct tcctctacag caagctcacc gtggacaaga
2581 gcaggtggca gcaggggaac gtcttctcat gctccgtgat gcatgaggct ctgcacaacc
2641 actacacgca gaagagcctc tccctgtctc ccggccgaaa gcggagagcc cccgtgaagc
2701 agaccctgaa cttcgacctg ctgaagctgg ccggcgacgt ggaaagcaac cctggcccta
2761 tgggatggtc atgtatcatc ctttttctag tagcaactgc aaccggtgta cattctgaca
2821 tccagatgac ccagtctcca tcctccctgt ctgcatctgt aggagatacc gtcactatca
2881 cttgccaggc aaacggctac ttaaattggt atcaacagag gcgagggaaa gccccaaaac
2941 tcctgatcta cgatgggtcc aaattggaaa gaggggtccc atcaaggttc agtggaagaa
3001 gatgggggca agaatataat ctgaccatca acaatctgca gcccgaagac attgcaacat
3061 atttttgtca agtgtatgag tttgtcgtcc ctgggaccag actggatttg aaacgtacgg
3121 tggctgcacc atctgtcttc atcttcccgc catctgatga gcagttgaaa tctggaactg
3181 cctctgttgt gtgcctgctg aataacttct accccagaga agccaaagtg cagtggaagg
3241 tggacaacgc cctgcagagc ggaaacagcc aggaaagcgt gacagagcag gattccaagg
3301 attccacata cagcctgagc agcacactga cactgtccaa ggccgactac gagaagcaca
3361 aggtgtacgc ctgcgaagtg acacaccagg gactgtcctc ccctgtgaca aagagcttca
3421 acagaggaga atgctgatga aagcttgcgg ccgcttcgag cagacatgat aagatacatt
3481 gatgagtttg gacaaaccac aactagaatg cagtgaaaaa aatgctttat ttgtgaaatt
3541 tgtgatgcta ttgctttatt tgtaaccatt ataagctgca ataaacaagt taacaacaac
3601 aattgcattc attttatgtt tcaggttcag ggggagatgt gggaggtttt ttaaagcaag
3661 taaaacctct acaaatgtgg taaaatcgat aaggatcttc ctagagcatg gctacgtaga
3721 taagtagcat ggcgggttaa tcattaacta caaggaaccc ctagtgatgg agttggccac
3781 tccctctctg cgcgctcgct cgctcactga ggccgggcga ccaaaggtcg cccgacgccc
3841 gggctttgcc cgggcggcct cagtgagcga gcgagcgcgc agccttaatt aacctaattc
3901 actggccgtc gttttacaac gtcgtgactg ggaaaaccct ggcgttaccc aacttaatcg
3961 ccttgcagca catccccctt tcgccagctg gcgtaatagc gaagaggccc gcaccgatcg
4021 cccttcccaa cagttgcgca gcctgaatgg cgaatgggac gcgccctgta gcggcgcatt
4081 aagcgcggcg ggtgtggtgg ttacgcgcag cgtgaccgct acacttgcca gcgccctagc
4141 gcccgctcct ttcgctttct tcccttcctt tctcgccacg ttcgccggct ttccccgtca
4201 agctctaaat cgggggctcc ctttagggtt ccgatttagt gctttacggc acctcgaccc
4261 caaaaaactt gattagggtg atggttcacg tagtgggcca tcgccctgat agacggtttt
4321 tcgccctttg acgttggagt ccacgttctt taatagtgga ctcttgttcc aaactggaac
4381 aacactcaac cctatctcgg tctattcttt tgatttataa gggattttgc cgatttcggc
4441 ctattggtta aaaaatgagc tgatttaaca aaaatttaac gcgaatttta acaaaatatt
4501 aacgcttaca atttaggtgg cacttttcgg ggaaatgtgc gcggaacccc tatttgttta
4561 tttttctaaa tacattcaaa tatgtatccg ctcatgagac aataaccctg ataaatgctt
4621 caataatatt gaaaaaggaa gagtatgagt attcaacatt tccgtgtcgc ccttattccc
4681 ttttttgcgg cattttgcct tcctgttttt gctcacccag aaacgctggt gaaagtaaaa
4741 gatgctgaag atcagttggg tgcacgagtg ggttacatcg aactggatct caacagcggt
4801 aagatccttg agagttttcg ccccgaagaa cgttttccaa tgatgagcac ttttaaagtt
4861 ctgctatgtg gcgcggtatt atcccgtatt gacgccgggc aagagcaact cggtcgccgc
4921 atacactatt ctcagaatga cttggttgag tactcaccag tcacagaaaa gcatcttacg
4981 gatggcatga cagtaagaga attatgcagt gctgccataa ccatgagtga taacactgcg
```

PLASMID SEQUENCES
FIG. 5J

```
5041 gccaacttac ttctgacaac gatcggagga ccgaaggagc taaccgcttt tttgcacaac
5101 atgggggatc atgtaactcg ccttgatcgt tgggaaccgg agctgaatga agccatacca
5161 aacgacgagc gtgacaccac gatgcctgta gcaatggcaa caacgttgcg caaactatta
5221 actggcgaac tacttactct agcttcccgg caacaattaa tagactggat ggaggcggat
5281 aaagttgcag gaccacttct gcgctcggcc cttccggctg gctggtttat tgctgataaa
5341 tctggagccg gtgagcgtgg gtctcgcggt atcattgcag cactggggcc agatggtaag
5401 ccctcccgta tcgtagttat ctacacgacg gggagtcagg caactatgga tgaacgaaat
5461 agacagatcg ctgagatagg tgcctcactg attaagcatt ggtaactgtc agaccaagtt
5521 tactcatata tactttagat tgatttaaaa cttcattttt aatttaaaag gatctaggtg
5581 aagatccttt ttgataatct catgaccaaa atcccttaac gtgagttttc gttccactga
5641 gcgtcagacc ccgtagaaaa gatcaaagga tcttcttgag atcctttttt tctgcgcgta
5701 atctgctgct tgcaaacaaa aaaaccaccg ctaccagcgg tggtttgttt gccggatcaa
5761 gagctaccaa ctctttttcc gaaggtaact ggcttcagca gagcgcagat accaaatact
5821 gttcttctag tgtagccgta gttaggccac cacttcaaga actctgtagc accgcctaca
5881 tacctcgctc tgctaatcct gttaccagtg gctgctgcca gtggcgataa gtcgtgtctt
5941 accgggttgg actcaagacg atagttaccg gataaggcgc agcggtcggg ctgaacgggg
6001 ggttcgtgca cacagcccag cttggagcga acgacctaca ccgaactgag atacctacag
6061 cgtgagctat gagaaagcgc cacgcttccc gaagggagaa aggcggacag gtatccggta
6121 agcggcaggg tcggaacagg agagcgcacg agggagcttc cagggggaaa cgcctggtat
6181 ctttatagtc ctgtcgggtt tcgccacctc tgacttgagc gtcgattttt gtgatgctcg
6241 tcaggggggc ggagcctatg gaaaaacgcc agcaacgcgg cctttttacg gttcctggcc
6301 ttttgctggc cttttgctca catgttcttt cctgcgttat cccctgattc tgtggataac
6361 cgtattaccg cctttgagtg agctgatacc gctcgccgca gccgaacgac cgagcgcagc
6421 gagtcagtga gcgaggaagc ggaagagcgc ccaatacgca aaccgcctct ccccgcgcgt
6481 tggccgattc attaatgcag ctggcacgac aggtttcccg actggaaagc gggcagtgag
6541 cgcaacgcaa ttaatgtgag ttagctcact cattaggcac cccaggcttt acactttatg
6601 cttccggctc gtatgttgtg tggaattgtg agcggataac aatttcacac aggaaacagc
6661 tatgaccatg attacgccag atttaattaa ggccttaatt agg
//
```

PLASMID SEQUENCES
FIG. 5K

SEQ ID NO: 15

```
pN250 3bn117 mini c-Myc F2A
LOCUS       pN250\3bn117\min        6754 bp    DNA     circular
FEATURES             Location/Qualifiers
     misc_feature    897..901
                     /vntifkey="21"
                     /label=TATA\box
     rep_origin      complement(4110..4565)
                     /vntifkey="33"
                     /label=f1\ori
     misc_feature    5727..6315
                     /vntifkey="21"
                     /label=COL\E1\Origin
     CDS             4696..5553
                     /vntifkey="4"
                     /label=Amp-R
     promoter        191..932
                     /vntifkey="29"
                     /label=human\CMV\I.E.\enhancer\&\promoter
     polyA_signal    3508..3739
                     /vntifkey="25"
                     /label=SV40\late\polyadenylation\signal
     intron          1047..1179
                     /vntifkey="15"
                     /label=Promega\chimeric\intron
     repeat_region   complement(3804..3933)
                     /vntifkey="34"
                     /label=ITR
     repeat_region   1..130
                     /vntifkey="34"
                     /label=ITR
     misc_feature    1758..2033
                     /vntifkey="21"
                     /label=CH1
     misc_feature    2854..3165
                     /vntifkey="21"
                     /label=3bnc117\light
     primer          complement(2490..2525)
                     /vntifkey="27"
                     /label=BG128R
     primer          complement(2490..2525)
                     /vntifkey="27"
                     /label=BG123R
     primer          1294..1322
                     /vntifkey="27"
                     /label=BG118F
     misc_feature    3181..3485
                     /vntifkey="21"
                     /label=CL
     misc_feature    3174..3179
                     /vntifkey="21"
                     /label=introduce\NarI\here\via\PCR
     misc_feature    1371..1756
                     /vntifkey="21"
                     /label=VH\IgG1
```

PLASMID SEQUENCES
FIG. 5L

```
     misc_feature    1311..1370
                     /vntifkey="21"
                     /label=IL2\signal\peptide
     misc_feature    1376..1394
                     /vntifkey="21"
                     /label=from\bg102f
     misc_feature    complement(2700..2792)
                     /vntifkey="21"
                     /label=reverse\primer\for\CHHCH23
     misc_feature    2775..2834
                     /vntifkey="21"
                     /label=forward\primer\for\VL\for\MAB
     misc_feature    2034..2722
                     /vntifkey="21"
                     /label=HCH23
     misc_feature    2034..2039
                     /vntifkey="21"
                     /label=need\a\site\here,\but\could\not\get\one\for\PG9-
\ended\up\SOWing...
     misc_feature    2739..2810
                     /vntifkey="21"
                     /label=F2A\linker
     misc_feature    2729..2738
                     /vntifkey="21"
                     /label=furin\site
     misc_feature    1248..1295
                     /vntifkey="21"
                     /label=c-myc\miniIRES\cloned\into\Nhe\site
BASE COUNT     1687 a     1766 c     1689 g     1612 t
ORIGIN
        1 ctgcgcgctc gctcgctcac tgaggccgcc cgggcaaagc ccgggcgtcg ggcgaccttt
       61 ggtcgcccgg cctcagtgag cgagcgagcg cgcagagagg gagtggccaa ctccatcact
      121 aggggttcct tgtagttaat gattaacccg ccatgctact tatctacgta gccatgctct
      181 aggaagatct tcaatattgg ccattagcca tattattcat tggttatata gcataaatca
      241 atattggcta ttggccattg catacgttgt atctatatca taatatgtac atttatattg
      301 gctcatgtcc aatatgaccg ccatgttggc attgattatt gactagttat taatagtaat
      361 caattacggg gtcattagtt catagcccat atatggagtt ccgcgttaca taacttacgg
      421 taaatggccc gcctggctga ccgcccaacg acccccgccc attgacgtca ataatgacgt
      481 atgttcccat agtaacgcca atagggactt tccattgacg tcaatgggtg gagtatttac
      541 ggtaaactgc ccacttggca gtacatcaag tgtatcatat gccaagtccg ccccctattg
      601 acgtcaatga cggtaaatgg cccgcctggc attatgccca gtacatgacc ttacgggact
      661 ttcctacttg gcagtacatc tacgtattag tcatcgctat taccatggtg atgcggtttt
      721 ggcagtacac caatgggcgt ggatagcggt ttgactcacg gggatttcca agtctccacc
      781 ccattgacgt caatgggagt ttgttttggc accaaaatca acgggacttt ccaaaatgtc
      841 gtaataaccc cgccccgttg acgcaaatgg gcggtaggcg tgtacggtgg gaggtctata
      901 taagcagagc tcgtttagtg aaccgtcaga tcactagaag ctttattgcg gtagtttatc
      961 acagttaaat tgctaacgca gtcagtgctt ctgacacaac agtctcgaac ttaagctgca
     1021 gaagttggtc gtgaggcact gggcaggtaa gtatcaaggt tacaagacag gtttaaggag
     1081 accaatagaa actgggcttg tcgagacaga gaagactctt gcgtttctga taggcaccta
     1141 ttggtcttac tgacatccac tttgcctttc tctccacagg tgtccactcc cagttcaatt
     1201 acagctctta aggctagagt acttaatacg actcactata ggctagcggg gactttgcac
     1261 tggaacttac aacacccgag caaggacgcg actctagcat cgatgccacc atgtacagga
     1321 tgcaactcct gtcttgcatt gcactaagtc ttgcacttgt cacaaacagt caggtccaat
     1381 tgttacagtc tggggcagcg gtgacgaagc ccggggcctc agtgagagtc tcctgcgagg
```

PLASMID SEQUENCES
FIG. 5M

```
1441 cttctggata caacattcgt gactacttta ttcattggtg gcgacaggcc ccaggacagg
1501 gccttcagtg ggtgggatgg atcaatccta agacaggtca gccaaacaat cctcgtcaat
1561 ttcagggtag agtcagtctg actcgacacg cgtcgtggga ctttgacaca ttttcctttt
1621 acatggacct gaaggcacta agatcggacg acacggccgt ttatttctgt gcgcgacagc
1681 gcagcgacta ttgggatttc gacgtctggg gcagtggaac ccaggtcact gtctcgtcag
1741 cgtcgaccaa ggggccctcg gtcttccccc tggcaccctc ctccaagagc acctctgggg
1801 gcacagcggc cctgggctgc ctggtcaagg actacttccc cgaaccggtg acggtgtcgt
1861 ggaactcagg cgccctgacc agcggcgtgc acaccttccc ggctgtccta cagtcctcag
1921 gactctactc cctcagcagc gtggtgaccg tgccctccag cagcttgggc acccagacct
1981 acatctgcaa cgtgaatcac aagcccagca acaccaaggt ggacaagaaa gttgagccca
2041 aatcttgtga caaaactcac acatgcccac cgtgcccagc acctgaactc ctggggggac
2101 cgtcagtctt cctcttcccc ccaaaaccca aggacaccct catgatctcc cggacccctg
2161 aggtcacatg cgtggtggtg gacgtgagcc acgaagaccc tgaggtcaag ttcaactggt
2221 acgtggacgg cgtggaggtg cataatgcca agacaaagcc gcgggaggag cagtacaaca
2281 gcacgtaccg tgtggtcagc gtcctcaccg tcctgcacca ggactggctg aatggcaagg
2341 agtacaagtg caaggtctcc aacaaagccc tcccagcccc catcgagaaa accatctcca
2401 aagccaaagg gcagccccga gaaccacagg tgtacaccct gcccccatcc cgggatgagc
2461 tgaccaagaa ccaggtcagc ctgacctgcc tggtcaaagg cttctatccc agcgacatcg
2521 ccgtggagtg ggagagcaat gggcagccgg agaacaacta caagaccacg cctcccgtgc
2581 tggactccga cggctccttc ttcctctaca gcaagctcac cgtggacaag agcaggtggc
2641 agcaggggaa cgtcttctca tgctccgtga tgcatgaggc tctgcacaac cactacacgc
2701 agaagagcct ctccctgtct cccggccgaa agcggagagc cccgtgaag cagaccctga
2761 acttcgacct gctgaagctg gccggcgacg tggaaagcaa ccctggccct atgggatggt
2821 catgtatcat cctttttcta gtagcaactg caaccggtgt acattctgac atccagatga
2881 cccagtctcc atcctccctg tctgcatctg taggagatac cgtcactatc acttgccagg
2941 caaacggcta cttaaattgg tatcaacaga ggcgagggaa agccccaaaa ctcctgatct
3001 acgatgggtc caaattggaa agaggggtcc catcaaggtt cagtggaaga agatgggggc
3061 aagaatataa tctgaccatc aacaatctgc agcccgaaga cattgcaaca tatttttgtc
3121 aagtgtatga gtttgtcgtc cctgggacca gactggattt gaaacgtacg gtggctgcac
3181 catctgtctt catcttcccg ccatctgatg agcagttgaa atctggaact gcctctgttg
3241 tgtgcctgct gaataacttc taccccagag aagccaaagt gcagtggaag gtggacaacg
3301 ccctgcagag cggaaacagc caggaaagcg tgacagagca ggattccaag gattccacat
3361 acagcctgag cagcacactg acactgtcca aggccgacta cgagaagcac aaggtgtacg
3421 cctgcgaagt gacacaccag ggactgtcct cccctgtgac aaagagcttc aacagaggag
3481 aatgctgatg aaagcttgcg gccgcttcga gcagacatga taagatacat tgatgagttt
3541 ggacaaacca caactagaat gcagtgaaaa aaatgcttta tttgtgaaat ttgtgatgct
3601 attgctttat ttgtaaccat tataagctgc aataaacaag ttaacaacaa caattgcatt
3661 cattttatgt ttcaggttca gggggagatg tgggaggttt tttaaagcaa gtaaaacctc
3721 tacaaatgtg gtaaaatcga taaggatctt cctagagcat ggctacgtag ataagtagca
3781 tggcgggtta atcattaact acaaggaacc cctagtgatg gagttggcca ctccctctct
3841 gcgcgctcgc tcgctcactg aggccgggcg accaaaggtc gcccgacgcc cgggctttgc
3901 ccgggcggcc tcagtgagcg agcgagcgcg cagccttaat taacctaatt cactggccgt
3961 cgttttacaa cgtcgtgact gggaaaaccc tggcgttacc caacttaatc gccttgcagc
4021 acatccccct ttcgccagct ggcgtaatag cgaagaggcc cgcaccgatc gcccttccca
4081 acagttgcgc agcctgaatg gcgaatggga cgcgccctgt agcggcgcat taagcgcggc
4141 gggtgtggtg gttacgcgca gcgtgaccgc tacacttgcc agcgccctag cgcccgctcc
4201 tttcgctttc ttcccttcct ttctcgccac gttcgccggc tttccccgtc aagctctaaa
4261 tcgggggctc cctttagggt tccgatttag tgctttacgg cacctcgacc ccaaaaaact
4321 tgattagggt gatggttcac gtagtgggcc atcgccctga tagacggttt ttcgcccttt
4381 gacgttggag tccacgttct ttaatagtgg actcttgttc caaactggaa caacactcaa
4441 ccctatctcg gtctattctt ttgatttata agggattttg ccgatttcgg cctattggtt
4501 aaaaaatgag ctgatttaac aaaaatttaa cgcgaatttt aacaaaatat taacgcttac
4561 aatttaggtg gcacttttcg gggaaatgtg cgcggaaccc ctatttgttt atttttctaa
4621 atacattcaa atatgtatcc gctcatgaga caataaccct gataaatgct tcaataatat
```

PLASMID SEQUENCES
FIG. 5N

```
4681 tgaaaaagga agagtatgag tattcaacat ttccgtgtcg cccttattcc cttttttgcg
4741 gcattttgcc ttcctgtttt tgctcaccca gaaacgctgg tgaaagtaaa agatgctgaa
4801 gatcagttgg gtgcacgagt gggttacatc gaactggatc tcaacagcgg taagatcctt
4861 gagagttttc gccccgaaga acgttttcca atgatgagca cttttaaagt tctgctatgt
4921 ggcgcggtat tatcccgtat tgacgccggg caagagcaac tcggtcgccg catacactat
4981 tctcagaatg acttggttga gtactcacca gtcacagaaa agcatcttac ggatggcatg
5041 acagtaagag aattatgcag tgctgccata accatgagtg ataacactgc ggccaactta
5101 cttctgacaa cgatcggagg accgaaggag ctaaccgctt ttttgcacaa catgggggat
5161 catgtaactc gccttgatcg ttgggaaccg gagctgaatg aagccatacc aaacgacgag
5221 cgtgacacca cgatgcctgt agcaatggca acaacgttgc gcaaactatt aactggcgaa
5281 ctacttactc tagcttcccg gcaacaatta atagactgga tggaggcgga taaagttgca
5341 ggaccacttc tgcgctcggc ccttccggct ggctggttta ttgctgataa atctggagcc
5401 ggtgagcgtg ggtctcgcgg tatcattgca gcactggggc cagatggtaa gccctcccgt
5461 atcgtagtta tctacacgac ggggagtcag gcaactatgg atgaacgaaa tagacagatc
5521 gctgagatag gtgcctcact gattaagcat tggtaactgt cagaccaagt ttactcatat
5581 atactttaga ttgatttaaa acttcatttt taatttaaaa ggatctaggt gaagatcctt
5641 tttgataatc tcatgaccaa aatcccttaa cgtgagtttt cgttccactg agcgtcagac
5701 cccgtagaaa agatcaaagg atcttcttga gatccttttt ttctgcgcgt aatctgctgc
5761 ttgcaaacaa aaaaaccacc gctaccagcg gtggtttgtt tgccggatca agagctacca
5821 actctttttc cgaaggtaac tggcttcagc agagcgcaga taccaaatac tgttcttcta
5881 gtgtagccgt agttaggcca ccacttcaag aactctgtag caccgcctac atacctcgct
5941 ctgctaatcc tgttaccagt ggctgctgcc agtggcgata agtcgtgtct taccgggttg
6001 gactcaagac gatagttacc ggataaggcg cagcggtcgg gctgaacggg gggttcgtgc
6061 acacagccca gcttggagcg aacgacctac accgaactga gatacctaca gcgtgagcta
6121 tgagaaagcg ccacgcttcc cgaagggaga aaggcggaca ggtatccggt aagcggcagg
6181 gtcggaacag gagagcgcac gagggagctt ccagggggaa acgcctggta tctttatagt
6241 cctgtcgggt ttcgccacct ctgacttgag cgtcgatttt tgtgatgctc gtcagggggg
6301 cggagcctat ggaaaaacgc cagcaacgcg gcctttttac ggttcctggc cttttgctgg
6361 ccttttgctc acatgttctt tcctgcgtta tcccctgatt ctgtggataa ccgtattacc
6421 gcctttgagt gagctgatac cgctcgccgc agccgaacga ccgagcgcag cgagtcagtg
6481 agcgaggaag cggaagagcg cccaatacgc aaaccgcctc tccccgcgcg ttggccgatt
6541 cattaatgca gctggcacga caggtttccc gactggaaag cgggcagtga gcgcaacgca
6601 attaatgtga gttagctcac tcattaggca ccccaggctt tacactttat gcttccggct
6661 cgtatgttgt gtggaattgt gagcggataa caatttcaca caggaaacag ctatgaccat
6721 gattacgcca gatttaatta aggccttaat tagg
//
```

PLASMID SEQUENCES

FIG. 5O

SEQ ID NO: 17

```
pN251 3bnc ORF 1 p2334
LOCUS       3bnc117\MAB\IRES       6748 bp    DNA     circular
FEATURES             Location/Qualifiers
     repeat_region   1..130
                     /vntifkey="34"
                     /label=ITR
     repeat_region   complement(3798..3927)
                     /vntifkey="34"
                     /label=ITR
     intron          1047..1179
                     /vntifkey="15"
                     /label=Promega\chimeric\intron
     polyA_signal    3502..3733
                     /vntifkey="25"
                     /label=SV40\late\polyadenylation\signal
     promoter        191..932
                     /vntifkey="29"
                     /label=human\CMV\I.E.\enhancer\&\promoter
     CDS             4690..5547
                     /vntifkey="4"
                     /label=Amp-R
     misc_feature    5721..6309
                     /vntifkey="21"
                     /label=COL\E1\Origin
     rep_origin      complement(4104..4559)
                     /vntifkey="33"
                     /label=f1\ori
     misc_feature    1248..1293
                     /vntifkey="21"
                     /label=c-myc\miniIRES\cloned\into\Nhe\site
     misc_feature    897..901
                     /vntifkey="21"
                     /label=TATA\box
     misc_feature    1294..3493
                     /vntifkey="21"
                     /label=3bnc\ORF\1
     misc_feature    1292..1297
                     /vntifkey="21"
                     /label=6bp\insertion
BASE COUNT     1654 a      1717 c      1771 g      1606 t
ORIGIN
        1 ctgcgcgctc gctcgctcac tgaggccgcc cgggcaaagc ccgggcgtcg ggcgaccttt
       61 ggtcgcccgg cctcagtgag cgagcgagcg cgcagagagg gagtggccaa ctccatcact
      121 aggggttcct tgtagttaat gattaacccg ccatgctact tatctacgta gccatgctct
      181 aggaagatct tcaatattgg ccattagcca tattattcat tggttatata gcataaatca
      241 atattggcta ttggccattg catacgttgt atctatatca taatatgtac atttatattg
      301 gctcatgtcc aatatgaccg ccatgttggc attgattatt gactagttat taatagtaat
      361 caattacggg gtcattagtt catagcccat atatggagtt ccgcgttaca taacttacgg
      421 taaatggccc gcctggctga ccgcccaacg acccccgccc attgacgtca ataatgacgt
      481 atgttcccat agtaacgcca atagggactt tccattgacg tcaatgggtg gagtatttac
      541 ggtaaactgc ccacttggca gtacatcaag tgtatcatat gccaagtccg ccccctattg
      601 acgtcaatga cggtaaatgg cccgcctggc attatgccca gtacatgacc ttacgggact
      661 ttcctacttg gcagtacatc tacgtattag tcatcgctat taccatggtg atgcggtttt
      721 ggcagtacac caatgggcgt ggatagcggt ttgactcacg gggatttcca agtctccacc
```

PLASMID SEQUENCES
FIG. 5P

```
 781 ccattgacgt caatgggagt ttgttttggc accaaaatca acgggacttt ccaaaatgtc
 841 gtaataaccc cgccccgttg acgcaaatgg gcggtaggcg tgtacggtgg gaggtctata
 901 taagcagagc tcgtttagtg aaccgtcaga tcactagaag ctttattgcg gtagtttatc
 961 acagttaaat tgctaacgca gtcagtgctt ctgacacaac agtctcgaac ttaagctgca
1021 gaagttggtc gtgaggcact gggcaggtaa gtatcaaggt tacaagacag gtttaaggag
1081 accaatagaa actgggcttg tcgagacaga gaagactctt gcgtttctga taggcaccta
1141 ttggtcttac tgacatccac tttgcctttc tctccacagg tgtccactcc cagttcaatt
1201 acagctctta aggctagagt acttaatacg actcactata ggctagcggg gactttgcac
1261 tggaacttac aacacccgag caaggacgcg actctagctc tagaaccatg taccgtatgc
1321 agctcctatc gtgcattgcc ttgtcgttgg ccttagttac aaacagtcag gtgcagcttt
1381 tgcagtccgg ggctgcagtg accaaacccg gcgcatctgt gagggtgtca tgcgaagcct
1441 cggggtacaa cattcgggac tactttatcc actggtggag gcaggcccca gggcagggat
1501 tacagtgggt ggggtggatc aacccgaaaa cagggcagcc taacaacccc cgacagttcc
1561 aggggcgcgt ctcgttgacg aggcacgcga gttgggattt cgacacattc agcttctaca
1621 tggacctcaa ggcgctgaga agtgacgaca cagccgtcta cttctgcgcg aggcagagat
1681 cggactattg ggacttcgac gtgtggggtt cgggaacgca agtgaccgtg tcctcagcgt
1741 ccacgaaagg gccatcagtg ttccctctgg cgccatcctc gaagtctacg tcaggcggga
1801 cggctgctct gggatgcctg gtgaaagact actttcccga gccggtgact gtctcgtgga
1861 attcaggcgc gttgacatcc ggtgttcaca cgttccccgc tgtgttgcag agcagcggac
1921 tgtactctct gagcagtgtg gtgacagtgc cctcctcatc gctggggacg cagacgtaca
1981 tctgcaacgt gaaccacaag ccgagcaaca cgaaggtgga caagaaggtc gagccgaagt
2041 cttgtgataa gactcacaca tgtcccccat gccccgctcc agagctgctg ggtggcccta
2101 gcgtgtttct gttcccaccg aagccaaagg acaccttgat gatcagcagg accccggaag
2161 tgacctgcgt tgtggtcgac gtgtcacatg aggaccccga agtgaagttt aactggtacg
2221 tggacggggt ggaggtgcat aacgcaaaga ctaagccccg ggaggagcaa tacaattcca
2281 cctaccgggt cgtgtcggtg ctgactgtgc tgcaccagga ctggctgaac gggaaggagt
2341 acaagtgcaa ggtgtcgaat aaggccctgc cagcacctat cgaaaagacg atatctaagg
2401 caaaggggca gccgcgggag ccccaagtat acacactgcc tccgtccagg gatgagttga
2461 ccaagaacca ggtgtctctg acctgcctgg ttaagggctt ctacccatcc gacatagcag
2521 tggagtggga gagcaacggc cagccggaga acaactataa gaccacaccc ccggtgctgg
2581 acagcgacgg ctcgttcttc ctgtacagta agttgaccgt cgacaagagc cggtggcagc
2641 aggggaatgt gttctcatgc agcgtgatgc acgaagccct gcacaatcac tacacccaga
2701 agtcactgtc gctgagccct ggccggaaaa ggagggcccc agtcaaacag actctgaact
2761 tcgacctgct gaagctcgcg ggggacgtgg agagtaatcc cgggccaatg tatcgcatgc
2821 agttgctgtc gtgcatcgcc ctgtctctgg cgctggtcac caattctgat attcagatga
2881 cgcagagccc tagcagcctc tctgcaagcg tgggggacac ggtgacgatt acatgccagg
2941 ctaacggata tctgaactgg taccaacagc ggagggggaa ggccccgaag ctgctcatct
3001 acgacgggtc caaattggag cgaggagtac cgtcccggtt ctcggggcgg agatgggggc
3061 aggaatacaa cctaaccata aacaacctac agcccgagga catcgccact tacttctgcc
3121 aggtgtacga gttcgtggtg cccggcacca ggctggacct gaagcggacc gtggccgcac
3181 ctagtgtgtt catcttccca ccgtccgatg agcagttgaa gagcgggaca gcgagcgtgg
3241 tgtgcctgct gaacaacttc tatccgcgcg aggccaaagt acagtggaag gtagataacg
3301 ccctccagtc cggaaacagc caggagtccg tgaccgagca ggactcaaag gattccacat
3361 actccctttc ctcaacactg acgctgagta aggcggatta cgagaagcac aaggtgtatg
3421 cgtgtgaggt gactcaccag ggctgtcct cacccgtgac gaaatcgttt aaccggggcg
3481 agtgttaatg agcggccgct tcgagcagac atgataagat acattgatga gtttggacaa
3541 accacaacta gaatgcagtg aaaaaaatgc tttatttgtg aaatttgtga tgctattgct
3601 ttatttgtaa ccattataag ctgcaataaa caagttaaca acaacaattg cattcatttt
3661 atgtttcagg ttcaggggga gatgtgggag gtttttaaa gcaagtaaaa cctctacaaa
3721 tgtggtaaaa tcgataagga tcttcctaga gcatggctac gtagataagt agcatggcgg
3781 gttaatcatt aactacaagg aacccctagt gatggagttg gccactccct ctctgcgcgc
3841 tcgctcgctc actgaggccg ggcgaccaaa ggtcgcccga cgcccgggct ttgcccgggc
3901 ggcctcagtg agcgagcgag cgcgcagcct taattaacct aattcactgg ccgtcgtttt
3961 acaacgtcgt gactgggaaa accctggcgt tacccaactt aatcgccttg cagcacatcc
```

PLASMID SEQUENCES
FIG. 5Q

```
4021 cccttttcgcc agctggcgta atagcgaaga ggcccgcacc gatcgccctt cccaacagtt
4081 gcgcagcctg aatggcgaat gggacgcgcc ctgtagcggc gcattaagcg cggcgggtgt
4141 ggtggttacg cgcagcgtga ccgctacact tgccagcgcc ctagcgcccg ctcctttcgc
4201 tttcttccct tcctttctcg ccacgttcgc cggctttccc cgtcaagctc taaatcgggg
4261 gctcccttta gggttccgat ttagtgcttt acggcacctc gaccccaaaa aacttgatta
4321 gggtgatggt tcacgtagtg ggccatcgcc ctgatagacg gtttttcgcc ctttgacgtt
4381 ggagtccacg ttctttaata gtggactctt gttccaaact ggaacaacac tcaaccctat
4441 ctcggtctat tcttttgatt tataagggat tttgccgatt tcggcctatt ggttaaaaaa
4501 tgagctgatt taacaaaaat ttaacgcgaa ttttaacaaa atattaacgc ttacaattta
4561 ggtggcactt ttcggggaaa tgtgcgcgga acccctattt gtttattttt ctaaatacat
4621 tcaaatatgt atccgctcat gagacaataa ccctgataaa tgcttcaata atattgaaaa
4681 aggaagagta tgagtattca acatttccgt gtcgccctta ttcccttttt tgcggcattt
4741 tgccttcctg tttttgctca cccagaaacg ctggtgaaag taaaagatgc tgaagatcag
4801 ttgggtgcac gagtgggtta catcgaactg gatctcaaca gcggtaagat ccttgagagt
4861 tttcgccccg aagaacgttt tccaatgatg agcactttta aagttctgct atgtggcgcg
4921 gtattatccc gtattgacgc cgggcaagag caactcggtc gccgcataca ctattctcag
4981 aatgacttgg ttgagtactc accagtcaca gaaaagcatc ttacggatgg catgacagta
5041 agagaattat gcagtgctgc cataaccatg agtgataaca ctgcggccaa cttacttctg
5101 acaacgatcg gaggaccgaa ggagctaacc gcttttttgc acaacatggg ggatcatgta
5161 actcgccttg atcgttggga accggagctg aatgaagcca taccaaacga cgagcgtgac
5221 accacgatgc ctgtagcaat ggcaacaacg ttgcgcaaac tattaactgg cgaactactt
5281 actctagctt cccggcaaca attaatagac tggatggagg cggataaagt tgcaggacca
5341 cttctgcgct cggcccttcc ggctggctgg tttattgctg ataaatctgg agccggtgag
5401 cgtgggtctc gcggtatcat tgcagcactg gggccagatg gtaagccctc ccgtatcgta
5461 gttatctaca cgacggggag tcaggcaact atggatgaac gaaatagaca gatcgctgag
5521 ataggtgcct cactgattaa gcattggtaa ctgtcagacc aagtttactc atatatactt
5581 tagattgatt taaaacttca tttttaattt aaaaggatct aggtgaagat cctttttgat
5641 aatctcatga ccaaaatccc ttaacgtgag ttttcgttcc actgagcgtc agaccccgta
5701 gaaaagatca aaggatcttc ttgagatcct ttttttctgc gcgtaatctg ctgcttgcaa
5761 acaaaaaaac caccgctacc agcggtggtt tgtttgccgg atcaagagct accaactctt
5821 tttccgaagg taactggctt cagcagagcg cagataccaa atactgttct tctagtgtag
5881 ccgtagttag gccaccactt caagaactct gtagcaccgc ctacatacct cgctctgcta
5941 atcctgttac cagtggctgc tgccagtggc gataagtcgt gtcttaccgg gttggactca
6001 agacgatagt taccggataa ggcgcagcgg tcgggctgaa cggggggttc gtgcacacag
6061 cccagcttgg agcgaacgac ctacaccgaa ctgagatacc tacagcgtga gctatgagaa
6121 agcgccacgc ttcccgaagg gagaaaggcg gacaggtatc cggtaagcgg cagggtcgga
6181 acaggagagc gcacgaggga gcttccaggg ggaaacgcct ggtatcttta tagtcctgtc
6241 gggtttcgcc acctctgact tgagcgtcga tttttgtgat gctcgtcagg ggggcggagc
6301 ctatggaaaa acgccagcaa cgcggccttt ttacggttcc tggccttttg ctggcctttt
6361 gctcacatgt tctttcctgc gttatcccct gattctgtgg ataaccgtat taccgccttt
6421 gagtgagctg ataccgctcg ccgcagccga acgaccgagc gcagcgagtc agtgagcgag
6481 gaagcggaag agcgcccaat acgcaaaccg cctctccccg cgcgttggcc gattcattaa
6541 tgcagctggc acgacaggtt tcccgactgg aaagcgggca gtgagcgcaa cgcaattaat
6601 gtgagttagc tcactcatta ggcaccccag gctttacact ttatgcttcc ggctcgtatg
6661 ttgtgtggaa ttgtgagcgg ataacaattt cacacaggaa acagctatga ccatgattac
6721 gccagattta attaaggcct taattagg
```

//

PLASMID SEQUENCES
FIG. 5R

SEQ ID NO: 16

```
pN252 3bnc ORF 2 p2753
LOCUS       3bnc117\MAB\IRES        6748 bp    DNA     circular
FEATURES             Location/Qualifiers
     repeat_region   1..130
                     /vntifkey="34"
                     /label=ITR
     repeat_region   complement(3798..3927)
                     /vntifkey="34"
                     /label=ITR
     intron          1047..1179
                     /vntifkey="15"
                     /label=Promega\chimeric\intron
     polyA_signal    3502..3733
                     /vntifkey="25"
                     /label=SV40\late\polyadenylation\signal
     promoter        191..932
                     /vntifkey="29"
                     /label=human\CMV\I.E.\enhancer\&\promoter
     CDS             4690..5547
                     /vntifkey="4"
                     /label=Amp-R
     misc_feature    5721..6309
                     /vntifkey="21"
                     /label=COL\E1\Origin
     rep_origin      complement(4104..4559)
                     /vntifkey="33"
                     /label=f1\ori
     misc_feature    1248..1293
                     /vntifkey="21"
                     /label=c-myc\miniIRES\cloned\into\Nhe\site
     misc_feature    897..901
                     /vntifkey="21"
                     /label=TATA\box
     misc_feature    1294..3493
                     /vntifkey="21"
                     /label=3nbc\ORF\2
     misc_feature    1292..1297
                     /vntifkey="21"
                     /label=6bp\insertion
BASE COUNT     1684 a      1691 c      1649 g      1724 t
ORIGIN
        1 ctgcgcgctc gctcgctcac tgaggccgcc cgggcaaagc ccgggcgtcg ggcgaccttt
       61 ggtcgcccgg cctcagtgag cgagcgagcg cgcagagagg gagtggccaa ctccatcact
      121 aggggttcct tgtagttaat gattaacccg ccatgctact tatctacgta gccatgctct
      181 aggaagatct tcaatattgg ccattagcca tattattcat tggttatata gcataaatca
      241 atattggcta ttggccattg catacgttgt atctatatca taatatgtac atttatattg
      301 gctcatgtcc aatatgaccg ccatgttggc attgattatt gactagttat taatagtaat
      361 caattacggg gtcattagtt catagcccat atatggagtt ccgcgttaca taacttacgg
      421 taaatggccc gcctggctga ccgcccaacg acccccgccc attgacgtca ataatgacgt
      481 atgttcccat agtaacgcca atagggactt tccattgacg tcaatgggtg gagtatttac
      541 ggtaaactgc ccacttggca gtacatcaag tgtatcatat gccaagtccg ccccctattg
      601 acgtcaatga cggtaaatgg cccgcctggc attatgccca gtacatgacc ttacgggact
      661 ttcctacttg gcagtacatc tacgtattag tcatcgctat taccatggtg atgcggtttt
      721 ggcagtacac caatgggcgt ggatagcggt ttgactcacg gggatttcca agtctccacc
```

PLASMID SEQUENCES
FIG. 5S

```
 781 ccattgacgt caatgggagt ttgttttggc accaaaatca acgggacttt ccaaaatgtc
 841 gtaataaccc cgccccgttg acgcaaatgg gcggtaggcg tgtacggtgg gaggtctata
 901 taagcagagc tcgtttagtg aaccgtcaga tcactagaag ctttattgcg gtagtttatc
 961 acagttaaat tgctaacgca gtcagtgctt ctgacacaac agtctcgaac ttaagctgca
1021 gaagttggtc gtgaggcact gggcaggtaa gtatcaaggt tacaagacag gtttaaggag
1081 accaatagaa actgggcttg tcgagacaga gaagactctt gcgtttctga taggcaccta
1141 ttggtcttac tgacatccac tttgcctttc tctccacagg tgtccactcc cagttcaatt
1201 acagctctta aggctagagt acttaatacg actcactata ggctagcggg gactttgcac
1261 tggaacttac aacacccgag caaggacgcg actctagctc tagaaccatg tatcggatgc
1321 agcttctctc ctgcattgcc ttaagtctcg cccttgtaac aaatagtcag gttcagcttt
1381 tacagagtgg cgccgcagtc accaaacccg gagcatccgt gcgagtctcc tgcgaagcca
1441 gtgggtacaa cattagggac tatttcatcc attggtggag gcaggcaccc ggccaaggac
1501 ttcagtgggt tgggtggatc aatcctaaga cgggacagcc caataacccg agacagtttc
1561 aggggcgcgt ctctcttact cgccatgctt cttgggattt tgacaccttt tctttctaca
1621 tggacctcaa agcccttcgc agcgacgata ccgctgtgta tttctgtgcc aggcagcgct
1681 ctgactactg ggactttgat gtttggggat ctggtacgca agtcacagtc tctagtgcaa
1741 gtaccaaagg ccccagtgtg tttcccctcg ctccgtctag caagtctacc tctggcggta
1801 ctgcagccct tggatgtctg gtcaaagact actttccaga gccggtgaca gtgagttgga
1861 attcgggtgc tctaacatct ggcgtgcaca cttttccggc tgtgctgcag tccagtggac
1921 tttactctct gagcagtgtg gttactgtgc cctctagttc tcttgggacg cagacctaca
1981 tctgcaatgt gaatcataag ccatctaata caaaggtgga taagaaggtg gaaccaaagt
2041 catgcgacaa aacccacacg tgcccaccat gtccagctcc ggagttactg ggcggaccct
2101 ctgtctttct gtttccgccc aagccgaagg atacactgat gatatctcgt accccagagg
2161 tgacatgcgt ggttgtcgat gtgtcccatg aggaccccga ggtgaagttt aactggtatg
2221 tggacggcgt ggaagtccat aatgctaaga ctaaaccaag ggaagaacag tacaattcca
2281 cgtaccgcgt cgttagcgtc ttgaccgtgc tccatcagga ctggctcaac ggaaaggagt
2341 ataagtgtaa ggtcagtaac aaggctcttc cggctccaat tgagaaaaca attagtaagg
2401 ctaaggggca gcctcgcgaa cctcaagtct acaccctacc accgtctcgc gacgaactca
2461 ctaagaatca ggtgtcgctc acctgcctcg tcaaaggttt ctatccctct gacatcgcag
2521 tagaatggga atccaatggc cagccggaga acaattacaa gaccaccccg ccagtgctag
2581 actcagacgg gagtttcttc ttatactcta agcttaccgt agataagtcc cggtggcagc
2641 agggcaatgt gttttcctgt tcagtgatgc atgaagcgct gcataatcac tatacacaaa
2701 agtcactttc tctgagtccc ggtcggaaga gaagagctcc tgttaaacag acactgaatt
2761 tcgatttgct caaactcgct ggagacgtag aaagcaatcc tggtcctatg taccgaatgc
2821 agcttttgtc ttgcatcgct ctgagccttg cgcttgttac gaatagcgac atacagatga
2881 cacagtctcc gagttctctt agtgctagtg tgggcgatac agtcactata acatgccagg
2941 ctaatggtta cctgaactgg taccaacaac gccgcggtaa agcccccaaa ctgctcatct
3001 atgatgggtc aaaacttgaa cgcggcgtcc cgagccgctt tagtggccgc cgttgggggc
3061 aggaatacaa tcttaccatc aacaatctac agcccgaaga tattgctact tacttttgcc
3121 aggtttacga atttgtcgtc ccgggaacgc gccttgatct taagcggact gtcgccgctc
3181 cgagtgtgtt tatctttcct ccatcagacg aacagcttaa gtcaggcacc gcttctgtgg
3241 tgtgcttgct gaataacttc tatccccggg aagccaaggt tcagtggaag gtcgacaatg
3301 ctcttcagtc tggtaatagc caggagtcag tgacagaaca ggactccaag gacagtacct
3361 actctctatc cagtacactg accctgagca aagctgacta cgaaaagcac aaagtctatg
3421 cttgtgaagt aacgcatcaa ggccttagct ctcctgttac caagagcttc aatagggtg
3481 aatgctaatg agcggccgct tcgagcagac atgataagat acattgatga gtttggacaa
3541 accacaacta gaatgcagtg aaaaaaatgc tttatttgtg aaatttgtga tgctattgct
3601 ttatttgtaa ccattataag ctgcaataaa caagttaaca acaacaattg cattcatttt
3661 atgtttcagg ttcaggggga gatgtgggag gtttttttaaa gcaagtaaaa cctctacaaa
3721 tgtggtaaaa tcgataagga tcttcctaga gcatggctac gtagataagt agcatggcgg
3781 gttaatcatt aactacaagg aacccctagt gatggagttg gccactccct ctctgcgcgc
3841 tcgctcgctc actgaggccg ggcgaccaaa ggtcgcccga cgcccgggct ttgcccgggc
3901 ggcctcagtg agcgagcgag cgcgcagcct taattaacct aattcactgg ccgtcgtttt
3961 acaacgtcgt gactgggaaa accctggcgt tacccaactt aatcgccttg cagcacatcc
```

PLASMID SEQUENCES
FIG. 5T

```
4021 ccctttcgcc agctggcgta atagcgaaga ggcccgcacc gatcgccctt cccaacagtt
4081 gcgcagcctg aatggcgaat gggacgcgcc ctgtagcggc gcattaagcg cggcgggtgt
4141 ggtggttacg cgcagcgtga ccgctacact tgccagcgcc ctagcgcccg ctcctttcgc
4201 tttcttccct tcctttctcg ccacgttcgc cggctttccc cgtcaagctc taaatcgggg
4261 gctcccttta gggttccgat ttagtgcttt acggcacctc gaccccaaaa aacttgatta
4321 gggtgatggt tcacgtagtg ggccatcgcc ctgatagacg gtttttcgcc ctttgacgtt
4381 ggagtccacg ttctttaata gtggactctt gttccaaact ggaacaacac tcaaccctat
4441 ctcggtctat tcttttgatt tataagggat tttgccgatt tcggcctatt ggttaaaaaa
4501 tgagctgatt taacaaaaat ttaacgcgaa ttttaacaaa atattaacgc ttacaattta
4561 ggtggcactt ttcggggaaa tgtgcgcgga acccctattt gtttattttt ctaaatacat
4621 tcaaatatgt atccgctcat gagacaataa ccctgataaa tgcttcaata atattgaaaa
4681 aggaagagta tgagtattca acatttccgt gtcgccctta ttcccttttt tgcggcattt
4741 tgccttcctg tttttgctca cccagaaacg ctggtgaaag taaaagatgc tgaagatcag
4801 ttgggtgcac gagtgggtta catcgaactg gatctcaaca gcggtaagat ccttgagagt
4861 tttcgccccg aagaacgttt tccaatgatg agcactttta aagttctgct atgtggcgcg
4921 gtattatccc gtattgacgc cgggcaagag caactcggtc gccgcataca ctattctcag
4981 aatgacttgg ttgagtactc accagtcaca gaaaagcatc ttacggatgg catgacagta
5041 agagaattat gcagtgctgc cataaccatg agtgataaca ctgcggccaa cttacttctg
5101 acaacgatcg gaggaccgaa ggagctaacc gcttttttgc acaacatggg ggatcatgta
5161 actcgccttg atcgttggga accggagctg aatgaagcca taccaaacga cgagcgtgac
5221 accacgatgc ctgtagcaat ggcaacaacg ttgcgcaaac tattaactgg cgaactactt
5281 actctagctt cccggcaaca attaatagac tggatggagg cggataaagt tgcaggacca
5341 cttctgcgct cggcccttcc ggctggctgg tttattgctg ataaatctgg agccggtgag
5401 cgtgggtctc gcggtatcat tgcagcactg gggccagatg gtaagccctc ccgtatcgta
5461 gttatctaca cgacggggag tcaggcaact atggatgaac gaaatagaca gatcgctgag
5521 ataggtgcct cactgattaa gcattggtaa ctgtcagacc aagtttactc atatatactt
5581 tagattgatt taaaacttca tttttaattt aaaaggatct aggtgaagat cctttttgat
5641 aatctcatga ccaaaatccc ttaacgtgag ttttcgttcc actgagcgtc agaccccgta
5701 gaaaagatca aaggatcttc ttgagatcct ttttttctgc gcgtaatctg ctgcttgcaa
5761 acaaaaaaac caccgctacc agcggtggtt tgtttgccgg atcaagagct accaactctt
5821 tttccgaagg taactggctt cagcagagcg cagataccaa atactgttct tctagtgtag
5881 ccgtagttag gccaccactt caagaactct gtagcaccgc ctacatacct cgctctgcta
5941 atcctgttac cagtggctgc tgccagtggc gataagtcgt gtcttaccgg gttggactca
6001 agacgatagt taccggataa ggcgcagcgg tcgggctgaa cggggggttc gtgcacacag
6061 cccagcttgg agcgaacgac ctacaccgaa ctgagatacc tacagcgtga gctatgagaa
6121 agcgccacgc ttcccgaagg gagaaaggcg gacaggtatc cggtaagcgg cagggtcgga
6181 acaggagagc gcacgaggga gcttccaggg ggaaacgcct ggtatcttta tagtcctgtc
6241 gggtttcgcc acctctgact tgagcgtcga tttttgtgat gctcgtcagg ggggcggagc
6301 ctatggaaaa acgccagcaa cgcggccttt ttacggttcc tggccttttg ctggcctttt
6361 gctcacatgt tctttcctgc gttatcccct gattctgtgg ataaccgtat taccgccttt
6421 gagtgagctg ataccgctcg ccgcagccga acgaccgagc gcagcgagtc agtgagcgag
6481 gaagcggaag agcgcccaat acgcaaaccg cctctccccg cgcgttggcc gattcattaa
6541 tgcagctggc acgacaggtt tcccgactgg aaagcgggca gtgagcgcaa cgcaattaat
6601 gtgagttagc tcactcatta ggcaccccag gctttacact ttatgcttcc ggctcgtatg
6661 ttgtgtggaa ttgtgagcgg ataacaattt cacacaggaa acagctatga ccatgattac
6721 gccagattta attaaggcct taattagg
//
```

PLASMID SEQUENCES
FIG. 5U

SEQ ID NO: 19

```
pN253 3bnc ORF 11 p2755
LOCUS       3bnc117\MAB\IRES        6748 bp    DNA     circular
FEATURES             Location/Qualifiers
     repeat_region   1..130
                     /vntifkey="34"
                     /label=ITR
     repeat_region   complement(3798..3927)
                     /vntifkey="34"
                     /label=ITR
     intron          1047..1179
                     /vntifkey="15"
                     /label=Promega\chimeric\intron
     polyA_signal    3502..3733
                     /vntifkey="25"
                     /label=SV40\late\polyadenylation\signal
     promoter        191..932
                     /vntifkey="29"
                     /label=human\CMV\I.E.\enhancer\&\promoter
     CDS             4690..5547
                     /vntifkey="4"
                     /label=Amp-R
     misc_feature    5721..6309
                     /vntifkey="21"
                     /label=COL\E1\Origin
     rep_origin      complement(4104..4559)
                     /vntifkey="33"
                     /label=f1\ori
     misc_feature    1248..1293
                     /vntifkey="21"
                     /label=c-myc\miniIRES\cloned\into\Nhe\site
     misc_feature    897..901
                     /vntifkey="21"
                     /label=TATA\box
     misc_feature    1294..3493
                     /vntifkey="21"
                     /label=3bnc\ORF\11
     misc_feature    1292..1297
                     /vntifkey="21"
                     /label=6\bp\insertion
BASE COUNT     1687 a      1686 c      1689 g      1686 t
ORIGIN
        1 ctgcgcgctc gctcgctcac tgaggccgcc cgggcaaagc ccgggcgtcg ggcgaccttt
       61 ggtcgcccgg cctcagtgag cgagcgagcg cgcagagagg gagtggccaa ctccatcact
      121 aggggttcct tgtagttaat gattaacccg ccatgctact tatctacgta gccatgctct
      181 aggaagatct tcaatattgg ccattagcca tattattcat tggttatata gcataaatca
      241 atattggcta ttggccattg catacgttgt atctatatca taatatgtac atttatattg
      301 gctcatgtcc aatatgaccg ccatgttggc attgattatt gactagttat taatagtaat
      361 caattacggg gtcattagtt catagcccat atatggagtt ccgcgttaca taacttacgg
      421 taaatggccc gcctggctga ccgcccaacg acccccgccc attgacgtca ataatgacgt
      481 atgttcccat agtaacgcca atagggactt tccattgacg tcaatgggtg gagtatttac
      541 ggtaaactgc ccacttggca gtacatcaag tgtatcatat gccaagtccg ccccctattg
      601 acgtcaatga cggtaaatgg cccgcctggc attatgccca gtacatgacc ttacgggact
      661 ttcctacttg gcagtacatc tacgtattag tcatcgctat taccatggtg atgcggtttt
      721 ggcagtacac caatgggcgt ggatagcggt ttgactcacg gggatttcca agtctccacc
```

PLASMID SEQUENCES
FIG. 5V

```
 781 ccattgacgt caatgggagt ttgttttggc accaaaatca acgggacttt ccaaaatgtc
 841 gtaataaccc cgccccgttg acgcaaatgg gcggtaggcg tgtacggtgg gaggtctata
 901 taagcagagc tcgtttagtg aaccgtcaga tcactagaag ctttattgcg gtagtttatc
 961 acagttaaat tgctaacgca gtcagtgctt ctgacacaac agtctcgaac ttaagctgca
1021 gaagttggtc gtgaggcact gggcaggtaa gtatcaaggt tacaagacag gtttaaggag
1081 accaatagaa actgggcttg tcgagacaga gaagactctt gcgtttctga taggcaccta
1141 ttggtcttac tgacatccac tttgcctttc tctccacagg tgtccactcc cagttcaatt
1201 acagctctta aggctagagt acttaatacg actcactata ggctagcggg gactttgcac
1261 tggaacttac aacacccgag caaggacgcg actctagctc tagaaccatg taccgcatgc
1321 aattactctc ctgtatcgct ctgtctctgg ctctggtgac aaacagccag gtccagctgc
1381 tgcagagtgg cgccgcagtg actaagcctg gcgctagtgt gagagtcagt tgcgaagcaa
1441 gcggctacaa cattcgcgat tactttatcc attggtggag gcaggctccc ggtcagggct
1501 tgcaatgggt cggctggatt aaccccaaaa ccgggcagcc caataaccct cgacaatttc
1561 agggacgcgt tagtttaacg aggcatgcgt catgggattt tgacacattt tcgttctata
1621 tggatctgaa ggctctgcgg tctgatgaca ccgctgtgta cttttgtgcc aggcaacggt
1681 ccgactattg ggactttgat gtgtgggggt cgggtacgca agtaacggtg tccagcgctt
1741 ccacaaaagg cccaagcgtg tttcccctcg ctccatcttc taagtctaca agcggcggca
1801 ccgctgctct gggctgtctg gtgaaagatt actttccaga gccggtcact gtgtcctgga
1861 atagcggcgc tctgacttct ggtgttcata cctttcccgc tgtcctgcaa agcagcggcc
1921 tgtacagcct gagctccgtg gtgaccgtac cctcctccag cttgggcaca cagacataca
1981 tatgcaatgt gaaccacaag cctagtaata ccaaggttga taagaaggta gaacctaaga
2041 gttgtgacaa gacccatact tgtccaccgt gtcctgcacc agaactgctc ggggggaccca
2101 gcgtctttct gtttccgcca aaacctaagg atactctaat gatttcccgt acccccgaag
2161 tcacttgcgt ggtcgtggac gtgtcacatg aggaccccga ggtaaagttt aactggtatg
2221 tggacggcgt ggaggttcat aacgccaaga ctaagccccg ggaggaacag tataacagta
2281 cgtatcgagt cgtaagcgtg ctgactgttc tgcaccaaga ctggttgaat gggaaggagt
2341 ataagtgtaa ggtcagcaac aaggctcttc ccgctcctat cgaaaagacc atttcaaaag
2401 ccaagggaca gccgcgggag cctcaagtgt ataccctgcc gccaagtaga gacgagctca
2461 ccaagaacca ggtttcactg acatgtctgg taaagggctt ctatccatcc gacattgccg
2521 tagaatggga gagtaacggc cagccagaga ataactataa gaccacgccc cctgtgttgg
2581 actccgacgg gtcattcttt ctgtatagca agctgacagt tgacaagtca cggtggcaac
2641 agggcaacgt gttttcatgt tccgtgatgc acgaagctct gcataaccac tatacccaga
2701 agtccctgtc tctgagccca gggaggaaga ggcgcgcacc agtgaaacag accttgaatt
2761 tcgacctgct gaagctggct ggcgatgttg aatccaaccc aggccccatg tatagaatgc
2821 agctgctgtc ttgtatcgcc ttgagcctgg ccttggtcac aaattcggat atccagatga
2881 cgcaatcccc ctcctccctc agcgcttcag taggtgacac agtaacaatt acatgtcagg
2941 ccaatgggta cctcaattgg tatcagcagc gaaggggcaa agctcctaag ttgctgatct
3001 atgacggctc taagttggaa cgcggcgttc cgagtaggtt tagtggccgg agatggggac
3061 aagagtataa cctgacgatc aacaacttgc aacccgagga cattgctacc tatttctgtc
3121 aggtgtatga atttgtagta ccaggcaccc ggctagatct gaaacggaca gtagctgccc
3181 ccagcgtgtt catattccct ccatctgacg aacagcttaa gtcgggcacc gcaagcgtgg
3241 tgtgcctgtt gaataacttc tatccgagag aggctaaggt gcagtggaag gtcgacaacg
3301 ccctacagtc tggcaattct caagaaagcg ttaccgaaca ggatagcaag gacagcacgt
3361 atagcttgtc ctccacactg acgctttcca aggcagacta tgaaaaacat aaggtgtacg
3421 cgtgtgaggt gactcatcag ggcctgtcca gcccggttac aaagtccttt aacaggggcg
3481 aatgctaatg agcggccgct tcgagcagac atgataagat acattgatga gtttggacaa
3541 accacaacta gaatgcagtg aaaaaaatgc tttatttgtg aaatttgtga tgctattgct
3601 ttatttgtaa ccattataag ctgcaataaa caagttaaca acaacaattg cattcatttt
3661 atgtttcagg ttcaggggga gatgtgggag gtttttttaaa gcaagtaaaa cctctacaaa
3721 tgtggtaaaa tcgataagga tcttcctaga gcatggctac gtagataagt agcatggcgg
3781 gttaatcatt aactacaagg aacccctagt gatggagttg gccactccct ctctgcgcgc
3841 tcgctcgctc actgaggccg ggcgaccaaa ggtcgcccga cgcccgggct ttgcccgggc
3901 ggcctcagtg agcgagcgag cgcgcagcct taattaacct aattcactgg ccgtcgtttt
3961 acaacgtcgt gactgggaaa accctggcgt tacccaactt aatcgccttg cagcacatcc
```

PLASMID SEQUENCES
FIG. 5W

```
4021 cccttttcgcc agctggcgta atagcgaaga ggcccgcacc gatcgccctt cccaacagtt
4081 gcgcagcctg aatggcgaat gggacgcgcc ctgtagcggc gcattaagcg cggcgggtgt
4141 ggtggttacg cgcagcgtga ccgctacact tgccagcgcc ctagcgcccg ctcctttcgc
4201 tttcttccct tcctttctcg ccacgttcgc cggctttccc cgtcaagctc taaatcgggg
4261 gctcccttta gggttccgat ttagtgcttt acggcacctc gaccccaaaa aacttgatta
4321 gggtgatggt tcacgtagtg ggccatcgcc ctgatagacg gtttttcgcc ctttgacgtt
4381 ggagtccacg ttctttaata gtggactctt gttccaaact ggaacaacac tcaaccctat
4441 ctcggtctat tcttttgatt tataagggat tttgccgatt tcggcctatt ggttaaaaaa
4501 tgagctgatt taacaaaaat ttaacgcgaa ttttaacaaa atattaacgc ttacaattta
4561 ggtggcactt ttcggggaaa tgtgcgcgga acccctattt gtttattttt ctaaatacat
4621 tcaaatatgt atccgctcat gagacaataa ccctgataaa tgcttcaata atattgaaaa
4681 aggaagagta tgagtattca acatttccgt gtcgccctta ttcccttttt tgcggcattt
4741 tgccttcctg tttttgctca cccagaaacg ctggtgaaag taaaagatgc tgaagatcag
4801 ttgggtgcac gagtgggtta catcgaactg gatctcaaca gcggtaagat ccttgagagt
4861 tttcgccccg aagaacgttt tccaatgatg agcactttta aagttctgct atgtggcgcg
4921 gtattatccc gtattgacgc cgggcaagag caactcggtc gccgcataca ctattctcag
4981 aatgacttgg ttgagtactc accagtcaca gaaaagcatc ttacggatgg catgacagta
5041 agagaattat gcagtgctgc cataaccatg agtgataaca ctgcggccaa cttacttctg
5101 acaacgatcg gaggaccgaa ggagctaacc gcttttttgc acaacatggg ggatcatgta
5161 actcgccttg atcgttggga accggagctg aatgaagcca taccaaacga cgagcgtgac
5221 accacgatgc ctgtagcaat ggcaacaacg ttgcgcaaac tattaactgg cgaactactt
5281 actctagctt cccggcaaca attaatagac tggatggagg cggataaagt tgcaggacca
5341 cttctgcgct cggcccttcc ggctggctgg tttattgctg ataaatctgg agccggtgag
5401 cgtgggtctc gcggtatcat tgcagcactg gggccagatg gtaagccctc ccgtatcgta
5461 gttatctaca cgacggggag tcaggcaact atggatgaac gaaatagaca gatcgctgag
5521 ataggtgcct cactgattaa gcattggtaa ctgtcagacc aagtttactc atatatactt
5581 tagattgatt taaaacttca tttttaattt aaaaggatct aggtgaagat cctttttgat
5641 aatctcatga ccaaaatccc ttaacgtgag ttttcgttcc actgagcgtc agaccccgta
5701 gaaaagatca aaggatcttc ttgagatcct ttttttctgc gcgtaatctg ctgcttgcaa
5761 acaaaaaaac caccgctacc agcggtggtt tgtttgccgg atcaagagct accaactctt
5821 tttccgaagg taactggctt cagcagagcg cagataccaa atactgttct tctagtgtag
5881 ccgtagttag gccaccactt caagaactct gtagcaccgc ctacatacct cgctctgcta
5941 atcctgttac cagtggctgc tgccagtggc gataagtcgt gtcttaccgg gttggactca
6001 agacgatagt taccggataa ggcgcagcgg tcgggctgaa cggggggttc gtgcacacag
6061 cccagcttgg agcgaacgac ctacaccgaa ctgagatacc tacagcgtga gctatgagaa
6121 agcgccacgc ttcccgaagg gagaaaggcg gacaggtatc cggtaagcgg cagggtcgga
6181 acaggagagc gcacgaggga gcttccaggg ggaaacgcct ggtatcttta tagtcctgtc
6241 gggtttcgcc acctctgact tgagcgtcga tttttgtgat gctcgtcagg ggggcggagc
6301 ctatggaaaa acgccagcaa cgcggccttt ttacggttcc tggccttttg ctggcctttt
6361 gctcacatgt tctttcctgc gttatcccct gattctgtgg ataaccgtat taccgccttt
6421 gagtgagctg ataccgctcg ccgcagccga acgaccgagc gcagcgagtc agtgagcgag
6481 gaagcggaag agcgcccaat acgcaaaccg cctctccccg cgcgttggcc gattcattaa
6541 tgcagctggc acgacaggtt tcccgactgg aaagcgggca gtgagcgcaa cgcaattaat
6601 gtgagttagc tcactcatta ggcaccccag gctttacact ttatgcttcc ggctcgtatg
6661 ttgtgtggaa ttgtgagcgg ataacaattt cacacaggaa acagctatga ccatgattac
6721 gccagattta attaaggcct taattagg
//
```

PLASMID SEQUENCES
FIG. 5X

SEQ ID NO: 20

```
pN254 3bnc ORF 26 p2757
LOCUS       3bnc117\MAB\IRES        6748 bp    DNA     circular
FEATURES             Location/Qualifiers
     repeat_region   1..130
                     /vntifkey="34"
                     /label=ITR
     repeat_region   complement(3798..3927)
                     /vntifkey="34"
                     /label=ITR
     intron          1047..1179
                     /vntifkey="15"
                     /label=Promega\chimeric\intron
     polyA_signal    3502..3733
                     /vntifkey="25"
                     /label=SV40\late\polyadenylation\signal
     promoter        191..932
                     /vntifkey="29"
                     /label=human\CMV\I.E.\enhancer\&\promoter
     CDS             4690..5547
                     /vntifkey="4"
                     /label=Amp-R
     misc_feature    5721..6309
                     /vntifkey="21"
                     /label=COL\E1\Origin
     rep_origin      complement(4104..4559)
                     /vntifkey="33"
                     /label=f1\ori
     misc_feature    1248..1293
                     /vntifkey="21"
                     /label=c-myc\miniIRES\cloned\into\Nhe\site
     misc_feature    897..901
                     /vntifkey="21"
                     /label=TATA\box
     misc_feature    1294..3493
                     /vntifkey="21"
                     /label=3bnc\ORF\26
     misc_feature    1292..1297
                     /vntifkey="21"
                     /label=6\bp\insertion
BASE COUNT     1668 a     1728 c     1674 g     1678 t
ORIGIN
        1 ctgcgcgctc gctcgctcac tgaggccgcc cgggcaaagc ccgggcgtcg ggcgaccttt
       61 ggtcgcccgg cctcagtgag cgagcgagcg cgcagagagg gagtggccaa ctccatcact
      121 aggggttcct tgtagttaat gattaacccg ccatgctact tatctacgta gccatgctct
      181 aggaagatct tcaatattgg ccattagcca tattattcat tggttatata gcataaatca
      241 atattggcta ttggccattg catacgttgt atctatatca taatatgtac atttatattg
      301 gctcatgtcc aatatgaccg ccatgttggc attgattatt gactagttat taatagtaat
      361 caattacggg gtcattagtt catagcccat atatggagtt ccgcgttaca taacttacgg
      421 taaatggccc gcctggctga ccgcccaacg acccccgccc attgacgtca ataatgacgt
      481 atgttcccat agtaacgcca atagggactt tccattgacg tcaatgggtg gagtatttac
      541 ggtaaactgc ccacttggca gtacatcaag tgtatcatat gccaagtccg ccccctattg
      601 acgtcaatga cggtaaatgg cccgcctggc attatgccca gtacatgacc ttacgggact
      661 ttcctacttg gcagtacatc tacgtattag tcatcgctat taccatggtg atgcggtttt
      721 ggcagtacac caatgggcgt ggatagcggt ttgactcacg gggatttcca agtctccacc
```

PLASMID SEQUENCES
FIG. 5Y

```
 781 ccattgacgt caatgggagt ttgttttggc accaaaatca acgggacttt ccaaaatgtc
 841 gtaataaccc cgccccgttg acgcaaatgg gcggtaggcg tgtacggtgg gaggtctata
 901 taagcagagc tcgtttagtg aaccgtcaga tcactagaag ctttattgcg gtagtttatc
 961 acagttaaat tgctaacgca gtcagtgctt ctgacacaac agtctcgaac ttaagctgca
1021 gaagttggtc gtgaggcact gggcaggtaa gtatcaaggt tacaagacag gtttaaggag
1081 accaatagaa actgggcttg tcgagacaga gaagactctt gcgtttctga taggcaccta
1141 ttggtcttac tgacatccac tttgcctttc tctccacagg tgtccactcc cagttcaatt
1201 acagctctta aggctagagt acttaatacg actcactata ggctagcggg gactttgcac
1261 tggaacttac aacacccgag caaggacgcg actctagctc tagaaccatg taccggatgc
1321 agttactttc gtgcatcgcc ctgtcactcg cccttgtgac taatagccag gtacagctac
1381 tgcagagcgg tgctgctgtg actaagccag ggcctctgt gcgggtgtct tgcgaggcgt
1441 cgggatacaa tatccgggac tactttatcc actggtggag acaggcaccg ggtcagggac
1501 ttcagtgggt gggctggatc aatcccaaaa caggccagcc caacaatccc cggcagttcc
1561 agggtcgcgt ctctctgact aggcacgcct cctgggattt cgacaccttc tcgttctata
1621 tggacctcaa ggctcttcgg tccgacgaca ccgccgtgta cttttgcgca cgccagagat
1681 ccgactactg ggactttgac gtttgggggt ccggaactca agtgacagtt agttctgcgt
1741 ctaccaaggg tccctcagtg ttccctctgg cccccctctag taagtcaacc tctggtggta
1801 ccgcggcctt aggctgtctg gtgaaagatt actttcccga acccgtgacc gtgtcttgga
1861 atagcggtgc tctcacgagt ggggtgcata cgtttcctgc cgtcctgcaa tcaagtggac
1921 tttacagctt gtcaagtgtc gtgacggtgc cgtccagctc actaggtacc cagacctaca
1981 tctgcaatgt gaatcataag ccttcgaata ccaaggtgga taagaaggtg gagcccaagt
2041 catgcgacaa gacccatacc tgtcctccct gccccgcacc tgagctgttg ggcggtccat
2101 ccgtgtttct gtttcccccct aagcccaagg acaccctgat gatatctcgc accccagagg
2161 tgacctgcgt agtggtcgac gtcagtcacg aggacccaga agtgaagttt aactggtacg
2221 tggacggcgt agaagtgcat aatgccaaaa ccaagccccg ggaagaacag tacaattcca
2281 cctaccgtgt ggtgtctgtt ttgaccgtgc tccaccagga ttggctgaat gggaaggaat
2341 acaagtgcaa ggtgtctaac aaggctctcc ctgcacccat tgagaaaacc atttccaagg
2401 ccaagggtca gccccgagaa ccccaagtgt acaccttacc gccctcccgc gacgaactga
2461 ccaaaaacca ggtgtccctt acctgcctgg tgaagggatt ctacccgagt gacatcgctg
2521 tggaatggga aagcaacggc cagcctgaaa acaattacaa gactacccca ccagtactcg
2581 attcagacgg aagctttttc ctttacagca agctcactgt ggacaagtct cgatggcagc
2641 agggcaatgt gttctcatgc tctgtgatgc atgaggcatt gcataaccac tatacacaga
2701 agtcattatc actctccccc ggcagaaaac gcagggctcc tgtgaagcag actcttaact
2761 ttgacctgct gaaacttgct ggtgacgtgg aatcaaaccc cggtccaatg tacagaatgc
2821 agcttttgtc atgcattgct ctcagcctag ctctagtgac caattcagat attcagatga
2881 ctcagagtcc aagtagtcta agcgcctcag tcggcgatac agtgacgatc acctgtcagg
2941 caaacggata cttgaattgg taccagcaga ggagggggaa ggctccgaag cttctgatct
3001 atgacggcag taagcttgaa cgcggtgtgc ctagccgctt ctccggtcgc cgctggggtc
3061 aggagtacaa cttaaccata aacaacctcc agcctgagga catagcaacc tatttctgtc
3121 aggtgtatga gtttgttgtg cccggtacaa ggctagacct caagcgaacc gtggccgctc
3181 catccgtctt tatctttcct cctagcgacg agcagctgaa gtccggcacc gcttcagtgg
3241 tctgcctcct caacaatttc taccccaggg aagccaaggt gcagtggaaa gtggacaatg
3301 cactgcagag tggaaattct caagagtctg tgaccgagca ggactcaaaa gactctacct
3361 acagcctgag ttcaaccctt accctgtcaa aggccgatta cgaaaagcat aaggtgtatg
3421 cttgcgaggt gacccaccag ggcctgtcga gccccgtgac caagagcttt aaccgtggag
3481 aatgctaatg agcggccgct tcgagcagac atgataagat acattgatga gtttggacaa
3541 accacaacta gaatgcagtg aaaaaaatgc tttatttgtg aaatttgtga tgctattgct
3601 ttatttgtaa ccattataag ctgcaataaa caagttaaca acaacaattg cattcatttt
3661 atgtttcagg ttcaggggga gatgtgggag gtttttttaaa gcaagtaaaa cctctacaaa
3721 tgtggtaaaa tcgataagga tcttcctaga gcatggctac gtagataagt agcatggcgg
3781 gttaatcatt aactacaagg aacccctagt gatggagttg gccactccct ctctgcgcgc
3841 tcgctcgctc actgaggccg ggcgaccaaa ggtcgcccga cgcccgggct ttgcccgggc
3901 ggcctcagtg agcgagcgag cgcgcagcct taattaacct aattcactgg ccgtcgtttt
3961 acaacgtcgt gactgggaaa accctggcgt tacccaactt aatcgccttg cagcacatcc
```

PLASMID SEQUENCES
FIG. 5Z

```
4021 ccctttcgcc agctggcgta atagcgaaga ggcccgcacc gatcgccctt cccaacagtt
4081 gcgcagcctg aatggcgaat gggacgcgcc ctgtagcggc gcattaagcg cggcgggtgt
4141 ggtggttacg cgcagcgtga ccgctacact tgccagcgcc ctagcgcccg ctcctttcgc
4201 tttcttccct tcctttctcg ccacgttcgc cggctttccc cgtcaagctc taaatcgggg
4261 gctcccttta gggttccgat ttagtgcttt acggcacctc gaccccaaaa aacttgatta
4321 gggtgatggt tcacgtagtg ggccatcgcc ctgatagacg gtttttcgcc ctttgacgtt
4381 ggagtccacg ttctttaata gtggactctt gttccaaact ggaacaacac tcaaccctat
4441 ctcggtctat tcttttgatt tataagggat tttgccgatt tcggcctatt ggttaaaaaa
4501 tgagctgatt taacaaaaat ttaacgcgaa ttttaacaaa atattaacgc ttacaattta
4561 ggtggcactt ttcggggaaa tgtgcgcgga acccctattt gtttattttt ctaaatacat
4621 tcaaatatgt atccgctcat gagacaataa ccctgataaa tgcttcaata atattgaaaa
4681 aggaagagta tgagtattca acatttccgt gtcgccctta ttcccttttt tgcggcattt
4741 tgccttcctg tttttgctca cccagaaacg ctggtgaaag taaaagatgc tgaagatcag
4801 ttgggtgcac gagtgggtta catcgaactg gatctcaaca gcggtaagat ccttgagagt
4861 tttcgccccg aagaacgttt tccaatgatg agcactttta aagttctgct atgtggcgcg
4921 gtattatccc gtattgacgc cgggcaagag caactcggtc gccgcataca ctattctcag
4981 aatgacttgg ttgagtactc accagtcaca gaaaagcatc ttacggatgg catgacagta
5041 agagaattat gcagtgctgc cataaccatg agtgataaca ctgcggccaa cttacttctg
5101 acaacgatcg gaggaccgaa ggagctaacc gcttttttgc acaacatggg ggatcatgta
5161 actcgccttg atcgttggga accggagctg aatgaagcca taccaaacga cgagcgtgac
5221 accacgatgc ctgtagcaat ggcaacaacg ttgcgcaaac tattaactgg cgaactactt
5281 actctagctt cccggcaaca attaatagac tggatggagg cggataaagt tgcaggacca
5341 cttctgcgct cggcccttcc ggctggctgg tttattgctg ataaatctgg agccggtgag
5401 cgtgggtctc gcggtatcat tgcagcactg gggccagatg gtaagccctc ccgtatcgta
5461 gttatctaca cgacggggag tcaggcaact atggatgaac gaaatagaca gatcgctgag
5521 ataggtgcct cactgattaa gcattggtaa ctgtcagacc aagtttactc atatatactt
5581 tagattgatt taaaacttca tttttaattt aaaaggatct aggtgaagat cctttttgat
5641 aatctcatga ccaaaatccc ttaacgtgag ttttcgttcc actgagcgtc agaccccgta
5701 gaaaagatca aaggatcttc ttgagatcct ttttttctgc gcgtaatctg ctgcttgcaa
5761 acaaaaaaac caccgctacc agcggtggtt tgtttgccgg atcaagagct accaactctt
5821 tttccgaagg taactggctt cagcagagcg cagataccaa atactgttct tctagtgtag
5881 ccgtagttag gccaccactt caagaactct gtagcaccgc ctacatacct cgctctgcta
5941 atcctgttac cagtggctgc tgccagtggc gataagtcgt gtcttaccgg gttggactca
6001 agacgatagt taccggataa ggcgcagcgg tcgggctgaa cggggggttc gtgcacacag
6061 cccagcttgg agcgaacgac ctacaccgaa ctgagatacc tacagcgtga gctatgagaa
6121 agcgccacgc ttcccgaagg gagaaaggcg gacaggtatc cggtaagcgg cagggtcgga
6181 acaggagagc gcacgaggga gcttccaggg ggaaacgcct ggtatcttta tagtcctgtc
6241 gggtttcgcc acctctgact tgagcgtcga tttttgtgat gctcgtcagg ggggcggagc
6301 ctatggaaaa acgccagcaa cgcggccttt ttacggttcc tggccttttg ctggcctttt
6361 gctcacatgt tctttcctgc gttatcccct gattctgtgg ataaccgtat taccgccttt
6421 gagtgagctg ataccgctcg ccgcagccga acgaccgagc gcagcgagtc agtgagcgag
6481 gaagcggaag agcgcccaat acgcaaaccg cctctccccg cgcgttggcc gattcattaa
6541 tgcagctggc acgacaggtt tcccgactgg aaagcgggca gtgagcgcaa cgcaattaat
6601 gtgagttagc tcactcatta ggcaccccag gctttacact ttatgcttcc ggctcgtatg
6661 ttgtgtggaa ttgtgagcgg ataacaattt cacacaggaa acagctatga ccatgattac
6721 gccagattta attaaggcct taattagg
```
//

PLASMID SEQUENCES
FIG. 5AA

SEQ ID NO: 21

```
pN255 3bnc ORF 42 p2759
LOCUS       3bnc117\MAB\IRES        6748 bp    DNA     circular
FEATURES             Location/Qualifiers
     repeat_region   1..130
                     /vntifkey="34"
                     /label=ITR
     repeat_region   complement(3798..3927)
                     /vntifkey="34"
                     /label=ITR
     intron          1047..1179
                     /vntifkey="15"
                     /label=Promega\chimeric\intron
     polyA_signal    3502..3733
                     /vntifkey="25"
                     /label=SV40\late\polyadenylation\signal
     promoter        191..932
                     /vntifkey="29"
                     /label=human\CMV\I.E.\enhancer\&\promoter
     CDS             4690..5547
                     /vntifkey="4"
                     /label=Amp-R
     misc_feature    5721..6309
                     /vntifkey="21"
                     /label=COL\E1\Origin
     rep_origin      complement(4104..4559)
                     /vntifkey="33"
                     /label=f1\ori
     misc_feature    1248..1293
                     /vntifkey="21"
                     /label=c-myc\miniIRES\cloned\into\Nhe\site
     misc_feature    897..901
                     /vntifkey="21"
                     /label=TATA\box
     misc_feature    1294..3493
                     /vntifkey="21"
                     /label=3bnc\ORF\42
     misc_feature    1292..1297
                     /vntifkey="21"
                     /label=6\bp\insertion
BASE COUNT     1726 a     1706 c     1616 g     1700 t
ORIGIN
        1 ctgcgcgctc gctcgctcac tgaggccgcc cgggcaaagc ccgggcgtcg ggcgaccttt
       61 ggtcgcccgg cctcagtgag cgagcgagcg cgcagagagg gagtggccaa ctccatcact
      121 aggggttcct tgtagttaat gattaacccg ccatgctact tatctacgta gccatgctct
      181 aggaagatct tcaatattgg ccattagcca tattattcat tggttatata gcataaatca
      241 atattggcta ttggccattg catacgttgt atctatatca taatatgtac atttatattg
      301 gctcatgtcc aatatgaccg ccatgttggc attgattatt gactagttat taatagtaat
      361 caattacggg gtcattagtt catagcccat atatggagtt ccgcgttaca taacttacgg
      421 taaatggccc gcctggctga ccgcccaacg acccccgccc attgacgtca ataatgacgt
      481 atgttcccat agtaacgcca atagggactt tccattgacg tcaatgggtg gagtatttac
      541 ggtaaactgc ccacttggca gtacatcaag tgtatcatat gccaagtccg ccccctattg
      601 acgtcaatga cggtaaatgg cccgcctggc attatgccca gtacatgacc ttacgggact
      661 ttcctacttg gcagtacatc tacgtattag tcatcgctat taccatggtg atgcggtttt
      721 ggcagtacac caatgggcgt ggatagcggt ttgactcacg gggatttcca agtctccacc
```

PLASMID SEQUENCES

FIG. 5BB

```
 781 ccattgacgt caatgggagt ttgttttggc accaaaatca acgggacttt ccaaaatgtc
 841 gtaataaccc cgccccgttg acgcaaatgg gcggtaggcg tgtacggtgg gaggtctata
 901 taagcagagc tcgtttagtg aaccgtcaga tcactagaag ctttattgcg gtagtttatc
 961 acagttaaat tgctaacgca gtcagtgctt ctgacacaac agtctcgaac ttaagctgca
1021 gaagttggtc gtgaggcact gggcaggtaa gtatcaaggt tacaagacag gtttaaggag
1081 accaatagaa actgggcttg tcgagacaga gaagactctt gcgtttctga taggcaccta
1141 ttggtcttac tgacatccac tttgcctttc tctccacagg tgtccactcc cagttcaatt
1201 acagctctta aggctagagt acttaatacg actcactata ggctagcggg gactttgcac
1261 tggaacttac aacacccgag caaggacgcg actctagctc tagaaccatg taccggatgc
1321 agctactgtc gtgtatcgct ctttcgttag cattagtcac aaactcgcaa gtccagctgc
1381 tgcagtcagg ggctgcagtg acaaagcccg gagcatcagt tcgcgtttca tgtgaggcca
1441 gtggctacaa catacgggac tatttcatcc actggtggag acaggcacca ggccagggat
1501 tacagtgggt tggctggatc aacccgaaaa caggccagcc caataacccg cgacagtttc
1561 agggccgtgt cagtctcacc cgccacgcat cttgggattt cgatacgttt tccttctaca
1621 tggatctgaa ggcactgcgc agcgacgata ccgcagttta cttctgcgca aggcagcgta
1681 gcgattactg ggacttcgat gtctgggggt caggcacaca agtaacggtt tcatccgctt
1741 ccacaaaagg gccatcagtg tttcccctgg caccctcctc aaaatctacc agcggaggca
1801 ccgcagctct cggctgtctg gttaaagact actttcccga acccgtcacc gtttcttgga
1861 attctggggc tctaacctca ggcgtgcaca cgttccccgc cgttctgcag agcagcggcc
1921 tgtactcctt atcaagtgta gtaactgttc catcatcaag cttgggcacc cagacctaca
1981 tctgcaatgt taatcacaaa ccttccaaca ctaaggtgga caagaaggtt gagccaaaaa
2041 gttgtgataa gacccacaca tgtcctccgt gtcccgctcc tgagctgcta ggtggcccca
2101 gtgtgttcct ctttccccct aaacccaaag acacactgat gatctcaagg acccctgaag
2161 ttacatgcgt tgttgttgat gtttcccacg aagatccaga agttaagttc aactggtatg
2221 ttgatggcgt tgaagttcac aacgcaaaaa ctaaaccgcg tgaagaacag tataactcta
2281 cataccgtgt ggtttcagtt cttacagtcc tgcatcagga ttggcttaac gggaaagaat
2341 acaaatgtaa agtatccaac aaagcacttc ccgcacccat tgagaaaacg atttcaaaag
2401 caaagggaca gcccagggaa ccccaagttt acacgctgcc gccatctcgt gatgagctga
2461 ccaagaatca ggtatctttg acgtgcctgg tcaaaggttt ctacccttcg gacatcgcgg
2521 ttgagtggga gtcaaacggc cagccagaaa acaattacaa aaccactcct cctgtcttgg
2581 acagcgatgg gtcattcttt ctttactcaa aactcactgt tgacaagtct cgatggcagc
2641 aaggcaacgt ctttagttgc tctgtgatgc atgaagccct ccacaatcac tatacacaga
2701 aaagtctatc actctcacct ggcagaaaac ggagggcacc cgtgaagcag acactcaatt
2761 tcgacttact gaaactggct ggggatgtcg aatctaatcc aggccctatg taccgcatgc
2821 aactactgtc atgtattgcc ctttcattag ctctcgtaac aaattctgat atccagatga
2881 cccagtcccc ctcatctctg tcagcatcgg ttggcgatac cgttactatt acgtgccagg
2941 caaatggcta cttgaactgg taccaacaac ggcgcggtaa agcacccaaa ctattgatat
3001 acgatggctc aaagttggaa agaggcgtgc cttcaagatt ctccggcaga cgctggggcc
3061 aggagtacaa cctaactatc aacaaccttc agccagagga tattgcaacc tacttctgtc
3121 aggtgtatga gtttgtggtg cccggcacgc gtctggattt gaagagaaca gtcgcggcac
3181 cctcagtgtt tatcttccct cccagtgatg agcagctgaa atcaggcacc gcctcagtgg
3241 tatgcctgtt gaacaacttc taccccgtg aggcaaaagt tcagtggaag gtggataatg
3301 ccttacagtc aggcaactca caagagagcg tcactgagca ggattcaaaa gattcaacat
3361 acagtcttag ctcaaccctg accctctcta aagcggatta cgaaaaacac aaagtttatg
3421 cctgcgaagt cacgcaccag ggtctgagta gccctgttac taaaagtttc aaccgaggcg
3481 aatgttaatg agcggccgct tcgagcagac atgataagat acattgatga gtttggacaa
3541 accacaacta gaatgcagtg aaaaaaatgc tttatttgtg aaatttgtga tgctattgct
3601 ttatttgtaa ccattataag ctgcaataaa caagttaaca acaacaattg cattcatttt
3661 atgtttcagg ttcaggggga gatgtgggag gtttttttaaa gcaagtaaaa cctctacaaa
3721 tgtggtaaaa tcgataagga tcttcctaga gcatggctac gtagataagt agcatggcgg
3781 gttaatcatt aactacaagg aacccctagt gatggagttg gccactccct ctctgcgcgc
3841 tcgctcgctc actgaggccg ggcgaccaaa ggtcgcccga cgcccgggct ttgcccgggc
3901 ggcctcagtg agcgagcgag cgcgcagcct taattaacct aattcactgg ccgtcgtttt
3961 acaacgtcgt gactgggaaa accctggcgt tacccaactt aatcgccttg cagcacatcc
```

PLASMID SEQUENCES
FIG. 5CC

```
4021 cccttttcgcc agctggcgta atagcgaaga ggcccgcacc gatcgccctt cccaacagtt
4081 gcgcagcctg aatggcgaat gggacgcgcc ctgtagcggc gcattaagcg cggcgggtgt
4141 ggtggttacg cgcagcgtga ccgctacact tgccagcgcc ctagcgcccg ctcctttcgc
4201 tttcttccct tcctttctcg ccacgttcgc cggctttccc cgtcaagctc taaatcgggg
4261 gctcccttta gggttccgat ttagtgcttt acggcacctc gaccccaaaa aacttgatta
4321 gggtgatggt tcacgtagtg ggccatcgcc ctgatagacg gtttttcgcc ctttgacgtt
4381 ggagtccacg ttctttaata gtggactctt gttccaaact ggaacaacac tcaaccctat
4441 ctcggtctat tcttttgatt tataagggat tttgccgatt tcggcctatt ggttaaaaaa
4501 tgagctgatt taacaaaaat ttaacgcgaa ttttaacaaa atattaacgc ttacaattta
4561 ggtggcactt ttcggggaaa tgtgcgcgga acccctattt gtttattttt ctaaatacat
4621 tcaaatatgt atccgctcat gagacaataa ccctgataaa tgcttcaata atattgaaaa
4681 aggaagagta tgagtattca acatttccgt gtcgccctta ttcccttttt tgcggcattt
4741 tgccttcctg tttttgctca cccagaaacg ctggtgaaag taaaagatgc tgaagatcag
4801 ttgggtgcac gagtgggtta catcgaactg gatctcaaca gcggtaagat ccttgagagt
4861 tttcgccccg aagaacgttt tccaatgatg agcactttta aagttctgct atgtggcgcg
4921 gtattatccc gtattgacgc cgggcaagag caactcggtc gccgcataca ctattctcag
4981 aatgacttgg ttgagtactc accagtcaca gaaaagcatc ttacggatgg catgacagta
5041 agagaattat gcagtgctgc cataaccatg agtgataaca ctgcggccaa cttacttctg
5101 acaacgatcg gaggaccgaa ggagctaacc gcttttttgc acaacatggg ggatcatgta
5161 actcgccttg atcgttggga accggagctg aatgaagcca taccaaacga cgagcgtgac
5221 accacgatgc ctgtagcaat ggcaacaacg ttgcgcaaac tattaactgg cgaactactt
5281 actctagctt cccggcaaca attaatagac tggatggagg cggataaagt tgcaggacca
5341 cttctgcgct cggcccttcc ggctggctgg tttattgctg ataaatctgg agccggtgag
5401 cgtgggtctc gcggtatcat tgcagcactg gggccagatg gtaagccctc ccgtatcgta
5461 gttatctaca cgacggggag tcaggcaact atggatgaac gaaatagaca gatcgctgag
5521 ataggtgcct cactgattaa gcattggtaa ctgtcagacc aagtttactc atatatactt
5581 tagattgatt taaaacttca tttttaattt aaaaggatct aggtgaagat cctttttgat
5641 aatctcatga ccaaaatccc ttaacgtgag ttttcgttcc actgagcgtc agaccccgta
5701 gaaaagatca aaggatcttc ttgagatcct ttttttctgc gcgtaatctg ctgcttgcaa
5761 acaaaaaaac caccgctacc agcggtggtt tgtttgccgg atcaagagct accaactctt
5821 tttccgaagg taactggctt cagcagagcg cagataccaa atactgttct tctagtgtag
5881 ccgtagttag gccaccactt caagaactct gtagcaccgc ctacatacct cgctctgcta
5941 atcctgttac cagtggctgc tgccagtggc gataagtcgt gtcttaccgg gttggactca
6001 agacgatagt taccggataa ggcgcagcgg tcgggctgaa cggggggttc gtgcacacag
6061 cccagcttgg agcgaacgac ctacaccgaa ctgagatacc tacagcgtga gctatgagaa
6121 agcgccacgc ttcccgaagg gagaaaggcg gacaggtatc cggtaagcgg cagggtcgga
6181 acaggagagc gcacgaggga gcttccaggg ggaaacgcct ggtatcttta tagtcctgtc
6241 gggtttcgcc acctctgact tgagcgtcga tttttgtgat gctcgtcagg ggggcggagc
6301 ctatggaaaa acgccagcaa cgcggccttt ttacggttcc tggccttttg ctggcctttt
6361 gctcacatgt tctttcctgc gttatcccct gattctgtgg ataaccgtat taccgccttt
6421 gagtgagctg ataccgctcg ccgcagccga acgaccgagc gcagcgagtc agtgagcgag
6481 gaagcggaag agcgcccaat acgcaaaccg cctctccccg cgcgttggcc gattcattaa
6541 tgcagctggc acgacaggtt tcccgactgg aaagcgggca gtgagcgcaa cgcaattaat
6601 gtgagttagc tcactcatta ggcaccccag gctttacact ttatgcttcc ggctcgtatg
6661 ttgtgtggaa ttgtgagcgg ataacaattt cacacaggaa acagctatga ccatgattac
6721 gccagattta attaaggcct taattagg
//
```

PLASMID SEQUENCES
FIG. 5DD

SEQ ID NO: 22

```
pN256 CMV 3bnc ORF 28 p2761
LOCUS       3bnc117\MAB\IRES        6748 bp    DNA     circular
FEATURES             Location/Qualifiers
     repeat_region   1..130
                     /vntifkey="34"
                     /label=ITR
     repeat_region   complement(3798..3927)
                     /vntifkey="34"
                     /label=ITR
     intron          1047..1179
                     /vntifkey="15"
                     /label=Promega\chimeric\intron
     polyA_signal    3502..3733
                     /vntifkey="25"
                     /label=SV40\late\polyadenylation\signal
     promoter        191..932
                     /vntifkey="29"
                     /label=human\CMV\I.E.\enhancer\&\promoter
     CDS             4690..5547
                     /vntifkey="4"
                     /label=Amp-R
     misc_feature    5721..6309
                     /vntifkey="21"
                     /label=COL\E1\Origin
     rep_origin      complement(4104..4559)
                     /vntifkey="33"
                     /label=f1\ori
     misc_feature    897..901
                     /vntifkey="21"
                     /label=TATA\box
     misc_feature    1294..3493
                     /vntifkey="21"
                     /label=AnnaT_TestRef\28
     misc_feature    1248..1295
                     /vntifkey="21"
                     /label=c-myc\miniIRES
                     /note="mini  c-myc"
BASE COUNT     1677 a      1688 c      1679 g      1704 t
ORIGIN
        1 ctgcgcgctc gctcgctcac tgaggccgcc cgggcaaagc ccgggcgtcg ggcgaccttt
       61 ggtcgcccgg cctcagtgag cgagcgagcg cgcagagagg gagtggccaa ctccatcact
      121 aggggttcct tgtagttaat gattaacccg ccatgctact tatctacgta gccatgctct
      181 aggaagatct tcaatattgg ccattagcca tattattcat tggttatata gcataaatca
      241 atattggcta ttggccattg catacgttgt atctatatca taatatgtac atttatattg
      301 gctcatgtcc aatatgaccg ccatgttggc attgattatt gactagttat taatagtaat
      361 caattacggg gtcattagtt catagcccat atatggagtt ccgcgttaca taacttacgg
      421 taaatggccc gcctggctga ccgcccaacg acccccgccc attgacgtca ataatgacgt
      481 atgttcccat agtaacgcca atagggactt tccattgacg tcaatgggtg gagtatttac
      541 ggtaaactgc ccacttggca gtacatcaag tgtatcatat gccaagtccg ccccctattg
      601 acgtcaatga cggtaaatgg cccgcctggc attatgccca gtacatgacc ttacgggact
      661 ttcctacttg gcagtacatc tacgtattag tcatcgctat taccatggtg atgcggtttt
      721 ggcagtacac caatgggcgt ggatagcggt ttgactcacg gggatttcca agtctccacc
      781 ccattgacgt caatgggagt ttgttttggc accaaaatca acgggacttt ccaaaatgtc
      841 gtaataaccc cgccccgttg acgcaaatgg gcggtaggcg tgtacggtgg gaggtctata
```

PLASMID SEQUENCES
FIG. 5EE

```
 901 taagcagagc tcgtttagtg aaccgtcaga tcactagaag ctttattgcg gtagtttatc
 961 acagttaaat tgctaacgca gtcagtgctt ctgacacaac agtctcgaac ttaagctgca
1021 gaagttggtc gtgaggcact gggcaggtaa gtatcaaggt tacaagacag gtttaaggag
1081 accaatagaa actgggcttg tcgagacaga gaagactctt gcgtttctga taggcaccta
1141 ttggtcttac tgacatccac tttgcctttc tctccacagg tgtccactcc cagttcaatt
1201 acagctctta aggctagagt acttaatacg actcactata ggctagcggg gactttgcac
1261 tggaacttac aacacccgag caaggacgcg actctagctc tagaaccatg tacagaatgc
1321 agcttctgtc ttgcattgca ctttctctgg ccttagtgac taactctcaa gtgcagctcc
1381 ttcagagcgg cgcagctgtg acaaagcctg ggccagcgt tagagtgtcg tgtgaggcat
1441 ccggctataa catcagagac tatttcattc attggtggcg ccaagcgccc ggtcagggac
1501 ttcagtgggt gggctggatc aatccaaaga cagggcagcc taacaatcca agacagtttc
1561 agggccgggt gtccttgact cggcatgcga gctgggattt tgatacgttc tccttttaca
1621 tggacctgaa ggccctaagg tctgacgaca ccgctgtgta tttctgcgcc aggcagagat
1681 cagactattg ggactttgat gtgtggggct ctggtactca agtgacagtg agcagtgcgt
1741 ctacaaaggg cccatcagtc tttcctctgg ccccttccag caagtctacg tccggcggga
1801 ctgccgccct cggatgctta gtgaaggact atttccctga gcccgtgacc gtgagctgga
1861 atagcggcgc tctgacgtct ggcgtgcaca cattccctgc tgtgctgcag agcagtggcc
1921 tttactccct tagtagcgtg gtgacagtgc cctctagttc tctaggcacc cagacataca
1981 tttgtaatgt aaatcacaaa cctagcaaca caaaggtgga caagaaggtg gaacctaaga
2041 gttgtgataa gacccataca tgtcccccat gcccagcccc agagcttctt ggcggtccat
2101 cagttttctt gtttcctcca aaacctaagg acactctgat gatttcgaga acaccggaag
2161 tcacttgtgt ggtcgtggat gtgtcacacg aggaccctga ggtcaagttc aattggtatg
2221 tggacggcgt ggaggtacat aacgccaaaa cgaagcctcg tgaggagcag tacaactcca
2281 cctatcgagt ggtcagcgtc cttaccgtgt tacaccagga ctggcttaac ggaaaggagt
2341 ataagtgtaa ggtatccaac aaagccctgc ctgcacctat tgagaaaact atatctaaag
2401 ccaagggcca gccgcgagag cctcaagttt acacacttcc tccttcgaga gacgagctca
2461 ccaagaatca ggtgtcactt acctgccttg tgaaaggctt ttaccctagt gatatcgcgg
2521 tggaatggga gagcaatggg cagcctgaga acaactataa gacaacccct cccgtactgg
2581 acagcgatgg cagcttcttt ctctattcta agctgaccgt cgataagagt cggtggcagc
2641 agggtaacgt gttctcttgt tctgtgatgc atgaggcatt gcacaatcat tacacgcaga
2701 agagtctgtc cctttctcct ggccgtaaaa ggcgagctcc tgtgaagcag actcttaact
2761 ttgacttgct caagctcgct ggcgatgtgg agtccaatcc tgggcccatg taccgaatgc
2821 aacttcttag ctgcatagca ctttcccttg cacttgtgac gaattctgac atccagatga
2881 cccagagtcc ctcctctttg agtgcaagtg tgggcgacac cgtgaccatc acttgtcagg
2941 ccaatggcta tctcaactgg tatcagcagc ggagagggaa ggcacctaag ctactcatct
3001 atgacggcag taaactggag agaggcgttc caagcagatt ctccggtcgc cgatggggcc
3061 aggaatacaa tcttaccatc aataacctgc agcccgagga cattgccacc tatttctgtc
3121 aggtgtatga gttcgtggtg cccggaacga gactcgatct caagagaact gtggctgccc
3181 ccagcgtgtt cattttccct ccttccgacg agcagcttaa gagtggcacc gcttcagtgg
3241 tgtgtttact aaacaatttc taccctcgag aggcgaaggt gcagtggaag gtggataatg
3301 cccttcagtc aggcaattct caagaaagtg tgaccgagca ggatagtaag gactctacat
3361 actcactctc ctcaaccctg acactcagta aggccgacta tgagaagcac aaggtgtacg
3421 cgtgcgaagt cacgcatcag ggcctatcta gccccgtcac aaagtcattc aataggggcg
3481 agtgctaatg agcggccgct tcgagcagac atgataagat acattgatga gtttggacaa
3541 accacaacta gaatgcagtg aaaaaaatgc tttatttgtg aaatttgtga tgctattgct
3601 ttatttgtaa ccattataag ctgcaataaa caagttaaca acaacaattg cattcatttt
3661 atgtttcagg ttcaggggga gatgtgggag gtttttaaa gcaagtaaaa cctctacaaa
3721 tgtggtaaaa tcgataagga tcttcctaga gcatggctac gtagataagt agcatggcgg
3781 gttaatcatt aactacaagg aacccctagt gatggagttg gccactccct ctctgcgcgc
3841 tcgctcgctc actgaggccg ggcgaccaaa ggtcgcccga cgcccgggct ttgcccgggc
3901 ggcctcagtg agcgagcgag cgcgcagcct taattaacct aattcactgg ccgtcgtttt
3961 acaacgtcgt gactgggaaa accctggcgt tacccaactt aatcgccttg cagcacatcc
4021 ccctttcgcc agctggcgta atagcgaaga ggcccgcacc gatcgccctt cccaacagtt
4081 gcgcagcctg aatggcgaat gggacgcgcc ctgtagcggc gcattaagcg cggcgggtgt
```

PLASMID SEQUENCES
FIG. 5FF

```
4141 ggtggttacg cgcagcgtga ccgctacact tgccagcgcc ctagcgcccg ctcctttcgc
4201 tttcttccct tcctttctcg ccacgttcgc cggctttccc cgtcaagctc taaatcgggg
4261 gctcccttta gggttccgat ttagtgcttt acggcacctc gaccccaaaa aacttgatta
4321 gggtgatggt tcacgtagtg ggccatcgcc ctgatagacg gtttttcgcc ctttgacgtt
4381 ggagtccacg ttctttaata gtggactctt gttccaaact ggaacaacac tcaaccctat
4441 ctcggtctat tcttttgatt tataagggat tttgccgatt tcggcctatt ggttaaaaaa
4501 tgagctgatt taacaaaaat ttaacgcgaa ttttaacaaa atattaacgc ttacaattta
4561 ggtggcactt ttcggggaaa tgtgcgcgga acccctattt gtttattttt ctaaatacat
4621 tcaaatatgt atccgctcat gagacaataa ccctgataaa tgcttcaata atattgaaaa
4681 aggaagagta tgagtattca acatttccgt gtcgccctta ttcccttttt tgcggcattt
4741 tgccttcctg tttttgctca cccagaaacg ctggtgaaag taaaagatgc tgaagatcag
4801 ttgggtgcac gagtgggtta catcgaactg gatctcaaca gcggtaagat ccttgagagt
4861 tttcgccccg aagaacgttt tccaatgatg agcactttta aagttctgct atgtggcgcg
4921 gtattatccc gtattgacgc cgggcaagag caactcggtc gccgcataca ctattctcag
4981 aatgacttgg ttgagtactc accagtcaca gaaaagcatc ttacggatgg catgacagta
5041 agagaattat gcagtgctgc cataaccatg agtgataaca ctgcggccaa cttacttctg
5101 acaacgatcg gaggaccgaa ggagctaacc gcttttttgc acaacatggg ggatcatgta
5161 actcgccttg atcgttggga accggagctg aatgaagcca taccaaacga cgagcgtgac
5221 accacgatgc ctgtagcaat ggcaacaacg ttgcgcaaac tattaactgg cgaactactt
5281 actctagctt cccggcaaca attaatagac tggatggagg cggataaagt tgcaggacca
5341 cttctgcgct cggcccttcc ggctggctgg tttattgctg ataaatctgg agccggtgag
5401 cgtgggtctc gcggtatcat tgcagcactg gggccagatg gtaagccctc ccgtatcgta
5461 gttatctaca cgacggggag tcaggcaact atggatgaac gaaatagaca gatcgctgag
5521 ataggtgcct cactgattaa gcattggtaa ctgtcagacc aagtttactc atatatactt
5581 tagattgatt taaaacttca tttttaattt aaaaggatct aggtgaagat cctttttgat
5641 aatctcatga ccaaaatccc ttaacgtgag ttttcgttcc actgagcgtc agaccccgta
5701 gaaaagatca aaggatcttc ttgagatcct ttttttctgc gcgtaatctg ctgcttgcaa
5761 acaaaaaaac caccgctacc agcggtggtt tgtttgccgg atcaagagct accaactctt
5821 tttccgaagg taactggctt cagcagagcg cagataccaa atactgttct tctagtgtag
5881 ccgtagttag gccaccactt caagaactct gtagcaccgc ctacatacct cgctctgcta
5941 atcctgttac cagtggctgc tgccagtggc gataagtcgt gtcttaccgg gttggactca
6001 agacgatagt taccggataa ggcgcagcgg tcgggctgaa cggggggttc gtgcacacag
6061 cccagcttgg agcgaacgac ctacaccgaa ctgagatacc tacagcgtga gctatgagaa
6121 agcgccacgc ttcccgaagg gagaaaggcg gacaggtatc cggtaagcgg cagggtcgga
6181 acaggagagc gcacgaggga gcttccaggg ggaaacgcct ggtatcttta tagtcctgtc
6241 gggtttcgcc acctctgact tgagcgtcga tttttgtgat gctcgtcagg ggggcggagc
6301 ctatggaaaa acgccagcaa cgcggccttt ttacggttcc tggccttttg ctggcctttt
6361 gctcacatgt tctttcctgc gttatcccct gattctgtgg ataaccgtat taccgccttt
6421 gagtgagctg ataccgctcg ccgcagccga acgaccgagc gcagcgagtc agtgagcgag
6481 gaagcggaag agcgcccaat acgcaaaccg cctctccccg cgcgttggcc gattcattaa
6541 tgcagctggc acgacaggtt tcccgactgg aaagcgggca gtgagcgcaa cgcaattaat
6601 gtgagttagc tcactcatta ggcaccccag gctttacact ttatgcttcc ggctcgtatg
6661 ttgtgtggaa ttgtgagcgg ataacaattt cacacaggaa acagctatga ccatgattac
6721 gccagattta attaaggcct taattagg
```

//

PLASMID SEQUENCES
FIG. 5GG

SEQ ID NO: 23

```
pN257 CMV 3bnc ORF 30 p2762
LOCUS       3bnc117\MAB\IRES        6748 bp    DNA     circular
FEATURES             Location/Qualifiers
     repeat_region   1..130
                     /vntifkey="34"
                     /label=ITR
     repeat_region   complement(3798..3927)
                     /vntifkey="34"
                     /label=ITR
     intron          1047..1179
                     /vntifkey="15"
                     /label=Promega\chimeric\intron
     polyA_signal    3502..3733
                     /vntifkey="25"
                     /label=SV40\late\polyadenylation\signal
     promoter        191..932
                     /vntifkey="29"
                     /label=human\CMV\I.E.\enhancer\&\promoter
     CDS             4690..5547
                     /vntifkey="4"
                     /label=Amp-R
     misc_feature    5721..6309
                     /vntifkey="21"
                     /label=COL\E1\Origin
     rep_origin      complement(4104..4559)
                     /vntifkey="33"
                     /label=f1\ori
     misc_feature    1248..1293
                     /vntifkey="21"
                     /label=c-myc\miniIRES\cloned\into\Nhe\site
     misc_feature    897..901
                     /vntifkey="21"
                     /label=TATA\box
     misc_feature    1294..3493
                     /vntifkey="21"
                     /label=AnnaT_TestRef\30
BASE COUNT     1710 a      1668 c      1651 g      1719 t
ORIGIN
        1 ctgcgcgctc gctcgctcac tgaggccgcc cgggcaaagc ccgggcgtcg ggcgaccttt
       61 ggtcgcccgg cctcagtgag cgagcgagcg cgcagagagg gagtggccaa ctccatcact
      121 aggggttcct tgtagttaat gattaacccg ccatgctact tatctacgta gccatgctct
      181 aggaagatct tcaatattgg ccattagcca tattattcat tggttatata gcataaatca
      241 atattggcta ttggccattg catacgttgt atctatatca taatatgtac atttatattg
      301 gctcatgtcc aatatgaccg ccatgttggc attgattatt gactagttat taatagtaat
      361 caattacggg gtcattagtt catagcccat atatggagtt ccgcgttaca taacttacgg
      421 taaatggccc gcctggctga ccgcccaacg acccccgccc attgacgtca ataatgacgt
      481 atgttcccat agtaacgcca atagggactt tccattgacg tcaatgggtg gagtatttac
      541 ggtaaactgc ccacttggca gtacatcaag tgtatcatat gccaagtccg ccccctattg
      601 acgtcaatga cggtaaatgg cccgcctggc attatgccca gtacatgacc ttacgggact
      661 ttcctacttg gcagtacatc tacgtattag tcatcgctat taccatggtg atgcggtttt
      721 ggcagtacac caatgggcgt ggatagcggt ttgactcacg gggatttcca agtctccacc
      781 ccattgacgt caatgggagt ttgttttggc accaaaatca acgggacttt ccaaaatgtc
      841 gtaataaccc cgccccgttg acgcaaatgg gcggtaggcg tgtacggtgg gaggtctata
      901 taagcagagc tcgtttagtg aaccgtcaga tcactagaag ctttattgcg gtagtttatc
```

PLASMID SEQUENCES
FIG. 5HH

```
 961 acagttaaat tgctaacgca gtcagtgctt ctgacacaac agtctcgaac ttaagctgca
1021 gaagttggtc gtgaggcact gggcaggtaa gtatcaaggt tacaagacag gtttaaggag
1081 accaatagaa actgggcttg tcgagacaga gaagactctt gcgtttctga taggcaccta
1141 ttggtcttac tgacatccac tttgcctttc tctccacagg tgtccactcc cagttcaatt
1201 acagctctta aggctagagt acttaatacg actcactata ggctagcggg gactttgcac
1261 tggaacttac aacacccgag caaggacgcg actctagctc tagaaccatg tatcgtatgc
1321 aacttctcag ctgcattgca cttagtctcg ctctggttac aaacagtcaa gttcagctgc
1381 ttcagtccgg cgctgccgtg accaagcctg gagcttcggt cagagtgtca tgtgaagcca
1441 gcgggtataa cattagagac tatttcattc actggtggag acaggcccct ggacaggggc
1501 ttcagtgggt cggctggatt aaccctaaaa ccggccagcc caacaatcca agacagtttc
1561 agggccgggt gtcccttacc cgacatgcca gctgggattt cgatacattt tcgttctata
1621 tggaccttaa ggctttgaga tctgatgata cagctgtgta tttctgtgca cgacagcggt
1681 ctgattactg ggattttgac gtgtgggggt ccggcacaca agtcacagtg tccagtgcat
1741 ccacaaaagg accttcagtc tttcctctcg ccccgtccag caagtcaacc agcgggggta
1801 cagcggcttt ggggtgcctt gtcaaggact actttcctga acccgtgact gtgtcatgga
1861 actcgggtgc cctgacatcg gggtccaca cttttcccgc tgtgctccag tcctcggggc
1921 tatactccct tagctcggtg gttacagtcc catcctcatc attagggaca cagacataca
1981 tctgtaatgt gaaccacaag ccttcaaata ctaaggttga taagaaagtt gaacccaagt
2041 cttgcgataa gacacacaca tgtccccctt gtcctgcacc agagctgctt ggcgggcctt
2101 cagtttttct tttcctcca aaacctaagg atacacttat gatctcaagg acaccagaag
2161 tcacatgcgt cgtggtggat gtgtcccatg aggaccccga ggtcaagttt aactggtatg
2221 tggatggggt cgaagtgcac aacgccaaaa caaagccacg cgaagagcaa tacaattcga
2281 cttacagagt cgtgagtgta ctgaccgtgc tgcaccagga ttggctgaac ggcaaagagt
2341 acaaatgcaa agtgagcaac aaagctctac cagctcccat agaaaagaca atctctaaag
2401 ctaaggggca gccgcgggag ccccaagtct ataccctacc tccttcccgc gacgaactca
2461 caaagaacca ggttagcctt acatgtctcg taaaggggtt ctatccttcg gatatcgctg
2521 tcgaatggga gtctaacggg cagcctgaaa acaactacaa aacaactccc cctgtgcttg
2581 atagcgacgg tagtttcttt ctgtacagca aacttacagt cgataagagt agatggcaac
2641 aggggaatgt gttttcttgt tccgtgatgc acgaggcact gcacaatcac tacacacaga
2701 agagtctcag cttatctcct ggaaggaaga gacgagctcc cgtcaaacag acgctaaact
2761 ttgacctgtt aaagcttgcc ggcgatgtcg aatccaatcc agggcctatg taccggatgc
2821 agctacttag ttgcatagct cttagccttg ctctcgtgac taacagcgac atccagatga
2881 cgcagtcacc ttcctccctg tcagcctcag tcggcgatac cgtaactata acatgtcagg
2941 cgaatgggta tctgaattgg tatcagcagc gacgtgggaa agctcctaag ttgcttatct
3001 atgatgggtc taagcttgag agaggggtgc caagtagatt ttctggacga aggtgggggc
3061 aggagtataa cttgaccatc aataaccttc agcctgaaga tatcgccaca tacttttgcc
3121 aggtatatga gtttgttgtg cccgggacga gacttgatct caaacgaacg gtggctgctc
3181 cttctgtgtt tatctttcct ccttctgatg agcagctcaa gagcggaaca gcatccgttg
3241 tctgtctgct caacaacttt taccctaggg aagctaaggt gcagtggaag gttgacaatg
3301 ctttacagag cggaaatagc caggagtccg tcacagaaca ggatagcaag gatagcacat
3361 atagcttgag ctccactctg acactcagta aggctgatta tgagaagcat aaggtatatg
3421 cctgtgaagt cacacatcaa ggcctttcat cccctgttac taagtctttc aacagagggg
3481 aatgctaatg agcggccgct tcgagcagac atgataagat acattgatga gtttggacaa
3541 accacaacta gaatgcagtg aaaaaaatgc tttatttgtg aaatttgtga tgctattgct
3601 ttatttgtaa ccattataag ctgcaataaa caagttaaca acaacaattg cattcatttt
3661 atgtttcagg ttcaggggga gatgtgggag gtttttaaa gcaagtaaaa cctctacaaa
3721 tgtggtaaaa tcgataagga tcttcctaga gcatggctac gtagataagt agcatggcgg
3781 gttaatcatt aactacaagg aacccctagt gatggagttg gccactccct ctctgcgcgc
3841 tcgctcgctc actgaggccg ggcgaccaaa ggtcgcccga cgcccgggct ttgcccgggc
3901 ggcctcagtg agcgagcgag cgcgcagcct taattaacct aattcactgg ccgtcgtttt
3961 acaacgtcgt gactgggaaa accctggcgt tacccaactt aatcgccttg cagcacatcc
4021 ccctttcgcc agctggcgta atagcgaaga ggcccgcacc gatcgccctt cccaacagtt
4081 gcgcagcctg aatggcgaat gggacgcgcc ctgtagcggc gcattaagcg cggcgggtgt
4141 ggtggttacg cgcagcgtga ccgctacact tgccagcgcc ctagcgcccg ctcctttcgc
```

PLASMID SEQUENCES
FIG. 5II

```
4201 tttcttccct tcctttctcg ccacgttcgc cggctttccc cgtcaagctc taaatcgggg
4261 gctcccttta gggttccgat ttagtgcttt acggcacctc gaccccaaaa aacttgatta
4321 gggtgatggt tcacgtagtg ggccatcgcc ctgatagacg gtttttcgcc ctttgacgtt
4381 ggagtccacg ttctttaata gtggactctt gttccaaact ggaacaacac tcaaccctat
4441 ctcggtctat tcttttgatt tataagggat tttgccgatt tcggcctatt ggttaaaaaa
4501 tgagctgatt taacaaaaat ttaacgcgaa ttttaacaaa atattaacgc ttacaattta
4561 ggtggcactt ttcggggaaa tgtgcgcgga acccctattt gtttattttt ctaaatacat
4621 tcaaatatgt atccgctcat gagacaataa ccctgataaa tgcttcaata atattgaaaa
4681 aggaagagta tgagtattca acatttccgt gtcgccctta ttcccttttt tgcggcattt
4741 tgccttcctg tttttgctca cccagaaacg ctggtgaaag taaaagatgc tgaagatcag
4801 ttgggtgcac gagtgggtta catcgaactg gatctcaaca gcggtaagat ccttgagagt
4861 tttcgccccg aagaacgttt tccaatgatg agcactttta aagttctgct atgtggcgcg
4921 gtattatccc gtattgacgc cgggcaagag caactcggtc gccgcataca ctattctcag
4981 aatgacttgg ttgagtactc accagtcaca gaaaagcatc ttacggatgg catgacagta
5041 agagaattat gcagtgctgc cataaccatg agtgataaca ctgcggccaa cttacttctg
5101 acaacgatcg gaggaccgaa ggagctaacc gcttttttgc acaacatggg ggatcatgta
5161 actcgccttg atcgttggga accggagctg aatgaagcca taccaaacga cgagcgtgac
5221 accacgatgc ctgtagcaat ggcaacaacg ttgcgcaaac tattaactgg cgaactactt
5281 actctagctt cccggcaaca attaatagac tggatggagg cggataaagt tgcaggacca
5341 cttctgcgct cggcccttcc ggctggctgg tttattgctg ataaatctgg agccggtgag
5401 cgtgggtctc gcggtatcat tgcagcactg gggccagatg gtaagccctc ccgtatcgta
5461 gttatctaca cgacggggag tcaggcaact atggatgaac gaaatagaca gatcgctgag
5521 ataggtgcct cactgattaa gcattggtaa ctgtcagacc aagtttactc atatatactt
5581 tagattgatt taaaacttca tttttaattt aaaaggatct aggtgaagat cctttttgat
5641 aatctcatga ccaaaatccc ttaacgtgag ttttcgttcc actgagcgtc agaccccgta
5701 gaaaagatca aaggatcttc ttgagatcct ttttttctgc gcgtaatctg ctgcttgcaa
5761 acaaaaaaac caccgctacc agcggtggtt tgtttgccgg atcaagagct accaactctt
5821 tttccgaagg taactggctt cagcagagcg cagataccaa atactgttct tctagtgtag
5881 ccgtagttag gccaccactt caagaactct gtagcaccgc ctacatacct cgctctgcta
5941 atcctgttac cagtggctgc tgccagtggc gataagtcgt gtcttaccgg gttggactca
6001 agacgatagt taccggataa ggcgcagcgg tcgggctgaa cggggggttc gtgcacacag
6061 cccagcttgg agcgaacgac ctacaccgaa ctgagatacc tacagcgtga gctatgagaa
6121 agcgccacgc ttcccgaagg gagaaaggcg gacaggtatc cggtaagcgg cagggtcgga
6181 acaggagagc gcacgaggga gcttccaggg ggaaacgcct ggtatcttta tagtcctgtc
6241 gggtttcgcc acctctgact tgagcgtcga tttttgtgat gctcgtcagg ggggcggagc
6301 ctatggaaaa acgccagcaa cgcggccttt ttacggttcc tggccttttg ctggcctttt
6361 gctcacatgt tctttcctgc gttatcccct gattctgtgg ataaccgtat taccgccttt
6421 gagtgagctg ataccgctcg ccgcagccga acgaccgagc gcagcgagtc agtgagcgag
6481 gaagcggaag agcgcccaat acgcaaaccg cctctccccg cgcgttggcc gattcattaa
6541 tgcagctggc acgacaggtt tcccgactgg aaagcgggca gtgagcgcaa cgcaattaat
6601 gtgagttagc tcactcatta ggcaccccag gctttacact ttatgcttcc ggctcgtatg
6661 ttgtgtggaa ttgtgagcgg ataacaattt cacacaggaa acagctatga ccatgattac
6721 gccagattta attaaggcct taattagg
//
```

PLASMID SEQUENCES
FIG. 5JJ

SEQ ID NO: 24

```
pN258 CMV 3bnc ORF 35 p2763
LOCUS       3bnc117\MAB\IRES        6748 bp    DNA     circular
FEATURES             Location/Qualifiers
     repeat_region   1..130
                     /vntifkey="34"
                     /label=ITR
     repeat_region   complement(3798..3927)
                     /vntifkey="34"
                     /label=ITR
     intron          1047..1179
                     /vntifkey="15"
                     /label=Promega\chimeric\intron
     polyA_signal    3502..3733
                     /vntifkey="25"
                     /label=SV40\late\polyadenylation\signal
     promoter        191..932
                     /vntifkey="29"
                     /label=human\CMV\I.E.\enhancer\&\promoter
     CDS             4690..5547
                     /vntifkey="4"
                     /label=Amp-R
     misc_feature    5721..6309
                     /vntifkey="21"
                     /label=COL\E1\Origin
     rep_origin      complement(4104..4559)
                     /vntifkey="33"
                     /label=f1\ori
     misc_feature    1248..1293
                     /vntifkey="21"
                     /label=c-myc\miniIRES\cloned\into\Nhe\site
     misc_feature    897..901
                     /vntifkey="21"
                     /label=TATA\box
     misc_feature    1294..3493
                     /vntifkey="21"
                     /label=AnnaT_TestRef\35
BASE COUNT     1685 a      1732 c      1648 g      1683 t
ORIGIN
        1 ctgcgcgctc gctcgctcac tgaggccgcc cgggcaaagc ccgggcgtcg ggcgaccttt
       61 ggtcgcccgg cctcagtgag cgagcgagcg cgcagagagg gagtggccaa ctccatcact
      121 aggggttcct tgtagttaat gattaacccg ccatgctact tatctacgta gccatgctct
      181 aggaagatct tcaatattgg ccattagcca tattattcat tggttatata gcataaatca
      241 atattggcta ttggccattg catacgttgt atctatatca taatatgtac atttatattg
      301 gctcatgtcc aatatgaccg ccatgttggc attgattatt gactagttat taatagtaat
      361 caattacggg gtcattagtt catagcccat atatggagtt ccgcgttaca taacttacgg
      421 taaatggccc gcctggctga ccgcccaacg acccccgccc attgacgtca ataatgacgt
      481 atgttcccat agtaacgcca atagggactt tccattgacg tcaatgggtg gagtatttac
      541 ggtaaactgc ccacttggca gtacatcaag tgtatcatat gccaagtccg ccccctattg
      601 acgtcaatga cggtaaatgg cccgcctggc attatgccca gtacatgacc ttacgggact
      661 ttcctacttg gcagtacatc tacgtattag tcatcgctat taccatggtg atgcggtttt
      721 ggcagtacac caatgggcgt ggatagcggt ttgactcacg gggatttcca agtctccacc
      781 ccattgacgt caatgggagt ttgttttggc accaaaatca acgggacttt ccaaaatgtc
      841 gtaataaccc cgccccgttg acgcaaatgg gcggtaggcg tgtacggtgg gaggtctata
      901 taagcagagc tcgtttagtg aaccgtcaga tcactagaag ctttattgcg gtagtttatc
```

PLASMID SEQUENCES
FIG. 5KK

```
 961 acagttaaat tgctaacgca gtcagtgctt ctgacacaac agtctcgaac ttaagctgca
1021 gaagttggtc gtgaggcact gggcaggtaa gtatcaaggt tacaagacag gtttaaggag
1081 accaatagaa actgggcttg tcgagacaga gaagactctt gcgtttctga taggcaccta
1141 ttggtcttac tgacatccac tttgcctttc tctccacagg tgtccactcc cagttcaatt
1201 acagctctta aggctagagt acttaatacg actcactata ggctagcggg gactttgcac
1261 tggaacttac aacacccgag caaggacgcg actctagctc tagaaccatg tataggatgc
1321 aactgttgtc gtgcattgct ctgagcctcg ccttagtgac caatagccaa gtacaactcc
1381 tccagtctgg agcagctgtt accaagccag gcgcttcggt tagggtttca tgcgaagcaa
1441 gtggctataa catccgggac tatttcatcc attggtggag acaagccccc ggacaagggc
1501 tgcaatgggt cggctggatt aacccaaaga ccggccaacc caacaacccc cggcagtttc
1561 aagggagggt gagcctgacc cgccatgcaa gctgggactt cgacactttt tccttctaca
1621 tggatctgaa agctctgagg tccgacgaca ccgccgtgta cttctgtgct cggcagagga
1681 gcgactattg ggactttgac gtttggggct ctggcaccca agttacagtt tcctcggctt
1741 ccacaaaggg cccctcggta tttcccttgg ccccctcgtc taagtccacc agcggaggaa
1801 ctgctgcttt aggctgcctt gttaaggact acttccccga gcccgtgact gtctcgtgga
1861 actcaggcgc gctcactagc ggggttcata cctttcccgc tgtgttgcag agcagtggct
1921 tgtatagcct gtctagcgtc gtgaccgttc ccagcagcag cctcgggacc cagacgtaca
1981 tttgtaacgt taatcataag ccttcaaaca ccaaagtcga taagaaggtg gaacccaaga
2041 gttgtgacaa aacccacacc tgcccgccct gtcccgcacc cgagctgtta ggtggtcctt
2101 ctgtctttct gtttcctccc aagccaaagg acacccttat gatatcgagg acccctgaag
2161 taacctgcgt cgtagttgac gtttcccacg aagatcccga ggtcaagttc aactggtatg
2221 tcgacggggt tgaagtgcac aacgcaaaaa caaagcctcg tgaggaacaa tacaactcaa
2281 cgtatagggt tgtctccgtt cttaccgttc tgcaccaaga ctggttgaac gggaaggagt
2341 acaaatgcaa agtatcgaac aaagccctgc ccgcacccat tgagaaaacc atttcgaagg
2401 ccaaaggcca accccgggaa ccccaagtgt ataccctccc accttccaga gatgaactga
2461 ccaagaatca ggtgtcgctg acctgcctgg tgaagggctt ctacccctct gatattgccg
2521 tggaatggga aagcaatggc caacccgaaa acaattacaa gaccactccc ccggttttag
2581 actcagacgg ctcattcttt ctgtattcaa agttgactgt tgacaagtcc agatggcagc
2641 aagggaacgt tttctcctgt agtgttatgc atgaagccct gcataatcat tacacccaga
2701 agtcgttgag cctatctccc ggtaggaaaa ggcgggctcc tgtgaagcaa actctgaact
2761 ttgacttgct gaagctcgcc ggtgacgtag aatcaaaccc tggacccatg tacagaatgc
2821 agctgttgtc ctgtattgca ctgagtctgg ctctcgtgac caattcagac atccagatga
2881 cccaatcacc ctccagcctt tccgcctcgg ttggagacac cgtaacaatt acttgtcagg
2941 ctaacggtta ccttaactgg tatcagcagc gccgagggaa agctcccaag ctactcatat
3001 acgacggctc taagctggaa cgcggcgttc cttcacggtt tagtggccgg aggtggggcc
3061 aggaatacaa cctgaccatt aacaacctgc agcccgaaga tattgccacc tatttctgtc
3121 aggtgtatga atttgttgtt cccgggaccc gactggactt gaagcggacc gttgcggcac
3181 ccagcgtctt tatctttccc ccatcggatg aacaactgaa atccggcacc gcctcagttg
3241 tttgcctgct gaacaacttc tatccgcggg aagcgaaggt ccagtggaaa gttgacaacg
3301 ccctgcagtc aggtaactcg caagaatctg tcaccgaaca ggacagcaag gactcgacct
3361 atagtctcag ctccacccta acgctgtcca aagccgatta tgagaagcac aaagtctatg
3421 cttgtgaggt tacgcaccaa gggctaagca gtcccgttac aaagtccttt aaccggggag
3481 agtgttaatg agcggccgct tcgagcagac atgataagat acattgatga gtttggacaa
3541 accacaacta gaatgcagtg aaaaaaatgc tttatttgtg aaatttgtga tgctattgct
3601 ttatttgtaa ccattataag ctgcaataaa caagttaaca acaacaattg cattcatttt
3661 atgtttcagg ttcaggggga gatgtgggag gtttttttaaa gcaagtaaaa cctctacaaa
3721 tgtggtaaaa tcgataagga tcttcctaga gcatggctac gtagataagt agcatggcgg
3781 gttaatcatt aactacaagg aacccctagt gatggagttg gccactccct ctctgcgcgc
3841 tcgctcgctc actgaggccg ggcgaccaaa ggtcgcccga cgcccgggct ttgcccgggc
3901 ggcctcagtg agcgagcgag cgcgcagcct taattaacct aattcactgg ccgtcgtttt
3961 acaacgtcgt gactgggaaa accctggcgt tacccaactt aatcgccttg cagcacatcc
4021 ccctttcgcc agctggcgta atagcgaaga ggcccgcacc gatcgccctt cccaacagtt
4081 gcgcagcctg aatggcgaat gggacgcgcc ctgtagcggc gcattaagcg cggcgggtgt
4141 ggtggttacg cgcagcgtga ccgctacact tgccagcgcc ctagcgcccg ctcctttcgc
```

PLASMID SEQUENCES

FIG. 5LL

```
4201 tttcttccct tcctttctcg ccacgttcgc cggctttccc cgtcaagctc taaatcgggg
4261 gctcccttta gggttccgat ttagtgcttt acggcacctc gaccccaaaa aacttgatta
4321 gggtgatggt tcacgtagtg ggccatcgcc ctgatagacg gtttttcgcc ctttgacgtt
4381 ggagtccacg ttctttaata gtggactctt gttccaaact ggaacaacac tcaaccctat
4441 ctcggtctat tcttttgatt tataagggat tttgccgatt tcggcctatt ggttaaaaaa
4501 tgagctgatt taacaaaaat ttaacgcgaa ttttaacaaa atattaacgc ttacaattta
4561 ggtggcactt ttcggggaaa tgtgcgcgga acccctattt gtttattttt ctaaatacat
4621 tcaaatatgt atccgctcat gagacaataa ccctgataaa tgcttcaata atattgaaaa
4681 aggaagagta tgagtattca acatttccgt gtcgccctta ttcccttttt tgcggcattt
4741 tgccttcctg tttttgctca cccagaaacg ctggtgaaag taaaagatgc tgaagatcag
4801 ttgggtgcac gagtgggtta catcgaactg gatctcaaca gcggtaagat ccttgagagt
4861 tttcgccccg aagaacgttt tccaatgatg agcactttta aagttctgct atgtggcgcg
4921 gtattatccc gtattgacgc cgggcaagag caactcggtc gccgcataca ctattctcag
4981 aatgacttgg ttgagtactc accagtcaca gaaaagcatc ttacggatgg catgacagta
5041 agagaattat gcagtgctgc cataaccatg agtgataaca ctgcggccaa cttacttctg
5101 acaacgatcg gaggaccgaa ggagctaacc gcttttttgc acaacatggg ggatcatgta
5161 actcgccttg atcgttggga accggagctg aatgaagcca taccaaacga cgagcgtgac
5221 accacgatgc ctgtagcaat ggcaacaacg ttgcgcaaac tattaactgg cgaactactt
5281 actctagctt cccggcaaca attaatagac tggatggagg cggataaagt tgcaggacca
5341 cttctgcgct cggcccttcc ggctggctgg tttattgctg ataaatctgg agccggtgag
5401 cgtgggtctc gcggtatcat tgcagcactg gggccagatg gtaagccctc ccgtatcgta
5461 gttatctaca cgacggggag tcaggcaact atggatgaac gaaatagaca gatcgctgag
5521 ataggtgcct cactgattaa gcattggtaa ctgtcagacc aagtttactc atatatactt
5581 tagattgatt taaaacttca tttttaattt aaaaggatct aggtgaagat cctttttgat
5641 aatctcatga ccaaaatccc ttaacgtgag ttttcgttcc actgagcgtc agaccccgta
5701 gaaaagatca aaggatcttc ttgagatcct ttttttctgc gcgtaatctg ctgcttgcaa
5761 acaaaaaaac caccgctacc agcggtggtt tgtttgccgg atcaagagct accaactctt
5821 tttccgaagg taactggctt cagcagagcg cagataccaa atactgttct tctagtgtag
5881 ccgtagttag gccaccactt caagaactct gtagcaccgc ctacatacct cgctctgcta
5941 atcctgttac cagtggctgc tgccagtggc gataagtcgt gtcttaccgg gttggactca
6001 agacgatagt taccggataa ggcgcagcgg tcgggctgaa cggggggttc gtgcacacag
6061 cccagcttgg agcgaacgac ctacaccgaa ctgagatacc tacagcgtga gctatgagaa
6121 agcgccacgc ttcccgaagg gagaaaggcg gacaggtatc cggtaagcgg cagggtcgga
6181 acaggagagc gcacgaggga gcttccaggg ggaaacgcct ggtatcttta tagtcctgtc
6241 gggtttcgcc acctctgact tgagcgtcga tttttgtgat gctcgtcagg ggggcggagc
6301 ctatggaaaa acgccagcaa cgcggccttt ttacggttcc tggccttttg ctggcctttt
6361 gctcacatgt tctttcctgc gttatcccct gattctgtgg ataaccgtat taccgccttt
6421 gagtgagctg ataccgctcg ccgcagccga acgaccgagc gcagcgagtc agtgagcgag
6481 gaagcggaag agcgcccaat acgcaaaccg cctctccccg cgcgttggcc gattcattaa
6541 tgcagctggc acgacaggtt tcccgactgg aaagcgggca gtgagcgcaa cgcaattaat
6601 gtgagttagc tcactcatta ggcaccccag gctttacact ttatgcttcc ggctcgtatg
6661 ttgtgtggaa ttgtgagcgg ataacaattt cacacaggaa acagctatga ccatgattac
6721 gccagattta attaaggcct taattagg
//
```

PLASMID SEQUENCES
FIG. 5MM

SEQ ID NO: 25

```
pN259 CMV 3bnc ORF 39 p2764
LOCUS       3bnc117\MAB\IRES        6748 bp    DNA     circular
FEATURES             Location/Qualifiers
     repeat_region   1..130
                     /vntifkey="34"
                     /label=ITR
     repeat_region   complement(3798..3927)
                     /vntifkey="34"
                     /label=ITR
     intron          1047..1179
                     /vntifkey="15"
                     /label=Promega\chimeric\intron
     polyA_signal    3502..3733
                     /vntifkey="25"
                     /label=SV40\late\polyadenylation\signal
     promoter        191..932
                     /vntifkey="29"
                     /label=human\CMV\I.E.\enhancer\&\promoter
     CDS             4690..5547
                     /vntifkey="4"
                     /label=Amp-R
     misc_feature    5721..6309
                     /vntifkey="21"
                     /label=COL\E1\Origin
     rep_origin      complement(4104..4559)
                     /vntifkey="33"
                     /label=f1\ori
     misc_feature    1248..1293
                     /vntifkey="21"
                     /label=c-myc\miniIRES\cloned\into\Nhe\site
     misc_feature    897..901
                     /vntifkey="21"
                     /label=TATA\box
     misc_feature    1294..3493
                     /vntifkey="21"
                     /label=AnnaT_TestRef\39
BASE COUNT     1706 a      1702 c      1646 g      1694 t
ORIGIN
        1 ctgcgcgctc gctcgctcac tgaggccgcc cgggcaaagc ccgggcgtcg ggcgaccttt
       61 ggtcgcccgg cctcagtgag cgagcgagcg cgcagagagg gagtggccaa ctccatcact
      121 aggggttcct tgtagttaat gattaacccg ccatgctact tatctacgta gccatgctct
      181 aggaagatct tcaatattgg ccattagcca tattattcat tggttatata gcataaatca
      241 atattggcta ttggccattg catacgttgt atctatatca taatatgtac atttatattg
      301 gctcatgtcc aatatgaccg ccatgttggc attgattatt gactagttat taatagtaat
      361 caattacggg gtcattagtt catagcccat atatggagtt ccgcgttaca taacttacgg
      421 taaatggccc gcctggctga ccgcccaacg acccccgccc attgacgtca ataatgacgt
      481 atgttcccat agtaacgcca atagggactt tccattgacg tcaatgggtg gagtatttac
      541 ggtaaactgc ccacttggca gtacatcaag tgtatcatat gccaagtccg ccccctattg
      601 acgtcaatga cggtaaatgg cccgcctggc attatgccca gtacatgacc ttacgggact
      661 ttcctacttg gcagtacatc tacgtattag tcatcgctat taccatggtg atgcggtttt
      721 ggcagtacac caatgggcgt ggatagcggt ttgactcacg gggatttcca agtctccacc
      781 ccattgacgt caatgggagt ttgttttggc accaaaatca acgggacttt ccaaaatgtc
      841 gtaataaccc cgccccgttg acgcaaatgg gcggtaggcg tgtacggtgg gaggtctata
      901 taagcagagc tcgtttagtg aaccgtcaga tcactagaag ctttattgcg gtagtttatc
```

PLASMID SEQUENCES
FIG. 5NN

```
 961 acagttaaat tgctaacgca gtcagtgctt ctgacacaac agtctcgaac ttaagctgca
1021 gaagttggtc gtgaggcact gggcaggtaa gtatcaaggt tacaagacag gtttaaggag
1081 accaatagaa actgggcttg tcgagacaga gaagactctt gcgtttctga taggcaccta
1141 ttggtcttac tgacatccac tttgcctttc tctccacagg tgtccactcc cagttcaatt
1201 acagctctta aggctagagt acttaatacg actcactata ggctagcggg gactttgcac
1261 tggaacttac aacacccgag caaggacgcg actctagctc tagaaccatg tataggatgc
1321 agttactctc atgcattgct ctctcactgg cacttgtaac caattctcaa gtgcagcttc
1381 tccagtctgg cgctgccgtc accaagccag gagccagcgt tcgagtttca tgcgaagctt
1441 ctgggtacaa tatcagagat tacttcattc actggtggcg ccaggctccc gggcaggggc
1501 tccagtgggt gggatggatt aaccccaaga cgggacagcc caacaatccc aggcagttcc
1561 aggggcgtgt tagcctgaca agacatgcct catgggactt tgatacattc agtttctata
1621 tggacttgaa agctctgaga agtgatgata ccgctgttta cttttgcgct cggcagcgat
1681 cagactattg ggatttcgat gtgtggggat caggcaccca agtgacggtg tcaagcgctt
1741 caacaaaagg accctcagtg ttccctctcg ccccttcatc taaatcaaca agcggtggca
1801 ccgctgcctt gggatgtctc gttaaggact actttcccga gcccgtcaca gtgagttgga
1861 attctggcgc tcttactagc ggggtgcata ctttccccgc tgtactgcag tccagcggcc
1921 tgtattcatt gtcatcagtg gttacagtac cctcatcgag tctgggcacg cagacctaca
1981 tctgcaacgt caaccataaa ccctctaaca ccaaagtcga taagaaagta gaacccaaat
2041 cttgcgacaa aacacataca tgcccaccat gtcccgctcc agagttgttg ggtggacccct
2101 ccgtgtttct gttccctccc aaacccaaag atacactcat gatttcgcgg acccccgagg
2161 tgacttgcgt cgtcgtggat gtgtcccacg aggaccccga ggtcaaattc aactggtatg
2221 ttgatggagt ggaggttcat aacgccaaga ccaaacccag agaggagcag tacaacagta
2281 cgtacagagt tgtgtctgtt ctcactgttc tacaccagga ctggcttaac ggaaaggagt
2341 ataagtgtaa agtgtccaac aaggcactcc ctgctcccat tgaaaagaca atctcaaaag
2401 ctaagggcca gcccagagaa ccgcaagtgt acacgctacc gcctagtcga gatgagctga
2461 ccaagaacca ggtgtccttg acttgcctcg ttaaagggtt ctatccctcg gatatagctg
2521 tcgagtggga gtcaaatggg caacccgaga ataactacaa gaccacaccc cctgtgctgg
2581 attcagacgg tagcttcttt ctatactcca aactgacggt tgacaaatcc cgttggcagc
2641 aggggaacgt tttctcatgc tcagttatgc atgaagcact gcataaccac tatacgcaga
2701 aatcattatc acttagtccc ggacggaaaa ggcgcgctcc cgtgaaacag accctcaact
2761 ttgacttact gaagctcgcc ggagacgtcg agtcaaatcc tggtccgatg tatagaatgc
2821 agctgctttc ttgcattgca ttgagtctcg ccctggtcac caacagtgat atccagatga
2881 cccagagtcc ttcatctctc tcagcttcag tgggagacac ggtcacgata acctgccagg
2941 ctaacggcta tctcaattgg taccagcagc gcaggggtaa agctcccaaa ctgctgatct
3001 atgatggttc aaaactggag cgcggcgtac cctcacggtt ttccggacga cgatggggcc
3061 aggagtacaa tctgactatc aacaacctgc agcccgagga catagcgacg tatttctgcc
3121 aggtatatga gtttgtcgtc cctgggaccc ggctggacct gaaaaggacg gtcgctgcac
3181 cctcagtatt catattccca ccctccgatg agcagttgaa aagcggaaca gcgtcagtcg
3241 tgtgcctcct caataacttc taccccccggg aagccaaagt tcagtggaaa gttgacaatg
3301 cacttcagtc tggaaatagt caggagagcg tgactgagca ggattcaaaa gattctacgt
3361 attccctgag ctcaacgctc acactgtcta aagctgatta tgagaaacat aaggtttatg
3421 cctgcgaggt aacgcatcag ggtctatcat cgccccgtcac gaaaagcttt aacagagggg
3481 agtgttaatg agcggccgct tcgagcagac atgataagat acattgatga gtttggacaa
3541 accacaacta gaatgcagtg aaaaaaatgc tttatttgtg aaatttgtga tgctattgct
3601 ttatttgtaa ccattataag ctgcaataaa caagttaaca acaacaattg cattcatttt
3661 atgtttcagg ttcaggggga gatgtgggag gtttttttaaa gcaagtaaaa cctctacaaa
3721 tgtggtaaaa tcgataagga tcttcctaga gcatggctac gtagataagt agcatggcgg
3781 gttaatcatt aactacaagg aacccctagt gatggagttg gccactccct ctctgcgcgc
3841 tcgctcgctc actgaggccg ggcgaccaaa ggtcgcccga cgcccgggct ttgcccgggc
3901 ggcctcagtg agcgagcgag cgcgcagcct taattaacct aattcactgg ccgtcgtttt
3961 acaacgtcgt gactgggaaa accctggcgt tacccaactt aatcgccttg cagcacatcc
4021 ccctttcgcc agctggcgta atagcgaaga ggcccgcacc gatcgccctt cccaacagtt
4081 gcgcagcctg aatggcgaat gggacgcgcc ctgtagcggc gcattaagcg cggcgggtgt
4141 ggtggttacg cgcagcgtga ccgctacact tgccagcgcc ctagcgcccg ctcctttcgc
```

PLASMID SEQUENCES
FIG. 5OO

```
4201 tttcttccct tcctttctcg ccacgttcgc cggctttccc cgtcaagctc taaatcgggg
4261 gctcccttta gggttccgat ttagtgcttt acggcacctc gaccccaaaa aacttgatta
4321 gggtgatggt tcacgtagtg ggccatcgcc ctgatagacg gtttttcgcc ctttgacgtt
4381 ggagtccacg ttctttaata gtggactctt gttccaaact ggaacaacac tcaaccctat
4441 ctcggtctat tcttttgatt tataagggat tttgccgatt tcggcctatt ggttaaaaaa
4501 tgagctgatt taacaaaaat ttaacgcgaa ttttaacaaa atattaacgc ttacaattta
4561 ggtggcactt ttcggggaaa tgtgcgcgga acccctattt gtttattttt ctaaatacat
4621 tcaaatatgt atccgctcat gagacaataa ccctgataaa tgcttcaata atattgaaaa
4681 aggaagagta tgagtattca acatttccgt gtcgccctta ttcccttttt tgcggcattt
4741 tgccttcctg tttttgctca cccagaaacg ctggtgaaag taaaagatgc tgaagatcag
4801 ttgggtgcac gagtgggtta catcgaactg gatctcaaca gcggtaagat ccttgagagt
4861 tttcgccccg aagaacgttt tccaatgatg agcactttta aagttctgct atgtggcgcg
4921 gtattatccc gtattgacgc cgggcaagag caactcggtc gccgcataca ctattctcag
4981 aatgacttgg ttgagtactc accagtcaca gaaaagcatc ttacggatgg catgacagta
5041 agagaattat gcagtgctgc cataaccatg agtgataaca ctgcggccaa cttacttctg
5101 acaacgatcg gaggaccgaa ggagctaacc gcttttttgc acaacatggg ggatcatgta
5161 actcgccttg atcgttggga accggagctg aatgaagcca taccaaacga cgagcgtgac
5221 accacgatgc ctgtagcaat ggcaacaacg ttgcgcaaac tattaactgg cgaactactt
5281 actctagctt cccggcaaca attaatagac tggatggagg cggataaagt tgcaggacca
5341 cttctgcgct cggcccttcc ggctggctgg tttattgctg ataaatctgg agccggtgag
5401 cgtgggtctc gcggtatcat tgcagcactg gggccagatg gtaagccctc ccgtatcgta
5461 gttatctaca cgacggggag tcaggcaact atggatgaac gaaatagaca gatcgctgag
5521 ataggtgcct cactgattaa gcattggtaa ctgtcagacc aagtttactc atatatactt
5581 tagattgatt taaaacttca tttttaattt aaaaggatct aggtgaagat cctttttgat
5641 aatctcatga ccaaaatccc ttaacgtgag ttttcgttcc actgagcgtc agaccccgta
5701 gaaaagatca aaggatcttc ttgagatcct ttttttctgc gcgtaatctg ctgcttgcaa
5761 acaaaaaaac caccgctacc agcggtggtt tgtttgccgg atcaagagct accaactctt
5821 tttccgaagg taactggctt cagcagagcg cagataccaa atactgttct tctagtgtag
5881 ccgtagttag gccaccactt caagaactct gtagcaccgc ctacatacct cgctctgcta
5941 atcctgttac cagtggctgc tgccagtggc gataagtcgt gtcttaccgg gttggactca
6001 agacgatagt taccggataa ggcgcagcgg tcgggctgaa cggggggttc gtgcacacag
6061 cccagcttgg agcgaacgac ctacaccgaa ctgagatacc tacagcgtga gctatgagaa
6121 agcgccacgc ttcccgaagg gagaaaggcg gacaggtatc cggtaagcgg cagggtcgga
6181 acaggagagc gcacgaggga gcttccaggg ggaaacgcct ggtatcttta tagtcctgtc
6241 gggtttcgcc acctctgact tgagcgtcga tttttgtgat gctcgtcagg ggggcggagc
6301 ctatggaaaa acgccagcaa cgcggccttt ttacggttcc tggccttttg ctggcctttt
6361 gctcacatgt tctttcctgc gttatcccct gattctgtgg ataaccgtat taccgccttt
6421 gagtgagctg ataccgctcg ccgcagccga acgaccgagc gcagcgagtc agtgagcgag
6481 gaagcggaag agcgcccaat acgcaaaccg cctctccccg cgcgttggcc gattcattaa
6541 tgcagctggc acgacaggtt tcccgactgg aaagcgggca gtgagcgcaa cgcaattaat
6601 gtgagttagc tcactcatta ggcaccccag gctttacact ttatgcttcc ggctcgtatg
6661 ttgtgtggaa ttgtgagcgg ataacaattt cacacaggaa acagctatga ccatgattac
6721 gccagattta attaaggcct taattagg
//
```

PLASMID SEQUENCES
FIG. 5PP

SEQ ID NO: 26

```
pN260 CMV 3bnc ORF 40 p2765
LOCUS       3bnc117\MAB\IRES        6748 bp    DNA     circular
FEATURES             Location/Qualifiers
     repeat_region   1..130
                     /vntifkey="34"
                     /label=ITR
     repeat_region   complement(3798..3927)
                     /vntifkey="34"
                     /label=ITR
     intron          1047..1179
                     /vntifkey="15"
                     /label=Promega\chimeric\intron
     polyA_signal    3502..3733
                     /vntifkey="25"
                     /label=SV40\late\polyadenylation\signal
     promoter        191..932
                     /vntifkey="29"
                     /label=human\CMV\I.E.\enhancer\&\promoter
     CDS             4690..5547
                     /vntifkey="4"
                     /label=Amp-R
     misc_feature    5721..6309
                     /vntifkey="21"
                     /label=COL\E1\Origin
     rep_origin      complement(4104..4559)
                     /vntifkey="33"
                     /label=f1\ori
     misc_feature    1248..1293
                     /vntifkey="21"
                     /label=c-myc\miniIRES\cloned\into\Nhe\site
     misc_feature    897..901
                     /vntifkey="21"
                     /label=TATA\box
     misc_feature    1294..3493
                     /vntifkey="21"
                     /label=AnnaT_TestRef\40
BASE COUNT     1705 a      1700 c      1678 g      1665 t
ORIGIN
        1 ctgcgcgctc gctcgctcac tgaggccgcc cgggcaaagc ccgggcgtcg ggcgaccttt
       61 ggtcgcccgg cctcagtgag cgagcgagcg cgcagagagg gagtggccaa ctccatcact
      121 aggggttcct tgtagttaat gattaacccg ccatgctact tatctacgta gccatgctct
      181 aggaagatct tcaatattgg ccattagcca tattattcat tggttatata gcataaatca
      241 atattggcta ttggccattg catacgttgt atctatatca taatatgtac atttatattg
      301 gctcatgtcc aatatgaccg ccatgttggc attgattatt gactagttat taatagtaat
      361 caattacggg gtcattagtt catagcccat atatggagtt ccgcgttaca taacttacgg
      421 taaatggccc gcctggctga ccgcccaacg acccccgccc attgacgtca ataatgacgt
      481 atgttcccat agtaacgcca atagggactt tccattgacg tcaatgggtg gagtatttac
      541 ggtaaactgc ccacttggca gtacatcaag tgtatcatat gccaagtccg ccccctattg
      601 acgtcaatga cggtaaatgg cccgcctggc attatgccca gtacatgacc ttacgggact
      661 ttcctacttg gcagtacatc tacgtattag tcatcgctat taccatggtg atgcggtttt
      721 ggcagtacac caatgggcgt ggatagcggt ttgactcacg gggatttcca agtctccacc
      781 ccattgacgt caatgggagt ttgttttggc accaaaatca acgggacttt ccaaaatgtc
      841 gtaataaccc cgccccgttg acgcaaatgg gcggtaggcg tgtacggtgg gaggtctata
      901 taagcagagc tcgtttagtg aaccgtcaga tcactagaag ctttattgcg gtagtttatc
```

PLASMID SEQUENCES
FIG. 5QQ

```
 961 acagttaaat tgctaacgca gtcagtgctt ctgacacaac agtctcgaac ttaagctgca
1021 gaagttggtc gtgaggcact gggcaggtaa gtatcaaggt tacaagacag gtttaaggag
1081 accaatagaa actgggcttg tcgagacaga gaagactctt gcgtttctga taggcaccta
1141 ttggtcttac tgacatccac tttgcctttc tctccacagg tgtccactcc cagttcaatt
1201 acagctctta aggctagagt acttaatacg actcactata ggctagcggg gactttgcac
1261 tggaacttac aacacccgag caaggacgcg actctagctc tagaaccatg taccgtatgc
1321 agcttctctc atgtatagcc ctgagtttag ccctagttac aaatagccag gtgcagctgc
1381 tacagagcgg ggctgcggtc acaaagcctg ggccagcgt tcgcgtgtcc tgtgaggctt
1441 ccgggtacaa tatccgcgat tactttatcc actggtggcg tcaagctccg ggtcaggggt
1501 tacagtgggt cggttggatc aatccaaaaa caggacagcc caacaatcct cgccagtttc
1561 aggggcgtgt cagccttaca cgtcacgcca gttgggattt tgacacattc agcttttaca
1621 tggacctgaa ggccctgcga agcgacgaca cagccgtgta cttttgcgcc agacagcgga
1681 gcgactactg ggactttgat gtgtggggga gcggtacaca agtgacagtc tccagcgcgt
1741 ccaccaaagg acccagcgtg tttcctctgg ccccatcttc caagtcaaca tccggcggaa
1801 ctgcggccct agggtgcctg gtgaaagact actttcctga gcccgtaact gtgagctgga
1861 actccggggc tctgacatcc ggggttcata cattccctgc agtacttcag tcctccggcc
1921 tgtatagctt atctagcgta gtaacagtgc cctcctcttc cttggggaca cagacctaca
1981 tttgcaatgt gaatcataag ccctccaaca caaaggtgga taagaaggtg gagccgaaat
2041 cctgcgacaa aacgcacact tgccctcctt gtccagcccc cgagctgcta gggggaccct
2101 ccgtttttct gtttccacca aaacccaagg acacccttat gatttcacgc acaccggagg
2161 taacctgtgt tgtggtagac gtgtcgcatg aagatccaga ggtcaagttt aactggtatg
2221 ttgatggagt ggaggtccat aacgcaaaga caaaacccag agaggagcag tacaatagta
2281 cttaccgtgt ggtttctgta ctgacagtat tacatcagga ctggttgaac gggaaagagt
2341 acaaatgtaa agttagtaac aaagcccttc ctgcacctat agaaaagacc atatccaaag
2401 ccaaaggcca gcccagagag ccccaagttt acacgctacc gccaagccga gacgagctga
2461 ctaagaatca ggtgtccctg acttgtctag tcaagggctt ttaccccagc gatattgctg
2521 tggagtggga gagcaatggc cagcccgaga ataactacaa aacaacaccc ccggtccttg
2581 actccgatgg gagtttcttt ctgtacagca aattgacagt agacaagagc agatggcagc
2641 aggggaatgt gtttagctgc agcgtgatgc atgaggctct ccataatcat tacacgcaga
2701 aatccctgag cttgtctccc gggcgtaaac gacgcgcacc cgtgaaacag acattgaatt
2761 tcgacttgct gaagttagcc ggggacgtcg agagtaatcc aggccctatg tacagaatgc
2821 agctcctgtc ctgcatagct ctcagcctgg cccttgtgac aaattctgat atacagatga
2881 cgcagtcgcc ctcaagcctc agtgcctccg tgggggatac tgttacaatc acatgtcagg
2941 ccaatggcta tctaaactgg tatcagcagc ggagggggaaa ggcacccaag ttactgatat
3001 acgacggctc caagttggag cgcggggtcc ccagcaggtt ttccggcagg agatgggggc
3061 aggagtacaa cctgaccata aacaatctcc agcctgagga tattgccaca tacttttgcc
3121 aggtatacga gtttgttgtg cctggcacac ggctcgatct gaaaaggacc gtggctgccc
3181 caagcgtgtt cattttccct cccagcgacg aacagcttaa gtctgggact gcgtccgtcg
3241 tatgtttgct gaacaacttc tatccccgtg aagccaaagt gcagtggaaa gtggacaatg
3301 cactgcagtc cgggaactcc caagagagcg tcacagagca ggactccaaa gactcgacct
3361 actctctaag ctccacactg acactcagca aggctgacta tgagaagcac aaagtttacg
3421 cctgtgaagt gactcatcag ggctcagct cccccgtgac aaaaagcttt aaccggggag
3481 aatgttaatg agcggccgct tcgagcagac atgataagat acattgatga gtttggacaa
3541 accacaacta gaatgcagtg aaaaaaatgc tttatttgtg aaatttgtga tgctattgct
3601 ttatttgtaa ccattataag ctgcaataaa caagttaaca acaacaattg cattcatttt
3661 atgtttcagg ttcaggggga gatgtgggag gtttttaaa gcaagtaaaa cctctacaaa
3721 tgtggtaaaa tcgataagga tcttcctaga gcatggctac gtagataagt agcatggcgg
3781 gttaatcatt aactacaagg aacccctagt gatggagttg gccactccct ctctgcgcgc
3841 tcgctcgctc actgaggccg ggcgaccaaa ggtcgcccga cgcccgggct ttgcccgggc
3901 ggcctcagtg agcgagcgag cgcgcagcct taattaacct aattcactgg ccgtcgtttt
3961 acaacgtcgt gactgggaaa accctggcgt tacccaactt aatcgccttg cagcacatcc
4021 ccctttcgcc agctggcgta atagcgaaga ggcccgcacc gatcgccctt cccaacagtt
4081 gcgcagcctg aatggcgaat gggacgcgcc ctgtagcggc gcattaagcg cggcgggtgt
4141 ggtggttacg cgcagcgtga ccgctacact tgccagcgcc ctagcgcccg ctcctttcgc
```

PLASMID SEQUENCES
FIG. 5RR

```
4201 tttcttccct tcctttctcg ccacgttcgc cggctttccc cgtcaagctc taaatcgggg
4261 gctcccttta gggttccgat ttagtgcttt acggcacctc gaccccaaaa aacttgatta
4321 gggtgatggt tcacgtagtg ggccatcgcc ctgatagacg gtttttcgcc ctttgacgtt
4381 ggagtccacg ttctttaata gtggactctt gttccaaact ggaacaacac tcaaccctat
4441 ctcggtctat tcttttgatt tataagggat tttgccgatt tcggcctatt ggttaaaaaa
4501 tgagctgatt taacaaaaat ttaacgcgaa ttttaacaaa atattaacgc ttacaattta
4561 ggtggcactt ttcggggaaa tgtgcgcgga acccctattt gtttattttt ctaaatacat
4621 tcaaatatgt atccgctcat gagacaataa ccctgataaa tgcttcaata atattgaaaa
4681 aggaagagta tgagtattca acatttccgt gtcgccctta ttcccttttt tgcggcattt
4741 tgccttcctg tttttgctca cccagaaacg ctggtgaaag taaaagatgc tgaagatcag
4801 ttgggtgcac gagtgggtta catcgaactg gatctcaaca gcggtaagat ccttgagagt
4861 tttcgccccg aagaacgttt tccaatgatg agcactttta aagttctgct atgtggcgcg
4921 gtattatccc gtattgacgc cgggcaagag caactcggtc gccgcataca ctattctcag
4981 aatgacttgg ttgagtactc accagtcaca gaaaagcatc ttacggatgg catgacagta
5041 agagaattat gcagtgctgc cataaccatg agtgataaca ctgcggccaa cttacttctg
5101 acaacgatcg gaggaccgaa ggagctaacc gcttttttgc acaacatggg ggatcatgta
5161 actcgccttg atcgttggga accggagctg aatgaagcca taccaaacga cgagcgtgac
5221 accacgatgc ctgtagcaat ggcaacaacg ttgcgcaaac tattaactgg cgaactactt
5281 actctagctt cccggcaaca attaatagac tggatggagg cggataaagt tgcaggacca
5341 cttctgcgct cggcccttcc ggctggctgg tttattgctg ataaatctgg agccggtgag
5401 cgtgggtctc gcggtatcat tgcagcactg gggccagatg gtaagccctc ccgtatcgta
5461 gttatctaca cgacggggag tcaggcaact atggatgaac gaaatagaca gatcgctgag
5521 ataggtgcct cactgattaa gcattggtaa ctgtcagacc aagtttactc atatatactt
5581 tagattgatt taaaacttca tttttaattt aaaaggatct aggtgaagat cctttttgat
5641 aatctcatga ccaaaatccc ttaacgtgag ttttcgttcc actgagcgtc agaccccgta
5701 gaaaagatca aaggatcttc ttgagatcct ttttttctgc gcgtaatctg ctgcttgcaa
5761 acaaaaaaac caccgctacc agcggtggtt tgtttgccgg atcaagagct accaactctt
5821 tttccgaagg taactggctt cagcagagcg cagataccaa atactgttct tctagtgtag
5881 ccgtagttag gccaccactt caagaactct gtagcaccgc ctacatacct cgctctgcta
5941 atcctgttac cagtggctgc tgccagtggc gataagtcgt gtcttaccgg gttggactca
6001 agacgatagt taccggataa ggcgcagcgg tcgggctgaa cggggggttc gtgcacacag
6061 cccagcttgg agcgaacgac ctacaccgaa ctgagatacc tacagcgtga gctatgagaa
6121 agcgccacgc ttcccgaagg gagaaaggcg gacaggtatc cggtaagcgg cagggtcgga
6181 acaggagagc gcacgaggga gcttccaggg ggaaacgcct ggtatcttta tagtcctgtc
6241 gggtttcgcc acctctgact tgagcgtcga tttttgtgat gctcgtcagg ggggcggagc
6301 ctatggaaaa acgccagcaa cgcggccttt ttacggttcc tggccttttg ctggcctttt
6361 gctcacatgt tctttcctgc gttatcccct gattctgtgg ataaccgtat taccgccttt
6421 gagtgagctg ataccgctcg ccgcagccga acgaccgagc gcagcgagtc agtgagcgag
6481 gaagcggaag agcgcccaat acgcaaaccg cctctccccg cgcgttggcc gattcattaa
6541 tgcagctggc acgacaggtt tcccgactgg aaagcgggca gtgagcgcaa cgcaattaat
6601 gtgagttagc tcactcatta ggcaccccag gctttacact ttatgcttcc ggctcgtatg
6661 ttgtgtggaa ttgtgagcgg ataacaattt cacacaggaa acagctatga ccatgattac
6721 gccagattta attaaggcct taattagg
//
```

PLASMID SEQUENCES
FIG. 5SS

SEQ ID NO: 27

```
pN261 CMV 3bncIA Usage p2766-VC
LOCUS       pAAV.CMV.PI.3bnI        6748 bp    DNA     circular
FEATURES             Location/Qualifiers
     repeat_region   1..130
                     /vntifkey="34"
                     /label=ITR
     repeat_region   complement(3798..3927)
                     /vntifkey="34"
                     /label=ITR
     intron          1047..1179
                     /vntifkey="15"
                     /label=Promega\chimeric\intron
     polyA_signal    3502..3733
                     /vntifkey="25"
                     /label=SV40\late\polyadenylation\signal
     promoter        191..932
                     /vntifkey="29"
                     /label=human\CMV\I.E.\enhancer\&\promoter
     CDS             4690..5547
                     /vntifkey="4"
                     /label=Amp-R
     misc_feature    5721..6309
                     /vntifkey="21"
                     /label=COL\E1\Origin
     rep_origin      complement(4104..4559)
                     /vntifkey="33"
                     /label=f1\ori
     misc_feature    1248..1293
                     /vntifkey="21"
                     /label=c-myc\miniIRES\cloned\into\Nhe\site
     misc_feature    897..901
                     /vntifkey="21"
                     /label=TATA\box
     misc_feature    1294..3493
                     /vntifkey="21"
                     /label=AnnaT_Test3bnIA_Usage
     misc_feature    3500..3500
                     /vntifkey="21"
                     /label=DELETION:\73bp
                     /note="Position: 3493: -
AAAATCAGCCTCGACTGTGCCTTCTAGTTGCCAGCCATCTGTTGTTTGCCCCTCCCCCGTGCCTTCCGGCCGC"
BASE COUNT     1710 a      1797 c      1691 g      1550 t
ORIGIN
        1 ctgcgcgctc gctcgctcac tgaggccgcc cgggcaaagc ccgggcgtcg ggcgaccttt
       61 ggtcgcccgg cctcagtgag cgagcgagcg cgcagagagg gagtggccaa ctccatcact
      121 aggggttcct tgtagttaat gattaacccg ccatgctact tatctacgta gccatgctct
      181 aggaagatct tcaatattgg ccattagcca tattattcat tggttatata gcataaatca
      241 atattggcta ttggccattg catacgttgt atctatatca taatatgtac atttatattg
      301 gctcatgtcc aatatgaccg ccatgttggc attgattatt gactagttat taatagtaat
      361 caattacggg gtcattagtt catagcccat atatggagtt ccgcgttaca taacttacgg
      421 taaatggccc gcctggctga ccgcccaacg acccccgccc attgacgtca ataatgacgt
      481 atgttcccat agtaacgcca atagggactt tccattgacg tcaatgggtg gagtatttac
      541 ggtaaactgc ccacttggca gtacatcaag tgtatcatat gccaagtccg ccccctattg
      601 acgtcaatga cggtaaatgg cccgcctggc attatgccca gtacatgacc ttacgggact
```

PLASMID SEQUENCES
FIG. 5TT

```
 661 ttcctacttg gcagtacatc tacgtattag tcatcgctat taccatggtg atgcggtttt
 721 ggcagtacac caatgggcgt ggatagcggt ttgactcacg gggatttcca agtctccacc
 781 ccattgacgt caatgggagt ttgttttggc accaaaatca acgggacttt ccaaaatgtc
 841 gtaataaccc cgccccgttg acgcaaatgg gcggtaggcg tgtacggtgg gaggtctata
 901 taagcagagc tcgtttagtg aaccgtcaga tcactagaag ctttattgcg gtagtttatc
 961 acagttaaat tgctaacgca gtcagtgctt ctgacacaac agtctcgaac ttaagctgca
1021 gaagttggtc gtgaggcact gggcaggtaa gtatcaaggt tacaagacag gtttaaggag
1081 accaatagaa actgggcttg tcgagacaga gaagactctt gcgtttctga taggcaccta
1141 ttggtcttac tgacatccac tttgcctttc tctccacagg tgtccactcc cagttcaatt
1201 acagctctta aggctagagt acttaatacg actcactata ggctagcggg gactttgcac
1261 tggaacttac aacacccgag caaggacgcg actctagctc tagaaccatg taccgaatgc
1321 aactgctgtc ctgcatcgcc ctgtccctgg cactggtcac caacagccag gtccagctgc
1381 tgcagagcgg agcagcagtc acaaaaccag gagccagcgt cagagtcagc tgcgaggcca
1441 gcgggtacaa cattcgggac tacttcatcc actggtggcg gcaggcacca gggcaggggc
1501 tgcagtgggt gggctggatc aaccctaaaa ccggacaacc caacaaccca cgacagtttc
1561 agggcagagt gagcctgacc agacacgcca gctgggactt tgacaccttt tccttctata
1621 tggatctgaa agcactgcga tccgacgata ccgccgtgta cttttgcgca cgacagcggt
1681 ccgattactg ggacttcgac gtctggggca gcgggacaca agtcacagtg tccagcgcct
1741 ccaccaaggg accaagcgtg tttccactgg caccatccag caagagcaca tccggaggca
1801 ccgcagcact gggctgcctg gtcaaggatt acttccctga accagtcacc gtcagctgga
1861 actccggagc cctgacaagc ggcgtgcaca ccttccctgc cgtgctgcag tccagcggcc
1921 tgtattccct gagctccgtg gtgaccgtgc ccagctccag cctgggcacc cagacctaca
1981 tttgcaatgt caaccataaa ccaagcaata ccaaagtcga caagaaagtc gagcccaaaa
2041 gctgcgacaa aacccacaca tgccctccat gccctgcccc agagctgctg gggggaccct
2101 ccgtctttct gtttccccct aaaccaaaag acaccctgat gatcagcaga acccccgaag
2161 tcacatgcgt ggtggtcgac gtcagccacg aggaccctga ggtcaagttc aattggtacg
2221 tcgacggggt cgaggtccac aatgccaaga ccaagcccag agaggaacag tataacagca
2281 cctaccgggt cgtgtccgtg ctgacagtgc tgcatcagga ctggctgaac ggaaaggagt
2341 acaagtgcaa ggtgtccaac aaggccctgc ccgcaccaat tgaaaagaca atcagcaagg
2401 ccaaggggca gccccgagag ccccaagtct ataccctgcc cccttcccga gatgaactga
2461 ccaagaacca agtcagcctg acatgcctgg tgaagggatt ctacccttcc gatatcgccg
2521 tcgagtggga atccaacggc caacccgaga ataactacaa aacaacccca cccgtgctgg
2581 acagcgacgg gtccttcttt ctgtatagca agctgaccgt ggacaaatcc cgatggcagc
2641 aaggaaacgt gttcagctgc agcgtgatgc atgaggccct gcacaaccac tatacccaga
2701 aaagcctgag cctgagccca ggccggaagc ggagagcccc agtcaaacag accctgaact
2761 tcgatctgct gaaactggca ggcgacgtgg agtccaaccc agggccaatg tatagaatgc
2821 agctgctgag ctgcattgcc ctgagcctgg ccctggtgac caattccgat atccagatga
2881 cccagagccc ctcctccctg agcgcatccg tcggagacac cgtgacaatc acatgccagg
2941 caaacggcta tctgaactgg tatcagcagc ggagagggaa ggcacctaag ctgctgatct
3001 acgacggaag caagctggaa cgaggcgtcc ccagccggtt cagcgggaga agatgggggc
3061 aggaatacaa cctgacaatc aacaatctgc agcccgagga cattgcaacc tacttctgcc
3121 aggtgtacga gtttgtcgtc ccagggacac gactggatct gaagcggaca gtggccgcac
3181 ccagcgtgtt tatcttccct ccctccgacg aacagctgaa gtccggcacc gcatccgtgg
3241 tgtgcctgct gaacaatttc tatcccagag aggccaaagt ccagtggaag gtggacaatg
3301 cactgcagtc cggaaatagc caagaaagcg tcaccgagca ggactccaag gactccacat
3361 actccctgag cagcacactg accctgagca aggcagacta cgagaagcac aaggtctacg
3421 cctgcgaagt cacccaccag ggactgtcct cccctgtgac caaatccttc aatagaggag
3481 agtgctaatg agcggccgct tcgagcagac atgataagat acattgatga gtttggacaa
3541 accacaacta gaatgcagtg aaaaaaatgc tttatttgtg aaatttgtga tgctattgct
3601 ttatttgtaa ccattataag ctgcaataaa caagttaaca acaacaattg cattcatttt
3661 atgtttcagg ttcaggggga gatgtgggag gtttttaaa gcaagtaaaa cctctacaaa
3721 tgtggtaaaa tcgataagga tcttcctaga gcatggctac gtagataagt agcatggcgg
3781 gttaatcatt aactacaagg aacccctagt gatggagttg gccactccct ctctgcgcgc
3841 tcgctcgctc actgaggccg ggcgaccaaa ggtcgcccga cgcccgggct ttgcccgggc
```

PLASMID SEQUENCES
FIG. 5UU

```
3901 ggcctcagtg agcgagcgag cgcgcagcct taattaacct aattcactgg ccgtcgtttt
3961 acaacgtcgt gactgggaaa accctggcgt tacccaactt aatcgccttg cagcacatcc
4021 ccctttcgcc agctggcgta atagcgaaga ggcccgcacc gatcgccctt cccaacagtt
4081 gcgcagcctg aatggcgaat gggacgcgcc ctgtagcggc gcattaagcg cggcgggtgt
4141 ggtggttacg cgcagcgtga ccgctacact tgccagcgcc ctagcgcccg ctcctttcgc
4201 tttcttccct tcctttctcg ccacgttcgc cggctttccc cgtcaagctc taaatcgggg
4261 gctcccttta gggttccgat ttagtgcttt acggcacctc gaccccaaaa aacttgatta
4321 gggtgatggt tcacgtagtg ggccatcgcc ctgatagacg gtttttcgcc ctttgacgtt
4381 ggagtccacg ttctttaata gtggactctt gttccaaact ggaacaacac tcaaccctat
4441 ctcggtctat tcttttgatt tataagggat tttgccgatt tcggcctatt ggttaaaaaa
4501 tgagctgatt taacaaaaat ttaacgcgaa ttttaacaaa atattaacgc ttacaattta
4561 ggtggcactt ttcggggaaa tgtgcgcgga acccctattt gtttattttt ctaaatacat
4621 tcaaatatgt atccgctcat gagacaataa ccctgataaa tgcttcaata atattgaaaa
4681 aggaagagta tgagtattca acatttccgt gtcgccctta ttcccttttt tgcggcattt
4741 tgccttcctg tttttgctca cccagaaacg ctggtgaaag taaaagatgc tgaagatcag
4801 ttgggtgcac gagtgggtta catcgaactg gatctcaaca gcggtaagat ccttgagagt
4861 tttcgccccg aagaacgttt tccaatgatg agcactttta aagttctgct atgtggcgcg
4921 gtattatccc gtattgacgc cgggcaagag caactcggtc gccgcataca ctattctcag
4981 aatgacttgg ttgagtactc accagtcaca gaaaagcatc ttacggatgg catgacagta
5041 agagaattat gcagtgctgc cataaccatg agtgataaca ctgcggccaa cttacttctg
5101 acaacgatcg gaggaccgaa ggagctaacc gcttttttgc acaacatggg ggatcatgta
5161 actcgccttg atcgttggga accggagctg aatgaagcca taccaaacga cgagcgtgac
5221 accacgatgc ctgtagcaat ggcaacaacg ttgcgcaaac tattaactgg cgaactactt
5281 actctagctt cccggcaaca attaatagac tggatggagg cggataaagt tgcaggacca
5341 cttctgcgct cggcccttcc ggctggctgg tttattgctg ataaatctgg agccggtgag
5401 cgtgggtctc gcggtatcat tgcagcactg gggccagatg gtaagccctc ccgtatcgta
5461 gttatctaca cgacggggag tcaggcaact atggatgaac gaaatagaca gatcgctgag
5521 ataggtgcct cactgattaa gcattggtaa ctgtcagacc aagtttactc atatatactt
5581 tagattgatt taaaacttca tttttaattt aaaaggatct aggtgaagat cctttttgat
5641 aatctcatga ccaaaatccc ttaacgtgag ttttcgttcc actgagcgtc agaccccgta
5701 gaaaagatca aaggatcttc ttgagatcct ttttttctgc gcgtaatctg ctgcttgcaa
5761 acaaaaaaac caccgctacc agcggtggtt tgtttgccgg atcaagagct accaactctt
5821 tttccgaagg taactggctt cagcagagcg cagataccaa atactgttct tctagtgtag
5881 ccgtagttag gccaccactt caagaactct gtagcaccgc ctacatacct cgctctgcta
5941 atcctgttac cagtggctgc tgccagtggc gataagtcgt gtcttaccgg gttggactca
6001 agacgatagt taccggataa ggcgcagcgg tcgggctgaa cggggggttc gtgcacacag
6061 cccagcttgg agcgaacgac ctacaccgaa ctgagatacc tacagcgtga gctatgagaa
6121 agcgccacgc ttcccgaagg gagaaaggcg gacaggtatc cggtaagcgg cagggtcgga
6181 acaggagagc gcacgaggga gcttccaggg ggaaacgcct ggtatcttta tagtcctgtc
6241 gggtttcgcc acctctgact tgagcgtcga tttttgtgat gctcgtcagg ggggcggagc
6301 ctatggaaaa acgccagcaa cgcggccttt ttacggttcc tggccttttg ctggcctttt
6361 gctcacatgt tctttcctgc gttatcccct gattctgtgg ataaccgtat taccgccttt
6421 gagtgagctg ataccgctcg ccgcagccga acgaccgagc gcagcgagtc agtgagcgag
6481 gaagcggaag agcgcccaat acgcaaaccg cctctccccg cgcgttggcc gattcattaa
6541 tgcagctggc acgacaggtt tcccgactgg aaagcgggca gtgagcgcaa cgcaattaat
6601 gtgagttagc tcactcatta ggcaccccag gctttacact ttatgcttcc ggctcgtatg
6661 ttgtgtggaa ttgtgagcgg ataacaattt cacacaggaa acagctatga ccatgattac
6721 gccagattta attaaggcct taattagg
//
```

PLASMID SEQUENCES
FIG. 5VV

SEQ ID NO: 28

```
pN262 CMV 3bncIAM Usage p2767
LOCUS       3bnc117\MAB\IRES        6748 bp    DNA     circular
FEATURES             Location/Qualifiers
     repeat_region   1..130
                     /vntifkey="34"
                     /label=ITR
     repeat_region   complement(3798..3927)
                     /vntifkey="34"
                     /label=ITR
     intron          1047..1179
                     /vntifkey="15"
                     /label=Promega\chimeric\intron
     polyA_signal    3502..3733
                     /vntifkey="25"
                     /label=SV40\late\polyadenylation\signal
     promoter        191..932
                     /vntifkey="29"
                     /label=human\CMV\I.E.\enhancer\&\promoter
     CDS             4690..5547
                     /vntifkey="4"
                     /label=Amp-R
     misc_feature    5721..6309
                     /vntifkey="21"
                     /label=COL\E1\Origin
     rep_origin      complement(4104..4559)
                     /vntifkey="33"
                     /label=f1\ori
     misc_feature    1248..1293
                     /vntifkey="21"
                     /label=c-myc\miniIRES\cloned\into\Nhe\site
     misc_feature    897..901
                     /vntifkey="21"
                     /label=TATA\box
     misc_feature    1294..3493
                     /vntifkey="21"
                     /label=AnnaT_Test3bnIAM_Usage
BASE COUNT     1671 a      1800 c      1735 g      1542 t
ORIGIN
        1 ctgcgcgctc gctcgctcac tgaggccgcc cgggcaaagc ccgggcgtcg ggcgaccttt
       61 ggtcgcccgg cctcagtgag cgagcgagcg cgcagagagg gagtggccaa ctccatcact
      121 aggggttcct tgtagttaat gattaacccg ccatgctact tatctacgta gccatgctct
      181 aggaagatct tcaatattgg ccattagcca tattattcat tggttatata gcataaatca
      241 atattggcta ttggccattg catacgttgt atctatatca taatatgtac atttatattg
      301 gctcatgtcc aatatgaccg ccatgttggc attgattatt gactagttat taatagtaat
      361 caattacggg gtcattagtt catagcccat atatggagtt ccgcgttaca taacttacgg
      421 taaatggccc gcctggctga ccgcccaacg acccccgccc attgacgtca ataatgacgt
      481 atgttcccat agtaacgcca atagggactt tccattgacg tcaatgggtg gagtatttac
      541 ggtaaactgc ccacttggca gtacatcaag tgtatcatat gccaagtccg ccccctattg
      601 acgtcaatga cggtaaatgg cccgcctggc attatgccca gtacatgacc ttacgggact
      661 ttcctacttg gcagtacatc tacgtattag tcatcgctat taccatggtg atgcggtttt
      721 ggcagtacac caatgggcgt ggatagcggt ttgactcacg gggatttcca agtctccacc
      781 ccattgacgt caatgggagt ttgttttggc accaaaatca acgggacttt ccaaaatgtc
      841 gtaataaccc cgccccgttg acgcaaatgg gcggtaggcg tgtacggtgg gaggtctata
      901 taagcagagc tcgtttagtg aaccgtcaga tcactagaag ctttattgcg gtagtttatc
```

PLASMID SEQUENCES
FIG. 5WW

```
 961 acagttaaat tgctaacgca gtcagtgctt ctgacacaac agtctcgaac ttaagctgca
1021 gaagttggtc gtgaggcact gggcaggtaa gtatcaaggt tacaagacag gtttaaggag
1081 accaatagaa actgggcttg tcgagacaga gaagactctt gcgtttctga taggcaccta
1141 ttggtcttac tgacatccac tttgcctttc tctccacagg tgtccactcc cagttcaatt
1201 acagctctta aggctagagt acttaatacg actcactata ggctagcggg gactttgcac
1261 tggaacttac aacacccgag caaggacgcg actctagctc tagaaccatg taccgaatgc
1321 aactgctgtc ctgcatcgcc ctgtccctgg cactggtcac caacagccag gtccagctgc
1381 tgcagagcgg cgccgccgtg acaaagccag gagccagcgt gcgggtcagc tgcgaggcct
1441 ccggctacaa cattcgggat tacttcatcc actggtggcg gcaggcccca ggccagggac
1501 tgcagtgggt gggctggatc aacccaaaga caggccagcc aaacaaccct cggcagttcc
1561 agggacgggt gagcctgacc cggcacgcca gctgggattt cgatacattc tccttctaca
1621 tggatctgaa agccctgcgg tccgacgata cagccgtgta cttctgcgcc cggcagcggt
1681 ccgattactg ggacttcgat gtgtggggaa gcggcacaca agtcaccgtc agcagcgcca
1741 gcaccaaggg cccttccgtg ttcccactgg ccccttccag caagtccacc tccggaggca
1801 cagccgccct gggctgcctg gtgaaagatt acttccctga gcccgtgacc gtgagctgga
1861 actccggagc cctgaccagc ggagtgcaca ccttccctgc cgtgctgcag tccagcggac
1921 tgtacagcct gtcctccgtg gtgacagtgc ccagctccag cctgggcacc cagacctaca
1981 tttgcaacgt caaccataag ccaagcaaca caaaggtgga taagaaagtg gagccaaaaa
2041 gctgtgacaa gacacacacc tgtcctccct gccccgcccc cgagctgctg ggcggaccaa
2101 gcgtgttcct gttccctcct aagcccaagg acacactgat gatcagccgg accccagagg
2161 tcacatgtgt ggtggtggat gtgagccacg aggaccctga ggtgaagttc aactggtacg
2221 tggatggagt cgaagtgcac aacgccaaaa ccaagcctcg ggaggagcag tacaacagca
2281 cctaccgggt ggtgagcgtg ctgaccgtgc tgcatcagga ctggctgaat ggaaaggaat
2341 acaagtgtaa agtgtccaac aaagccctgc cagcccccat cgaaaagaca atttccaaag
2401 ccaagggaca gccacgggag ccacaagtgt acaccctgcc cccaagccgg gatgagctga
2461 caaagaatca ggtcagcctg acatgtctgg tcaagggctt ctacccaagc gatatcgccg
2521 tggagtggga gtccaatggc cagcccgaaa acaactacaa gaccacccca ccagtgctgg
2581 actccgatgg ctccttcttc ctgtactcca agctgaccgt ggacaaaagc cggtggcagc
2641 agggaaacgt gttcagctgt agcgtgatgc acgaagccct gcacaaccac tacacccaga
2701 aaagcctgag cctgagccca ggccggaagc ggcgggcccc agtgaaacag accctgaatt
2761 tcgatctgct gaagctggcc ggagatgtgg aaagcaaccc cggacccatg taccggatgc
2821 agctgctgag ctgtatcgcc ctgagcctgg ccctggtgac caattccgat attcagatga
2881 cacagagccc cagctccctg agcgccagcg tgggcgatac cgtcaccatc acatgccagg
2941 ccaacggata cctgaactgg taccagcagc ggcggggaaa ggccccaaag ctgctgatct
3001 acgatggaag caagctggag cggggagtgc ccagccggtt cagcggacgg cggtggggcc
3061 aggaatacaa cctgaccatc aacaatctgc agccagagga catcgccacc tacttctgcc
3121 aggtctacga gttcgtggtg cctggaaccc ggctggatct gaagcggaca gtggccgccc
3181 cctccgtgtt catcttcccc cctagcgacg agcagctgaa atccggaaca gccagcgtgg
3241 tctgtctgct gaacaacttc taccctcggg aggccaaagt gcagtggaag gtcgataacg
3301 ccctgcagtc cggaaacagc caggagtccg tgaccgagca ggattccaag gatagcacct
3361 acagcctgag ctccaccctg acactgtcca aggccgatta cgagaaacac aaggtgtacg
3421 cctgcgaagt gacccatcag ggactgagca gcccagtgac caagagcttc aatcggggag
3481 aatgctaatg agcggccgct tcgagcagac atgataagat acattgatga gtttggacaa
3541 accacaacta gaatgcagtg aaaaaaatgc tttatttgtg aaatttgtga tgctattgct
3601 ttatttgtaa ccattataag ctgcaataaa caagttaaca acaacaattg cattcatttt
3661 atgtttcagg ttcaggggga gatgtgggag gtttttaaa gcaagtaaaa cctctacaaa
3721 tgtggtaaaa tcgataagga tcttcctaga gcatggctac gtagataagt agcatggcgg
3781 gttaatcatt aactacaagg aacccctagt gatggagttg gccactccct ctctgcgcgc
3841 tcgctcgctc actgaggccg ggcgaccaaa ggtcgcccga cgcccgggct ttgcccgggc
3901 ggcctcagtg agcgagcgag cgcgcagcct taattaacct aattcactgg ccgtcgtttt
3961 acaacgtcgt gactgggaaa accctggcgt tacccaactt aatcgccttg cagcacatcc
4021 ccctttcgcc agctggcgta atagcgaaga ggcccgcacc gatcgccctt cccaacagtt
4081 gcgcagcctg aatggcgaat gggacgcgcc ctgtagcggc gcattaagcg cggcgggtgt
4141 ggtggttacg cgcagcgtga ccgctacact tgccagcgcc ctagcgcccg ctcctttcgc
```

PLASMID SEQUENCES
FIG. 5XX

```
4201 tttcttccct tcctttctcg ccacgttcgc cggctttccc cgtcaagctc taaatcgggg
4261 gctcccttta gggttccgat ttagtgcttt acggcacctc gaccccaaaa aacttgatta
4321 gggtgatggt tcacgtagtg ggccatcgcc ctgatagacg gtttttcgcc ctttgacgtt
4381 ggagtccacg ttctttaata gtggactctt gttccaaact ggaacaacac tcaaccctat
4441 ctcggtctat tcttttgatt tataagggat tttgccgatt tcggcctatt ggttaaaaaa
4501 tgagctgatt taacaaaaat ttaacgcgaa ttttaacaaa atattaacgc ttacaattta
4561 ggtggcactt ttcggggaaa tgtgcgcgga acccctattt gtttattttt ctaaatacat
4621 tcaaatatgt atccgctcat gagacaataa ccctgataaa tgcttcaata atattgaaaa
4681 aggaagagta tgagtattca acatttccgt gtcgccctta ttcccttttt tgcggcattt
4741 tgccttcctg tttttgctca cccagaaacg ctggtgaaag taaaagatgc tgaagatcag
4801 ttgggtgcac gagtgggtta catcgaactg gatctcaaca gcggtaagat ccttgagagt
4861 tttcgccccg aagaacgttt tccaatgatg agcactttta aagttctgct atgtggcgcg
4921 gtattatccc gtattgacgc cgggcaagag caactcggtc gccgcataca ctattctcag
4981 aatgacttgg ttgagtactc accagtcaca gaaaagcatc ttacggatgg catgacagta
5041 agagaattat gcagtgctgc cataaccatg agtgataaca ctgcggccaa cttacttctg
5101 acaacgatcg gaggaccgaa ggagctaacc gcttttttgc acaacatggg ggatcatgta
5161 actcgccttg atcgttggga accggagctg aatgaagcca taccaaacga cgagcgtgac
5221 accacgatgc ctgtagcaat ggcaacaacg ttgcgcaaac tattaactgg cgaactactt
5281 actctagctt cccggcaaca attaatagac tggatggagg cggataaagt tgcaggacca
5341 cttctgcgct cggcccttcc ggctggctgg tttattgctg ataaatctgg agccggtgag
5401 cgtgggtctc gcggtatcat tgcagcactg gggccagatg gtaagccctc ccgtatcgta
5461 gttatctaca cgacggggag tcaggcaact atggatgaac gaaatagaca gatcgctgag
5521 ataggtgcct cactgattaa gcattggtaa ctgtcagacc aagtttactc atatatactt
5581 tagattgatt taaaacttca tttttaattt aaaaggatct aggtgaagat cctttttgat
5641 aatctcatga ccaaaatccc ttaacgtgag ttttcgttcc actgagcgtc agaccccgta
5701 gaaaagatca aaggatcttc ttgagatcct ttttttctgc gcgtaatctg ctgcttgcaa
5761 acaaaaaaac caccgctacc agcggtggtt tgtttgccgg atcaagagct accaactctt
5821 tttccgaagg taactggctt cagcagagcg cagataccaa atactgttct tctagtgtag
5881 ccgtagttag gccaccactt caagaactct gtagcaccgc ctacatacct cgctctgcta
5941 atcctgttac cagtggctgc tgccagtggc gataagtcgt gtcttaccgg gttggactca
6001 agacgatagt taccggataa ggcgcagcgg tcgggctgaa cggggggttc gtgcacacag
6061 cccagcttgg agcgaacgac ctacaccgaa ctgagatacc tacagcgtga gctatgagaa
6121 agcgccacgc ttcccgaagg gagaaaggcg gacaggtatc cggtaagcgg cagggtcgga
6181 acaggagagc gcacgaggga gcttccaggg ggaaacgcct ggtatcttta tagtcctgtc
6241 gggtttcgcc acctctgact tgagcgtcga tttttgtgat gctcgtcagg ggggcggagc
6301 ctatggaaaa acgccagcaa cgcggccttt ttacggttcc tggccttttg ctggcctttt
6361 gctcacatgt tctttcctgc gttatcccct gattctgtgg ataaccgtat taccgccttt
6421 gagtgagctg ataccgctcg ccgcagccga acgaccgagc gcagcgagtc agtgagcgag
6481 gaagcggaag agcgcccaat acgcaaaccg cctctccccg cgcgttggcc gattcattaa
6541 tgcagctggc acgacaggtt tcccgactgg aaagcgggca gtgagcgcaa cgcaattaat
6601 gtgagttagc tcactcatta ggcaccccag gctttacact ttatgcttcc ggctcgtatg
6661 ttgtgtggaa ttgtgagcgg ataacaattt cacacaggaa acagctatga ccatgattac
6721 gccagattta attaaggcct taattagg
//
```

PLASMID SEQUENCES

FIG. 5YY

SEQ ID NO: 29

```
pRN008 [CMV.SDA.VRC01H.IgG1B12H.BGH.VRC8552]
LOCUS       pRN008\[CMV.SDA.        5826 bp    DNA     circular
FEATURES             Location/Qualifiers
     misc_feature    1380..1384
                     /vntifkey="21"
                     /label=KOZAK
     misc_feature    1385..2800
                     /vntifkey="21"
                     /label=VRC01H\[VRC01VH-B12CH)
BASE COUNT     1442 a      1567 c      1438 g      1379 t
ORIGIN
        1 tcgcgcgttt cggtgatgac ggtgaaaacc tctgacacat gcagctcccg gagacggtca
       61 cagcttgtct gtaagcggat gccgggagca gacaagcccg tcagggcgcg tcagcgggtg
      121 ttggcgggtg tcggggctgg cttaactatg cggcatcaga gcagattgta ctgagagtgc
      181 accatatgcg gtgtgaaata ccgcacagat gcgtaaggag aaaataccgc atcagattgg
      241 ctattggcca ttgcatacgt tgtatccata tcataatatg tacatttata ttggctcatg
      301 tccaacatta ccgccatgtt gacattgatt attgactagt tattaatagt aatcaattac
      361 ggggtcatta gttcatagcc catatatgga gttccgcgtt acataactta cggtaaatgg
      421 cccgcctggc tgaccgccca acgacccccg cccattgacg tcaataatga cgtatgttcc
      481 catagtaacg ccaataggga ctttccattg acgtcaatgg gtggagtatt tacggtaaac
      541 tgcccacttg gcagtacatc aagtgtatca tatgccaagt acgcccccta ttgacgtcaa
      601 tgacggtaaa tggcccgcct ggcattatgc ccagtacatg accttatggg actttcctac
      661 ttggcagtac atctacgtat tagtcatcgc tattaccatg gtgatgcggt tttggcagta
      721 catcaatggg cgtggatagc ggtttgactc acggggattt ccaagtctcc accccattga
      781 cgtcaatggg agtttgtttt ggcaccaaaa tcaacgggac tttccaaaat gtcgtaacaa
      841 ctccgcccca ttgacgcaaa tgggcggtag gcgtgtacgg tgggaggtct atataagcag
      901 agctcgttta gtgaaccgtc agatcgcctg gagacgccat ccacgctgtt ttgacctcca
      961 tagaagacac cgggaccgat ccagcctcca tcggctcgca tctctccttc acgcgcccgc
     1021 cgccctacct gaggccgcca tccacgccgg ttgagtcgcg ttctgccgcc tcccgcctgt
     1081 ggtgcctcct gaactgcgtc cgccgtctag gtaagtttaa agctcaggtc gagaccgggc
     1141 ctttgtccgg cgctcccttg gagcctacct agactcagcc ggctctccac gctttgcctg
     1201 accctgcttg ctcaactcta gttaacggtg gagggcagtg tagtctgagc agtactcgtt
     1261 gctgccgcgc gcgccaccag acataatagc tgacagacta acagactgtt cctttccatg
     1321 ggtcttttct gcagtcaccg tcgtcgacac gtgtgatcag atatcgcggc cgctctagac
     1381 caccatggga tggtcatgta tcatcctttt tctagtagca actgcaaccg gtgtacattc
     1441 ccaggtgcag ctggtgcagt ctggaggtca gatgaagaag cctggcgagt cgatgagaat
     1501 ttcttgtcgg gcttctggat atgaatttat tgattgtacg ctaaattgga ttcgtctggc
     1561 ccccggaaaa aggcctgagt ggatgggatg gctgaagcct cggggggggg ccgtcaacta
     1621 cgcacgtcca cttcagggca gagtgaccat gactcgagac gtttattccg acacagcctt
     1681 tttggagctg cgctcgttga cagtagacga cacggccgtc tacttttgta ctaggggaaa
     1741 aaactgtgat tacaattggg acttcgaaca ctggggccgg ggcaccccgg tcatcgtctc
     1801 atcaccgtcg accaagggcc catcggtctt ccccctggca ccctcctcca agagcacctc
     1861 tgggggcaca gcggccctgg gctgcctggt caaggactac ttccccgaac cggtgacggt
     1921 gtcgtggaac tcaggcgccc tgaccagcgg cgtgcacacc ttcccggctg tcctacagtc
     1981 ctcaggactc tactccctca gcagcgtggt gaccgtgccc tccagcagct tgggcaccca
     2041 gacctacatc tgcaacgtga atcacaagcc cagcaacacc aaggtggaca agaaagttga
     2101 gcccaaatct tgtgacaaaa ctcacacatg cccaccgtgc ccagcacctg aactcctggg
     2161 gggaccgtca gtcttcctct tccccccaaa acccaaggac accctcatga tctcccggac
     2221 ccctgaggtc acatgcgtgg tggtggacgt gagccacgaa gaccctgagg tcaagttcaa
     2281 ctggtacgtg gacggcgtgg aggtgcataa tgccaagaca aagccgcggg aggagcagta
     2341 caacagcacg taccgtgtgg tcagcgtcct caccgtcctg caccaggact ggctgaatgg
     2401 caaggagtac aagtgcaagg tctccaacaa agccctccca gcccccatcg agaaaaccat
     2461 ctccaaagcc aaagggcagc cccgagaacc acaggtgtac accctgcccc catcccggga
     2521 tgagctgacc aagaaccagg tcagcctgac ctgcctggtc aaaggcttct atcccagcga
```

PLASMID SEQUENCES
FIG. 5ZZ

```
2581 catcgccgtg gagtgggaga gcaatgggca gccggagaac aactacaaga ccacgcctcc
2641 cgtgctggac tccgacggct ccttcttcct ctacagcaag ctcaccgtgg acaagagcag
2701 gtggcagcag gggaacgtct tctcatgctc cgtgatgcat gaggctctgc acaaccacta
2761 cacgcagaag agcctctccc tgtctccggg taaatgatga ggatccagat ctgctgtgcc
2821 ttctagttgc cagccatctg ttgtttgccc ctcccccgtg ccttccttga ccctggaagg
2881 tgccactccc actgtccttt cctaataaaa tgaggaaatt gcatcgcatt gtctgagtag
2941 gtgtcattct attctggggg gtggggtggg gcaggacagc aagggggagg attgggaaga
3001 caatagcagg catgctgggg atgcggtggg ctctatgggt acccaggtgc tgaagaattg
3061 acccggttcc tcctgggcca gaaagaagca ggcacatccc cttctctgtg acacaccctg
3121 tccacgcccc tggttcttag ttccagcccc actcatagga cactcatagc tcaggagggc
3181 tccgccttca atcccacccg ctaaagtact tggagcggtc tctccctccc tcatcagccc
3241 accaaaccaa acctagcctc caagagtggg aagaaattaa agcaagatag gctattaagt
3301 gcagagggag agaaaatgcc tccaacatgt gaggaagtaa tgagagaaat catagaattt
3361 taaggccatg atttaaggcc atcatggcct taatcttccg cttcctcgct cactgactcg
3421 ctgcgctcgg tcgttcggct gcggcgagcg gtatcagctc actcaaaggc ggtaatacgg
3481 ttatccacag aatcagggga taacgcagga aagaacatgt gagcaaaagg ccagcaaaag
3541 gccaggaacc gtaaaaaggc cgcgttgctg gcgtttttcc ataggctccg cccccctgac
3601 gagcatcaca aaaatcgacg ctcaagtcag aggtggcgaa acccgacagg actataaaga
3661 taccaggcgt ttccccctgg aagctccctc gtgcgctctc ctgttccgac cctgccgctt
3721 accggatacc tgtccgcctt tctcccttcg ggaagcgtgg cgctttctca tagctcacgc
3781 tgtaggtatc tcagttcggt gtaggtcgtt cgctccaagc tgggctgtgt gcacgaaccc
3841 cccgttcagc ccgaccgctg cgccttatcc ggtaactatc gtcttgagtc caacccggta
3901 agacacgact tatcgccact ggcagcagcc actggtaaca ggattagcag agcgaggtat
3961 gtaggcggtg ctacagagtt cttgaagtgg tggcctaact acggctacac tagaagaaca
4021 gtatttggta tctgcgctct gctgaagcca gttaccttcg gaaaaagagt tggtagctct
4081 tgatccggca aacaaaccac cgctggtagc ggtggttttt ttgtttgcaa gcagcagatt
4141 acgcgcagaa aaaaaggatc tcaagaagat cctttgatct tttctacggg gtctgacgct
4201 cagtggaacg aaaactcacg ttaagggatt ttggtcatga gattatcaaa aaggatcttc
4261 acctagatcc ttttaaatta aaaatgaagt tttaaatcaa tctaaagtat atatgagtaa
4321 acttggtctg acagttacca atgcttaatc agtgaggcac ctatctcagc gatctgtcta
4381 tttcgttcat ccatagttgc ctgactcggg gggggggggc gctgaggtct gcctcgtgaa
4441 gaaggtgttg ctgactcata ccaggcctga atcgccccat catccagcca gaaagtgagg
4501 gagccacggt tgatgagagc tttgttgtag gtggaccagt tggtgatttt gaacttttgc
4561 tttgccacgg aacggtctgc gttgtcggga agatgcgtga tctgatcctt caactcagca
4621 aaagttcgat ttattcaaca aagccgccgt cccgtcaagt cagcgtaatg ctctgccagt
4681 gttacaacca attaaccaat tctgattaga aaaactcatc gagcatcaaa tgaaactgca
4741 atttattcat atcaggatta tcaataccat atttttgaaa aagccgtttc tgtaatgaag
4801 gagaaaactc accgaggcag ttccatagga tggcaagatc ctggtatcgg tctgcgattc
4861 cgactcgtcc aacatcaata caacctatta atttcccctc gtcaaaaata aggttatcaa
4921 gtgagaaatc accatgagtg acgactgaat ccggtgagaa tggcaaaagc ttatgcattt
4981 ctttccagac ttgttcaaca ggccagccat tacgctcgtc atcaaaatca ctcgcatcaa
5041 ccaaaccgtt attcattcgt gattgcgcct gagcgagacg aaatacgcga tcgctgttaa
5101 aaggacaatt acaaacagga atcgaatgca accggcgcag gaacactgcc agcgcatcaa
5161 caatattttc acctgaatca ggatattctt ctaatacctg gaatgctgtt ttcccgggga
5221 tcgcagtggt gagtaaccat gcatcatcag gagtacggat aaaatgcttg atggtcggaa
5281 gaggcataaa ttccgtcagc cagtttagtc tgaccatctc atctgtaaca tcattggcaa
5341 cgctaccttt gccatgtttc agaaacaact ctggcgcatc gggcttccca tacaatcgat
5401 agattgtcgc acctgattgc ccgacattat cgcgagccca tttataccca tataaatcag
5461 catccatgtt ggaatttaat cgcggcctcg agcaagacgt ttcccgttga atatggctca
5521 taacacccct tgtattactg tttatgtaag cagacagttt tattgttcat gatgatatat
5581 ttttatcttg tgcaatgtaa catcagagat tttgagacac aacgtggctt tccccccccc
5641 cccattattg aagcatttat cagggttatt gtctcatgag cggatacata tttgaatgta
5701 tttagaaaaa taaacaaata ggggttccgc gcacatttcc ccgaaaagtg ccacctgacg
5761 tctaagaaac cattattatc atgacattaa cctataaaaa taggcgtatc acgaggccct
```

PLASMID SEQUENCES
FIG. 5AAA 5821 ttcgtc

Effect of variable codon use on expression of 3bnc117 in liver
ug/ml of serum :

FIG 9A

>3bc via 201

Atggagttcgggctgagctgggtctttctggtggccctgctgaagggagtccagtgccaggtgcagctgctgcagtccggagccgccgtg
accaaaccaggaggaagcgtgcgggtgagctgtgaggcctccggctacaacatccgggattacttcatccactggtggaggcaggcccc
cggccagggactgcagtgggtggggtggatcaacccaaagaccggacagccaaacaacccacggcagttccagggaagggtgagcct
gacccggcacgccagctgggatttcgataccttcagcttctacatggatctgaaggccctgcggagcgatgataccgccgtgtacttctgcg
caaggcagcggagcgattactgggacttcgatgtgtggggaagcggaacccaggtcacagtgtcaagcgcgtcgaccaaggggccctc
aagcggcggaggaggcagcggaggaggagggtccggaggcgggggatctgcagatatccagatgacacagtccccaagcagcctgt
ccgccagcgtgggagatactgtgaccattacctgtcaggctaacggctacctgaactggtaccagcagcgacggggaaaggcccctaag
ctgctgatctatgatggatccaagctggagcggggagtgcccagcaggttctcaggccggcggtggggacaggagtacaacctgaccat
caacaacctgcagccagaggacatcgccacctacttctgccaggtgtacgagttcgtggtgccaggcactcggctggatctgaaacgtacg
acctgccctccatgtccagcccccgaactgctgggcgggcctagcgtgttcctgtttccccctaagcctaaagatacactgatgattagtaga
accccagaggtcacatgcgtggtcgtggacgtgtcccacgaagagcctgacgtgaagttcaactggtacgtggatggcgtggaggtgcac
aatgctaagactaaaccacgcgaagagcagtataatagtacataccgagtcgtgtcagtcctgacagtgctgcaccaggattggctgaacg
gcaaggagtataagtgcaaggtgtctaacaaggccctgcccgcccctatcgagaaaacaattagcaaggccaaagggcagccacggga
accccaggtgtacactctgccaccctcaagagatgaactgactaagaaccaggtcagcctgacctgtctggtgaaaggcttctaccccagc
gacatcgccgtggagtgggaaagtaacggccagcctgagaataactacaagactacccctccagtgctggatagcgacgggtccttcttcc
tgtacagcaagctgacagtggacaaatcccgctggcagcagggaaacgtcttttcctgttctgtgatgcatgaggccctgcacaatcattaca
cccagaagagtctgtcactgagccccggcaaa

FIG 9B

>3bc via human atgtaccggatgcaactcctgtcttgcattgcactaagtcttgcacttgtcacaaacagtcaggtccaattgttacagtctggggcagcggtga
cgaagcccggggcctcagtgagagtctcctgcgaggcttctggatacaacattcgtgactactttattcattggtggcgacaggccccagga
cagggccttcagtgggtgggatggatcaatcctaagacaggtcagccaaacaatcctcgtcaatttcagggtagagtcagtctgactcgaca
cgcgtcgtgggactttgacacattttccttttacatggacctgaaggcactaagatcggacgacacggccgtttatttctgtgcgcgacagcgc
agcgactattgggatttcgacgtctggggcagtggaacccaggtcactgtctcgtcagcgtcgaccaaggggccctcaagcggcggagg
aggcagcggaggaggagggtccggaggcgggggatctgcagacatccagatgacccagtctccatcctccctgtctgcatctgtaggag
ataccgtcactatcacttgccaggcaaacggctacttaaattggtatcaacagaggcgagggaaagccccaaaactcctgatctacgatgg
gtccaaattggaaagaggggtcccatcaaggttcagtggaagaagatgggggcaagaatataatctgaccatcaacaatctgcagcccga
agacattgcaacatattttgtcaagtgtatgagtttgtcgtccctgggaccagactggatttgaaacgtacgacatgcccaccgtgcccagca
cctgaactcctggggggaccgtcagtcttcctcttccccccaaaacccaaggacaccctcatgatctcccggacccctgaggtcacatgcgt
ggtggtggacgtgagccacgaagaccctgaggtcaagttcaactggtacgtggacggcgtggaggtgcataatgccaagacaaagccgc
gggaggagcagtacaacagcacgtaccgtgtggtcagcgtcctcaccgtcctgcaccaggactggctgaatggcaaggagtacaagtgc
aaggtctccaacaaagccctcccagcccccatcgagaaaaccatctccaaagccaaagggcagccccgagaaccacaggtgtacaccct
gcccccatcccgggatgagctgaccaagaaccaggtcagcctgacctgcctggtcaaaggcttctatcccagcgatatcgccgtggaatg
ggagagcaacggccagcccgagaacaactacaagaccacccccccctgtgctggacagcgacggctcattcttcctgtacagcaagctga
ccgtggacaagagccggtggcagcagggcaacgtgttcagctgcagcgtgatgcacgaggccctgcacaaccactacacccagaagtc
cctgagcctgagccccggcaag

FIG. 10A

>201
atggagttcgggctgagctgggtctttctggtggccctgctgaagggagtccagtgcgaggtgcagctgctggaatccggacctggcctgg
tgaaaccatctgagacactgagtctgacttgtgctgtctccggcctgtctatcagctccgatttctcctgggcatggattaggcagacccccgg
caaggccctggaatatgtggggtacatccgcgggaacaccggagatacatactataatcctagtctgaagtcaaggctgactatctcaaag
gacaccagcaaaaaccaaatctacctgaatctgtctagtgtcaccgctggcgatgccgccgtgtactattgcgcaagggaccgggtgtgcg
acgatgactacggatactattacaccgaggtgtgcttcggcctggattcttgggggcagggaatcgtggtcacagtgtcaagcggcggagg
aggcagcggaggaggagggtccggaggcgggggatctgcagaactggtcatgacacagtccccactgagcctgtccgtcgctccagga
cagactgcatctattagttgtcgatcctctcagtccctggactatgctaacggcaatacctacctgtcttggtttcaccagcgaccaggacagc
cacctcggagactgatctatcagatttccaacagagattctggagtgcccgacaggttctcaggcagcggagcaggaactgagtttaccctg
cgaatcagtcggatggaatcagatgacgtggggatctactactgcggacaggggaccacattcccacggacatttggacagggcactaag
gtggagatcaaaacctgtggaggaggaagcaagccaccaacctgccctccatgtacatctcccgaactgctgggcgggcctagcgtgttc
ctgtttccccctaagcctaaagatacactgatgattagtagaaccccagaggtcacatgcgtggtcgtggacgtgtcccaggaagatcctga
cgtgaagttcaactggtacgtgaatggcgccgaggtgcaccatgctcagactaaaccacgcgaaacccagtataatagtacataccgagtc
gtgtcagtcctgacagtgactcaccaggattggctgaacggcaaggagtatacctgcaaggtgtctaacaaggccctgcccgcccctatcc
agaaaacaattagcaaggacaaagggcagccacgggaaccccaggtgtacactctgccaccctcaagagaggaactgactaagaacca
ggtcagcctgacctgtctggtgaaaggcttctaccccagcgatatcgtcgtggagtgggaaagttcaggccagcctgagaatacttacaag
actacccctccagtgctggatagcgacgggtcctatttcctgtacagcaagctgacagtggacaaatcccgctggcagcagggaaacgtct
ttcctgttctgtgatgcatgaggccctgcacaatcattacacccagaagagtctgtcactgagccccggcaaa

FIG. 10B

>10A atgggcagcaccgccatcctggctctgctgctggcagtgctgcagggcgtctgggcagaggtgcagctggtccagagcggagcagagat
gaagcgaccaggagaatcactgagaatcagctgcaaaacttctggctacagtttcaccaacgactggattacatgggtgcgacagatgcct
ggcaaggggctggagtggatgggcatgatctaccctgccgattctgaaacaagatattctccaagtgtgcaggggcaggtcactctgagcg
tggacaaatcaattagcaccgcctacctgcagtggagctccctgaaggccagcgataccgctacatactattgcgctaaactgggcccttgc
acttccgtcacctgttatttcgctctggacttttggggacagggcgcagtggtcaccgtgtctagtggaggaggaggcagtggaggaggag
ggtcaggaggaggaggcagccagtctgtcctgacacagccacctagtgcatcaggagcaccaggacagagcgtgactatcagctgttcc
ggctcaagctccaacattgaggggaattacgtgcactggtatcagcatctgtctgggaaggcccccaaactgctgatctacaacgacaatga
aaggccaagcggagtgcccgatcgcttctctggaagtaaatcaggcaccagcgccagcctggcaatctccggactgcagtctaaagacg
aagcagattactattgtagcacatgggacctgtccctgaatgattatatttttgggtctggaacacggctgactgtgctgggccagcccaagg
ctagtaaacgggtcgagatcaagacttgtggaggcgggtctaaacccccctacttgcccaccctgtaccagccctgaactgctgggaggccc
atccgtgttcctgtttcctccaaagcctaaagacaccctgatgatttccagaaccccagaggtgacatgcgtcgtggtcgatgtctctcaggaa
gaccctgatgtgaagtttaactggtacgtgaatggcgcagaggtccaccatgcccagacaaaaccacgagaaactcagtataactctaccta
ccgggtggtcagtgtgctgaccgtcacacaccaggactggctgaacgggaaggagtatacctgcaaggtgagtaacaaggccctgccag
ctcccatccagaaaacaattagcaaggataaaggacagccaagagaaccccaggtgtacactctgccccttctagggaggaactgacta
agaaccaggtgagtctgacctgtctggtcaaaggcttctatcccagcgacatcgtggtcgagtgggaaagctccgggcagcctgagaatac
atacaagaccacaccacccgtgctggacagtgatggctcatatttcctgtactccaagctgaccgtggataaatctcgatggcagcaggga
acgtgtttagttgttcagtcatgcatgaggcactgcacaatcattatacacagaagagcctgtccctgtctccaggaaagtga

TISSUE PREFERENTIAL CODON MODIFIED EXPRESSION CASSETTES, VECTORS CONTAINING SAME, AND USES THEREOF

CROSS REFERENCE TO RELATED APPLICATIONS

This application is a continuation of U.S. patent application Ser. No. 14/787,622, filed Oct. 28, 2015, now pending, which is a national stage application under 35 USC § 371 of PCT/US14/035880, filed Apr. 29, 2014, expired, which claims the benefit under 35 USC § 119(e) of the priority of U.S. Patent Application No. 61/817,110, filed Apr. 29, 2013, expired. Each of these applications is hereby incorporated by reference in their entirety.

STATEMENT OF GOVERNMENT INTEREST

This invention was made with government support under grant no. W911NF-13-2-0036 awarded by Defense Advanced Research Projects Agency. The government has certain rights in the invention.

BACKGROUND OF THE INVENTION

Various therapies in gene therapy rely upon the expression of recombinant genes in heterologous systems. A variety of viral vectors have been described for delivery of immunogenic and therapeutic products to a host. One vector system which has been described in the literature as very attractive for long-term expression of a transgene product is a recombinant adeno-associated virus, due to its relatively low immunogenicity and the fact that it is not associated with any clinical sequelae in humans. Adeno-associated virus (AAV) is a small, non-enveloped human parvovirus that packages a linear strand of single stranded DNA genome that is 4.7 kb. The capsid of an AAV contains 60 copies (in total) of three viral proteins (VPs), VP1, VP2, and VP3, in a predicted ratio of 1:1:10-20, arranged with T=1 icosahedral symmetry [H-J Nam, et al., J Virol., 81(22): 12260-12271 (November 2007)]. The three VPs are translated from the same mRNA, with VP1 containing a unique N-terminal domain in addition to the entire VP2 sequence at its C-terminal region [Nam et al., cited above]. VP2 contains an extra N-terminal sequence in addition to VP3 at its C terminus.

Codon usage bias has been reported for numerous organisms, from viruses to eukaryotes. Since the genetic code is degenerate (i.e., each amino acid can be coded by on average three different codons), the DNA sequence can be modified by synonymous nucleotide substitutions without altering the amino acid sequence of the encoded protein. Such synonymous codon optimization has been performed for the purpose of optimizing expression in a desired host, as described in the scientific literature and in patent documents. See, U.S. Pat. Nos. 5,786,464 and 6,114,148. Much of the early work in this called optimization, focused on altering the rare codons in the target gene so that they more closely reflect the codon usage of the host without modifying the amino acid sequence of the encoded protein. Since the early published work in this area, a variety of different algorithms have been described for modifying coding sequences for expression in different bacterial and eukaryotic host cell species.

In 2004, Plotkin, et al, Proc Natl Acad Sci. USA, 1010: 12588-12591 (2004) reported significant differences in synonymous codon usage between genes specifically expressed in different tissues. However, more recent work by Sémon et al, Mol Biol Evol, 23(3):523-529 (2006) re-evaluated that work and concluded that variability of synonymous codon usage between tissues is much smaller than variability within tissues. Semon et al further report that the synonymous codon usage variability reported by Plotkin et al was due only to GC-content differences, which affects introns and intergenic regions as well as synonymous codon positions.

For a variety of reasons, including cost, efficiency, and safety, there remains a need in the art for vectors which expression higher levels of gene products in a target cell.

SUMMARY OF THE INVENTION

Expression cassettes and vectors containing a gene which is designed to enhance expression in a selected type of tissue are provided herein. In one aspect, the present invention provides a gene sequence which is designed to preferentially express in a non-secretory tissue (e.g., muscle). In another aspect, the present invention provides a gene which has codons designed to preferentially express in a secretory tissue (e.g., muscle, respiratory epithelium or liver). And in another aspect, codon frequency tables are described which can be used to design a gene sequence for other, unrelated gene products, for example FIX, LDLR, unrelated antibodies, or any other therapeutic transgenes. to optimize tissue specific expression.

In a further aspect, the invention provides an AAV comprising a modified gene which has been designed to express in higher levels in muscle. In one example, the AAV has an AAV8 capsid. In another example, the modified gene is a modified antibody gene.

In still another aspect, the invention provides an AAV comprising a modified gene which has been codon optimized to express in higher levels in respiratory epithelium. In one example, the AAV has an AAV8 capsid.

In another aspect, the invention provides an expression cassette comprising an open reading frame (ORF) under the control of regulatory sequences which direct expression of the product in a muscle cell, which ORF has been modified to preferentially increase expression levels in muscle, wherein the modified ORF have\\s a sequence selected from the group consisting of ORF1 (SEQ ID NO: 9), ORF26 (SEQ ID NO: 6), ORF 28 (SEQ ID NO: 5), ORF 30 (SEQ ID NO: 4), ORF35 (SEQ ID NO: 3), ORF39 (SEQ ID NO: 2), ORF40 (SEQ ID NO: 1), ORF42 (SEQ ID NO: 30), IA (SEQ ID NO: 10), 201 (SEQ ID NO: 31) and IAM (SEQ ID NO: 11). In one example, the modified ORF is selected from ORF35 and ORF39. In another example, the modified ORF is ORF40. In a further example, the modified ORF is selected from ORF26 and ORF30. In another example, the modified ORF is selected from ORF26, ORF35 and ORFIAU. In one embodiment, the expression cassette comprises a tissue preferential promoter. When designed for packaging into a recombinant AAV, the expression cassette may comprise AAV inverted terminal repeats (ITRs) flanking (i.e., both 3' and 5/upstream and downstream) of the coding sequence. Optionally, the ITRs are from a different source AAV than the AAV which provides the capsid. In another aspect, the invention provides an expression cassette comprising an open reading frame under the control of regulatory sequences which direct expression of the product in liver cells, where the ORF has been modified to preferentially increase expression levels in liver. Expression cassettes for directing expression in respiratory epithelium or other tissue are described.

In a further aspect, the invention provides a vector comprising the expression cassette described herein and other genetic elements. In one embodiment, the vector is a recombinant adeno-associated virus (AAV) having an AAV capsid in which the expression cassette is packaged.

In still a further aspect, the invention provides a recombinant AAV comprising an AAV8 capsid and an expression cassette for an anti-HIV antibody, wherein the expression cassette is adapted for expression in a selected target tissue, said expression cassette comprising a modified ORF having a sequence selected from the group consisting of ORF1 (SEQ ID NO: 9), ORF26 (SEQ ID NO: 6), ORF 28 (SEQ ID NO: 5), ORF 30 (SEQ ID NO: 4), ORF35 (SEQ ID NO: 3), ORF39 (SEQ ID NO: 2), ORF40 (SEQ ID NO: 1), ORF42 (SEQ ID NO: 30), IA (SEQ ID NO: 10), 201 (SEQ ID NO: 31) and IAM (SEQ ID NO: 11).

In another aspect, the invention provides a pharmaceutical composition comprising one or more vectors, each containing one or more expression cassettes. Each expression cassette comprises a modified ORF. In one embodiment, the ORF is selected from ORF26 (SEQ ID NO: 6), ORF 28 (SEQ ID NO: 5), ORF 30 (SEQ ID NO: 4), ORF35 (SEQ ID NO: 3), ORF39 (SEQ ID NO: 2), ORF40 (SEQ ID NO: 1), ORF42 (SEQ ID NO: 30), IA (SEQ ID NO: 10), IAM (SEQ ID NO: 11), and 201 (SEQ ID NO: 31).

Still other aspects and advantages will be apparent from the detailed description of the invention.

BRIEF DESCRIPTION OF THE DRAWINGS

FIG. 1A-1J is an alignment of the sequences of genes all encoding the same anti-HIV antibody protein construct. The gene constructs use different synonymous codons for the same amino acids and are aligned with the parental (base) gene sequences as a frame of reference.

FIG. 5A-5AAA provides the sequences and features of the plasmid constructs used in Example 1 below.

FIG. 9A provides the nucleic acid sequences of the 3bcn117 antibody following modification according to the 201 frequency table (Table 16) (SEQ ID NO: 33).

FIG. 9B provides the nucleic acid sequences of the 3bcn117 antibody following modification according to the human frequency table (Table 2) (SEQ ID NO: 34).

FIG. 10A provides the nucleic acid sequences of the 201 construct (SEQ ID NO: 31).

FIG. 10B provides the nucleic acid sequences of the 10A construct (SEQ ID NO: 32).

DETAILED DESCRIPTION OF THE INVENTION

Figure 2:
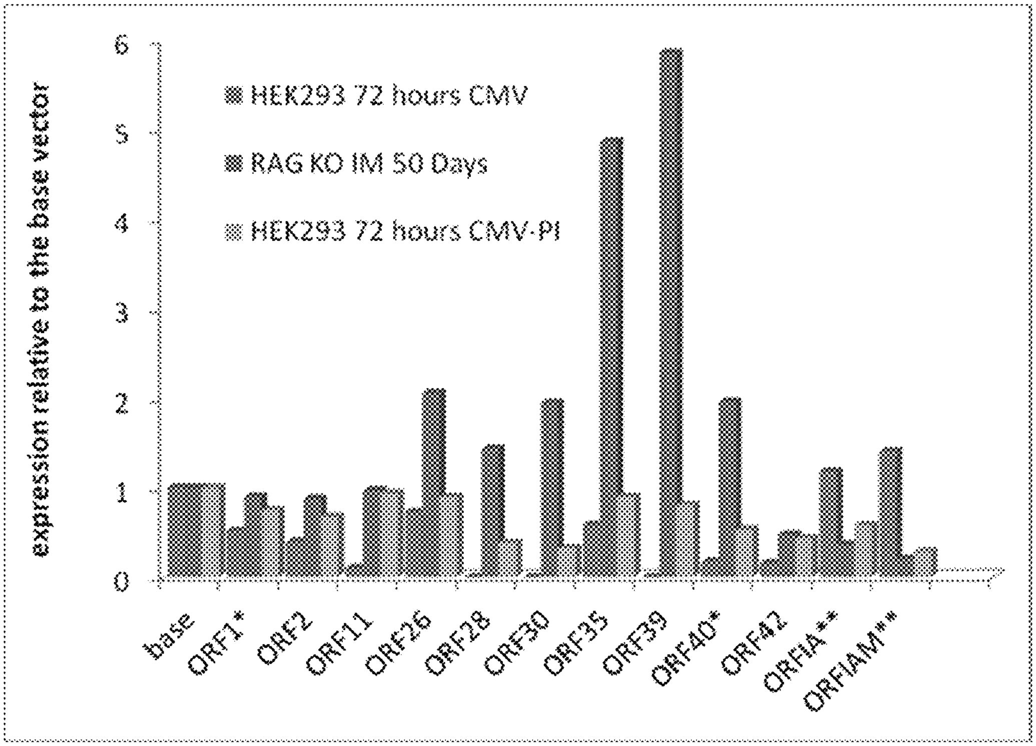
FIG. 2 is a bar chart illustrating AAV-mediated expression of gene constructs modified according to 12 different schemas as compared to a base vector containing the original parental sequence. The codon frequencies used for those modifications are shown in the Tables 1-12, and the parent codon frequency is shown in Table 13. Table 14 shows the codon frequencies which are used in most mammalian codon optimization protocols. Expression of the gene under the control of human cytomegalovirus promoter (CMV(first bar)) or a CMV promoter with a commercially available enhancer (Promega intron, PI)(third bar) were assessed in HEK 293 cells at 72 hours post-infection. These were compared to expression observed with the CMV-PI construct in RAG knock-out mice injected intramuscularly as described in the Example (middle bar).
Figure 3:
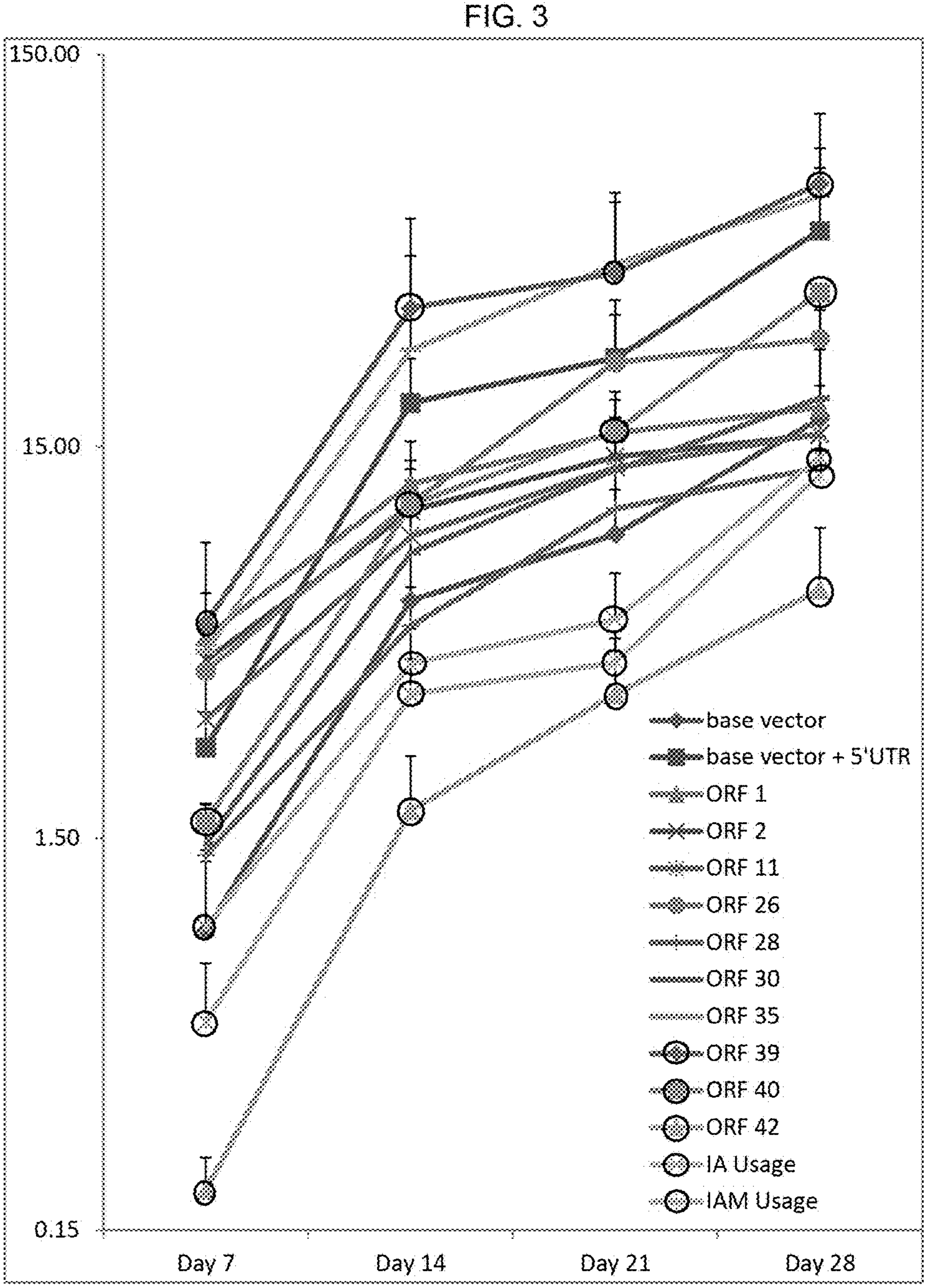
FIG. 3 is a line graph illustrating AAV-mediated expression of 12 codon biased constructs.
Figure 4:
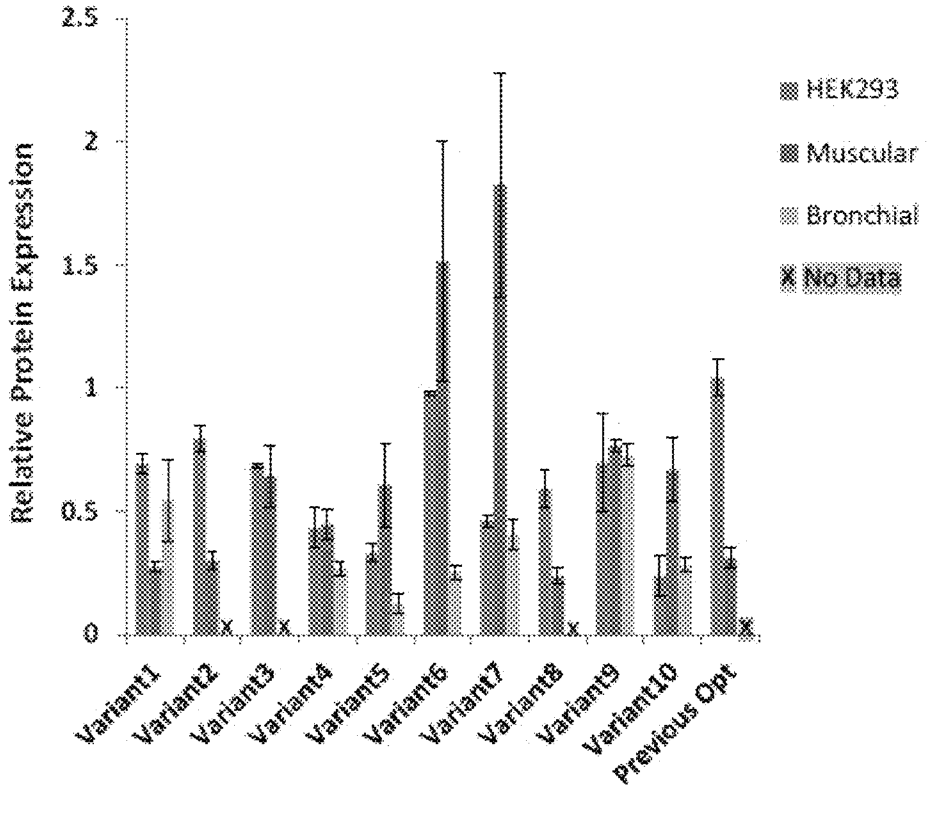
FIG. 4 is a bar chart of the data illustrated in FIG. 2 presented in a different format. For muscle expression, n=3 mice; for bronchial lavage n=2 mice; for transfections, n=2 wells, in addition two independent transfections were performed on different days with similar outcome. Each "n" was assayed by ELISA in duplicate (serum for muscle expression and transfections at 4 different dilutions and bronchial lavage at 2 different dilutions) using protein A capture, and detected using biotinylated anti-human IgG1 antibodies as primary, and streptavidin conjugated HRP as secondary. Affinity purified MAB was used as a standard to make 8 point calibration curve. Constructs were packaged into AAV8 vector using triple transfection production method in HEK293 cells and purified by tangential flow filtration followed by gradient centrifugation. Viral titer was determined by qPCR. $2\times10^{10}$ GC(genome copies)/mouse were administered intramuscularly in 30 μl injection into RAG KO mice. For bronchial lavage $8\times10^{10}$ GC/mouse were administered by intranasal instillation in 50 μl into C57B16 mice. For IM injections, blood samples were collected weekly for 2 months via orbital bleeding, and serum was assayed by ELISA. For bronchial lavage, mice were sacrificed on day 7 after vector administration, and 1 ml of PBS was used to lavage the airways. Concentrations that are in the table are not recalculated for the mucosal surfaces, but rather are straight concentrations in the lavage sample. Transfections were done on 6 well plates using lipofectamine, using standard conditions with the recommended amount of the DNA as manufacturer suggests.

The present invention provides expression cassettes and vectors containing genes which are designed to enhance expression in a desired type of tissue. The present invention provides nucleic acid molecules and vectors carrying genes with codons which are designed for expression in various tissues (e.g., muscle, liver, respiratory epithelium, etc).

"Coding sequence" refers to a DNA sequence that encodes a specific amino acid sequence. An open reading frame (ORF) is a continuous sequence of DNA that contains a start codon, a subsequent region which usually has a length which is a multiple of 3 nucleotides, and a stop codon in the same reading frame.

Since the genetic code is degenerate (i.e., each amino acid can be coded by different codons), the DNA sequence can be modified by nucleotide substitutions without altering the amino acid sequence of the encoded protein. Such changes are referred to herein as synonymous codon modifications.

Base combinations which encode some of the standard amino acids are provided below.

CODON TABLE 1

| | DNA | mRNA | tRNA Anti-codon |
|---|---|---|---|
| alanine (Ala, A) | CGA | GCU | CGA |
| | CGG | GCC | CGG |
| | CGT | GCA | CGU |
| | CGC | GCG | CGC |
| arginine (Arg, R) | GCA | CGU | GCA |
| | GCG | CGC | GCG |
| | GCT | CGA | GCU |
| | GCC | CGG | GCC |
| | TCT | AGA | UCU |
| | TCC | AGG | UCC |
| asparagine (Asn, N) | TTA | AAU | UUA |
| | TTG | AAC | UUG |
| aspartate (Asp, D) | CTA | GAU | CUA |
| | CTG | GAC | CUG |
| cysteine (Cys, C) | ACA | UGU | ACA |
| | ACG | UGC | ACG |
| glutamate (Glu, E) | CTT | GAA | CUU |
| | CTC | GAG | CUC |
| glutamine (Gln, Q) | GTT | CAA | GUU |
| | GTC | CAG | GUC |
| glycine (Gly, G) | CCA | GGU | CCA |
| | CCG | GGC | CCG |
| | CCT | GGA | CCU |
| | CCC | GGG | CCC |
| histidine (His, H) | GTA | CAU | GUA |
| | GTG | CAC | GUG |
| isoleucine (Ile, I) | TAA | AUU | UAA |
| | TAG | AUC | UAG |
| | TAT | AUA | UAU |
| leucine (Leu, L) | AAT | UUA | AAU |
| | AAC | UUG | AAC |
| | GAA | CUU | GAA |
| | GAG | CUC | GAG |
| | GAT | CUA | GAU |
| | GAC | CUG | GAC |
| lysine (Lys, K) | TTT | AAA | UUU |
| | TTC | AAG | UUC |
| methionine (Met, M) | TAC | AUG | UAC |
| phenylalanine (Phe, F) | AAA | UUU | AAA |
| | AAG | UUC | AAG |
| proline (Pro, P) | GGA | CCU | GGA |
| | GGG | CCC | GGG |
| | GGT | CCA | GGU |
| | GGC | CCG | GGC |
| serine (Ser, S) | AGA | UCU | AGA |
| | AGG | UCC | AGG |
| | AGT | UCA | AGU |
| | AGC | UCG | AGC, |
| | TCA | AGU | UCA |
| | TCG | AGC | UCG |
| stop | ATG | UAA | AUG |
| | ATT | UAG | AUU |
| | ACT | UGA | ACU |
| threonine (Thr, T) | TGA | ACU | UGA |
| | TGG | ACC | UGG |
| | TGT | ACA | UGU |
| | TGC | ACG | UGC |
| tryptophan (Trp, W) | ACC | UGG | ACC |
| tyrosine (Tyr, Y) | ATA | UAU | AUA |
| | ATG | UAC | AUG |
| valine (Val, V) | CAA | GUU | CAA |
| | CAG | GUC | CAG |
| | CAT | GUA | CAU |
| | CAC | GUG | CAC |

The term “codon usage bias” refers to differences in the frequency of occurrence of synonymous codons in coding DNA. A variety of statistical methods have been described to analyze codon frequency in the literature. Additionally, there are many computer programs available to implement these statistical analyses enumerated above, including CodonW, GCUA, INCA, etc. Methods of codon optimization for expression in a specific species have been described.

For example, Table 2 provides a conventional codon frequency for *Homo sapiens* (human) as reported by the Codon Usage Database: kazusa.or.jp/codon/. These codon frequency are reported as frequency of an mRNA triplet (codon) per thousand codons. Given a table of codon frequencies presented based on the mRNA sequence, the corresponding cDNA or tRNA triplets may be readily determined by one of skill in the art, e.g., using Table 1 above.

TABLE 2

| Sequence | Codon (frequency: per thousand) | | | | | | | |
|---|---|---|---|---|---|---|---|---|
| HUMAN | UUU | 17.6 | UCU | 15.2 | UAU | 12.2 | UGU | 10.6 |
| | UUC | 20.3 | UCC | 17.7 | UAC | 15.3 | UGC | 12.6 |
| | UUA | 7.7 | UCA | 12.2 | UAA | 1 | UGA | 1.6 |
| | UUG | 12.9 | UCG | 4.4 | UAG | 0.8 | UGG | 13.2 |
| | CUU | 13.2 | CCU | 17.5 | CAU | 10.9 | CGU | 4.5 |
| | CUC | 19.6 | CCC | 19.8 | CAC | 15.1 | CGC | 10.4 |
| | CUA | 7.2 | CCA | 16.9 | CAA | 12.3 | CGA | 6.2 |
| | CUG | 39.6 | CCG | 6. | CAG | 34.2 | CGG | 11.4 |
| | AUU | 16 | ACU | 13.1 | AAU | 17 | AGU | 12.1 |
| | AUC | 20.8 | ACC | 18.9 | AAC | 19.1 | AGC | 19.5 |
| | AUA | 7.5 | ACA | 15.1 | AAA | 24.4 | AGA | 12.2 |
| | AUG | 22 | ACG | 6.1 | AAG | 31.9 | AGG | 12 |
| | GUU | 11 | GCU | 18.4 | GAU | 21.8 | GGU | 10.8 |
| | GUC | 14.5 | GCC | 27.7 | GAC | 25.1 | GGC | 22.2 |
| | GUA | 7.1 | GCA | 15.8 | GAA | 29 | GGA | 16 |
| | GUG | 28.1 | GCG | 7.4 | GAG | 39.6 | GGG | 16.5 |

As described in the examples below, a study was designed to test whether codons play a role in expression levels which can be achieved in different tissues. The results of this study shows that modified codons do not express at the same levels in all cell or tissue types within a species (e.g., humans).

Using the information provided herein (e.g., in one or more of Table 3, Table 4, Table 5, Table 6, Table 7, Table 8, Table 9, Table 10, Table 11, Table 12, Table 16, and/or Table 17), one may design modified genes having codons which preferentially enhance expression levels in a selected target tissue. In one example, the target tissue is an organ, tissue, or cell type with natural secretory pathways, e.g., liver, lung, epithelial cells (e.g., lung, gastrointestinal, exocrine, etc), sebaceous glands, hormone secretory cells, tears (meibomiah glands), among others. The target tissue may be a secreting or non-secreting organ, tissue or cell type, e.g., skeletal muscle, brain, ocular photoreceptor cells, etc. In another example, the codons are selected for a more specific target, e.g., for skeletal muscle, or for respiratory epithelium, or liver. In one embodiment, the codons are optimized for a selected tissue or organ (e.g., muscle), using the triplet frequency shown in the analytic table for orf35 (Table 6), or a frequency within about 10% thereof. In another embodiment, the codons are optimized for a target (e.g., muscle), using the triplet frequency shown in the analytic table for orf39 (Table 5) or a frequency within 10% thereof. According to the invention, the nucleic acid sequence encoding the product is modified with synonymous codon sequences in a tissue-preferential manner. Suitably, the entire length of the open reading frame (ORF) for the product is modified. However, in some embodiments, only a fragment of the ORF may be altered.

In one embodiment, the codons are generated based on the codon frequency of a selected table, or a frequency within about 10%, within about 5%, within about 3%, or within about 1% of the codon frequency of any one of the Tables provided herein. As used herein, “within about 10% frequency” may encompass the frequency of codons for a selected amino acid (e.g., Ala) within a selected Table, or the codon frequencies within a selected Table may be within 10% for each represented amino acid within a selected Table. For example, computer programs currently exist (e.g., Vector NTI® (Life Technologies)) and/or may be readily designed, which allow importation or use of a codon frequency such as that of any of the tables provided herein and the backtranslation of a nucleic acid sequence (e.g., mRNA or cDNA). The resulting sequence may be synthesized or modified using genetic engineering techniques.

By utilizing a codon frequency selected from one or more of the Tables 3-12, 16, 17, or a frequency within about 10% thereof (or optionally Table 13, 14 or 15), one can apply the codon frequencies to a selected polypeptide sequence, and produce a nucleic acid fragment of a codon-optimized coding region which encodes the polypeptide, but which uses codons more optimal for a given tissue. Suitably, the entire length of the open reading frame (ORF) for the product is modified. However, in some embodiments, only a fragment of the ORF may be altered. By using one of these methods, one can apply the frequencies to any given protein, enzyme, polypeptide, peptide or other amino acid sequence, and produce a nucleic acid fragment of a codon-optimized coding region which encodes the amino acid product.

TABLE 3

| Sequence | Codon (frequency: per thousand) | | | | | | | |
|---|---|---|---|---|---|---|---|---|
| ORF 42 | UUU | 12.4 | UCU | 17.9 | UAU | 8.3 | UGU | 13.8 |
| | UUC | 22 | UCC | 13.8 | UAC | 31.7 | UGC | 11 |
| | UUA | 9.6 | UCA | 45.5 | UAA | 0 | UGA | 0 |
| | UUG | 11 | UCG | 6.9 | UAG | 0 | UGG | 20.7 |
| | CUU | 11 | CCU | 17.9 | CAU | 2.8 | CGU | 9.6 |
| | CUC | 12.4 | CCC | 30.3 | CAC | 15.2 | CGC | 8.3 |
| | CUA | 9.6 | CCA | 12.4 | CAA | 11 | CGA | 4.1 |
| | CUG | 33.1 | CCG | 6.9 | CAG | 42.7 | CGG | 5.5 |
| | AUU | 6.9 | ACU | 12.4 | AAU | 16.5 | AGU | 15.2 |
| | AUC | 12.4 | ACC | 24.8 | AAC | 28.9 | AGC | 13.8 |
| | AUA | 2.8 | ACA | 20.7 | AAA | 42.7 | AGA | 8.3 |
| | AUG | 11 | ACG | 12.4 | AAG | 19.3 | AGG | 5.5 |
| | GUU | 41.3 | GCU | 11 | GAU | 33.1 | GGU | 5.5 |
| | GUC | 17.9 | GCC | 9.6 | GAC | 13.8 | GGC | 37.2 |
| | GUA | 9.6 | GCA | 28.9 | GAA | 22 | GGA | 5.5 |
| | GUG | 20.7 | GCG | 4.1 | GAG | 19.3 | GGG | 9.6 |

TABLE 4

| Sequence | Codon (frequency: per thousand) | | | | | | | |
|---|---|---|---|---|---|---|---|---|
| ORF 40 | UUU | 24.8 | UCU | 11 | UAU | 8.3 | UGU | 13.8 |
| | UUC | 9.6 | UCC | 39.9 | UAC | 31.7 | UGC | 11 |
| | UUA | 8.3 | UCA | 5.5 | UAA | 0 | UGA | 0 |
| | UUG | 11 | UCG | 4.1 | UAG | 0 | UGG | 20.7 |
| | CUU | 11 | CCU | 17.9 | CAU | 12.4 | CGU | 9.6 |
| | CUC | 12.4 | CCC | 30.3 | CAC | 5.5 | CGC | 8.3 |
| | CUA | 11 | CCA | 12.4 | CAA | 5.5 | CGA | 4.1 |
| | CUG | 33.1 | CCG | 6.9 | CAG | 48.2 | CGG | 5.5 |
| | AUU | 6.9 | ACU | 12.4 | AAU | 24.8 | AGU | 9.6 |
| | AUC | 5.5 | ACC | 11 | AAC | 20.7 | AGC | 42.7 |
| | AUA | 9.6 | ACA | 41.3 | AAA | 33.1 | AGA | 8.3 |
| | AUG | 11 | ACG | 5.5 | AAG | 28.9 | AGG | 5.5 |
| | GUU | 16.5 | GCU | 12.4 | GAU | 16.5 | GGU | 4.1 |
| | GUC | 16.5 | GCC | 27.5 | GAC | 30.3 | GGC | 13.8 |
| | GUA | 15.2 | GCA | 8.3 | GAA | 8.3 | GGA | 9.6 |
| | GUG | 41.3 | GCG | 5.5 | GAG | 33.1 | GGG | 30.3 |

TABLE 5

| Sequence | Codon (frequency: per thousand) | | | | | | | |
|---|---|---|---|---|---|---|---|---|
| ORF 39 | UUU | 12.4 | UCU | 17.9 | UAU | 22 | UGU | 5.5 |
| | UUC | 22 | UCC | 13.8 | UAC | 17.9 | UGC | 19.3 |
| | UUA | 4.1 | UCA | 45.5 | UAA | 0 | UGA | 0 |
| | UUG | 11 | UCG | 5.5 | UAG | 0 | UGG | 20.7 |
| | CUU | 9.6 | CCU | 12.4 | CAU | 12.4 | CGU | 2.8 |
| | CUC | 24.8 | CCC | 44.1 | CAC | 5.5 | CGC | 5.5 |
| | CUA | 5.5 | CCA | 6.9 | CAA | 5.5 | CGA | 6.9 |
| | CUG | 31.7 | CCG | 4.1 | CAG | 48.2 | CGG | 8.3 |
| | AUU | 8.3 | ACU | 9.6 | AAU | 16.5 | AGU | 15.2 |
| | AUC | 8.3 | ACC | 22 | AAC | 28.9 | AGC | 15.2 |
| | AUA | 5.5 | ACA | 17.9 | AAA | 42.7 | AGA | 11 |
| | AUG | 11 | ACG | 20.7 | AAG | 19.3 | AGG | 6.9 |
| | GUU | 24.8 | GCU | 28.9 | GAU | 26.2 | GGU | 9.6 |
| | GUC | 22 | GCC | 13.8 | GAC | 20.7 | GGC | 13.8 |
| | GUA | 11 | GCA | 8.3 | GAA | 8.3 | GGA | 20.7 |
| | GUG | 31.7 | GCG | 2.8 | GAG | 33.1 | GGG | 13.8 |

TABLE 6

| Sequence | Codon (frequency: per thousand) | | | | | | | |
|---|---|---|---|---|---|---|---|---|
| ORF 35 | UUU | 19.3 | UCU | 12.4 | UAU | 22 | UGU | 13.8 |
| | UUC | 15.2 | UCC | 23.4 | UAC | 17.9 | UGC | 11 |
| | UUA | 5.5 | UCA | 17.9 | UAA | 0 | UGA | 0 |
| | UUG | 13.8 | UCG | 20.7 | UAG | 0 | UGG | 20.7 |
| | CUU | 6.9 | CCU | 12.4 | CAU | 9.6 | CGU | 1.4 |
| | CUC | 13.8 | CCC | 44.1 | CAC | 8.3 | CGC | 4.1 |
| | CUA | 5.5 | CCA | 6.9 | CAA | 27.5 | CGA | 2.8 |
| | CUG | 41.3 | CCG | 4.1 | CAG | 26.2 | CGG | 13.8 |
| | AUU | 13.8 | ACU | 11 | AAU | 9.6 | AGU | 11 |
| | AUC | 5.5 | ACC | 46.8 | AAC | 35.8 | AGC | 27.5 |
| | AUA | 2.8 | ACA | 6.9 | AAA | 20.7 | AGA | 5.5 |
| | AUG | 11 | ACG | 5.5 | AAG | 41.3 | AGG | 13.8 |
| | GUU | 41.3 | GCU | 19.3 | GAU | 11 | GGU | 8.3 |
| | GUC | 17.9 | GCC | 19.3 | GAC | 35.8 | GGC | 26.2 |
| | GUA | 9.6 | GCA | 11 | GAA | 28.9 | GGA | 9.6 |
| | GUG | 20.7 | GCG | 4.1 | GAG | 12.4 | GGG | 13.8 |

TABLE 7

| Sequence | Codon (frequency: per thousand) | | | | | | | |
|---|---|---|---|---|---|---|---|---|
| ORF 30 | UUU | 24.8 | UCU | 16.5 | UAU | 22 | UGU | 13.8 |
| | UUC | 9.6 | UCC | 26.2 | UAC | 17.9 | UGC | 11 |
| | UUA | 5.5 | UCA | 17.9 | UAA | 0 | UGA | 0 |
| | UUG | 6.9 | UCG | 11 | UAG | 0 | UGG | 20.7 |
| | CUU | 31.7 | CCU | 37.2 | CAU | 5.5 | CGU | 2.8 |
| | CUC | 16.5 | CCC | 15.2 | CAC | 12.4 | CGC | 2.8 |
| | CUA | 6.9 | CCA | 12.4 | CAA | 9.6 | CGA | 8.3 |
| | CUG | 19.3 | CCG | 2.8 | CAG | 44.1 | CGG | 5.5 |
| | AUU | 5.5 | ACU | 12.4 | AAU | 16.5 | AGU | 13.8 |
| | AUC | 12.4 | ACC | 11 | AAC | 28.9 | AGC | 27.5 |
| | AUA | 4.1 | ACA | 41.3 | AAA | 20.7 | AGA | 16.5 |
| | AUG | 11 | ACG | 5.5 | AAG | 41.3 | AGG | 5.5 |
| | GUU | 15.2 | GCU | 27.5 | GAU | 33.1 | GGU | 4.1 |
| | GUC | 28.9 | GCC | 15.2 | GAC | 13.8 | GGC | 13.8 |
| | GUA | 6.9 | GCA | 8.3 | GAA | 22 | GGA | 9.6 |
| | GUG | 38.6 | GCG | 2.8 | GAG | 19.3 | GGG | 30.3 |

TABLE 8

| Sequence | Codon (frequency: per thousand) | | | | | | | |
|---|---|---|---|---|---|---|---|---|
| ORF 28 | UUU | 12.4 | UCU | 27.5 | UAU | 22 | UGU | 13.8 |
| | UUC | 22 | UCC | 20.7 | UAC | 17.9 | UGC | 11 |
| | UUA | 5.5 | UCA | 13.8 | UAA | 0 | UGA | 0 |
| | UUG | 6.9 | UCG | 4.1 | UAG | 0 | UGG | 20.7 |
| | CUU | 31.7 | CCU | 37.2 | CAU | 9.6 | CGU | 2.8 |
| | CUC | 16.5 | CCC | 15.2 | CAC | 8.3 | CGC | 2.8 |
| | CUA | 6.9 | CCA | 12.4 | CAA | 8.3 | CGA | 8.3 |
| | CUG | 19.3 | CCG | 2.8 | CAG | 45.5 | CGG | 5.5 |
| | AUU | 9.6 | ACU | 13.8 | AAU | 24.8 | AGU | 22 |
| | AUC | 9.6 | ACC | 24.8 | AAC | 20.7 | AGC | 24.8 |
| | AUA | 2.8 | ACA | 20.7 | AAA | 12.4 | AGA | 16.5 |

TABLE 8-continued

| Sequence | Codon (frequency: per thousand) | | | | | | | |
|---|---|---|---|---|---|---|---|---|
| | AUG | 11 | ACG | 11 | AAG | 49.6 | AGG | 5.5 |
| | GUU | 5.5 | GCU | 11 | GAU | 16.5 | GGU | 6.9 |
| | GUC | 12.4 | GCC | 22 | GAC | 30.3 | GGC | 37.2 |
| | GUA | 5.5 | GCA | 12.4 | GAA | 8.3 | GGA | 5.5 |
| | GUG | 66.1 | GCG | 8.3 | GAG | 33.1 | GGG | 8.3 |

TABLE 9

| Sequence | Codon (frequency: per thousand) | | | | | | | |
|---|---|---|---|---|---|---|---|---|
| ORF 26 | UUU | 19.3 | UCU | 22 | UAU | 8.3 | UGU | 5.5 |
| | UUC | 15.2 | UCC | 19.3 | UAC | 31.7 | UGC | 19.3 |
| | UUA | 6.9 | UCA | 26.2 | UAA | 0 | UGA | 0 |
| | UUG | 8.3 | UCG | 6.9 | UAG | 0 | UGG | 20.7 |
| | CUU | 17.9 | CCU | 17.9 | CAU | 9.6 | CGU | 2.8 |
| | CUC | 17.9 | CCC | 30.3 | CAC | 8.3 | CGC | 12.4 |
| | CUA | 8.3 | CCA | 12.4 | CAA | 5.5 | CGA | 4.1 |
| | CUG | 27.5 | CCG | 6.9 | CAG | 48.2 | CGG | 8.3 |
| | AUU | 5.5 | ACU | 11 | AAU | 24.8 | AGU | 17.9 |
| | AUC | 12.4 | ACC | 46.8 | AAC | 20.7 | AGC | 20.7 |
| | AUA | 4.1 | ACA | 6.9 | AAA | 12.4 | AGA | 5.5 |
| | AUG | 11 | ACG | 5.5 | AAG | 49.6 | AGG | 8.3 |
| | GUU | 5.5 | GCU | 19.3 | GAU | 11 | GGU | 22 |
| | GUC | 11 | GCC | 19.3 | GAC | 35.8 | GGC | 16.5 |
| | GUA | 5.5 | GCA | 11 | GAA | 22 | GGA | 12.4 |
| | GUG | 67.5 | GCG | 4.1 | GAG | 19.3 | GGG | 6.9 |

TABLE 10

| Sequence | Codon (frequency: per thousand) | | | | | | | |
|---|---|---|---|---|---|---|---|---|
| ORF 11 | UUU | 23.4 | UCU | 16.5 | UAU | 27.5 | UGU | 17.9 |
| | UUC | 11 | UCC | 30.3 | UAC | 12.4 | UGC | 6.9 |
| | UUA | 2.8 | UCA | 11 | UAA | 0 | UGA | 0 |
| | UUG | 16.5 | UCG | 5.5 | UAG | 0 | UGG | 20.7 |
| | CUU | 4.1 | CCU | 15.2 | CAU | 12.4 | CGU | 1.4 |
| | CUC | 8.3 | CCC | 22 | CAC | 5.5 | CGC | 6.9 |
| | CUA | 4.1 | CCA | 19.3 | CAA | 17.9 | CGA | 4.1 |
| | CUG | 51 | CCG | 11 | CAG | 35.8 | CGG | 11 |
| | AUU | 9.6 | ACU | 12.4 | AAU | 16.5 | AGU | 15.2 |
| | AUC | 9.6 | ACC | 24.8 | AAC | 28.9 | AGC | 34.4 |
| | AUA | 2.8 | ACA | 20.7 | AAA | 12.4 | AGA | 6.9 |
| | AUG | 11 | ACG | 12.4 | AAG | 49.6 | AGG | 11 |
| | GUU | 15.2 | GCU | 28.9 | GAU | 16.5 | GGU | 5.5 |
| | GUC | 16.5 | GCC | 13.8 | GAC | 30.3 | GGC | 37.2 |
| | GUA | 16.5 | GCA | 8.3 | GAA | 22 | GGA | 5.5 |
| | GUG | 41.3 | GCG | 2.8 | GAG | 19.3 | GGG | 9.6 |

TABLE 11

| Sequence | Codon (frequency: per thousand) | | | | | | | |
|---|---|---|---|---|---|---|---|---|
| ORF 2 | UUU | 22 | UCU | 37.2 | UAU | 13.8 | UGU | 8.3 |
| | UUC | 12.4 | UCC | 15.2 | UAC | 26.2 | UGC | 16.5 |
| | UUA | 5.5 | UCA | 11 | UAA | 0 | UGA | 0 |
| | UUG | 5.5 | UCG | 2.8 | UAG | 0 | UGG | 20.7 |
| | CUU | 31.7 | CCU | 11 | CAU | 12.4 | CGU | 2.8 |
| | CUC | 16.5 | CCC | 19.3 | CAC | 5.5 | CGC | 17.9 |
| | CUA | 6.9 | CCA | 16.5 | CAA | 9.6 | CGA | 2.8 |
| | CUG | 20.7 | CCG | 20.7 | CAG | 44.1 | CGG | 6.9 |
| | AUU | 6.9 | ACU | 12.4 | AAU | 33.1 | AGU | 30.3 |
| | AUC | 11 | ACC | 26.2 | AAC | 12.4 | AGC | 16.5 |
| | AUA | 4.1 | ACA | 20.7 | AAA | 20.7 | AGA | 4.1 |
| | AUG | 11 | ACG | 11 | AAG | 41.3 | AGG | 6.9 |
| | GUU | 15.2 | GCU | 28.9 | GAU | 16.5 | GGU | 13.8 |
| | GUC | 28.9 | GCC | 13.8 | GAC | 30.3 | GGC | 19.3 |
| | GUA | 6.9 | GCA | 8.3 | GAA | 28.9 | GGA | 13.8 |
| | GUG | 38.6 | GCG | 2.8 | GAG | 12.4 | GGG | 11 |

TABLE 12

| Sequence | Codon (frequency: per thousand) | | | | | | | |
|---|---|---|---|---|---|---|---|---|
| ORF 1 | UUU | 6.9 | UCU | 12.4 | UAU | 8.3 | UGU | 5.5 |
| | UUC | 27.5 | UCC | 24.8 | UAC | 31.7 | UGC | 19.3 |
| | UUA | 2.8 | UCA | 16.5 | UAA | 0 | UGA | 0 |
| | UUG | 16.5 | UCG | 22 | UAG | 0 | UGG | 20.7 |
| | CUU | 2.8 | CCU | 11 | CAU | 2.8 | CGU | 1.4 |
| | CUC | 8.3 | CCC | 20.7 | CAC | 15.2 | CGC | 4.1 |
| | CUA | 4.1 | CCA | 16.5 | CAA | 5.5 | CGA | 2.8 |
| | CUG | 52.3 | CCG | 19.3 | CAG | 48.2 | CGG | 15.2 |
| | AUU | 5.5 | ACU | 9.6 | AAU | 9.6 | AGU | 11 |
| | AUC | 12.4 | ACC | 22 | AAC | 35.8 | AGC | 26.2 |
| | AUA | 4.1 | ACA | 17.9 | AAA | 12.4 | AGA | 4.1 |
| | AUG | 11 | ACG | 20.7 | AAG | 49.6 | AGG | 13.8 |
| | GUU | 5.5 | GCU | 8.3 | GAU | 11 | GGU | 4.1 |
| | GUC | 12.4 | GCC | 19.3 | GAC | 35.8 | GGC | 13.8 |
| | GUA | 5.5 | GCA | 11 | GAA | 8.3 | GGA | 9.6 |
| | GUG | 66.1 | GCG | 15.2 | GAG | 33.1 | GGG | 30.3 |

TABLE 13

| Sequence | Codon (frequency: per thousand) | | | | | | | |
|---|---|---|---|---|---|---|---|---|
| IAU | UUU | 13.8 | UCU | 0 | UAU | 13.8 | UGU | 0 |
| | UUC | 20.7 | UCC | 51 | UAC | 26.2 | UGC | 24.8 |
| | UUA | 0 | UCA | 0 | UAA | 0 | UGA | 0 |
| | UUG | 0 | UCG | 0 | UAG | 0 | UGG | 20.7 |
| | CUU | 0 | CCU | 16.5 | CAU | 4.1 | CGU | 0 |
| | CUC | 0 | CCC | 26.2 | CAC | 13.8 | CGC | 0 |
| | CUA | 0 | CCA | 24.8 | CAA | 11 | CGA | 12.4 |
| | CUG | 86.8 | CCG | 0 | CAG | 42.7 | CGG | 12.4 |
| | AUU | 6.9 | ACU | 0 | AAU | 15.2 | AGU | 0 |
| | AUC | 15.2 | ACC | 45.5 | AAC | 30.3 | AGC | 62 |
| | AUA | 0 | ACA | 24.8 | AAA | 23.4 | AGA | 16.5 |
| | AUG | 11 | ACG | 0 | AAG | 38.6 | AGG | 0 |
| | GUU | 0 | GCU | 0 | GAU | 12.4 | GGU | 0 |
| | GUC | 46.8 | GCC | 27.5 | GAC | 34.4 | GGC | 19.3 |
| | GUA | 0 | GCA | 26.2 | GAA | 15.2 | GGA | 20.7 |
| | GUG | 42.7 | GCG | 0 | GAG | 26.2 | GGG | 17.9 |

TABLE 14

| Sequence | Codon (frequency: per thousand) | | | | | | | |
|---|---|---|---|---|---|---|---|---|
| IAM | UUU | 0 | UCU | 0 | UAU | 0 | UGU | 11 |
| | UUC | 34.4 | UCC | 41.3 | UAC | 39.9 | UGC | 13.8 |
| | UUA | 0 | UCA | 0 | UAA | 0 | UGA | 0 |
| | UUG | 0 | UCG | 0 | UAG | 0 | UGG | 20.7 |
| | CUU | 0 | CCU | 17.9 | CAU | 4.1 | CGU | 0 |
| | CUC | 0 | CCC | 20.7 | CAC | 13.8 | CGC | 0 |
| | CUA | 0 | CCA | 28.9 | CAA | 4.1 | CGA | 1.4 |
| | CUG | 86.8 | CCG | 0 | CAG | 49.6 | CGG | 39.9 |
| | AUU | 5.5 | ACU | 0 | AAU | 9.6 | AGU | 0 |
| | AUC | 16.5 | ACC | 44.1 | AAC | 35.8 | AGC | 71.6 |
| | AUA | 0 | ACA | 26.2 | AAA | 19.3 | AGA | 0 |
| | AUG | 11 | ACG | 0 | AAG | 42.7 | AGG | 0 |
| | GUU | 0 | GCU | 0 | GAU | 33.1 | GGU | 0 |
| | GUC | 19.3 | GCC | 52.3 | GAC | 13.8 | GGC | 23.4 |
| | GUA | 0 | GCA | 1.4 | GAA | 12.4 | GGA | 34.4 |
| | GUG | 70.2 | GCG | 0 | GAG | 28.9 | GGG | 0 |

TABLE 15

| Sequence | Codon (frequency: per thousand) | | | | | | | |
|---|---|---|---|---|---|---|---|---|
| BASE | UUU | 11 | UCU | 19.3 | UAU | 9.7 | UGU | 5.5 |
| | UUC | 24.8 | UCC | 31.7 | UAC | 29 | UGC | 19.3 |
| | UUA | 2.8 | UCA | 11 | UAA | 0 | UGA | 0 |
| | UUG | 6.9 | UCG | 8.3 | UAG | 0 | UGG | 22.1 |
| | CUU | 5.5 | CCU | 13.8 | CAU | 5.5 | CGU | 5.5 |
| | CUC | 16.6 | CCC | 26.2 | CAC | 13.8 | CGC | 1.4 |
| | CUA | 5.5 | CCA | 17.9 | CAA | 8.3 | CGA | 8.3 |
| | CUG | 45.5 | CCG | 9.7 | CAG | 44.1 | CGG | 5.5 |

TABLE 15-continued

| Sequence | Codon (frequency: per thousand) | | | | | | | |
|---|---|---|---|---|---|---|---|---|
| | AUU | 5.5 | ACU | 9.7 | AAU | 13.8 | AGU | 6.9 |
| | AUC | 17.9 | ACC | 33.1 | AAC | 30.3 | AGC | 34.5 |
| | AUA | 0 | ACA | 19.3 | AAA | 20.7 | AGA | 13.8 |
| | AUG | 9.7 | ACG | 9.7 | AAG | 41.4 | AGG | 5.5 |
| | GUU | 4.1 | GCU | 5.5 | GAU | 11 | GGU | 4.1 |
| | GUC | 34.5 | GCC | 24.8 | GAC | 35.9 | GGC | 20.7 |
| | GUA | 4.1 | GCA | 16.6 | GAA | 16.6 | GGA | 17.9 |
| | GUG | 48.3 | GCG | 6.9 | GAG | 24.8 | GGG | 17.9 |

TABLE 16

| Sequence | Codon (frequency: per thousand) | | | | | | | |
|---|---|---|---|---|---|---|---|---|
| 201 | UUU | 11.8 | UCU | 23.5 | UAU | 17.6 | UGU | 11.8 |
| | UUC | 17.6 | UCC | 27.5 | UAC | 33.3 | UGC | 15.7 |
| | UUA | 0 | UCA | 17.6 | UAA | 0 | UGA | 0 |
| | UUG | 0 | UCG | 0 | UAG | 0 | UGG | 17.6 |
| | CUU | 0 | CCU | 21.6 | CAU | 5.9 | CGU | 0 |
| | CUC | 0 | CCC | 17.6 | CAC | 7.8 | CGC | 5.9 |
| | CUA | 0 | CCA | 27.5 | CAA | 2 | CGA | 7.8 |
| | CUG | 78.4 | CCG | 0 | CAG | 47.1 | CGG | 9.8 |
| | AUU | 9.8 | ACU | 21.6 | AAU | 13.7 | AGU | 17.6 |
| | AUC | 21.6 | ACC | 31.4 | AAC | 17.6 | AGC | 29.4 |
| | AUA | 0 | ACA | 25.5 | AAA | 19.6 | AGA | 7.8 |
| | AUG | 9.8 | ACG | 0 | AAG | 31.4 | AGG | 7.8 |
| | GUU | 0 | GCU | 9.8 | GAU | 23.5 | GGU | 0 |
| | GUC | 27.5 | GCC | 15.7 | GAC | 23.5 | GGC | 33.3 |
| | GUA | 0 | GCA | 9.8 | GAA | 19.6 | GGA | 45.1 |
| | GUG | 54.9 | GCG | 0 | GAG | 25.5 | GGG | 21.6 |

TABLE 17

| Sequence | Codon (frequency: per thousand) | | | | | | | |
|---|---|---|---|---|---|---|---|---|
| 10A | UUU | 9.8 | UCU | 29.3 | UAU | 21.5 | UGU | 13.7 |
| | UUC | 11.7 | UCC | 21.5 | UAC | 23.4 | UGC | 11.7 |
| | UUA | 0 | UCA | 15.6 | UAA | 0 | UGA | 0 |
| | UUG | 0 | UCG | 0 | UAG | 0 | UGG | 23.4 |
| | CUU | 0 | CCU | 21.5 | CAU | 7.8 | CGU | 0 |
| | CUC | 0 | CCC | 19.5 | CAC | 7.8 | CGC | 2 |
| | CUA | 0 | CCA | 27.3 | CAA | 0 | CGA | 7.8 |
| | CUG | 78.1 | CCG | 0 | CAG | 50.8 | CGG | 5.9 |
| | AUU | 11.7 | ACU | 19.5 | AAU | 11.7 | AGU | 23.4 |
| | AUC | 17.6 | ACC | 31.2 | AAC | 17.6 | AGC | 39.1 |
| | AUA | 0 | ACA | 25.4 | AAA | 27.3 | AGA | 7.8 |
| | AUG | 13.7 | ACG | 0 | AAG | 33.2 | AGG | 3.9 |
| | GUU | 0 | GCU | 11.7 | GAU | 19.5 | GGU | 0 |
| | GUC | 31.2 | GCC | 15.6 | GAC | 21.5 | GGC | 33.2 |
| | GUA | 0 | GCA | 19.5 | GAA | 19.5 | GGA | 43 |
| | GUG | 48.8 | GCG | 0 | GAG | 23.4 | GGG | 19.5 |

For example, the codon frequency of Table 5 or Table 6, or a codon frequency within 10% thereof, is particularly well suited to enhance expression of a selected gene product in muscle, and more particularly, skeletal muscle. In another example, the codon frequency of Table 9, Table 10, or Table 11, or a codon frequency within 10% thereof, is particularly well suited to enhance expression of a selected gene product in liver. In still another example, the codon frequency of Table 16 is particularly well suited to enhance expression of a selected gene product in respiratory epithelium (e.g., lung). In one embodiment, expression is mediated by an AAV. However, the codon frequency of these tables are useful in other methods and for other delivery vectors.

The methods provided herein are designed as the primary consideration to select the frequently used codon for a given amino acid as the primary consideration. However, as a secondary or tertiary consideration, the methods described herein may further select a codon or modify a selected sequence to exclude undesirable structural elements, e.g., (a) restriction sites, CpG islands, (b) exclusion of a hairpin turn in the initial polynucleotide sequence; (c) exclusion of a repeat element in the initial polynucleotide sequence; (d) exclusion of a ribosome binding site in the initial polynucleotide sequence; (e) exclusion of a polyadenylation signal in the initial polynucleotide sequence; (f) exclusion of a splice site in the initial polynucleotide sequence; (g) exclusion of an open reading frame in each possible 5' reading frame in the initial polynucleotide sequence; (h) exclusion of a polynucleotide sequence that facilitates RNA degradation in the initial polynucleotide sequence; (i) exclusion of an RNA polymerase termination signal in the initial polynucleotide sequence; (j) exclusion of a transcriptional promoter in the initial polynucleotide sequence; (k) exclusion of an immunostimulatory sequence in the initial polynucleotide sequence; (l) incorporation of an immunostimulatory sequence in the initial polynucleotide sequence; (mi) exclusion of an RNA methylation signal in the initial polynucleotide sequence; (n) exclusion of a selenocysteine incorporation signal in the initial polynucleotide sequence; (o) exclusion of an RNA editing sequence in the initial polynucleotide sequence; (p) exclusion of an RNAi-targeted sequence in the initial polynucleotide sequence; and/or (q) exclusion of an inverted repeat within the first 45 nucleotides encoding said synthetic polypeptide in the initial polynucleotide sequence. See, e.g., US Patent Publication No. 20130196864, which is incorporated by reference herein.

Methods of modifying an existing nucleic acid sequence to provide a synonymous codon for a selected amino acid and/or back-translating a selected amino acid sequence into a desired nucleic acid have been described. For example, web-based or commercially available computer programs, as well as service based companies may be used to back translate the amino acids sequences to nucleic acid coding sequences, including both RNA and/or cDNA. See, e.g., backtranseq by EMBOSS, ebi.ac.uk/Tools/st/; Gene Infinity (geneinfinity org/sms-/sms_backtranslation.html); ExPasy (expasy.org/tools/). A number of options are available for performing the changes to the codons or for synthesizing the codon-optimized coding regions designed as described herein. Such modifications or synthesis can be performed using standard and routine molecular biological manipulations well known to those of ordinary skill in the art. In one approach, a series of complementary oligonucleotide pairs of 80-90 nucleotides each in length and spanning the length of the desired sequence are synthesized by standard methods. These oligonucleotide pairs are synthesized such that upon annealing, they form double stranded fragments of 80-90 base pairs, containing cohesive ends, e.g., each oligonucleotide in the pair is synthesized to extend 3, 4, 5, 6, 7, 8, 9, 10, or more bases beyond the region that is complementary to the other oligonucleotide in the pair. The single-stranded ends of each pair of oligonucleotides is designed to anneal with the single-stranded end of another pair of oligonucleotides. The oligonucleotide pairs are allowed to anneal, and approximately five to six of these double-stranded fragments are then allowed to anneal together via the cohesive single stranded ends, and then they ligated together and cloned into a standard bacterial cloning vector, for example, a TOPO® vector available from Invitrogen Corporation, Carlsbad, Calif. The construct is then sequenced by standard methods. Several of these constructs consisting of 5 to 6 fragments of 80 to 90 base pair fragments ligated together, i.e., fragments of about 500 base pairs, are prepared, such that the entire desired sequence is represented in a series of plasmid constructs. The inserts of these plasmids are then cut with appropriate restriction enzymes and ligated together to form the final construct. The final construct is then cloned into a standard bacterial cloning vector, and sequenced. Additional methods would be immediately apparent to the skilled artisan. In addition, gene synthesis is readily available commercially.

As described above, the term "about" when used to modify a numerical value means a variation of ±10%, unless otherwise specified.

The terms "identical" or percent "identity," in the context of two or more nucleic acids or polypeptide sequences, refer to two or more sequences or subsequences that are the same or have a specified percentage of amino acid residues or nucleotides that are the same (i.e., about 70% identity, preferably 75%, 80%, 85%, 90%, 91%, 92%, 93%, 94%, 95%, 96%, 97%, 98%, 99%, or higher identity) over a specified region (e.g., any one of the modified ORFs provided herein when compared and aligned for maximum correspondence over a comparison window or designated region) as measured using a BLAST or BLAST 2.0 sequence comparison algorithms with default parameters described below, or by manual alignment and visual inspection (see, e.g., NCBI web site or the like). As another example, polynucleotide sequences can be compared using Fasta, a program in GCG Version 6.1. Fasta provides alignments and percent sequence identity of the regions of the best overlap between the query and search sequences. For instance, percent sequence identity between nucleic acid sequences can be determined using Fasta with its default parameters (a word size of 6 and the NOPAM factor for the scoring matrix) as provided in GCG Version 6.1, herein incorporated by reference. Generally, these programs are used at default settings, although one skilled in the art can alter these settings as needed. Alternatively, one of skill in the art can utilize another algorithm or computer program that provides at least the level of identity or alignment as that provided by the referenced algorithms and programs. This definition also refers to, or can be applied to, the compliment of a sequence. The definition also includes sequences that have deletions and/or additions, as well as those that have substitutions. As described below, the preferred algorithms can account for gaps and the like. Preferably, identity exists over a region that is at least about 25, 50, 75, 100, 150, 200 amino acids or nucleotides in length, and oftentimes over a region that is 225, 250, 300, 350, 400, 450, 500 amino acids or nucleotides in length or over the full-length of an amino acid or nucleic acid sequences.

Typically, when an alignment is prepared based upon an amino acid sequence, the alignment contains insertions and deletions which are so identified with respect to a reference AAV sequence and the numbering of the amino acid residues is based upon a reference scale provided for the alignment. However, any given AAV sequence may have fewer amino acid residues than the reference scale. In the present invention, when discussing the parental sequence, the term "the same position" or the "corresponding position" refers to the amino acid located at the same residue number in each of the sequences, with respect to the reference scale for the aligned sequences. However, when taken out of the alignment, each of the proteins may have these amino acids located at different residue numbers. Alignments are performed using any of a variety of publicly or commercially available Multiple Sequence Alignment Programs. Sequence alignment programs are available for amino acid sequences, e.g., the "Clustal X", "MAP", "PIMA", "MSA", "BLOCKMAKER", "MEME", and "Match-Box" programs. Generally, any of these programs are used at default settings, although one of skill in the art can alter these settings as needed. Alternatively, one of skill in the art can utilize another algorithm or computer program which provides at least the level of identity or alignment as that provided by the referenced algorithms and programs. See, e.g., J. D. Thomson et al, *Nucl. Acids. Res.*, "A comprehensive comparison of multiple sequence alignments", 27(13):2682-2690 (1999).

As used throughout this specification and the claims, the terms "comprise" and "contain" and its variants including, "comprises", "comprising", "contains" and "containing", among other variants, is inclusive of other components, elements, integers, steps and the like. The term "consists of" or "consisting of" are exclusive of other components, elements, integers, steps and the like.

Gene Products

As described herein, a synonymously modified gene designed as described herein is typically engineered into an expression cassette. An expression cassette as described herein contains the modified gene which has codons preferentially modified and selected to express a product in a target tissue, which is operably linked to expression control sequences which direct expression thereof. Such an expression cassette may also include expression control sequences useful for transcription initiation, termination, promoter and enhancer sequences; efficient RNA processing signals such as splicing and polyadenylation (polyA) signals; sequences that stabilize cytoplasmic mRNA; sequences that enhance translation efficiency (i.e., Kozak consensus sequence); sequences that enhance protein stability; and when desired, sequences that enhance secretion of the encoded product. Alternatively, or additionally, such regulatory expression elements may be located outside of the expression cassette, e.g., within another region of a vector into which the expression cassette is engineered.

Figure 5:
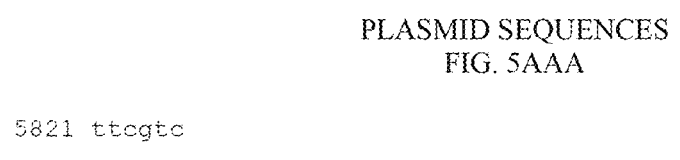

Provided in FIG. 5 and the sequence listing (SEQ ID Nos: 13-29), herein are the plasmid constructs utilized the Example below. The plasmids contain sequences encoding an anti-HIV antibody (3bcn117 antibody. See, Scheid et al, Sequence and structural convergence of broad and potent HIV antibodies that mimic CD4 binding. Science. 2011 Sep. 16; 333(6049):1633-7. Epub 2011 Jul. 14, which is incorporated herein by reference). Specific fragments of the sequences are identified and are, in one embodiment, of particular interest. These fragments may be used in conjunction with other fragments described herein, or other complementary fragments as known in the art. For example, certain fragments of interest include the constant regions of the heavy and light chains of an antibody such as the anti-SIV or anti-HIV antibody of the examples. These sequences, having been optimized for expression in a particular tissue type (e.g., liver, respiratory epithelial cells (e.g., lung)) may be utilized in conjunction with the variable regions of other antibodies, as described further below. The variable regions may be optimized for expression in the desired tissue using the codon frequency tables described herein. See Tables 3-12, 16, 17. Optionally, Tables 2, 23, 24, 15 may be used in conjunction with the methods and constructs described herein.

Desirable fragments of the plasmids include 5' and 3' ITR sequences, promoters, enhancers, TATA box, introns, IRES, F2A linkers, furin sites, forward primers, reverse primers, polyA signals. Other desirable fragments include the following:

| Region | Position (nt) | | |
|---|---|---|---|
| | SEQ ID NO: 14 | SED ID NO: 15 | SEQ ID NO: 18 |
| VH (variable region heavy chain) | 1365-1750 | 1371-1756 | 1320-1705 |
| CH1 (constant region 1 heavy chain) | 1752-2027 | 1758-2033 | 1707-1982 |
| HCH23 (constant region 2-3 heavy chain) | 2028-2716 | 2034-2722 | 1983-2671 |
| CL (constant region light chain) | 3111-3415 | 3181-3485 | 3130-3434 |
| 3nbc117 light | 2798-3095 | 2854-3165 | 2803-3114 |

Corresponding regions of the ORFs described herein or other desirable sequences can be readily determined using standard alignment techniques known in the art and described herein.

Therapeutic Transgenes

A nucleotide sequence encoding any of a number of different therapeutic transgenes may be selected for codon modification to enhance tissue-preferential expression as described herein. Useful therapeutic products encoded by the transgene include hormones and growth and differentiation factors including, without limitation, insulin, glucagon, growth hormone (GH), parathyroid hormone (PTH), growth hormone releasing factor (GRF), follicle stimulating hormone (FSH), luteinizing hormone (LH), human chorionic gonadotropin (hCG), vascular endothelial growth factor (VEGF), angiopoietins, angiostatin, granulocyte colony stimulating factor (GCSF), erythropoietin (EPO), connective tissue growth factor (CTGF), basic fibroblast growth factor (bFGF), acidic fibroblast growth factor (aFGF), epidermal growth factor (EGF), platelet-derived growth factor (PDGF), insulin growth factors I and II (IGF-I and IGF-II), any one of the transforming growth factor α superfamily, including TGFα, activins, inhibins, or any of the bone morphogenic proteins (BMP) BMPs 1-15 as well as TGFb proteins, any one of the heregluin/neuregulin/ARIA/neu differentiation factor (NDF) family of growth factors, nerve growth factor (NGF), brain-derived neurotrophic factor (BDNF), neurotrophins NT-3 and NT-4/5, ciliary neurotrophic factor (CNTF), glial cell line derived neurotrophic factor (GDNF), neurturin, agrin, any one of the family of semaphorins/collapsins, netrin-1 and netrin-2, hepatocyte growth factor (HGF), ephrins, noggin, sonic hedgehog and tyrosine hydroxylase.

Other useful transgene products include proteins that regulate the immune system including, without limitation, cytokines and lymphokines such as thrombopoietin (TPO), interleukins (IL) IL-1 through IL-25 (including IL-2, IL-4, IL-12 and IL-18), monocyte chemoattractant protein, leukemia inhibitory factor, granulocyte-macrophage colony stimulating factor, Fas ligand, tumor necrosis factors α and β, interferons α, β, TGFb and γ, stem cell factor, flk-2/flt3 ligand. Gene products produced by the immune system are also useful in the invention. These include, without limitations, immunoglobulins IgG, IgM, IgA, IgD and IgE, chimeric immunoglobulins, humanized antibodies, single chain antibodies, T cell receptors, chimeric T cell receptors, single chain T cell receptors, class I and class II MHC molecules, as well as engineered immunoglobulins and MHC molecules. Useful gene products also include complement regulatory proteins such as complement regulatory proteins, membrane cofactor protein (MCP), decay accelerating factor (DAF), CR1, CF2 and CD59.

Still other useful gene products include any one of the receptors for the hormones, growth factors, cytokines, lymphokines, regulatory proteins and immune system proteins. The invention encompasses receptors for cholesterol regulation and/or lipid modulation, including the low density lipoprotein (LDL) receptor, high density lipoprotein (HDL) receptor, the very low density lipoprotein (VLDL) receptor, and scavenger receptors. The invention also encompasses gene products such as members of the steroid hormone receptor superfamily including glucocorticoid receptors and estrogen receptors, Vitamin D receptors and other nuclear receptors. In addition, useful gene products include transcription factors such as jun, fos, max, mad, serum response factor (SRF), AP-1, AP2, myb, MyoD and myogenin, ETS-box containing proteins, TFE3, E2F, ATF1, ATF2, ATF3, ATF4, ZF5, NFAT, CREB, HNF-4, C/EBP, SP1, CCAAT-box binding proteins, interferon regulation factor (IRF-1), Wilms tumor protein, ETS-binding protein, STAT, GATA-box binding proteins, e.g., GATA-3, and the forkhead family of winged helix proteins.

Other useful gene products include, carbamoyl synthetase I, ornithine transcarbamylase, arginosuccinate synthetase, arginosuccinate lyase, arginase, fumarylacetacetate hydrolase, phenylalanine hydroxylase, alpha-1 antitrypsin, glucose-6-phosphatase, porphobilinogen deaminase, cystathione beta-synthase, branched chain ketoacid decarboxylase, albumin, isovaleryl-coA dehydrogenase, propionyl CoA carboxylase, methyl malonyl CoA mutase, glutaryl CoA dehydrogenase, insulin, beta-glucosidase, pyruvate carboxylate, hepatic phosphorylase, phosphorylase kinase, glycine decarboxylase, H-protein, T-protein, a cystic fibrosis transmembrane regulator (CFTR) sequence, and a dystrophin cDNA sequence. Still other useful gene products include enzymes such as may be useful in enzyme replacement therapy, which is useful in a variety of conditions resulting from deficient activity of enzyme. For example, enzymes that contain mannose-6-phosphate may be utilized in therapies for lysosomal storage diseases (e.g., a suitable gene includes that encoding β-glucuronidase (GUSB)).

Still other useful gene products include those used for treatment of hemophilia, including hemophilia B (including Factor IX) and hemophilia A (including Factor VIII and its variants, such as the light chain and heavy chain of the heterodimer and the B-deleted domain; U.S. Pat. Nos. 6,200,560 and 6,221,349). The present invention is not limited to any specific Factor VIII sequence. Many natural and recombinant forms of Factor VIII have been isolated and generated. Examples of naturally occurring and recombinant forms of Factor VII can be found in the patent and scientific literature including, U.S. Pat. Nos. 5,563,045, 5,451,521, 5,422,260, 5,004,803, 4,757,006, 5,661,008, 5,789,203, 5,681,746, 5,595,886, 5,045,455, 5,668,108, 5,633,150, 5,693,499, 5,587,310, 5,171,844, 5,149,637, 5,112,950, 4,886,876, WO 94/11503, WO 87/07144, WO 92/16557, WO 91/09122, WO 97/03195, WO 96/21035, WO 91/07490, EP 0 672 138, EP 0 270 618, EP 0 182 448, EP 0 162 067, EP 0 786 474, EP 0 533 862, EP 0 506 757, EP 0 874 057, EP 0 795 021, EP 0 670 332, EP 0 500 734, EP 0 232 112, EP 0 160 457, Sanberg et al., XXth Int. Congress of the World Fed. Of Hemophilia (1992), and Lind et al., Eur. J. Biochem., 232:19 (1995).

Also included herein are non-naturally occurring gene sequences include antisense molecules and catalytic nucleic acids, such as ribozymes, which could be used to reduce overexpression of a target. "Knockdown gene therapy" is directed towards a gene product which is associated with a disease or conditions in which the targeted gene is overexpressed, but which is not entirely extinguished by the therapy. Molecules such as microRNA and small interfering RNA (siRNA) may be delivered to accomplish knock out or knock down.

Reduction and/or modulation of expression of a gene is particularly desirable for treatment of hyperproliferative conditions characterized by hyperproliferating cells, as are cancers and psoriasis. Target polypeptides include those polypeptides which are produced exclusively or at higher levels in hyperproliferative cells as compared to normal cells. Target antigens include polypeptides encoded by oncogenes such as myb, myc, fyn, and the translocation gene bcr/abl, ras, src, P53, neu, trk and EGRF. In addition to oncogene products as target antigens, target polypeptides for anti-cancer treatments and protective regimens include variable regions of antibodies made by B cell lymphomas and variable regions of T cell receptors of T cell lymphomas which, in some embodiments, are also used as target antigens for autoimmune disease. Other tumor associated polypeptides can be used as target polypeptides such as polypeptides which are found at higher levels in tumor cells including the polypeptide recognized by monoclonal antibody 17 1A and folate binding polypeptides.

Other suitable therapeutic polypeptides and proteins include those which may be useful for treating individuals suffering from autoimmune diseases and disorders by conferring a broad based protective immune response against targets that are associated with autoimmunity including cell receptors and cells which produce "self"-directed antibodies. T cell mediated autoimmune diseases include Rheumatoid arthritis (RA), multiple sclerosis (MS), Sjögren's syndrome, sarcoidosis, insulin dependent diabetes mellitus (IDDM), autoimmune thyroiditis, reactive arthritis, ankylosing spondylitis, scleroderma, polymyositis, dermatomyositis, psoriasis, vasculitis, Wegener's granulomatosis, Crohn's disease and ulcerative colitis. Each of these diseases is characterized by T cell receptors (TCRs) and antibodies (Ab) that bind to endogenous antigens and initiate the inflammatory cascade associated with autoimmune diseases.

Other suitable therapeutic polypeptides and protein include those useful for treating individuals suffering from a rare disease. Such rare disease include, e.g., acrocephalosyndactylia, Acrodermatitis, Addison Disease, Adie Syndrome, Alagille Syndrome, Amylose, Amyotrophic Lateral Sclerosis, Angelman Syndrome, Angiolymphoid Hyperplasia with Eosinophilia, Arnold-Chiari Malformation, juvenile rheumatoid arthritis, Asperger Syndrome, Bardet-Biedl Syndrome, Barrett Esophagus, Beckwith-Wiedemann Syndrome, Behcet Syndrome, Bloom Syndrome, Bowen's Disease, Brachial Plexus Neuropathies, Brown-Sequard Syndrome, Budd-Chiari Syndrome, Burkitt Lymphoma, Carcinoma 256, Walker Caroli Disease, Charcot-Marie-Tooth Disease, Chediak-Higashi Syndrome, Chiari-Frommel Syndrome, Chondrodysplasia Punctata, Colonic Pseudo-Obstruction, Colorectal Neoplasms, Hereditary Nonpolyposis, Craniofacial Dysostosis, Creutzfeldt-Jakob Syndrome, Crohn Disease, Cushing Syndrome, Cystic Fibrosis, Dandy-Walker Syndrome, De Lange Syndrome, Dementia, Vascular Dermatitis, Herpetiformis, DiGeorge Syndrome, Diffuse Cerebral Sclerosis of Schilder, Duane Retraction Syndrome, Dupuytren Contracture, Ebstein Anomaly, Eisenmenger Complex, Ellis-Van Creveld Syndrome, Encephalitis, Enchondromatosis, Epidermal Necrolysis, Toxic Facial Hemiatrophy, Factor XII Deficiency, Fanconi Anemia, Felty's Syndrome, Fibrous Dysplasia, Polyostotic, Fox-Fordyce Disease, Friedreich Ataxia, Fusobacterium, Gardner Syndrome, Gaucher Disease, Gerstmann Syndrome, Giant Lymph Node Hyperplasia, Glycogen Storage Disease Type I, Glycogen Storage Disease Type II, Glycogen Storage Disease Type IV, Glycogen Storage Disease Type V, Glycogen Storage Disease Type VII, Goldenhar Syndrome, Guillain-Barre Syndrome, Hallermann's Syndrome, Hamartoma Syndrome, Multiple Hartnup Disease, Hepatolenticular Degeneration, Hepatolenticular Degeneration, Hereditary Sensory and Motor Neuropathy Hirschsprung Disease, Histiocytic Necrotizing Lymphadenitis, Histiocytosis, Langerhans-Cell Hodgkin Disease, Horner Syndrome, Huntington Disease, Hyperaldosteronism, Hyperostosis, Diffuse Idiopathic Skeletal, Hypopituitarism, Inappropriate ADH Syndrome, Intestinal Polyps Isaacs Syndrome, Kartagener Syndrome, Kearns-Sayre Syndrome, Klippel-Feil Syndrome, Klippel-Trenaunay-Weber Syndrome, Kluver-Bucy Syndrome, Korsakoff Syndrome, Lafora Disease, Lambert-Eaton Myasthenic Syndrome, Landau-Kleffner Syndrome, Langer-Giedion Syndrome, Leigh Disease, Lesch-Nyhan Syndrome, Leukodystrophy, Globoid Cell, Li-Fraumeni Syndrome, Long QT Syndrome, Machado-Joseph Disease, Mallory-Weiss Syndrome, Marek Disease, Marfan Syndrome, Meckel Diverticulum, Meige Syndrome, Melkersson-Rosenthal Syndrome, Meniere Disease, Mikulicz' Disease, Miller Fisher Syndrome, Mobius Syndrome, Moyamoya Disease, Mucocutaneous Lymph Node Syndrome, Mucopolysaccharidosis I, Mucopolysaccharidosis II, Mucopolysaccharidosis III, Mucopolysaccharidosis IV, Mucopolysaccharidosis VI, Multiple Endocrine Neoplasia Type 1, Munchausen Syndrome by Proxy, Muscular Atrophy, Spinal Neuroaxonal Dystrophies, Neuromyelitis Optica, Neuronal Ceroid-Lipofuscinoses, Niemann-Pick Diseases, Noonan Syndrome, Optic Atrophies, Hereditary Osteitis Deformans, Osteochondritis, Osteochondrodysplasias, Osteolysis, Essential, Paget Disease Extramammary, Paget's Disease, Mammary, Panniculitis, Nodular Nonsuppurative, Papillon-Lefevre Disease, Paralysis, Pelizaeus-Merzbacher Disease, Pemphigus, Benign Familial Penile Induration, Pericarditis, Constrictive, Peroxisomal Disorders, Peutz-Jeghers Syndrome, Pick Disease of the Brain, Pierre Robin Syndrome, Pigmentation Disorders, Pityriasis Lichenoides, Polycystic Ovary Syndrome, Polyendocrinopathies, Autoimmune Prader-Willi Syndrome, Pupil Disorders, Rett Syndrome, Reye Syndrome, Rubinstein-Taybi Syndrome, Sandhoff Disease, Sarcoma, Ewing's, Sjogren's Syndrome, Sjogren-Larsson Syndrome, Smith-Lemli-Opitz Syndrome, Spinal Muscular Atrophies of Childhood, Sturge-Weber Syndrome, Sweating, Gustatory, Takayasu Arteritis, Tangier Disease, Tay-Sachs Disease, Thromboangiitis Obliterans, Thyroiditis, Autoimmune, Tietze's Syndrome, Togaviridae Infections, Tolosa-Hunt Syndrome, Tourette Syndrome, Uveomeningoencephalitic Syndrome Waardenburg's Syndrome, Wegener Granulomatosis, Weil Disease, Werner Syndrome, Williams Syndrome, Wilms Tumor, Wolff-Parkinson-White Syndrome, Wolfram Syndrome, Wolman Disease, Zellweger Syndrome, Zollinger-Ellison Syndrome, and von Willebrand Diseases.

Immunogenic Transgenes

The nucleotide sequence encoding of any of a number of immunogenic transgenes may be selected for codon modification to enhance tissue-preferential expression as described herein. Examples of suitable immunogenic transgenes include those selected from a variety of viral families. Example of desirable viral families against which an immune response would be desirable include, the picornavirus family, which includes the genera rhinoviruses, which are responsible for about 50% of cases of the common cold; the genera enteroviruses, which include polioviruses, coxsackieviruses, echoviruses, and human enteroviruses such as hepatitis A virus; and the genera apthoviruses, which are responsible for foot and mouth diseases, primarily in non-human animals. Within the picornavirus family of viruses, target antigens include the VP1, VP2, VP3, VP4, and VPG. Other viral families include the astroviruses and the calcivirus family. The calcivirus family encompasses the Norwalk group of viruses, which are an important causative agent of epidemic gastroenteritis. Still another viral family desirable for use in targeting antigens for inducing immune responses in humans and non-human animals is the togavirus family, which includes the genera alphavirus, which include Sindbis viruses, RossRiver virus, and Venezuelan, Eastern & Western Equine encephalitis, and rubivirus, including Rubella virus. The flaviviridae family includes dengue, yellow fever, Japanese encephalitis, St. Louis encephalitis and tick borne encephalitis viruses. Other target antigens may be generated from the Hepatitis C or the coronavirus family, which includes a number of non-human viruses such as infectious bronchitis virus (poultry), porcine transmissible gastroenteric virus (pig), porcine hemagglutinatin encephalomyelitis virus (pig), feline infectious peritonitis virus (cats), feline enteric coronavirus (cat), canine coronavirus (dog), and human respiratory coronaviruses, which may cause the common cold and/or non A, B or C hepatitis, and which include the putative cause of sudden acute respiratory syndrome (SARS). Within the coronavirus family, target antigens include the E1 (also called M or matrix protein), E2 (also called S or Spike protein), E3 (also called HE or hemagglutin elterose) glycoprotein (not present in all coronaviruses), or N (nucleocapsid). Still other antigens may be targeted against the arterivirus family and the rhabdovirus family. The rhabdovirus family includes the genera vesiculovirus (e.g., Vesicular Stomatitis Virus), and the general lyssavirus (e.g., rabies). Within the rhabdovirus family, suitable antigens may be derived from the G protein or the N protein. The family filoviridae, which includes hemorrhagic fever viruses such as Marburg and Ebola virus may be a suitable source of antigens. The paramyxovirus family includes parainfluenza Virus Type 1, parainfluenza Virus Type 3, bovine parainfluenza Virus Type 3, rubulavirus (mumps virus, parainfluenza Virus Type 2, parainfluenza virus Type 4, Newcastle disease virus (chickens), rinderpest, morbillivirus, which includes measles and canine distemper, and pneumovirus, which includes respiratory syncytial virus. The influenza virus is classified within the family orthomyxovirus and is a suitable source of antigen (e.g., the HA protein, the N1 protein). The bunyavirus family includes the genera bunyavirus (California encephalitis, La Crosse), phlebovirus (Rift Valley Fever), hantavirus (puremala is a hemahagin fever virus), nairovirus (Nairobi sheep disease) and various unassigned bungaviruses. The arenavirus family provides a source of antigens against LCM and Lassa fever virus. Another source of antigens is the bornavirus family. The reovirus family includes the genera reovirus, rotavirus (which causes acute gastroenteritis in children), orbiviruses, and cultivirus (Colorado Tick fever, Lebombo (humans), equine encephalosis, blue tongue). The retrovirus family includes the sub family oncorivirinal which encompasses such human and veterinary diseases as feline leukemia virus, HTLVI and HTLVII, lentivirinal (which includes HIV, simian immunodeficiency virus, feline immunodeficiency virus, equine infectious anemia virus, and spumavirinal). The papovavirus family includes the sub-family polyomaviruses (BKU and JCU viruses) and the sub family papillomavirus (associated with cancers or malignant progression of papilloma). The adenovirus family includes viruses (EX, AD7, ARD, O.B.) which cause respiratory disease and/or enteritis. The parvovirus family feline parvovirus (feline enteritis), feline panleucopeniavirus, canine parvovirus, and porcine parvovirus. The herpesvirus family includes the sub family alphaherpesvirinae, which encompasses the genera simplexvirus (HSVI, HSVII), varicellovirus (pseudorabies, varicella zoster) and the sub-family betaherpesvirinae, which includes the genera cytomegalovirus (HCMV, muromegalovirus) and the sub family gammaherpesvirinae, which includes the genera lymphocryptovirus, EBV (Burkitts lymphoma), human herpesviruses 6A, 6B and 7, Kaposi's sarcoma-associated herpesvirus and cercopithecine herpesvirus (B virus), infectious rhinotracheitis, Marek's disease virus, and rhadinovirus. The poxvirus family includes the sub family chordopoxvirinae, which encompasses the genera orthopoxvirus (Variola major (Smallpox) and Vaccinia (Cowpox)), parapoxvirus, avipoxvirus, capripoxvirus, leporipoxvirus, suipoxvirus, and the sub family entomopoxvirinae. The hepadnavirus family includes the Hepatitis B virus. One unclassified virus which may be suitable source of antigens is the Hepatitis delta virus, Hepatitis E virus, and prions. Another virus which is a source of antigens is Nipan Virus. Still other viral sources may include avian infectious bursal disease virus and porcine respiratory and reproductive syndrome virus. The alphavirus family includes equine arteritis virus and various Encephalitis viruses.

The present invention may also encompass immunogens which are useful to immunize a human or non-human animal against other pathogens including bacteria, fungi, parasitic microorganisms or multicellular parasites which infect human and non-human vertebrates, or from a cancer cell or tumor cell. Examples of bacterial pathogens include pathogenic gram positive cocci include pneumococci; staphylococci (and the toxins produced thereby, e.g., enterotoxin B); and streptococci. Pathogenic gram negative cocci include meningococcus; gonococcus. Pathogenic enteric gram negative bacilli include enterobacteriaceae; *pseudomonas*, acinetobacteria and eikenella; melioidosis; *salmonella; shigella; haemophilus; moraxella; H. ducreyi* (which causes chancroid); *brucella* species (brucellosis); *Francisella tularensis* (which causes tularemia); *Yersinia pestis* (plague) and other *yersinia* (*pasteurella*); *streptobacillus moniliformis* and spirillum; Gram-positive bacilli include *listeria monocytogenes*; erysipelothrix rhusiopathiae; *Corynebacterium diphtheria* (diphtheria); cholera; *B. anthracis* (anthrax); donovanosis (granuloma inguinale); and bartonellosis. Diseases caused by pathogenic anaerobic bacteria include tetanus; botulism (*Clostridum botulinum* and its toxin); *Clostridium perfringens* and its epsilon toxin; other clostridia; tuberculosis; leprosy; and other mycobacteria. Pathogenic spirochetal diseases include syphilis; treponematoses: yaws, pinta and endemic syphilis; and leptospirosis. Other infections caused by higher pathogen bacteria and pathogenic fungi include glanders (*Burkholderia mallei*); actinomycosis; nocardiosis; cryptococcosis, blastomycosis, histoplasmosis and coccidioidomycosis; candidiasis, aspergillosis, and mucormycosis; sporotrichosis; paracoccidiodomycosis, petriellidiosis, torulopsosis, mycetoma and chromomycosis; and dermatophytosis. Rickettsial infections include Typhus fever, Rocky Mountain spotted fever, Q fever (*Coxiella burnetti*), and Rickettsialpox. Examples of *mycoplasma* and chlamydial infections include: *mycoplasma pneumoniae; lymphogranuloma venereum; psittacosis; and perinatal chlamydial infections. Pathogenic eukaryotes encompass pathogenic protozoans and helminths and infections produced thereby include: amebiasis; malaria; leishmaniasis; trypanosomiasis; toxoplasmosis; Pneumocystis carinii*; Trichans; *Toxoplasma gondii*; babesiosis; giardiasis; trichinosis; filariasis; schistosomiasis; nematodes; trematodes or flukes; and cestode (tapeworm) infections.

Many of these organisms and/or the toxins produced thereby have been identified by the Centers for Disease Control [(CDC), Department of Health and Human Services, USA], as agents which have potential for use in biological attacks. For example, some of these biological agents, include, *Bacillus anthracis* (anthrax), *Clostridium botulinum* and its toxin (botulism), *Yersinia pestis* (plague), variola major (smallpox), *Francisella tularensis* (tularemia), and viral hemorrhagic fevers [filoviruses (e.g., Ebola, Marburg], and arenaviruses [e.g., Lassa, Machupo]), all of which are currently classified as Category A agents; *Coxiella burnetti* (Q fever); *Brucella* species (brucellosis), *Burkholderia mallei* (glanders), *Burkholderia pseudomallei* (meloidosis), *Ricinus communis* and its toxin (ricin toxin), *Clostridium perfringens* and its toxin (epsilon toxin), *Staphylococcus* species and their toxins (enterotoxin B), *Chlamydia psittaci* (psittacosis), water safety threats (e.g., *Vibrio cholerae, Crytosporidium parvum*), Typhus fever (*Richettsia powazekii*), and viral encephalitis (alphaviruses, e.g., Venezuelan equine encephalitis; eastern equine encephalitis; western equine encephalitis); all of which are currently classified as Category B agents; and Nipan virus and hantaviruses, which are currently classified as Category C agents. In addition, other organisms, which are so classified or differently classified, may be identified and/or used for such a purpose in the future. It will be readily understood that the viral vectors and other constructs described herein are useful to deliver antigens from these organisms, viruses, their toxins or other by-products, which will prevent and/or treat infection or other adverse reactions with these biological agents.

The vectors of the invention can be used to deliver immunogens. In rheumatoid arthritis (RA), several specific variable regions of T-cell receptors (TCRs) which are involved in the disease have been characterized. These TCRs include V 3, V 14, and V 17. Thus, delivery of a nucleic acid sequence that encodes at least one of these polypeptides will elicit an immune response that will target T cells involved in RA. In multiple sclerosis (MS), several specific variable regions of TCRs which are involved in the disease have been characterized. These TCRs include V 7 and V 10. Thus, delivery of a nucleic acid sequence that encodes at least one of these polypeptides will elicit an immune response that will target T cells involved in MS. In scleroderma, several specific variable regions of TCRs which are involved in the disease have been characterized. These TCRs include V 6, V 8, V 14, V 3C, V 7, V 14, V 15, V 16, V 28 and V 12. Thus, delivery of a nucleic acid molecule that encodes at least one of these polypeptides will elicit an immune response that will target T cells involved in scleroderma.

Other useful products include an "anti-pathogen construct" which is a protein, peptide, or other molecule encoded by a nucleic acid sequence carried on a viral vector as described herein, which is capable of providing passive immunity against the selected pathogenic agent or a cross-reactive strain of the pathogenic agent. In one embodiment, the anti-pathogen construct is a neutralizing antibody construct against the pathogenic agent, e.g., a virus, bacterium, fungus, or a pathogenic toxin of said agent (e.g., anthrax toxin). Examples of such pathogens are provided herein. As used herein, a "neutralizing antibody" is an antibody which defends a cell from an antigen or infectious body by inhibiting or neutralizing its biological effect. In one embodiment, "neutralizes" and grammatical variations thereof, refer to an activity of an antibody that prevents entry or translocation of the pathogen into the cytoplasm of a cell susceptible to infection. As used herein a "neutralizing antibody construct" includes a full-length antibody (an immunoglobulin molecule), as well as antibody fragments or artificial constructs which have the ability to inhibit or neutralize an antigen or infectious agent. These antibody fragments or artificial constructs may include a single chain antibody, a Fab fragment, a univalent antibody, or an immunoadhesin. The neutralizing antibody construct may be a monoclonal antibody, a "humanized" antibody, a polyclonal antibody, or another suitable construct. An "immunoglobulin molecule" is a protein containing the immunologically-active portions of an immunoglobulin heavy chain and immunoglobulin light chain covalently coupled together and capable of specifically combining with an antigen Immunoglobulin molecules are of any type (e.g., IgG, IgE, IgM, IgD, IgA and IgY), class (e.g., IgG1, IgG2, IgG3, IgG4, IgA1 and IgA2) or subclass. The terms "antibody" and "immunoglobulin" may be used interchangeably herein. An "immunoglobulin heavy chain" is a polypeptide that contains at least a portion of the antigen binding domain of an immunoglobulin and at least a portion of a variable region of an immunoglobulin heavy chain or at least a portion of a constant region of an immunoglobulin heavy chain. Thus, the immunoglobulin derived heavy chain has significant regions of amino acid sequence homology with a member of the immunoglobulin gene superfamily. For example, the heavy chain in a Fab fragment is an immunoglobulin-derived heavy chain. An "immunoglobulin light chain" is a polypeptide that contains at least a portion of the antigen binding domain of an immunoglobulin and at least a portion of the variable region or at least a portion of a constant region of an immunoglobulin light chain. Thus, the immunoglobulin-derived light chain has significant regions of amino acid homology with a member of the immunoglobulin gene superfamily. An "immunoadhesin" is a chimeric, antibody-like molecule that combines the functional domain of a binding protein, usually a receptor, ligand, or cell-adhesion molecule, with immunoglobulin constant domains, usually including the hinge and Fc regions. A ""fragment antigen-binding" (Fab) fragment" is a region on an antibody that binds to antigens. It is composed of one constant and one variable domain of each of the heavy and the light chain. With respect to immunoglobulins or antibodies as described herein, a fragment of an immunoglobulin coding sequence may be modified according to the methods described herein. Suitable fragments may include the coding region for one or more of, e.g., a heavy chain, a light chain, and/or fragments thereof such as the constant region of a heavy chain (CH1, CH2 and/or CH3) and/or or the constant region of a light chain. Alternatively, variable regions of a heavy chain or light chain may be modified. Examples of such fragments include, without limitation:

| | Position (nt) | | |
|---|---|---|---|
| Region | SEQ ID NO: 14 | SED ID NO: 15 | SEQ ID NO: 18 |
| VH (variable region heavy chain) | 1365-1750 | 1371-1756 | 1320-1705 |
| CH1 (constant region 1 heavy chain) | 1752-2027 | 1758-2033 | 1707-1982 |
| HCH23 (constant region 2-3 heavy chain) | 2028-2716 | 2034-2722 | 1983-2671 |
| CL (constant region light chain) | 3111-3415 | 3181-3485 | 3130-3434 |
| 3nbc117 light | 2798-3095 | 2854-3165 | 2803-3114 |

Still other immunoglobulin coding regions may be modified.

Expression Cassette

For use in producing a viral vector (e.g., a recombinant (r) AAV), the expression cassette can be carried on any suitable vector, e.g., a plasmid, which is delivered to a packaging host cell. "Suitable regulatory sequences" refer to nucleotide sequences located upstream (5' non-coding sequences), within, or downstream (3' non-coding sequences) of a coding sequence, and which influence the transcription, RNA processing or stability, or translation of the associated coding sequence. Regulatory sequences may include promoters, translation leader sequences, introns, polyadenylation recognition sequences, RNA processing sites, effector binding sites and stem-loop structures. Suitable transfection techniques and packaging host cells are known and/or can be readily designed by one of skill in the art.

Examples of constitutive promoters suitable for controlling expression of the transgenes include, but are not limited to chicken β-actin (CB) promoter, human cytomegalovirus (CMV) promoter, the early and late promoters of simian virus 40 (SV40), U6 promoter, metallothionein promoters, EF1α promoter, ubiquitin promoter, hypoxanthine phosphoribosyl transferase (HPRT) promoter, dihydrofolate reductase (DHFR) promoter (Scharfmann et al., Proc. Natl. Acad. Sci. USA 88:4626-4630 (1991), adenosine deaminase promoter, phosphoglycerol kinase (PGK) promoter, pyruvate kinase promoter phosphoglycerol mutase promoter, the β-actin promoter (Lai et al., Proc. Natl. Acad. Sci. USA 86: 10006-10010 (1989)), the long terminal repeats (LTR) of Moloney Leukemia Virus and other retroviruses, the thymidine kinase promoter of Herpes Simplex Virus and other constitutive promoters known to those of skill in the art. Examples of tissue- or cell-preferential promoters suitable for use in the present invention include, but are not limited to, endothelin-I (ET-I) and Flt-I, which are for endothelial cells, FoxJ1 (that targets ciliated cells), human thyroxine binding globulin (TBG) and alpha-1 anti-trypsin (A1AT) for liver, troponin and T (TnT) for heart, clara cell 10 (CC10), surfactant protein C (SPC) and FoxJ1 for heart; synapsin, tyrosine hydroxylase, CaMKII (Ca2+/calmodulin-dependent protein kinase) for central nervous system/brain, insulin and elastase-I for pancrease, Ap2 and adiponector for adipocyte, desmin and MHC for muscle, and VMD for retina. Still others are known in the art.

Inducible promoters suitable for controlling expression of the transgene include promoters responsive to exogenous agents (e.g., pharmacological agents) or to physiological cues. These response elements include, but are not limited to a hypoxia response element (HRE) that binds HIF-Iα and β, a metal-ion response element such as described by Mayo et al. (1982, Cell 29:99-108); Brinster et al. (1982, Nature 296:39-42) and Searle et al. (1985, Mol. Cell. Biol. 5:1480-1489); or a heat shock response element such as described by Nouer et al. (in: Heat Shock Response, ed. Nouer, L., CRC, Boca Raton, Fla., ppI67-220, 1991).

Examples of regulatable promoters which are ligand-dependent transcription factor complexes that may be used in the invention include, without limitation, members of the nuclear receptor superfamily activated by their respective ligands (e.g., glucocorticoid, estrogen, progestin, retinoid, ecdysone, and analogs and mimetics thereof) and rTTA activated by tetracycline. In one aspect of the invention, the gene switch is an EcR-based gene switch. Examples of such systems include, without limitation, the systems described in U.S. Pat. Nos. 6,258,603, 7,045,315, U.S. Published Patent Application Nos. 2006/0014711, 2007/0161086, and International Published Application No. WO 01/70816. Examples of chimeric ecdysone receptor systems are described in U.S. Pat. No. 7,091,038, U.S. Published Patent Application Nos. 2002/0110861, 2004/0033600, 2004/0096942, 2005/0266457, and 2006/0100416, and International Published Application Nos. WO 01/70816, WO 02/066612, WO 02/066613, WO 02/066614, WO 02/066615, WO 02/29075, and WO 2005/108617, each of which is incorporated by reference in its entirety. An example of a non-steroidal ecdysone agonist-regulated system is the RheoSwitch® Mammalian Inducible Expression System (New England Biolabs, Ipswich, Mass.).

Still other promoter systems may include response elements including but not limited to a tetracycline (tet) response element (such as described by Gossen & Bujard (1992, Proc. Natl. Acad. Sci. USA 89:5547-551); or a hormone response element such as described by Lee et al. (1981, Nature 294:228-232); Hynes et al. (1981, Proc. Natl. Acad. Sci. USA 78:2038-2042); Klock et al. (1987, Nature 329:734-736); and Israel & Kaufman (1989, Nucl. Acids Res. 17:2589-2604) and other inducible promoters known in the art. Using such promoters, expression of the neutralizing antibody construct can be controlled, for example, by the Tet-on/off system (Gossen et al., 1995, Science 268:1766-9; Gossen et al., 1992, Proc. Natl. Acad. Sci. USA., 89(12): 5547-51); the TetR-KRAB system (Urrutia R., 2003, Genome Biol., 4(10):231; Deuschle U et al., 1995, Mol Cell Biol. (4):1907-14); the mifepristone (RU486) regulatable system (Geneswitch; Wang Y et al., 1994, Proc. Natl. Acad. Sci. USA., 91(17):8180-4; Schillinger et al., 2005, Proc. Natl. Acad. Sci. USA. 102(39):13789-94); the humanized tamoxifen-dep regulatable system (Roscilli et al., 2002, Mol. Ther. 6(5):653-63). In one system, a gene switch is based on heterodimerization of FK506 binding protein (FKBP) with FKBP rapamycin associated protein (FRAP) and is regulated through rapamycin or its non-immunosuppressive analogs. Examples of such systems, include, without limitation, the ARGENT™ Transcriptional Technology (ARIAD Pharmaceuticals, Cambridge, Mass.) and the systems described in U.S. Pat. Nos. 6,015,709, 6,117,680, 6,479,653, 6,187,757, and 6,649,595, U.S. Publication No. 2002/0173474, U.S. Publication No. 200910100535, U.S. Pat. Nos. 5,834,266, 7,109,317, 7,485,441, 5,830,462, 5,869,337, 5,871,753, 6,011,018, 6,043,082, 6,046,047, 6,063,625, 6,140,120, 6,165,787, 6,972,193, 6,326,166, 7,008,780, 6,133,456, 6,150,527, 6,506,379, 6,258,823, 6,693,189, 6,127,521, 6,150,137, 6,464,974, 6,509,152, 6,015,709, 6,117,680, 6,479,653, 6,187,757, 6,649,595, 6,984,635, 7,067,526, 7,196,192, 6,476,200, 6,492,106, WO 94/18347, WO 96/20951, WO 96/06097, WO 97/31898, WO 96/41865, WO 98/02441, WO 95/33052, WO 99110508, WO 99110510, WO 99/36553, WO 99/41258, WO 01114387, ARGENT™ Regulated Transcription Retrovirus Kit, Version 2.0 (9109102), and ARGENT™ Regulated Transcription Plasmid Kit, Version 2.0 (9109/02), each of which is incorporated herein by reference in its entirety. The Ariad system is designed to be induced by rapamycin and analogs thereof referred to as "rapalogs". Examples of suitable rapamycins are provided in the documents listed above in connection with the description of the ARGENT™ system. In one embodiment, the molecule is rapamycin [e.g., marketed as Rapamune™ by Pfizer]. In another embodiment, a rapalog known as AP21967 [ARIAD] is used. Examples of these dimerizer molecules that can be used in the present invention include, but are not limited to rapamycin, FK506, FK1012 (a homodimer of FK506), rapamycin analogs ("rapalogs") which are readily prepared by chemical modifications of the natural product to add a "bump" that reduces or eliminates affinity for endogenous FKBP and/or FRAP. Examples of rapalogs include, but are not limited to such as AP26113 (Ariad), AP1510 (Amara, J. F., et al., 1997, Proc Natl Acad Sci USA, 94(20): 10618-23) AP22660, AP22594, AP21370, AP22594, AP23054, AP1855, AP1856, AP1701, AP1861, AP1692 and AP1889, with designed 'bumps' that minimize interactions with endogenous FKBP. Still other rapalogs may be selected, e.g., AP23573 [Merck].

In addition to the elements identified above for the expression cassette, the vector may also include conventional control elements which are operably linked to the coding sequence in a manner which permits transcription, translation and/or expression of the encoded product (e.g., a neutralizing antibody or a portion thereof) in a cell transfected with the plasmid vector or infected with the virus produced by the invention. As used herein, "operably linked" sequences include both expression control sequences that are contiguous with the gene of interest and expression control sequences that act in trans or at a distance to control the gene of interest.

The term "heterologous" when used with reference to a protein or a nucleic acid indicates that the protein or the nucleic acid comprises two or more sequences or subsequences which are not found in the same relationship to each other in nature. For instance, the nucleic acid is typically recombinantly produced, having two or more sequences from unrelated genes arranged to make a new functional nucleic acid. For example, in one embodiment, the nucleic acid has a promoter from one gene arranged to direct the expression of a coding sequence from a different gene. Thus, with reference to the coding sequence, the promoter is heterologous.

As exemplified herein, the vector may be a plasmid and/or a recombinant AAV viral vector. However, it will be readily understood that the expression cassettes containing nucleic acid sequences generated as described herein may be engineered onto any number of vectors including, other viral vectors such as baculovirus, adenovirus, retroviruses, and the like. Methods for generating and isolating AAVs suitable for use as vectors are known in the art. See generally, e.g., Grieger & Samulski, 2005, "Adeno-associated virus as a gene therapy vector: Vector development, production and clinical applications," *Adv. Biochem. Engin/Biotechnol.* 99: 119-145; Buning et al., 2008, "Recent developments in adeno-associated virus vector technology," *J Gene Med.* 10:717-733; and the references cited below, each of which is incorporated herein by reference in its entirety.

An adeno-associated virus (AAV) viral vector is an AAV DNase-resistant particle having an AAV protein capsid into which is packaged nucleic acid sequences for delivery to target cells. In one embodiment, the AAV sequences on the expression cassette comprise only minimal AAV sequences to avoid the risk of replication. In one embodiment, the minimal AAV sequences include the AAV inverted terminal repeat sequences (ITR). In one embodiment, the 5' ITR and the 3' ITR are the minimal AAV sequences required in cis in order to express a transgene encoded by a nucleic acid sequence packaged in the AAV capsid. Typically, the ITRs flank the modified coding sequence for a selected gene product. In one embodiment, the AAV vector contains AAV 5' and 3' ITRs, which may be of the same AAV origin as the capsid, or which may be of a different AAV origin (to produce an AAV pseudotype). In one embodiment, the coding sequences for the replication (rep) and/or capsid (cap) are removed from the AAV genome and supplied in trans or by a packaging cell line in order to generate the AAV vector.

An AAV capsid is composed of 60 capsid protein subunits, VP1, VP2, and VP3, that are arranged in an icosahedral symmetry in a ratio of approximately 1:1:10 to 1:1:20, depending upon the selected AAV. The capsid type does play a role in tissue specificity. The sequences of a variety of AAV have been described, as have methods of generating vectors having the AAV capsids. Examples of AAV which may be selected as sources for capsids of AAV viral vectors (DNase resistant viral particles) include, e.g., AAV1, AAV2, AAV3, AAV4, AAV5, AAV6, AAV6.2, AAV7, AAV8, AAV9, rh10, AAVrh64R1, AAVrh64R2, rh8 [See, e.g., US Published Patent Application No. 2007-0036760-A1; US Published Patent Application No. 2009-0197338-A1; EP 1310571]. See also, WO 2003/042397 (AAV7 and other simian AAV), U.S. Pat. Nos. 7,790,449 and 7,282,199 (AAV8), WO 2005/033321 and U.S. Pat. No. 7,906,111 (AAV9), and WO 2006/110689]. As yet to be discovered AAV, or a recombinant AAV based thereon, may be used as a source for the AAV capsid. These documents also describe other AAV which may be selected for generating AAV and are incorporated by reference. In some embodiments, an AAV cap for use in the viral vector can be generated by mutagenesis (i.e., by insertions, deletions, or substitutions) of one of the aforementioned AAV Caps or its encoding nucleic acid. In some embodiments, the AAV capsid is chimeric, comprising domains from two or three or four or more of the aforementioned AAV capsid proteins. In some embodiments, the AAV capsid is a mosaic of Vp1, Vp2, and Vp3 monomers from two or three different AAVs or recombinant AAVs. In some embodiments, an rAAV composition comprises more than one of the aforementioned Caps.

For packaging a transgene into virions, the ITRs are the only AAV components required in cis in the same construct as the transgene. The cap and rep genes can be supplied in trans. Accordingly, DNA constructs can be designed so that the AAV ITRs flank the coding sequence, thus defining the region to be amplified and packaged—the only design constraint being the upper limit of the size of the DNA to be packaged (approximately 4.5 kb). Adeno-associated virus engineering and design choices that can be used to save space are known in the art.

The components required to be cultured in the host cell to package an AAV minigene in an AAV capsid may be provided to the host cell in trans. Alternatively, any one or more of the required components (e g., minigene, rep sequences, cap sequences, and/or helper functions) may be provided by a stable host cell which has been engineered to contain one or more of the required components using methods known to those of skill in the art. Most suitably, such a stable host cell will contain the required component (s) under the control of an inducible promoter. However, the required component(s) may be under the control of a constitutive promoter. Examples of suitable inducible and constitutive promoters are provided herein, in the discussion of regulatory elements suitable for use with the transgene. In still another alternative, a selected stable host cell may contain selected component(s) under the control of a constitutive promoter and other selected component(s) under the control of one or more inducible promoters. For example, a stable host cell may be generated which is derived from 293 cells (which contain E1 helper functions under the control of a constitutive promoter), but which contains the rep and/or cap proteins under the control of inducible promoters. Still other stable host cells may be generated by one of skill in the art.

The minigene, rep sequences, cap sequences, and helper functions required for producing the rAAV of the invention may be delivered to the packaging host cell in the form of any genetic element which transfer the sequences carried thereon. The selected genetic element may be delivered by any suitable method, including those described herein. The methods used to construct any embodiment of this invention are known to those with skill in nucleic acid manipulation and include genetic engineering, recombinant engineering, and synthetic techniques. See, e.g., Sambrook et al, Molecular Cloning: A Laboratory Manual, Cold Spring Harbor Press, Cold Spring Harbor, N.Y. Similarly, methods of generating rAAV virions are well known and the selection of a suitable method is not a limitation on the present invention. See, e.g., K. Fisher et al, (1993) *J Virol.*, 70:520-532 and U.S. Pat. No. 5,478,745.

Unless otherwise specified, the AAV ITRs, and other selected AAV components described herein, may be readily selected from among any AAV. Further, more than one AAV source may provide elements to an AAV vector. For example, as described above, a pseudotyped AAV may contain ITRs from a source which differs from the source of the AAV capsid. Additionally or alternatively, a chimeric AAV capsid may be utilized. Still other AAV components may be selected. Sources of such AAV sequences are described herein and may also be isolated or obtained from academic, commercial, or public sources (e.g., the American Type Culture Collection, Manassas, Va.). Alternatively, the AAV sequences may be obtained through synthetic or other suitable means by reference to published sequences such as are available in the literature or in databases such as, e.g., GenBank®, PubMed®, or the like.

In one embodiment, the pharmaceutical compositions include a single vector containing an expression cassette comprising a modified ORF as described above. In another embodiment, the composition includes more than one vector, each containing one or more expression cassettes. Each expression cassette comprises a modified ORF. In another embodiment, the composition includes multiple viral vectors, each containing one or more expression cassettes as described herein.

The AAV vectors may be suspended in a physiologically compatible carrier for administration to a human or non-human mammalian patient. Suitable carriers may be readily selected by one of skill in the art in view of the route of delivery. For example, one suitable carrier includes saline, which may be formulated with a variety of buffering solutions (e.g., phosphate buffered saline). Other exemplary carriers include sterile saline, lactose, sucrose, calcium phosphate, gelatin, dextran, agar, pectin, peanut oil, sesame oil, and water. The selection of the carrier is not a limitation of the present invention. Optionally, the compositions of the invention may contain, in addition to the rAAV and carrier (s), other conventional pharmaceutical ingredients, such as preservatives, or chemical stabilizers. Suitable exemplary preservatives include chlorobutanol, potassium sorbate, sorbic acid, sulfur dioxide, propyl gallate, the parabens, ethyl vanillin, glycerin, phenol, and parachlorophenol. Suitable chemical stabilizers include gelatin and albumin.

The following examples are illustrative only and are not a limitation on the invention described herein.

EXAMPLE 1

Modification of Open Reading Frame (ORF) of Anti-HIV Antibody

The ORF of an anti-SIV antibody which had previously been shown to express at unusually high levels in liver as compared to other tissue types and other ORFs. From this observation, the study described herein was designed. Using an anti-HIV antibody coding sequence as a base sequence for proof-of-principal, 12 alternative synonymous codon modified ORFs were generated using different methods by DNA2.0 [Menlo Park, Calif.]. These sequences are provided in FIG. 1, which is incorporated by reference herein. The ORF for the anti-HIV antibody which served as the base ORF in the study described herein had previously been altered in our laboratory and was observed to preferentially express at very high levels in liver. The base sequence, which served as the control, was modified using the coding frequencies for human, as provided by kazusa.or.jp/codon/cgi-bin/showcodon.cgi?species=9606 (Table 2). Additional modifications were made by hand to remove restriction sites and other non-desirable features (e.g., CpG islands).

The following Table 18 provides a comparison of the identity of the modified ORFs generated and studied herein. The sequences of the ORFs are contained in SEQ ID NOs: 1-12 and 30. An alignment of the sequences is provided in FIGS. 1A-1J.

TABLE 18

Comparison of Identity of Modified ORFs

|         | ORF1 | ORFBASE | ORFIAM | ORFIAU | ORF11 | ORF2 | ORF26 | ORF28 | ORF30 | ORF35 | ORF42 | ORF39 | ORF40 |
|---------|------|---------|--------|--------|-------|------|-------|-------|-------|-------|-------|-------|-------|
| ORF1    |      | 77      | 79     | 79     | 77    | 76   | 77    | 77    | 75    | 76    | 76    | 76    | 77    |
| ORFBASE |      |         | 80     | 80     | 75    | 75   | 76    | 76    | 76    | 75    | 75    | 75    | 76    |
| ORFIAM  |      |         |        | 85     | 78    | 75   | 78    | 78    | 76    | 76    | 76    | 76    | 78    |
| ORFIAU  |      |         |        |        | 79    | 76   | 77    | 77    | 76    | 76    | 76    | 76    | 78    |
| ORF11   |      |         |        |        |       | 76   | 75    | 76    | 76    | 77    | 75    | 76    | 77    |
| ORF2    |      |         |        |        |       |      | 77    | 76    | 76    | 74    | 74    | 76    | 75    |
| ORF26   |      |         |        |        |       |      |       | 77    | 74    | 77    | 76    | 76    | 76    |
| ORF28   |      |         |        |        |       |      |       |       | 77    | 76    | 75    | 75    | 76    |
| ORF30   |      |         |        |        |       |      |       |       |       | 75    | 74    | 76    | 75    |
| ORF35   |      |         |        |        |       |      |       |       |       |       | 77    | 76    | 75    |
| ORF42   |      |         |        |        |       |      |       |       |       |       |       | 76    | 76    |
| ORF39   |      |         |        |        |       |      |       |       |       |       |       |       | 76    |
| ORF40   |      |         |        |        |       |      |       |       |       |       |       |       |       |

These ORFs were engineered into a plasmid construct (F2A) and expression levels were assessed in HEK 293 cells. The sequences of these plasmids are provided in the attached FIG. 5 (SEQ ID NOs: 13-29), which is incorporated by reference herein.

The data in Table 19 provides the results on an in vitro assessment of the plasmid constructs in HEK 293 cells. As shown in FIG. 2, expression of the gene under the control of human cytomegalovirus promoter (CMV(first bar)) or a CMV promoter with a commercially available enhancer (Promega intron, PI)(third bar) were assessed in HEK 293 cells at 72 hours post-transfection. Cells were transfected with $2\times10^{10}$ GC/per mouse and expression levels were assessed at day 50. The pZac is an empty vector carrying only the promoter and enhancer. F2A is a plasmid containing the "base" or parental anti-HIV antibody ORF under the control of the CMV-IE promoter. Mini-C is similar to the F2a, in that it contains the "base" or parental anti-HIV antibody ORF under the control of the CMV-IE promoter, but it further contains a 5'UTR.

Protein levels determined by ELISA for 2-3 transfections (HEK) approximately 72 hours (three days) after the last transfection.

TABLE 19

| | | ng/ml -- 72 hours post transfection -- serum free supernatant | | | |
|---|---|---|---|---|---|
| | | HEK293-CMV | | HEK293-CMV-PI | |
| NAME | DESCRIPTION | AVE | STDEV | AVE | STDEV |
| pZac | empty vector CMV-PI | 1.33 | 1.89 | 0 | 0 |
| F2A | base vector (BV) CMV-PI | | | 593.11 | 59.61 |
| mini C | BV (CMV-PI) + 5'UTR | | | 568.19 | 24.16 |
| ORF 1 | ORF 1 | 233.11 | 46.55 | 377.71 | 125.58 |
| ORF 2 | ORF 2 | 151.37 | 18.73 | 394.76 | 31.7 |
| ORF 11 | ORF 11 | 54.44 | 0.95 | 451.54 | 42.98 |
| ORF26 | ORF26 | 508.44 | 316.51 | 391.6 | 5.69 |
| ORF 28 | ORF 28 | 19.15 | 0.48 | 245.54 | 66.1 |
| ORF 30 | ORF 30 | 12.55 | 1.05 | 188.01 | 30.46 |
| ORF 35 | ORF 35 | 183.19 | 17.72 | 557.51 | 7.94 |
| ORF 39 | ORF 39 | 40.4 | 8.45 | 262.2 | 20.99 |
| ORF 40 | ORF 40 | 114.43 | 15.01 | 368.84 | 92.69 |

TABLE 19-continued

| | | ng/ml -- 72 hours post transfection -- serum free supernatant | | | |
|---|---|---|---|---|---|
| | | HEK293-CMV | | HEK293-CMV-PI | |
| NAME | DESCRIPTION | AVE | STDEV | AVE | STDEV |
| ORF 42 | ORF 42 | 66.22 | 8.53 | 335.76 | 62.74 |
| IA U | IA USAGE | 537.17 | 66.15 | 397.79 | 159.8 |
| IAM U | IAM USAGE | 463.23 | 60.76 | 135.78 | 66.53 |

Open squares indicate that the study was not done to date.

As shown in Table 19, in the 293 cells, there were significant differences in expression levels for all modified genes expressed from the CMV promoter, with the ORF26, IA U and IAM U constructs showing the strongest expression levels. There were also significant differences in in vitro expression levels for all modified genes expressed under the CMV promoter with the enhancer (CMV-IE). These data show that none of the modified constructs provide expression levels significantly higher than the base vector. With the promoter-enhancer, ORF 35 show the strongest expression levels followed by ORF11.

The plasmids carrying the genes described above expressed under the CMV-PI promoter/enhancer were packaged into AAV8 capsids using published methods and the resulting AAV.CMV-IE.modified genes were expressed in a non-secretory tissue (muscle) and a secretory tissue (lung). Except where otherwise specified, animals (RAG KO) were delivered $2\times10^{10}$ genomic particles/mL. For those animals injected im, serum levels of protein were determined on day 50 post-injection by ELISA (FIG. 2 (middle bars)). For those animals for which the constructs were delivered by nasal installation, protein levels in bronchial lavage were determined by ELISA seven days following installation. Table 20 provides the results.

TABLE 20

| | | μg/ml - SERUM ROA: INTRAMUSCULAR | | | | ng/ml -- BRONCHIAL LAVAGE ROA: INTRANASAL INSTILLATION | |
|---|---|---|---|---|---|---|---|
| NAME | DESCRIPTION | AVE | STDEV | AVE | STDEV | AVE | STDEV |
| F2A | base vector (BV) CMV-PI | 23.76 | 5.10 | **21.94 | 10.45 | | |
| mini C | BV(CMV-PI) + 5'UTR | 76.31 | 19.71 | **63.59 | 21.35 | 24.79 | 0.12 |
| ORF 1 | ORF 1 | *21.34 | *0.94 | | | 8.77 | 0.01 |
| ORF 2 | ORF 2 | 20.95 | 2.71 | | | 13.58 | 5.82 |
| ORF 11 | ORF 11 | 23.00 | 4.58 | | | | |
| ORF26 | ORF26 | 48.98 | 16.75 | | | | |
| ORF 28 | ORF 28 | 34.14 | 7.97 | | | 6.69 | 0.97 |
| ORF 30 | ORF 30 | 46.26 | 22.32 | | | 3.15 | 1.45 |
| ORF 35 | ORF 35 | 115.68 | 64.61 | | | 6.31 | 1.03 |
| ORF 39 | ORF 39 | 139.30 | 60.16 | | | 10.07 | 2.09 |
| ORF 40 | ORF 40 | *46.54 | *20.12 | | | 14.73 | 1.76 |
| ORF 42 | ORF 42 | | | **15.24 | 3.69 | | |
| IA U | IA USAGE | | | **48.82 | 2.29 | 18.04 | 1.55 |
| IAM U | IAM USAGE | | | **42.60 | 14.18 | 7.04 | 1.1 |

Open squares indicate that the study was not done to date.

*Vector $1\times10^{10}$

**Day 35, rather than day 50

With the exception of AAV8 vectors carrying ORF2 and ORF11 which were approximately the same as the parental gene, the tested constructs outperformed the vector expressing the parental gene in muscle. The muscle expression levels observed for the ORF1 vector was about the same as for the vector carrying the parental gene, but at half the dose. The highest expression levels for muscle were observed for ORF35 and ORF39, which were both approximately four times the expression level of the parental gene.

In respiratory epithelium, the expression levels observed for vector carrying the parental gene were higher than those for the vectors carrying the other modified genes. Significant variations in expression levels were observed, with the vectors carrying IA U, ORF40 and ORF2 expressing at higher levels that the other vectors with the exception of the vector carrying the parental gene.

These observations demonstrate that in vitro assessment of codon optimization is not predictive of expression levels in all tissues. As seen above, in the HEK 293 cells, none of the codon modified genes tested expressed at a higher level than the parental gene. It is possible that the derivation of the 293 cell line from human embryonic kidney cells would be predictive of expression levels in kidney. While in this example, the results observed in 293 cells are consistent with the expression levels observed in lung, significantly different expression results were observed in muscle. This suggests that there are tissue-specific codon patterns and that one can select an algorithmic schema for modification of a selected gene which will preferentially enhance its expression in a selected target tissue.

EXAMPLE 2

A further study was conducted using, $2\times10^{10}$ GC/mouse of AAV8 containing modified transgenes were injected IV for liver expression into RAG KO mice (n=5 mice per construct) as described above. Expression of circulating antibody in serum was monitored by ELISA for 56 days. The results are shown the following Table 21 and demonstrate significant differences in expression in liver between the modified open reading frames. For example, the ORF2, ORF11, ORF26, ORF35 and IAU constructs consistently expressed at a higher level in liver than the 5' UTR construct, which served as a control. ORF39 expressed slightly higher in liver than the control at longer time periods, while ORF 42, ORF28 and ORF1 expressed at a similar level to the control. The IAM construct showed consistently low levels of expression in liver.

TABLE 21

| | ORF1 | | ORF2 | | ORF11 | |
|---|---|---|---|---|---|---|
| | Average | stdev. | average | stdev. | average | stdev. |
| Day 0 | 0.00 | | 0.00 | | 0.00 | |
| Day 7 | 46.82 | 18.21 | 215.47 | 106.95 | 222.35 | 54.94 |
| Day 14 | 118.62 | 67.49 | 587.67 | 310.10 | 554.69 | 143.95 |
| Day 21 | 186.39 | 96.52 | 692.40 | 370.28 | 653.54 | 138.25 |
| Day 28 | 160.17 | 86.25 | 930.70 | 463.55 | 903.50 | 269.02 |
| Day 35 | 170.25 | 93.65 | 636.50 | 270.23 | 745.29 | 223.72 |
| Day 42 | 227.29 | 105.22 | 918.11 | 406.00 | 855.00 | 325.39 |
| Day 49 | 158.40 | 98.97 | 544.80 | 277.30 | 776.80 | 244.22 |
| Day 56 | 169.89 | 101.71 | 670.25 | 267.16 | 723.00 | 239.23 |

| | ORF26 | | ORF28 | | ORF35 | | ORF39 | |
|---|---|---|---|---|---|---|---|---|
| | Average | stdev. | average | stdev. | average | stdev. | average | stdev. |
| Day 0 | 0.00 | | 0.00 | | 0.00 | | 0.00 | |
| Day 7 | 175.90 | 40.07 | 35.63 | 26.45 | 77.92 | 14.59 | 67.62 | 4.14 |
| Day 14 | 469.47 | 69.45 | 96.84 | 76.09 | 153.03 | 38.47 | 165.09 | 42.15 |
| Day 21 | 537.23 | 25.46 | 132.45 | 94.81 | 164.75 | 41.16 | 164.05 | 49.03 |
| Day 28 | 748.77 | 168.21 | 181.26 | 130.79 | 321.21 | 135.05 | 352.53 | 79.62 |
| Day 35 | 561.00 | 112.60 | 165.43 | 100.77 | 207.27 | 67.00 | 181.73 | 59.40 |
| Day 42 | 722.25 | 83.83 | 135.64 | 93.70 | 173.80 | 64.06 | 146.20 | 50.80 |
| Day 49 | 505.40 | 145.27 | 135.82 | 90.23 | 147.54 | 46.28 | 128.63 | 47.71 |
| Day 56 | 434.22 | 105.62 | 153.39 | 115.28 | 160.80 | 52.88 | 149.05 | 47.03 |

| | ORF40 | | ORF42 | | IAU | | IAM | | 5'UTR (mini C) (Control) | |
|---|---|---|---|---|---|---|---|---|---|---|
| | Average | stdev. | average | stdev. | average | stdev. | average | stdev. | average | stdev. |
| Day 0 | 0.00 | | 0.00 | | 0.00 | | 0.00 | | 0.00 | |
| Day 7 | 24.27 | 9.77 | 39.76 | 21.52 | 97.67 | 48.61 | 12.20 | 4.71 | 69.92 | 50.36 |
| Day 14 | 51.19 | 20.44 | 95.10 | 49.91 | 265.20 | 108.20 | 16.36 | 8.31 | 104.01 | 77.79 |
| Day 21 | 62.95 | 25.19 | 88.78 | 49.39 | 330.53 | 162.77 | 15.54 | 6.32 | 104.33 | 64.62 |
| Day 28 | 62.13 | 23.99 | 121.84 | 63.78 | 485.02 | 212.38 | 16.88 | 7.47 | 178.63 | 98.22 |
| Day 35 | 53.33 | 23.81 | 141.57 | 78.12 | 303.62 | 112.68 | 11.24 | 5.86 | 108.76 | 61.08 |
| Day 42 | 60.89 | 27.56 | 92.60 | 56.49 | 369.47 | 144.21 | 10.88 | 5.07 | 107.73 | 44.34 |
| Day 49 | 53.40 | 23.19 | 96.15 | 61.31 | 320.29 | 164.55 | 16.89 | 8.70 | 118.86 | 53.48 |
| Day 56 | 53.47 | 21.99 | 105.53 | 64.25 | 377.35 | 158.09 | 12.24 | 6.49 | 93.13 | 37.43 |

EXAMPLE 3

Figure 6:
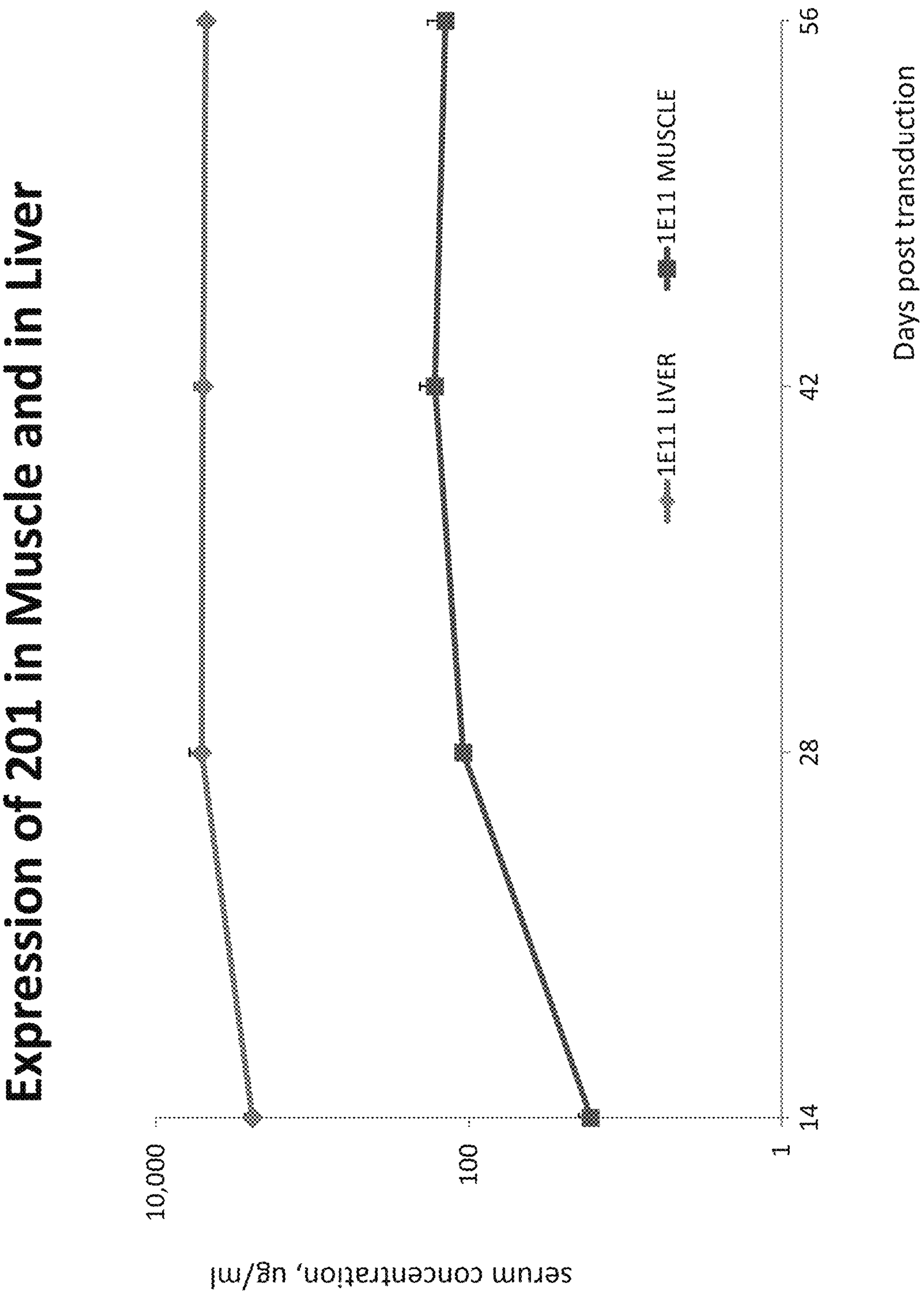
FIG. 6 is a graph showing the expression of the 201 construct in muscle (bottom line) and liver (top line) of mice versus time post transduction. 5 mice per group were injected at the indicated dosages ($1\times10^{10}$ GC/per mouse or $1\times10^{11}$ GC/mouse). Concentrations were determined by ELISA. Capture accomplished by binding to SIV mac251 gp120; detection by Fc chain antibody (IgG1) conjugated with biotin, followed by HRP-streptavidin.

AAV8 containing one of two modified constructs, 10A (SEQ ID NO: 32) or 201 (SEQ ID NO: 31), were injected into mice as described above ($1\times10^{11}$ GC/mouse). Expression in muscle and liver was determined by ELISA. FIG. 6 is a graph showing the expression of the 201 construct in muscle (bottom line) and liver (top line) of mice versus time post transduction. 5 mice per group were injected at the indicated dosages ($1\times10^{10}$ or $1\times10^{11}$ GC/per mouse). Concentrations were determined by ELISA. Capture accomplished by binding to SIV mac251 gp120; detection by Fc chain antibody (IgG1) conjugated with biotin, followed by HRP-streptavidin.

Figure 7:
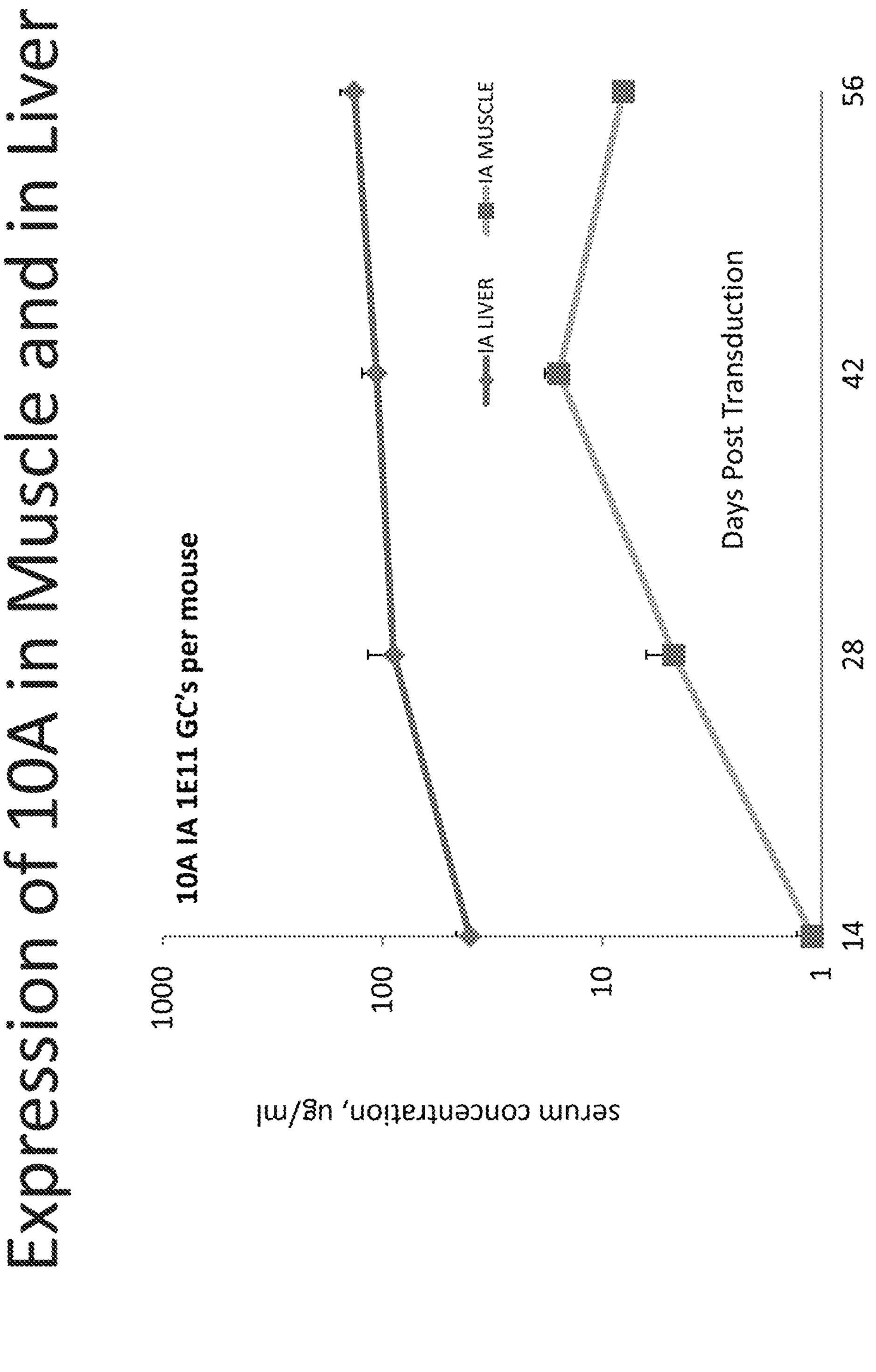
FIG. 7 is a graph showing the expression of the 10A construct in muscle (bottom line) and liver (top line) of mice versus time post transduction. 5 mice per group were injected at the dosage of $1\times10^{11}$ GC/per mouse. CMV promoter was used for IM injections; TBG promoter was used for IV injections.

FIG. 7 is a graph showing the expression of the 10A construct in muscle (bottom line) and liver (top line) of mice versus time post transduction. 5 mice per group were injected at the dosage of $1\times10^{11}$ GC/per mouse. CMV promoter was used for IM injections; TBG promoter was used for IV injections.

A comparison of these two figures shows that, in both muscle and liver, the 201 construct expresses levels greater than 10 fold as compared to the 10A construct.

Figure 8:
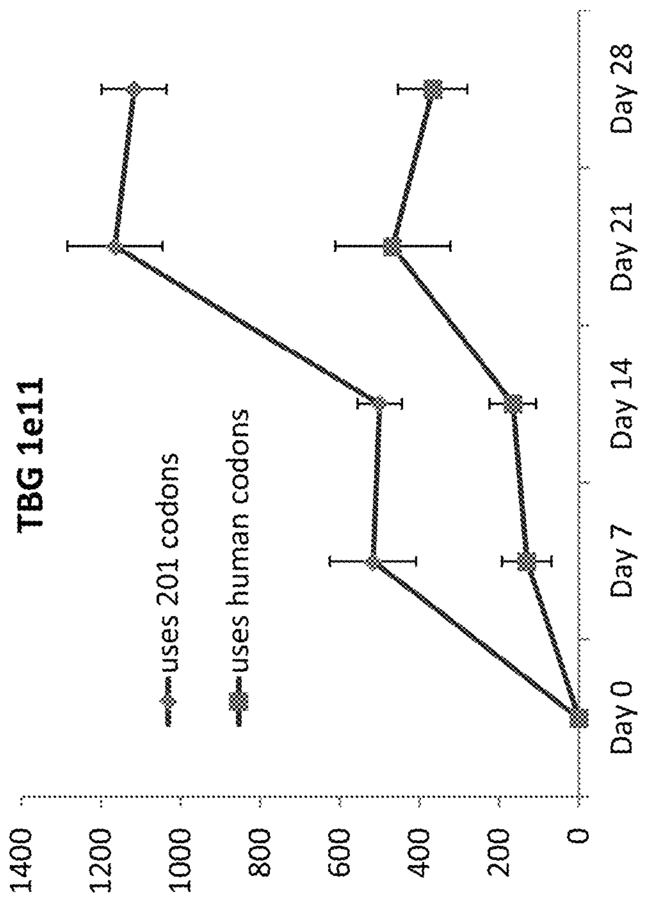
FIG. 8 is a graph demonstrating the effect of variable codon usage on expression of 3bnc117 in liver. The 3bnc117 antibody coding sequence was optimized using the codon frequency of human (Table 2)(top line) or 201 (Table 16)(bottom line). Expression is shown as μg/mL serum. The TBG promoter construct was used at a dosage of $1\times10^{11}$ GC/per mouse.

The 3bnc117 antibody coding sequence was optimized using the codon frequency of human (Table 2) or 201 (Table 16) manually. The codon frequencies for the final sequences are shown in tables 22 (human) and 23 (201) below. AAV8 constructs utilizing the TBM promoter and incorporating 3bnC117/hum (SEQ ID NO: 34) or 3bnC117/201 (SEQ ID NO: 33) sequence were injected intravenously into mice at a dosage of $1\times10^{11}$ GC/per mouse. Expression in liver is shown in FIG. 8. Expression of the 3bnC117/201 in liver was ~2.5 to over 3 times greater than expression using the human codon frequency optimized sequence.

TABLE 22

| Sequence | Codon (frequency: per thousand) | | | | | | | |
|---|---|---|---|---|---|---|---|---|
| 3bnC117/HUM | UUU | 14.3 | UCU | 14.3 | UAU | 14.3 | UGU | 4.1 |
| | UUC | 20.4 | UCC | 22.4 | UAC | 28.5 | UGC | 18.3 |
| | UUA | 4.1 | UCA | 12.2 | UAA | 0 | UGA | 0 |
| | UUG | 6.1 | UCG | 8.1 | UAG | 0 | UGG | 26.5 |
| | CUU | 6.1 | CCU | 14.3 | CAU | 4.1 | CGU | 8.1 |
| | CUC | 14.3 | CCC | 24.4 | CAC | 12.2 | CGC | 2 |
| | CUA | 4.1 | CCA | 22.4 | CAA | 12.2 | CGA | 10.2 |
| | CUG | 42.8 | CCG | 6.1 | CAG | 46.8 | CGG | 10.2 |
| | AUU | 8.1 | ACU | 8.1 | AAU | 14.3 | AGU | 10.2 |
| | AUC | 18.3 | ACC | 34.6 | AAC | 28.5 | AGC | 32.6 |
| | AUA | 0 | ACA | 14.3 | AAA | 20.4 | AGA | 14.3 |
| | AUG | 12.2 | ACG | 8.1 | AAG | 34.6 | AGG | 4.1 |
| | GUU | 2 | GCU | 2 | GAU | 12.2 | GGU | 4.1 |
| | GUC | 40.7 | GCC | 20.4 | GAC | 36.7 | GGC | 26.5 |
| | GUA | 2 | GCA | 18.3 | GAA | 14.3 | GGA | 28.5 |
| | GUG | 36.7 | GCG | 8.1 | GAG | 26.5 | GGG | 24.4 |

TABLE 23

| Sequence | Codon (frequency: per thousand) | | | | | | | |
|---|---|---|---|---|---|---|---|---|
| 3bnC117/201 | UUU | 6.1 | UCU | 6.1 | UAU | 6.1 | UGU | 10.2 |
| | UUC | 32.7 | UCC | 20.4 | UAC | 34.7 | UGC | 12.2 |
| | UUA | 0 | UCA | 12.2 | UAA | 0 | UGA | 0 |
| | UUG | 0 | UCG | 2 | UAG | 0 | UGG | 28.6 |
| | CUU | 0 | CCU | 18.4 | CAU | 4.1 | CGU | 2 |
| | CUC | 0 | CCC | 20.4 | CAC | 12.2 | CGC | 4.1 |
| | CUA | 0 | CCA | 28.6 | CAA | 0 | CGA | 4.1 |
| | CUG | 75.5 | CCG | 0 | CAG | 59.2 | CGG | 24.5 |
| | AUU | 6.1 | ACU | 12.2 | AAU | 8.2 | AGU | 8.2 |
| | AUC | 18.4 | ACC | 32.7 | AAC | 32.7 | AGC | 46.9 |
| | AUA | 0 | ACA | 16.3 | AAA | 18.4 | AGA | 4.1 |
| | AUG | 10.2 | ACG | 2 | AAG | 38.8 | AGG | 8.2 |
| | GUU | 0 | GCU | 4.1 | GAU | 34.7 | GGU | 0 |
| | GUC | 18.4 | GCC | 34.7 | GAC | 14.3 | GGC | 28.6 |
| | GUA | 0 | GCA | 4.1 | GAA | 12.2 | GGA | 44.9 |
| | GUG | 67.3 | GCG | 2 | GAG | 30.6 | GGG | 16.3 |

Table for Free Text in Feature <220>

| SEQ ID NO: | 221 | <220><223> Feature |
|---|---|---|
| 1 | Artificial sequence | synthetic sequence |
| 2 | Artificial sequence | synthetic sequence |
| 3 | Artificial sequence | synthetic sequence |
| 4 | Artificial sequence | synthetic sequence |
| 5 | Artificial sequence | synthetic sequence |
| 6 | Artificial sequence | synthetic sequence |
| 7 | Artificial sequence | synthetic sequence |
| 8 | Artificial sequence | synthetic sequence |
| 9 | Artificial sequence | synthetic sequence |
| 10 | Artificial sequence | synthetic sequence |
| 11 | Artificial sequence | synthetic sequence |
| 12 | Artificial sequence | synthetic sequence |
| 13 | Artificial sequence | synthetic sequence |
| 14 | Artificial sequence | synthetic sequence |
| 15 | Artificial sequence | synthetic sequence |
| 16 | Artificial sequence | synthetic sequence |
| 17 | Artificial sequence | synthetic sequence |
| 18 | Artificial sequence | synthetic sequence |
| 19 | Artificial sequence | synthetic sequence |
| 20 | Artificial sequence | synthetic sequence |
| 21 | Artificial sequence | synthetic sequence |
| 22 | Artificial sequence | synthetic sequence |
| 23 | Artificial sequence | synthetic sequence |
| 24 | Artificial sequence | synthetic sequence |
| 25 | Artificial sequence | synthetic sequence |
| 26 | Artificial sequence | synthetic sequence |
| 27 | Artificial sequence | synthetic sequence |
| 28 | Artificial sequence | synthetic sequence |
| 29 | Artificial sequence | synthetic sequence |
| 30 | Artificial sequence | synthetic sequence |
| 31 | Artificial sequence | synthetic sequence |
| 32 | Artificial sequence | synthetic sequence |
| 33 | Artificial sequence | synthetic sequence |
| 34 | Artificial sequence | synthetic sequence |

This application contains sequences and a sequence listing, filed herewith as a text file named Z6688PCT_SEQ_LIST_042914_ST25. All publications, patents, and patent applications cited in this application are hereby incorporated by reference in their entireties as if each individual publication or patent application were specifically and individually indicated to be incorporated by reference. Although the foregoing invention has been described in some detail by way of illustration and example for purposes of clarity of understanding, it will be readily apparent to those of ordinary skill in the art in light of the teachings of this invention that certain changes and modifications can be made thereto without departing from the spirit or scope of the appended claims.

The invention claimed is:

1. A method for improving expression of a selected gene product in a selected type of target tissue within a selected species, said method comprising:

constructing an expression cassette comprising a coding sequence for a selected gene product generated with a selected codon frequency of Table 3, Table 4, Table 5, Table 6, Table 7, Table 8, Table 9, Table 10, Table 11, Table 12, Table 16, or Table 17.

2. The method according to claim 1, wherein the target tissue is selected from liver, skeletal muscle, and respiratory epithelium.

3. The method according to claim 1, wherein the target tissue is skeletal muscle and the selected codon frequency is Table 5, or Table 6.

4. The method according to claim 1, wherein the target tissue is liver and the selected codon frequency is Table 9, Table 10, or Table 11.

5. The method according to claims 1, wherein the target tissue is respiratory epithelium and the selected codon frequency is Table 16.

6. An expression cassette comprising an open reading frame (ORF) for an antibody construct under the control of regulatory sequences which direct expression of the product in a cell, which ORF has been modified to preferentially increase expression levels in target tissue cells, wherein the modified ORF is characterized by a triplet frequency of any one of Tables 3 to 12.

7. The expression cassette according to claim 6, wherein the cell is a liver cell.

8. A vector comprising the expression cassette according to claim 6.

9. The vector according to claim 8, wherein said vector is a recombinant adeno-associated virus (AAV) having an AAV capsid in which the expression cassette is packaged.

10. The vector according to claim 9, wherein the expression cassette comprises AAV inverted terminal repeat (ITR) sequences flanking the modified ORF.

11. The vector according to claim 10, wherein the ITRs are from a different AAV than the AAV donor for the capsid.

12. An expression cassette comprising an open reading frame (ORF) for an antibody construct under the control of regulatory sequences which direct expression of the product in cell, which ORF has been modified to preferentially increase expression levels in non-secretory cells, wherein the modified ORF is characterized by a triplet frequency of Table 16 or Table 17.

13. A pharmaceutical composition comprising a vector which comprises one or more expression cassettes of claim 12.

14. A composition comprising multiple vectors, wherein each vector comprises an expression cassette of claim 12.

15. An expression cassette comprising an open reading frame (ORF) for an antibody construct under the control of regulatory sequences which direct expression of the product in a muscle cell, which ORF has been modified to preferentially increase expression levels in muscle, wherein the modified ORF has a sequence selected from: ORF1 having a sequence of SEQ ID NO: 9, ORF 2 having a sequence of SEQ ID NO: 8, ORF11 having a sequence of SEQ ID NO: 7, ORF26 having a sequence of SEQ ID NO: 6, ORF 28 having a sequence of SEQ ID NO: 5, ORF 30 having a sequence of SEQ ID NO: 4, ORF35 having a sequence of SEQ ID NO: 3, ORF39 having a sequence of SEQ ID NO: 2, ORF40 having a sequence of SEQ ID NO: 1, ORF42 having a sequence of SEQ ID NO: 30, IA having a sequence of SEQ ID NO: 10, or IAM having a sequence of SEQ ID NO: 11.

16. The expression cassette according to claim 15, wherein the modified ORF is selected from ORF35 having a sequence of SEQ ID NO: 3 and ORF39 having a sequence of SEQ ID NO: 2.

17. The expression cassette according to claim 15, wherein the modified ORF is ORF40 having a sequence of SEQ ID NO: 1.

18. The expression cassette according to claim 15, wherein the modified ORF is selected from ORF26 having a sequence of SEQ ID NO: 6 and ORF30 having a sequence of SEQ ID NO: 4.

19. The expression cassette according to claim 15, wherein the modified ORF is selected from ORF2 having a sequence of SEQ ID NO: 8, ORF 11 having a sequence of SEQ ID NO: 7, ORF26 having a sequence of SEQ ID NO: 6, ORF35 having a sequence of SEQ ID NO: 3 and IA having a sequence of SEQ ID NO: 10.

20. A packaging host cell in culture comprising the expression cassette according to claim 15.

21. An rAAV production system comprising (a) a packaging host cell culture comprising the expression cassette according to claim 15, (b) AAV rep sequences, AAV cap sequence, and necessary helper functions required for producing the rAAV.

22. A recombinant AAV comprising an AAV8 capsid and an expression cassette for an anti-HIV antibody, wherein the expression cassette is adapted for expression in a selected target tissue, said expression cassette comprising a modified ORF having a sequence selected from the group consisting of ORF1 having a sequence of SEQ ID NO: 9, ORF 2 having a sequence of SEQ ID NO: 8, ORF11 having a sequence of SEQ ID NO: 7, ORF26 having a sequence of SEQ ID NO: 6, ORF 28 having a sequence of SEQ ID NO: 5, ORF 30 having a sequence of SEQ ID NO: 4, ORF35 having a sequence of SEQ ID NO: 3, ORF39 having a sequence of SEQ ID NO: 2, ORF40 having a sequence of SEQ ID NO: 1, ORF42 having a sequence of SEQ ID NO: 30, IA having a sequence of SEQ ID NO: 10, and IAM having a sequence of SEQ ID NO: 11.

* * * * *

SEQUENCE LISTING

```
<160> NUMBER OF SEQ ID NOS: 34

<210> SEQ ID NO 1
<211> LENGTH: 2178
<212> TYPE: DNA
```

-continued

<213> ORGANISM: Artificial Sequence
<220> FEATURE:
<223> OTHER INFORMATION: Synthetic sequence

<400> SEQUENCE: 1
atgtaccgta tgcagcttct ctcatgtata gccctgagtt tagccctagt tacaaatagc 60
caggtgcagc tgctacagag cggggctgcg gtcacaaagc ctggggccag cgttcgcgtg 120
tcctgtgagg cttccgggta caatatccgc gattacttta tccactggtg gcgtcaagct 180
ccgggtcagg ggttacagtg ggtcggttgg atcaatccaa aaacaggaca gcccaacaat 240
cctcgccagt ttcaggggcg tgtcagcctt acacgtcacg ccagttggga ttttgacaca 300
ttcagctttt acatggacct gaaggccctg cgaagcgacg acacagccgt gtacttttgc 360
gccagacagc ggagcgacta ctgggacttt gatgtgtggg ggagcggtac acaagtgaca 420
gtctccagcg cgtccaccaa aggacccagc gtgtttcctc tggccccatc ttccaagtca 480
acatccggcg gaactgcggc cctagggtgc ctggtgaaag actactttcc tgagcccgta 540
actgtgagct ggaactccgg ggctctgaca tccggggttc atacattccc tgcagtactt 600
cagtcctccg gcctgtatag cttatctagc gtagtaacag tgccctcctc ttccttgggg 660
acacagacct acatttgcaa tgtgaatcat aagccctcca acacaaaggt ggataagaag 720
gtggagccga aatcctgcga caaaacgcac acttgccctc cttgtccagc cccgagctg 780
ctagggggac cctccgtttt tctgtttcca ccaaaaccca aggacaccct tatgatttca 840
cgcacaccgg aggtaacctg tgttgtggta gacgtgtcgc atgaagatcc agaggtcaag 900
tttaactggt atgttgatgg agtggaggtc cataacgcaa agacaaaacc cagagaggag 960
cagtacaata gtacttaccg tgtggtttct gtactgacag tattacatca ggactggttg 1020
aacgggaaag agtacaaatg taaagttagt aacaaagccc ttcctgcacc tatagaaaag 1080
accatatcca aagccaaagg ccagcccaga gagccccaag tttacacgct accgccaagc 1140
cgagacgagc tgactaagaa tcaggtgtcc ctgacttgtc tagtcaaggg cttttacccc 1200
agcgatattg ctgtggagtg ggagagcaat ggccagcccg agaataacta caaaacaaca 1260
cccccggtcc ttgactccga tgggagtttc tttctgtaca gcaaattgac agtagacaag 1320
agcagatggc agcaggggaa tgtgtttagc tgcagcgtga tgcatgaggc tctccataat 1380
cattacacgc agaaatccct gagcttgtct cccgggcgta aacgacgcgc acccgtgaaa 1440
cagacattga atttcgactt gctgaagtta gccggggacg tcgagagtaa tccaggccct 1500
atgtacagaa tgcagctcct gtcctgcata gctctcagcc tggcccttgt gacaaattct 1560
gatatacaga tgacgcagtc gccctcaagc ctcagtgcct ccgtggggga tactgttaca 1620
atcacatgtc aggccaatgg ctatctaaac tggtatcagc agcggagggg aaaggcaccc 1680
aagttactga tatacgacgg ctccaagttg gagcgcgggg tccccagcag gttttccggc 1740
aggagatggg ggcaggagta caacctgacc ataaacaatc tccagcctga ggatattgcc 1800
acatactttt gccaggtata cgagtttgtt gtgcctggca cacggctcga tctgaaaagg 1860
accgtggctg ccccaagcgt gttcattttc cctcccagcg acgaacagct taagtctggg 1920
actgcgtccg tcgtatgttt gctgaacaac ttctatcccc gtgaagccaa agtgcagtgg 1980
aaagtggaca atgcactgca gtccgggaac tcccaagaga gcgtcacaga gcaggactcc 2040
aaagactcga cctactctct aagctccaca ctgacactca gcaaggctga ctatgagaag 2100
cacaaagttt acgcctgtga agtgactcat caggggctca gctcccccgt gacaaaaagc 2160
tttaaccggg gagaatgt 2178

<210> SEQ ID NO 2
<211> LENGTH: 2178
<212> TYPE: DNA
<213> ORGANISM: Artificial Sequence
<220> FEATURE:
<223> OTHER INFORMATION: Synthetic sequence

<400> SEQUENCE: 2
atgtatagga tgcagttact ctcatgcatt gctctctcac tggcacttgt aaccaattct 60
caagtgcagc ttctccagtc tggcgctgcc gtcaccaagc caggagccag cgttcgagtt 120
tcatgcgaag cttctgggta caatatcaga gattacttca ttcactggtg gcgccaggct 180
cccgggcagg ggctccagtg ggtgggatgg attaacccca agacgggaca gcccaacaat 240
cccaggcagt tccaggggcg tgttagcctg acaagacatg cctcatggga ctttgataca 300
ttcagtttct atatggactt gaaagctctg agaagtgatg ataccgctgt ttacttttgc 360
gctcggcagc gatcagacta ttgggatttc gatgtgtggg gatcaggcac ccaagtgacg 420
gtgtcaagcg cttcaacaaa aggaccctca gtgttccctc tcgccccttc atctaaatca 480
acaagcggtg gcaccgctgc cttgggatgt ctcgttaagg actactttcc cgagcccgtc 540
acagtgagtt ggaattctgg cgctcttact agcggggtgc atactttccc cgctgtactg 600
cagtccagcg gcctgtattc attgtcatca gtggttacag taccctcatc gagtctgggc 660
acgcagacct acatctgcaa cgtcaaccat aaaccctcta acaccaaagt cgataagaaa 720
gtagaaccca aatcttgcga caaaacacat acatgcccac catgtcccgc tccagagttg 780
ttgggtggac cctccgtgtt tctgttccct cccaaaccca aagatacact catgatttcg 840
cggacccccg aggtgacttg cgtcgtcgtg gatgtgtccc acgaggaccc cgaggtcaaa 900
ttcaactggt atgttgatgg agtggaggtt cataacgcca agaccaaacc cagagaggag 960
cagtacaaca gtacgtacag agttgtgtct gttctcactg ttctacacca ggactggctt 1020
aacggaaagg agtataagtg taaagtgtcc aacaaggcac tccctgctcc cattgaaaag 1080
acaatctcaa aagctaaggg ccagcccaga gaaccgcaag tgtacacgct accgcctagt 1140
cgagatgagc tgaccaagaa ccaggtgtcc ttgacttgcc tcgttaaagg gttctatccc 1200
tcggatatag ctgtcgagtg ggagtcaaat gggcaacccg agaataacta caagaccaca 1260
ccccctgtgc tggattcaga cggtagcttc tttctatact ccaaactgac ggttgacaaa 1320
tcccgttggc agcaggggaa cgttttctca tgctcagtta tgcatgaagc actgcataac 1380
cactatacgc agaaatcatt atcacttagt cccggacgga aaaggcgcgc tcccgtgaaa 1440
cagaccctca actttgactt actgaagctc gccggagacg tcgagtcaaa tcctggtccg 1500
atgtatagaa tgcagctgct ttcttgcatt gcattgagtc tcgccctggt caccaacagt 1560
gatatccaga tgacccagag tccttcatct ctctcagctt cagtgggaga cacggtcacg 1620
ataacctgcc aggctaacgg ctatctcaat tggtaccagc agcgcagggg taaagctccc 1680
aaactgctga tctatgatgg ttcaaaactg gagcgcggcg taccctcacg gttttccgga 1740
cgacgatggg gccaggagta caatctgact atcaacaacc tgcagcccga ggacatagcg 1800
acgtatttct gccaggtata tgagtttgtc gtccctggga cccggctgga cctgaaaagg 1860
acggtcgctg caccctcagt attcatattc ccaccctccg atgagcagtt gaaaagcgga 1920
acagcgtcag tcgtgtgcct cctcaataac ttctaccccc gggaagccaa agttcagtgg 1980
aaagttgaca atgcacttca gtctggaaat agtcaggaga gcgtgactga gcaggattca 2040
aaagattcta cgtattccct gagctcaacg ctcacactgt ctaaagctga ttatgagaaa 2100
cataaggttt atgcctgcga ggtaacgcat cagggtctat catcgcccgt cacgaaaagc 2160
tttaacagag gggagtgt 2178

<210> SEQ ID NO 3
<211> LENGTH: 2178
<212> TYPE: DNA
<213> ORGANISM: Artificial Sequence
<220> FEATURE:
<223> OTHER INFORMATION: Synthetic sequence

<400> SEQUENCE: 3
atgtatagga tgcaactgtt gtcgtgcatt gctctgagcc tcgccttagt gaccaatagc 60
caagtacaac tcctccagtc tggagcagct gttaccaagc caggcgcttc ggttagggtt 120
tcatgcgaag caagtggcta taacatccgg gactatttca tccattggtg gagacaagcc 180
cccggacaag ggctgcaatg ggtcggctgg attaacccaa agaccggcca acccaacaac 240
ccccggcagt ttcaagggag ggtgagcctg acccgccatg caagctggga cttcgacact 300
ttttccttct acatggatct gaaagctctg aggtccgacg acaccgccgt gtacttctgt 360
gctcggcaga ggagcgacta ttgggacttt gacgtttggg gctctggcac ccaagttaca 420
gtttcctcgg cttccacaaa gggcccctcg gtatttccct tggcccccctc gtctaagtcc 480 accagcggag gaactgctgc tttaggctgc cttgttaagg actacttccc cgagcccgtg 540
actgtctcgt ggaactcagg cgcgctcact agcggggttc ataccttttcc cgctgtgttg 600 cagagcagtg gcttgtatag cctgtctagc gtcgtgaccg ttcccagcag cagcctcggg 660
acccagacgt acatttgtaa cgttaatcat aagccttcaa acaccaaagt cgataagaag 720
gtggaaccca agagttgtga caaaacccac acctgcccgc cctgtcccgc acccgagctg 780
ttaggtggtc cttctgtctt tctgtttcct cccaagccaa aggacaccct tatgatatcg 840
aggacccctg aagtaacctg cgtcgtagtt gacgtttccc acgaagatcc cgaggtcaag 900
ttcaactggt atgtcgacgg ggttgaagtg cacaacgcaa aaacaaagcc tcgtgaggaa 960
caatacaact caacgtatag ggttgtctcc gttcttaccg ttctgcacca agactggttg 1020
aacgggaagg agtacaaatg caaagtatcg aacaaagccc tgcccgcacc cattgagaaa 1080
accatttcga aggccaaagg ccaaccccgg gaaccccaag tgtataccct cccaccttcc 1140
agagatgaac tgaccaagaa tcaggtgtcg ctgacctgcc tggtgaaggg cttctacccc 1200
tctgatattg ccgtggaatg ggaaagcaat ggccaacccg aaaacaatta caagaccact 1260
cccccggttt tagactcaga cggctcattc tttctgtatt caaagttgac tgttgacaag 1320
tccagatggc agcaagggaa cgttttctcc tgtagtgtta tgcatgaagc cctgcataat 1380
cattacaccc agaagtcgtt gagcctatct cccggtagga aaaggcgggc tcctgtgaag 1440
caaactctga actttgactt gctgaagctc gccggtgacg tagaatcaaa ccctggaccc 1500
atgtacagaa tgcagctgtt gtcctgtatt gcactgagtc tggctctcgt gaccaattca 1560
gacatccaga tgacccaatc accctccagc ctttccgcct cggttggaga caccgtaaca 1620
attacttgtc aggctaacgg ttaccttaac tggtatcagc agcgccgagg gaaagctccc 1680
aagctactca tatacgacgg ctctaagctg gaacgcggcg ttccttcacg gtttagtggc 1740
cggaggtggg gccaggaata caacctgacc attaacaacc tgcagcccga agatattgcc 1800
acctatttct gtcaggtgta tgaatttgtt gttcccggga cccgactgga cttgaagcgg 1860
accgttgcgg cacccagcgt ctttatcttt cccccatcgg atgaacaact gaaatccggc 1920
accgcctcag ttgtttgcct gctgaacaac ttctatccgc gggaagcgaa ggtccagtgg 1980
aaagttgaca acgccctgca gtcaggtaac tcgcaagaat ctgtcaccga acaggacagc 2040
aaggactcga cctatagtct cagctccacc ctaacgctgt ccaaagccga ttatgagaag 2100
cacaaagtct atgcttgtga ggttacgcac caagggctaa gcagtcccgt tacaaagtcc 2160
tttaaccggg gagagtgt 2178

<210> SEQ ID NO 4
<211> LENGTH: 2178
<212> TYPE: DNA
<213> ORGANISM: Artificial Sequence
<220> FEATURE:
<223> OTHER INFORMATION: Synthetic sequence

<400> SEQUENCE: 4
atgtatcgta tgcaacttct cagctgcatt gcacttagtc tcgctctggt tacaaacagt 60
caagttcagc tgcttcagtc cggcgctgcc gtgaccaagc ctggagcttc ggtcagagtg 120
tcatgtgaag ccagcgggta taacattaga gactatttca ttcactggtg gagacaggcc 180
cctggacagg ggcttcagtg ggtcggctgg attaacccta aaaccggcca gcccaacaat 240
ccaagacagt ttcagggccg ggtgtccctt acccgacatg ccagctggga tttcgataca 300
ttttcgttct atatggacct taaggctttg agatctgatg atacagctgt gtatttctgt 360
gcacgacagc ggtctgatta ctgggatttt gacgtgtggg ggtccggcac acaagtcaca 420
gtgtccagtg catccacaaa aggaccttca gtctttcctc tcgccccgtc cagcaagtca 480
accagcgggg gtacagcggc tttggggtgc cttgtcaagg actactttcc tgaacccgtg 540
actgtgtcat ggaactcggg tgccctgaca tcgggggtcc acacttttcc cgctgtgctc 600
cagtcctcgg ggctatactc ccttagctcg gtggttacag tcccatcctc atcattaggg 660
acacagacat acatctgtaa tgtgaaccac aagccttcaa atactaaggt tgataagaaa 720
gttgaaccca agtcttgcga taagacacac acatgtcccc cttgtcctgc accagagctg 780
cttggcgggc cttcagtttt tctttttcct ccaaaaccta aggatacact tatgatctca 840
aggacaccag aagtcacatg cgtcgtggtg gatgtgtccc atgaggaccc cgaggtcaag 900
tttaactggt atgtggatgg ggtcgaagtg cacaacgcca aaacaaagcc acgcgaagag 960
caatacaatt cgacttacag agtcgtgagt gtactgaccg tgctgcacca ggattggctg 1020
aacggcaaag agtacaaatg caaagtgagc aacaaagctc taccagctcc catagaaaag 1080
acaatctcta aagctaaggg gcagccgcgg gagccccaag tctataccct acctccttcc 1140
cgcgacgaac tcacaaagaa ccaggttagc cttacatgtc tcgtaaaggg gttctatcct 1200
tcggatatcg ctgtcgaatg ggagtctaac gggcagcctg aaaacaacta caaaacaact 1260
ccccctgtgc ttgatagcga cggtagtttc tttctgtaca gcaaacttac agtcgataag 1320
agtagatggc aacaggggaa tgtgttttct tgttccgtga tgcacgaggc actgcacaat 1380
cactacacac agaagagtct cagcttatct cctggaagga agagacgagc tcccgtcaaa 1440
cagacgctaa actttgacct gttaaagctt gccggcgatg tcgaatccaa tccagggcct 1500
atgtaccgga tgcagctact tagttgcata gctcttagcc ttgctctcgt gactaacagc 1560
gacatccaga tgacgcagtc accttcctcc ctgtcagcct cagtcggcga taccgtaact 1620
ataacatgtc aggcgaatgg gtatctgaat tggtatcagc agcgacgtgg gaaagctcct 1680
aagttgctta tctatgatgg gtctaagctt gagagagggg tgccaagtag atttctgga 1740 cgaaggtggg ggcaggagta taacttgacc atcaataacc ttcagcctga agatatcgcc 1800
acatactttt gccaggtata tgagtttgtt gtgcccggga cgagacttga tctcaaacga 1860
acggtggctg ctccttctgt gtttatcttt cctccttctg atgagcagct caagagcgga 1920
acagcatccg ttgtctgtct gctcaacaac ttttacccta gggaagctaa ggtgcagtgg 1980
aaggttgaca atgctttaca gagcggaaat agccaggagt ccgtcacaga acaggatagc 2040
aaggatagca catatagctt gagctccact ctgacactca gtaaggctga ttatgagaag 2100
cataaggtat atgcctgtga agtcacacat caaggccttt catcccctgt tactaagtct 2160
ttcaacagag gggaatgc 2178

<210> SEQ ID NO 5
<211> LENGTH: 2178
<212> TYPE: DNA
<213> ORGANISM: Artificial Sequence
<220> FEATURE:
<223> OTHER INFORMATION: Synthetic sequence

<400> SEQUENCE: 5
atgtacagaa tgcagcttct gtcttgcatt gcactttctc tggccttagt gactaactct 60
caagtgcagc tccttcagag cggcgcagct gtgacaaagc ctggggccag cgttagagtg 120
tcgtgtgagg catccggcta taacatcaga gactatttca ttcattggtg gcgccaagcg 180
cccggtcagg gacttcagtg ggtgggctgg atcaatccaa agacagggca gcctaacaat 240
ccaagacagt ttcagggccg ggtgtccttg actcggcatg cgagctggga ttttgatacg 300
ttctcctttt acatggacct gaaggcccta aggtctgacg acaccgctgt gtatttctgc 360
gccaggcaga gatcagacta ttgggacttt gatgtgtggg gctctggtac tcaagtgaca 420
gtgagcagtg cgtctacaaa gggcccatca gtctttcctc tggccccttc cagcaagtct 480
acgtccggcg ggactgccgc cctcggatgc ttagtgaagg actatttccc tgagcccgtg 540
accgtgagct ggaatagcgg cgctctgacg tctggcgtgc acacattccc tgctgtgctg 600
cagagcagtg gcctttactc ccttagtagc gtggtgacag tgccctctag ttctctaggc 660
acccagacat acatttgtaa tgtaaatcac aaacctagca acacaaaggt ggacaagaag 720
gtggaaccta agagttgtga taagacccat acatgtcccc catgcccagc cccagagctt 780
cttggcggtc catcagtttt cttgtttcct ccaaaaccta aggacactct gatgatttcg 840
agaacaccgg aagtcacttg tgtggtcgtg gatgtgtcac acgaggaccc tgaggtcaag 900
ttcaattggt atgtggacgg cgtggaggta cataacgcca aaacgaagcc tcgtgaggag 960
cagtacaact ccacctatcg agtggtcagc gtccttaccg tgttacacca ggactggctt 1020
aacggaaagg agtataagtg taaggtatcc aacaaagccc tgcctgcacc tattgagaaa 1080
actatatcta aagccaaggg ccagccgcga gagcctcaag tttacacact tcctccttcg 1140
agagacgagc tcaccaagaa tcaggtgtca cttacctgcc ttgtgaaagg cttttaccct 1200
agtgatatcg cggtggaatg ggagagcaat gggcagcctg agaacaacta taagacaacc 1260
cctcccgtac tggacagcga tggcagcttc tttctctatt ctaagctgac cgtcgataag 1320
agtcggtggc agcagggtaa cgtgttctct tgttctgtga tgcatgaggc attgcacaat 1380
cattacacgc agaagagtct gtccctttct cctggccgta aaaggcgagc tcctgtgaag 1440
cagactctta actttgactt gctcaagctc gctggcgatg tggagtccaa tcctgggccc 1500
atgtaccgaa tgcaacttct tagctgcata gcactttccc ttgcacttgt gacgaattct 1560
gacatccaga tgacccagag tccctcctct ttgagtgcaa gtgtgggcga caccgtgacc 1620
atcacttgtc aggccaatgg ctatctcaac tggtatcagc agcggagagg gaaggcacct 1680
aagctactca tctatgacgg cagtaaactg gagagaggcg ttccaagcag attctccggt 1740
cgccgatggg gccaggaata caatcttacc atcaataacc tgcagcccga ggacattgcc 1800
acctatttct gtcaggtgta tgagttcgtg gtgcccggaa cgagactcga tctcaagaga 1860
actgtggctg cccccagcgt gttcattttc cctccttccg acgagcagct taagagtggc 1920
accgcttcag tggtgtgttt actaaacaat ttctaccctc gagaggcgaa ggtgcagtgg 1980
aaggtggata atgcccttca gtcaggcaat tctcaagaaa gtgtgaccga gcaggatagt 2040
aaggactcta catactcact ctcctcaacc ctgacactca gtaaggccga ctatgagaag 2100
cacaaggtgt acgcgtgcga agtcacgcat cagggcctat ctagccccgt cacaaagtca 2160
ttcaataggg gcgagtgc 2178

<210> SEQ ID NO 6
<211> LENGTH: 2178
<212> TYPE: DNA
<213> ORGANISM: Artificial Sequence
<220> FEATURE:
<223> OTHER INFORMATION: Synthetic sequence

<400> SEQUENCE: 6
atgtaccgga tgcagttact ttcgtgcatc gccctgtcac tcgcccttgt gactaatagc 60
caggtacagc tactgcagag cggtgctgct gtgactaagc caggggcctc tgtgcgggtg 120
tcttgcgagg cgtcgggata caatatccgg gactacttta tccactggtg gagacaggca 180
ccgggtcagg gacttcagtg ggtgggctgg atcaatccca aaacaggcca gcccaacaat 240
ccccggcagt tccagggtcg cgtctctctg actaggcacg cctcctggga tttcgacacc 300
ttctcgttct atatggacct caaggctctt cggtccgacg acaccgccgt gtacttttgc 360
gcacgccaga gatccgacta ctgggacttt gacgtttggg ggtccggaac tcaagtgaca 420
gttagttctg cgtctaccaa gggtccctca gtgttccctc tggccccctc tagtaagtca 480
acctctggtg gtaccgcggc cttaggctgt ctggtgaaag attactttcc cgaacccgtg 540
accgtgtctt ggaatagcgg tgctctcacg agtggggtgc atacgtttcc tgccgtcctg 600
caatcaagtg gactttacag cttgtcaagt gtcgtgacgg tgccgtccag ctcactaggt 660
acccagacct acatctgcaa tgtgaatcat aagccttcga ataccaaggt ggataagaag 720
gtggagccca agtcatgcga caagacccat acctgtcctc cctgccccgc acctgagctg 780
ttgggcggtc catccgtgtt tctgtttccc cctaagccca aggacaccct gatgatatct 840
cgcaccccag aggtgacctg cgtagtggtc gacgtcagtc acgaggaccc agaagtgaag 900
tttaactggt acgtggacgg cgtagaagtg cataatgcca aaaccaagcc ccgggaagaa 960
cagtacaatt ccacctaccg tgtggtgtct gttttgaccg tgctccacca ggattggctg 1020
aatgggaagg aatacaagtg caaggtgtct aacaaggctc tccctgcacc cattgagaaa 1080
accatttcca aggccaaggg tcagccccga gaaccccaag tgtacacctt accgccctcc 1140
cgcgacgaac tgaccaaaaa ccaggtgtcc cttacctgcc tggtgaaggg attctacccg 1200
agtgacatcg ctgtggaatg ggaaagcaac ggccagcctg aaaacaatta caagactacc 1260
ccaccagtac tcgattcaga cggaagcttt ttcctttaca gcaagctcac tgtggacaag 1320
tctcgatggc agcagggcaa tgtgttctca tgctctgtga tgcatgaggc attgcataac 1380
cactatacac agaagtcatt atcactctcc cccggcagaa aacgcagggc tcctgtgaag 1440

-continued

```
cagactctta actttgacct gctgaaactt gctggtgacg tggaatcaaa ccccggtcca   1500

atgtacagaa tgcagctttt gtcatgcatt gctctcagcc tagctctagt gaccaattca   1560

gatattcaga tgactcagag tccaagtagt ctaagcgcct cagtcggcga tacagtgacg   1620

atcacctgtc aggcaaacgg atacttgaat tggtaccagc agaggagggg gaaggctccg   1680

aagcttctga tctatgacgg cagtaagctt gaacgcggtg tgcctagccg cttctccggt   1740

cgccgctggg gtcaggagta caacttaacc ataaacaacc tccagcctga ggacatagca   1800

acctatttct gtcaggtgta tgagtttgtt gtgcccggta caaggctaga cctcaagcga   1860

accgtggccg ctccatccgt ctttatcttt cctcctagcg acgagcagct gaagtccggc   1920

accgcttcag tggtctgcct cctcaacaat ttctacccca gggaagccaa ggtgcagtgg   1980

aaagtggaca atgcactgca gagtggaaat tctcaagagt ctgtgaccga gcaggactca   2040

aaagactcta cctacagcct gagttcaacc cttaccctgt caaaggccga ttacgaaaag   2100

cataaggtgt atgcttgcga ggtgacccac cagggcctgt cgagccccgt gaccaagagc   2160

tttaaccgtg gagaatgc                                                 2178
```

<210> SEQ ID NO 7
<211> LENGTH: 2178
<212> TYPE: DNA
<213> ORGANISM: Artificial Sequence
<220> FEATURE:
<223> OTHER INFORMATION: Synthetic sequence

<400> SEQUENCE: 7

```
atgtaccgca tgcaattact ctcctgtatc gctctgtctc tggctctggt gacaaacagc     60

caggtccagc tgctgcagag tggcgccgca gtgactaagc ctggcgctag tgtgagagtc    120

agttgcgaag caagcggcta caacattcgc gattacttta tccattggtg gaggcaggct    180

cccggtcagg gcttgcaatg ggtcggctgg attaacccca aaaccgggca gcccaataac    240

cctcgacaat ttcagggacg cgttagttta acgaggcatg cgtcatggga ttttgacaca    300

ttttcgttct atatggatct gaaggctctg cggtctgatg acaccgctgt gtacttttgt    360

gccaggcaac ggtccgacta ttgggacttt gatgtgtggg ggtcgggtac gcaagtaacg    420

gtgtccagcg cttccacaaa aggcccaagc gtgtttcccc tcgctccatc ttctaagtct    480

acaagcggcg gcaccgctgc tctgggctgt ctggtgaaag attactttcc agagccggtc    540

actgtgtcct ggaatagcgg cgctctgact tctggtgttc atacctttcc cgctgtcctg    600

caaagcagcg gcctgtacag cctgagctcc gtggtgaccg taccctcctc cagcttgggc    660

acacagacat acatatgcaa tgtgaaccac aagcctagta ataccaaggt tgataagaag    720

gtagaaccta agagttgtga caagacccat acttgtccac cgtgtcctgc accagaactg    780

ctcgggggac ccagcgtctt tctgtttccg ccaaaaccta aggatactct aatgatttcc    840

cgtacccccg aagtcacttg cgtggtcgtg gacgtgtcac atgaggaccc cgaggtaaag    900

tttaactggt atgtggacgg cgtggaggtt cataacgcca agactaagcc ccgggaggaa    960

cagtataaca gtacgtatcg agtcgtaagc gtgctgactg ttctgcacca agactggttg   1020

aatgggaagg agtataagtg taaggtcagc aacaaggctc ttcccgctcc tatcgaaaag   1080

accatttcaa aagccaaggg acagccgcgg gagcctcaag tgtataccct gccgccaagt   1140

agagacgagc tcaccaagaa ccaggtttca ctgacatgtc tggtaaaggg cttctatcca   1200

tccgacattg ccgtagaatg ggagagtaac ggccagccag agaataacta taagaccacg   1260

ccccctgtgt tggactccga cgggtcattc tttctgtata gcaagctgac agttgacaag   1320
```

-continued

```
tcacggtggc aacagggcaa cgtgttttca tgttccgtga tgcacgaagc tctgcataac   1380

cactataccc agaagtccct gtctctgagc ccagggagga agaggcgcgc accagtgaaa   1440

cagaccttga atttcgacct gctgaagctg gctggcgatg ttgaatccaa cccaggcccc   1500

atgtatagaa tgcagctgct gtcttgtatc gccttgagcc tggccttggt cacaaattcg   1560

gatatccaga tgacgcaatc cccctcctcc ctcagcgctt cagtaggtga cacagtaaca   1620

attacatgtc aggccaatgg gtacctcaat tggtatcagc agcgaagggg caaagctcct   1680

aagttgctga tctatgacgg ctctaagttg gaacgcggcg ttccgagtag gtttagtggc   1740

cggagatggg gacaagagta taacctgacg atcaacaact tgcaacccga ggacattgct   1800

acctatttct gtcaggtgta tgaatttgta gtaccaggca cccggctaga tctgaaacgg   1860

acagtagctg cccccagcgt gttcatattc cctccatctg acgaacagct taagtcgggc   1920

accgcaagcg tggtgtgcct gttgaataac ttctatccga gagaggctaa ggtgcagtgg   1980

aaggtcgaca acgccctaca gtctggcaat tctcaagaaa gcgttaccga acaggatagc   2040

aaggacagca cgtatagctt gtcctccaca ctgacgcttt ccaaggcaga ctatgaaaaa   2100

cataaggtgt acgcgtgtga ggtgactcat cagggcctgt ccagcccggt tacaaagtcc   2160

tttaacaggg gcgaatgc                                                 2178
```

<210> SEQ ID NO 8
<211> LENGTH: 2178
<212> TYPE: DNA
<213> ORGANISM: Artificial Sequence
<220> FEATURE:
<223> OTHER INFORMATION: Synthetic sequence

<400> SEQUENCE: 8

```
atgtatcgga tgcagcttct ctcctgcatt gccttaagtc tcgcccttgt aacaaatagt     60

caggttcagc ttttacagag tggcgccgca gtcaccaaac ccggagcatc cgtgcgagtc    120

tcctgcgaag ccagtgggta caacattagg gactatttca tccattggtg gaggcaggca    180

cccggccaag gacttcagtg ggttgggtgg atcaatccta agacgggaca gcccaataac    240

ccgagacagt ttcaggggcg cgtctctctt actcgccatg cttcttggga ttttgacacc    300

ttttctttct acatggacct caaagccctt cgcagcgacg ataccgctgt gtatttctgt    360

gccaggcagc gctctgacta ctgggacttt gatgtttggg gatctggtac gcaagtcaca    420

gtctctagtg caagtaccaa aggccccagt gtgtttcccc tcgctccgtc tagcaagtct    480

acctctggcg gtactgcagc ccttggatgt ctggtcaaag actactttcc agagccggtg    540

acagtgagtt ggaattcggg tgctctaaca tctggcgtgc acacttttcc ggctgtgctg    600

cagtccagtg gactttactc tctgagcagt gtggttactg tgccctctag ttctcttggg    660

acgcagacct acatctgcaa tgtgaatcat aagccatcta atacaaaggt ggataagaag    720

gtggaaccaa agtcatgcga caaaacccac acgtgcccac catgtccagc tccggagtta    780

ctgggcggac cctctgtctt tctgtttccg cccaagccga aggatacact gatgatatct    840

cgtaccccag aggtgacatg cgtggttgtc gatgtgtccc atgaggaccc cgaggtgaag    900

tttaactggt atgtggacgg cgtggaagtc cataatgcta agactaaacc aagggaagaa    960

cagtacaatt ccacgtaccg cgtcgttagc gtcttgaccg tgctccatca ggactggctc   1020

aacggaaagg agtataagtg taaggtcagt aacaaggctc ttccggctcc aattgagaaa   1080

acaattagta aggctaaggg gcagcctcgc gaacctcaag tctacaccct accaccgtct   1140
```

-continued

```
cgcgacgaac tcactaagaa tcaggtgtcg ctcacctgcc tcgtcaaagg tttctatccc   1200
tctgacatcg cagtagaatg ggaatccaat ggccagccgg agaacaatta caagaccacc   1260
ccgccagtgc tagactcaga cgggagtttc ttcttatact ctaagcttac cgtagataag   1320
tcccggtggc agcagggcaa tgtgttttcc tgttcagtga tgcatgaagc gctgcataat   1380
cactatacac aaaagtcact ttctctgagt cccggtcgga agagaagagc tcctgttaaa   1440
cagacactga atttcgattt gctcaaactc gctggagacg tagaaagcaa tcctggtcct   1500
atgtaccgaa tgcagctttt gtcttgcatc gctctgagcc ttgcgcttgt tacgaatagc   1560
gacatacaga tgacacagtc tccgagttct cttagtgcta gtgtgggcga tacagtcact   1620
ataacatgcc aggctaatgg ttacctgaac tggtaccaac aacgccgcgg taaagccccc   1680
aaactgctca tctatgatgg gtcaaaactt gaacgcggcg tcccgagccg ctttagtggc   1740
cgccgttggg ggcaggaata caatcttacc atcaacaatc tacagcccga agatattgct   1800
acttactttt gccaggttta cgaatttgtc gtcccgggaa cgcgccttga tcttaagcgg   1860
actgtcgccg ctccgagtgt gtttatcttt cctccatcag acgaacagct taagtcaggc   1920
accgcttctg tggtgtgctt gctgaataac ttctatcccc gggaagccaa ggttcagtgg   1980
aaggtcgaca atgctcttca gtctggtaat agccaggagt cagtgacaga acaggactcc   2040
aaggacagta cctactctct atccagtaca ctgaccctga gcaaagctga ctacgaaaag   2100
cacaaagtct atgcttgtga agtaacgcat caaggcctta gctctcctgt taccaagagc   2160
ttcaataggg gtgaatgc                                                 2178
```

<210> SEQ ID NO 9
<211> LENGTH: 2178
<212> TYPE: DNA
<213> ORGANISM: Artificial Sequence
<220> FEATURE:
<223> OTHER INFORMATION: Synthetic sequence

<400> SEQUENCE: 9

```
atgtaccgta tgcagctcct atcgtgcatt gccttgtcgt tggccttagt tacaaacagt     60
caggtgcagc ttttgcagtc cggggctgca gtgaccaaac ccggcgcatc tgtgagggtg    120
tcatgcgaag cctcggggta caacattcgg gactacttta tccactggtg gaggcaggcc    180
ccagggcagg gattacagtg ggtggggtgg atcaacccga aaacagggca gcctaacaac    240
ccccgacagt tccaggggcg cgtctcgttg acgaggcacg cgagttggga tttcgacaca    300
ttcagcttct acatggacct caaggcgctg agaagtgacg acacagccgt ctacttctgc    360
gcgaggcaga gatcggacta ttgggacttc gacgtgtggg gttcgggaac gcaagtgacc    420
gtgtcctcag cgtccacgaa agggccatca gtgttccctc tggcgccatc ctcgaagtct    480
acgtcaggcg ggacggctgc tctgggatgc ctggtgaaag actactttcc cgagccggtg    540
actgtctcgt ggaattcagg cgcgttgaca tccggtgttc acacgttccc cgctgtgttg    600
cagagcagcg gactgtactc tctgagcagt gtggtgacag tgccctcctc atcgctgggg    660
acgcagacgt acatctgcaa cgtgaaccac aagccgagca acacgaaggt ggacaagaag    720
gtcgagccga agtcttgtga taagactcac acatgtcccc catgccccgc tccagagctg    780
ctgggtggcc ctagcgtgtt tctgttccca ccgaagccaa aggacacctt gatgatcagc    840
aggaccccgg aagtgacctg cgttgtggtc gacgtgtcac atgaggaccc cgaagtgaag    900
tttaactggt acgtggacgg ggtggaggtg cataacgcaa agactaagcc ccgggaggag    960
caatacaatt ccacctaccg ggtcgtgtcg gtgctgactg tgctgcacca ggactggctg   1020
```

aacgggaagg agtacaagtg caaggtgtcg aataaggccc tgccagcacc tatcgaaaag 1080
acgatatcta aggcaaaggg gcagccgcgg gagccccaag tatacacact gcctccgtcc 1140
agggatgagt tgaccaagaa ccaggtgtct ctgacctgcc tggttaaggg cttctaccca 1200
tccgacatag cagtggagtg ggagagcaac ggccagccgg agaacaacta taagaccaca 1260
cccccggtgc tggacagcga cggctcgttc ttcctgtaca gtaagttgac cgtcgacaag 1320
agccggtggc agcaggggaa tgtgttctca tgcagcgtga tgcacgaagc cctgcacaat 1380
cactacaccc agaagtcact gtcgctgagc cctggccgga aaaggagggc cccagtcaaa 1440
cagactctga acttcgacct gctgaagctc gcgggggacg tggagagtaa tcccgggcca 1500
atgtatcgca tgcagttgct gtcgtgcatc gccctgtctc tggcgctggt caccaattct 1560
gatattcaga tgacgcagag ccctagcagc ctctctgcaa gcgtggggga cacggtgacg 1620
attacatgcc aggctaacgg atatctgaac tggtaccaac agcggagggg gaaggccccg 1680
aagctgctca tctacgacgg gtccaaattg gagcgaggag taccgtcccg gttctcgggg 1740
cggagatggg ggcaggaata caacctaacc ataaacaacc tacagcccga ggacatcgcc 1800
acttacttct gccaggtgta cgagttcgtg gtgcccggca ccaggctgga cctgaagcgg 1860
accgtggccg cacctagtgt gttcatcttc ccaccgtccg atgagcagtt gaagagcggg 1920
acagcgagcg tggtgtgcct gctgaacaac ttctatccgc gcgaggccaa agtacagtgg 1980
aaggtagata acgccctcca gtccggaaac agccaggagt ccgtgaccga gcaggactca 2040
aaggattcca catactccct ttcctcaaca ctgacgctga gtaaggcgga ttacgagaag 2100
cacaaggtgt atgcgtgtga ggtgactcac caggggctgt cctcacccgt gacgaaatcg 2160
tttaaccggg gcgagtgt 2178

<210> SEQ ID NO 10
<211> LENGTH: 2178
<212> TYPE: DNA
<213> ORGANISM: Artificial Sequence
<220> FEATURE:
<223> OTHER INFORMATION: Synthetic sequence

<400> SEQUENCE: 10
atgtaccgaa tgcaactgct gtcctgcatc gccctgtccc tggcactggt caccaacagc 60
caggtccagc tgctgcagag cggagcagca gtcacaaaac caggagccag cgtcagagtc 120
agctgcgagg ccagcgggta caacattcgg gactacttca tccactggtg gcggcaggca 180
ccagggcagg ggctgcagtg ggtgggctgg atcaacccta aaaccggaca acccaacaac 240
ccacgacagt ttcagggcag agtgagcctg accagacacg ccagctggga ctttgacacc 300
ttttccttct atatggatct gaaagcactg cgatccgacg ataccgccgt gtacttttgc 360
gcacgacagc ggtccgatta ctgggacttc gacgtctggg gcagcgggac acaagtcaca 420
gtgtccagcg cctccaccaa gggaccaagc gtgtttccac tggcaccatc cagcaagagc 480
acatccggag gcaccgcagc actgggctgc ctggtcaagg attacttccc tgaaccagtc 540
accgtcagct ggaactccgg agccctgaca agcggcgtgc acaccttccc tgccgtgctg 600
cagtccagcg gcctgtattc cctgagctcc gtggtgaccg tgcccagctc cagcctgggc 660
acccagacct acatttgcaa tgtcaaccat aaaccaagca ataccaaagt cgacaagaaa 720
gtcgagccca aaagctgcga caaaacccac acatgccctc catgccctgc cccagagctg 780 ctgggggggac cctccgtctt tctgtttccc cctaaaccaa aagacaccct gatgatcagc 840

-continued

```
agaacccccg aagtcacatg cgtggtggtc gacgtcagcc acgaggaccc tgaggtcaag    900

ttcaattggt acgtcgacgg ggtcgaggtc cacaatgcca agaccaagcc cagagaggaa    960

cagtataaca gcacctaccg ggtcgtgtcc gtgctgacag tgctgcatca ggactggctg   1020

aacggaaagg agtacaagtg caaggtgtcc aacaaggccc tgcccgcacc aattgaaaag   1080

acaatcagca aggccaaggg gcagccccga gagccccaag tctataccct gccccccttcc  1140

cgagatgaac tgaccaagaa ccaagtcagc ctgacatgcc tggtgaaggg attctaccct   1200

tccgatatcg ccgtcgagtg ggaatccaac ggccaacccg agaataacta caaaacaacc   1260

ccacccgtgc tggacagcga cgggtccttc tttctgtata gcaagctgac cgtggacaaa   1320

tcccgatggc agcaaggaaa cgtgttcagc tgcagcgtga tgcatgaggc cctgcacaac   1380

cactataccc agaaaagcct gagcctgagc ccaggccgga agcggagagc ccccagtcaaa  1440

cagaccctga acttcgatct gctgaaactg gcaggcgacg tggagtccaa cccagggcca   1500

atgtatagaa tgcagctgct gagctgcatt gccctgagcc tggccctggt gaccaattcc   1560

gatatccaga tgacccagag cccctcctcc ctgagcgcat ccgtcggaga caccgtgaca   1620

atcacatgcc aggcaaacgg ctatctgaac tggtatcagc agcggagagg gaaggcacct   1680

aagctgctga tctacgacgg aagcaagctg gaacgaggcg tccccagccg gttcagcggg   1740

agaagatggg ggcaggaata caacctgaca atcaacaatc tgcagcccga ggacattgca   1800

acctacttct gccaggtgta cgagtttgtc gtcccaggga cacgactgga tctgaagcgg   1860

acagtggccg cacccagcgt gtttatcttc cctccctccg acgaacagct gaagtccggc   1920

accgcatccg tggtgtgcct gctgaacaat ttctatccca gagaggccaa agtccagtgg   1980

aaggtggaca atgcactgca gtccggaaat agccaagaaa gcgtcaccga gcaggactcc   2040

aaggactcca catactccct gagcagcaca ctgaccctga gcaaggcaga ctacgagaag   2100

cacaaggtct acgcctgcga agtcacccac cagggactgt cctcccctgt gaccaaatcc   2160

ttcaatagag gagagtgc                                                 2178
```

<210> SEQ ID NO 11
<211> LENGTH: 2178
<212> TYPE: DNA
<213> ORGANISM: Artificial Sequence
<220> FEATURE:
<223> OTHER INFORMATION: Synthetic sequence

<400> SEQUENCE: 11

```
atgtaccgaa tgcaactgct gtcctgcatc gccctgtccc tggcactggt caccaacagc     60

caggtccagc tgctgcagag cggcgccgcc gtgacaaagc caggagccag cgtgcgggtc    120

agctgcgagg cctccggcta caacattcgg gattacttca tccactggtg gcggcaggcc    180

ccaggccagg gactgcagtg ggtgggctgg atcaacccaa agacaggcca gccaaacaac    240

cctcggcagt tccagggacg ggtgagcctg acccggcacg ccagctggga tttcgataca    300

ttctccttct acatggatct gaaagccctg cggtccgacg atacagccgt gtacttctgc    360

gcccggcagc ggtccgatta ctgggacttc gatgtgtggg gaagcggcac acaagtcacc    420

gtcagcagcg ccagcaccaa gggcccttcc gtgttcccac tggccccttc cagcaagtcc    480

acctccggag gcacagccgc cctgggctgc ctggtgaaag attacttccc tgagcccgtg    540

accgtgagct ggaactccgg agccctgacc agcggagtgc acaccttccc tgccgtgctg    600

cagtccagcg gactgtacag cctgtcctcc gtggtgacag tgcccagctc cagcctgggc    660

acccagacct acatttgcaa cgtcaaccat aagccaagca acacaaaggt ggataagaaa    720
```

-continued gtggagccaa aaagctgtga caagacacac acctgtcctc cctgccccgc ccccgagctg 780
ctgggcggac caagcgtgtt cctgttccct cctaagccca aggacacact gatgatcagc 840
cggaccccag aggtcacatg tgtggtggtg gatgtgagcc acgaggaccc tgaggtgaag 900
ttcaactggt acgtggatgg agtcgaagtg cacaacgcca aaaccaagcc tcgggaggag 960
cagtacaaca gcacctaccg ggtggtgagc gtgctgaccg tgctgcatca ggactggctg 1020
aatggaaagg aatacaagtg taaagtgtcc aacaaagccc tgccagcccc catcgaaaag 1080
acaatttcca aagccaaggg acagccacgg gagccacaag tgtacaccct gcccccaagc 1140
cgggatgagc tgacaaagaa tcaggtcagc ctgacatgtc tggtcaaggg cttctaccca 1200
agcgatatcg ccgtggagtg ggagtccaat ggccagcccg aaaacaacta caagaccacc 1260
ccaccagtgc tggactccga tggctccttc ttcctgtact ccaagctgac cgtggacaaa 1320
agccggtggc agcagggaaa cgtgttcagc tgtagcgtga tgcacgaagc cctgcacaac 1380
cactacaccc agaaaagcct gagcctgagc ccaggccgga agcggcgggc cccagtgaaa 1440
cagaccctga atttcgatct gctgaagctg gccggagatg tggaaagcaa ccccggaccc 1500
atgtaccgga tgcagctgct gagctgtatc gccctgagcc tggccctggt gaccaattcc 1560
gatattcaga tgacacagag ccccagctcc ctgagcgcca gcgtgggcga taccgtcacc 1620
atcacatgcc aggccaacgg atacctgaac tggtaccagc agcggcgggg aaaggcccca 1680
aagctgctga tctacgatgg aagcaagctg gagcggggag tgcccagccg gttcagcgga 1740
cggcggtggg gccaggaata caacctgacc atcaacaatc tgcagccaga ggacatcgcc 1800
acctacttct gccaggtcta cgagttcgtg gtgcctggaa cccggctgga tctgaagcgg 1860
acagtggccg ccccctccgt gttcatcttc ccccctagcg acgagcagct gaaatccgga 1920
acagccagcg tggtctgtct gctgaacaac ttctaccctc gggaggccaa agtgcagtgg 1980
aaggtcgata acgccctgca gtccggaaac agccaggagt ccgtgaccga gcaggattcc 2040
aaggatagca cctacagcct gagctccacc ctgacactgt ccaaggccga ttacgagaaa 2100
cacaaggtgt acgcctgcga agtgacccat cagggactga gcagcccagt gaccaagagc 2160
ttcaatcggg gagaatgc 2178

<210> SEQ ID NO 12
<211> LENGTH: 2175
<212> TYPE: DNA
<213> ORGANISM: Artificial Sequence
<220> FEATURE:
<223> OTHER INFORMATION: Synthetic sequence

<400> SEQUENCE: 12
atgtacagga tgcaactcct gtcttgcatt gcactaagtc ttgcacttgt cacaaacagt 60
caggtccaat tgttacagtc tggggcagcg gtgacgaagc ccggggcctc agtgagagtc 120
tcctgcgagg cttctggata caacattcgt gactacttta ttcattggtg gcgacaggcc 180
ccaggacagg gccttcagtg ggtgggatgg atcaatccta agacaggtca gccaaacaat 240
cctcgtcaat ttcagggtag agtcagtctg actcgacacg cgtcgtggga ctttgacaca 300
ttttcctttt acatggacct gaaggcacta agatcggacg acacggccgt ttatttctgt 360
gcgcgacagc gcagcgacta ttgggatttc gacgtctggg gcagtggaac ccaggtcact 420
gtctcgtcag cgtcgaccaa ggggccctcg gtcttccccc tggcaccctc ctccaagagc 480
acctctgggg gcacagcggc cctgggctgc ctggtcaagg actacttccc cgaaccggtg 540

-continued

```
acggtgtcgt ggaactcagg cgccctgacc agcggcgtgc acaccttccc ggctgtccta    600

cagtcctcag gactctactc cctcagcagc gtggtgaccg tgccctccag cagcttgggc    660

acccagacct acatctgcaa cgtgaatcac aagcccagca acaccaaggt ggacaagaaa    720

gttgagccca aatcttgtga caaaactcac acatgcccac cgtgcccagc acctgaactc    780

ctggggggac cgtcagtctt cctcttcccc ccaaaaccca aggacaccct catgatctcc    840

cggacccctg aggtcacatg cgtggtggtg gacgtgagcc acgaagaccc tgaggtcaag    900

ttcaactggt acgtggacgg cgtggaggtg cataatgcca agacaaagcc gcgggaggag    960

cagtacaaca gcacgtaccg tgtggtcagc gtcctcaccg tcctgcacca ggactggctg   1020

aatggcaagg agtacaagtg caaggtctcc aacaaagccc tcccagcccc catcgagaaa   1080

accatctcca aagccaaagg gcagccccga gaaccacagg tgtacaccct gcccccatcc   1140

cgggatgagc tgaccaagaa ccaggtcagc ctgacctgcc tggtcaaagg cttctatccc   1200

agcgacatcg ccgtggagtg ggagagcaat gggcagccgg agaacaacta caagaccacg   1260

cctcccgtgc tggactccga cggctccttc ttcctctaca gcaagctcac cgtggacaag   1320

agcaggtggc agcaggggaa cgtcttctca tgctccgtga tgcatgaggc tctgcacaac   1380

cactacacgc agaagagcct ctccctgtct cccggccgaa agcggagagc cccccgtgaag   1440

cagaccctga acttcgacct gctgaagctg gccggcgacg tggaaagcaa ccctggccct   1500

atgggatggt catgtatcat cctttttcta gtagcaactg caaccggtgt acattctgac   1560

atccagatga cccagtctcc atcctccctg tctgcatctg taggagatac cgtcactatc   1620

acttgccagg caaacggcta cttaaattgg tatcaacaga ggcgagggaa agccccaaaa   1680

ctcctgatct acgatgggtc caaattggaa agaggggtcc catcaaggtt cagtggaaga   1740

agatgggggc aagaatataa tctgaccatc aacaatctgc agcccgaaga cattgcaaca   1800

tatttttgtc aagtgtatga gtttgtcgtc cctgggacca gactggattt gaaacgtacg   1860

gtggctgcac catctgtctt catcttcccg ccatctgatg agcagttgaa atctggaact   1920

gcctctgttg tgtgcctgct gaataacttc taccccagag aagccaaagt gcagtggaag   1980

gtggacaacg ccctgcagag cggaaacagc caggaaagcg tgacagagca ggattccaag   2040

gattccacat acagcctgag cagcacactg acactgtcca aggccgacta cgagaagcac   2100

aaggtgtacg cctgcgaagt gacacaccag ggactgtcct cccctgtgac aaagagcttc   2160

aacagaggag aatgc                                                    2175
```

```
<210> SEQ ID NO 13
<211> LENGTH: 5102
<212> TYPE: DNA
<213> ORGANISM: Artificial Sequence
<220> FEATURE:
<223> OTHER INFORMATION: Synthetic sequence
<220> FEATURE:
<221> NAME/KEY: misc_feature
<222> LOCATION: (1380)..(1384)
<223> OTHER INFORMATION: KOZAK
<220> FEATURE:
<221> NAME/KEY: misc_feature
<222> LOCATION: (1385)..(2077)
<223> OTHER INFORMATION: VRC01L\[VRC01VL-B12CL]

<400> SEQUENCE: 13
```

```
tcgcgcgttt cggtgatgac ggtgaaaacc tctgacacat gcagctcccg gagacggtca     60

cagcttgtct gtaagcggat gccgggagca gacaagcccg tcagggcgcg tcagcgggtg    120

ttggcgggtg tcggggctgg cttaactatg cggcatcaga gcagattgta ctgagagtgc    180
```

-continued

```
accatatgcg gtgtgaaata ccgcacagat gcgtaaggag aaaataccgc atcagattgg    240
ctattggcca ttgcatacgt tgtatccata tcataatatg tacatttata ttggctcatg    300
tccaacatta ccgccatgtt gacattgatt attgactagt tattaatagt aatcaattac    360
ggggtcatta gttcatagcc catatatgga gttccgcgtt acataactta cggtaaatgg    420
cccgcctggc tgaccgccca acgacccccg cccattgacg tcaataatga cgtatgttcc    480
catagtaacg ccaataggga ctttccattg acgtcaatgg gtggagtatt tacggtaaac    540
tgcccacttg gcagtacatc aagtgtatca tatgccaagt acgcccccta ttgacgtcaa    600
tgacggtaaa tggcccgcct ggcattatgc ccagtacatg accttatggg actttcctac    660
ttggcagtac atctacgtat tagtcatcgc tattaccatg gtgatgcggt tttggcagta    720
catcaatggg cgtggatagc ggtttgactc acggggattt ccaagtctcc accccattga    780
cgtcaatggg agtttgtttt ggcaccaaaa tcaacgggac tttccaaaat gtcgtaacaa    840
ctccgcccca ttgacgcaaa tgggcggtag gcgtgtacgg tgggaggtct atataagcag    900
agctcgttta gtgaaccgtc agatcgcctg gagacgccat ccacgctgtt ttgacctcca    960
tagaagacac cgggaccgat ccagcctcca tcggctcgca tctctccttc acgcgcccgc   1020
cgccctacct gaggccgcca tccacgccgg ttgagtcgcg ttctgccgcc tcccgcctgt   1080
ggtgcctcct gaactgcgtc cgccgtctag gtaagtttaa agctcaggtc gagaccgggc   1140
ctttgtccgg cgctcccttg gagcctacct agactcagcc ggctctccac gctttgcctg   1200
accctgcttg ctcaactcta gttaacggtg gagggcagtg tagtctgagc agtactcgtt   1260
gctgccgcgc gcgccaccag acataatagc tgacagacta acagactgtt cctttccatg   1320
ggtcttttct gcagtcaccg tcgtcgacac gtgtgatcag atatcgcggc cgctctagac   1380
caccatggga tggtcatgta tcatcctttt tctagtagca actgcaaccg gtgtacattc   1440
agaaattgtg ttgacacagt ctccaggcac cctgtctttg tctccagggg aaacagccat   1500
catctcttgt cggaccagtc agtatggttc cttagcctgg tatcaacaga ggcccggcca   1560
ggcccccagg ctcgtcatct attcgggctc tactcgggcc gctggcatcc cagacaggtt   1620
cagcggcagt cggtgggggc cagactacaa tctcaccatc agcaacctgg agtcgggaga   1680
ttttggtgtt tattattgcc agcagtatga attttttggc caggggacca aggtccaggt   1740
cgacattaaa cgtacggtgg ctgcaccatc tgtcttcatc ttcccgccat ctgatgagca   1800
gttgaaatct ggaactgcct ctgttgtgtg cctgctgaat aacttctacc ccagagaagc   1860
caaagtgcag tggaaggtgg acaacgccct gcagagcgga aacagccagg aaagcgtgac   1920
agagcaggat tccaaggatt ccacatacag cctgagcagc acactgacac tgtccaaggc   1980
cgactacgag aagcacaagg tgtacgcctg cgaagtgaca caccagggac tgtcctcccc   2040
tgtgacaaag agcttcaaca gaggagaatg ctgataggat ccagatctgc tgtgccttct   2100
agttgccagc catctgttgt ttgcccctcc cccgtgcctt ccttgaccct ggaaggtgcc   2160
actcccactg tcctttccta ataaaatgag gaaattgcat cgcattgtct gagtaggtgt   2220
cattctattc tggggggtgg ggtggggcag gacagcaagg gggaggattg ggaagacaat   2280
agcaggcatg ctggggatgc ggtgggctct atgggtaccc aggtgctgaa gaattgaccc   2340
ggttcctcct gggccagaaa gaagcaggca catccccttc tctgtgacac accctgtcca   2400
cgcccctggt tcttagttcc agccccactc ataggacact catagctcag gagggctccg   2460
ccttcaatcc cacccgctaa agtacttgga gcggtctctc cctccctcat cagcccacca   2520
```

-continued

```
aaccaaacct agcctccaag agtgggaaga aattaaagca agataggcta ttaagtgcag   2580
agggagagaa aatgcctcca acatgtgagg aagtaatgag agaaatcata gaattttaag   2640
gccatgattt aaggccatca tggccttaat cttccgcttc ctcgctcact gactcgctgc   2700
gctcggtcgt tcggctgcgg cgagcggtat cagctcactc aaaggcggta atacggttat   2760
ccacagaatc aggggataac gcaggaaaga acatgtgagc aaaaggccag caaaaggcca   2820
ggaaccgtaa aaaggccgcg ttgctggcgt ttttccatag gctccgcccc cctgacgagc   2880
atcacaaaaa tcgacgctca agtcagaggt ggcgaaaccc gacaggacta taaagatacc   2940
aggcgtttcc ccctggaagc tccctcgtgc gctctcctgt tccgaccctg ccgcttaccg   3000
gatacctgtc cgcctttctc ccttcgggaa gcgtggcgct ttctcatagc tcacgctgta   3060
ggtatctcag ttcggtgtag gtcgttcgct ccaagctggg ctgtgtgcac gaaccccccg   3120
ttcagcccga ccgctgcgcc ttatccggta actatcgtct tgagtccaac ccggtaagac   3180
acgacttatc gccactggca gcagccactg gtaacaggat tagcagagcg aggtatgtag   3240
gcggtgctac agagttcttg aagtggtggc ctaactacgg ctacactaga agaacagtat   3300
ttggtatctg cgctctgctg aagccagtta ccttcggaaa aagagttggt agctcttgat   3360
ccggcaaaca aaccaccgct ggtagcggtg gtttttttgt ttgcaagcag cagattacgc   3420
gcagaaaaaa aggatctcaa gaagatcctt tgatcttttc tacggggtct gacgctcagt   3480
ggaacgaaaa ctcacgttaa gggattttgg tcatgagatt atcaaaaagg atcttcacct   3540
agatcctttt aaattaaaaa tgaagtttta aatcaatcta aagtatatat gagtaaactt   3600
ggtctgacag ttaccaatgc ttaatcagtg aggcacctat ctcagcgatc tgtctatttc   3660
gttcatccat agttgcctga ctcggggggg gggggcgctg aggtctgcct cgtgaagaag   3720
gtgttgctga ctcataccag gcctgaatcg ccccatcatc cagccagaaa gtgagggagc   3780
cacggttgat gagagctttg ttgtaggtgg accagttggt gattttgaac ttttgctttg   3840
ccacggaacg gtctgcgttg tcgggaagat gcgtgatctg atccttcaac tcagcaaaag   3900
ttcgatttat tcaacaaagc cgccgtcccg tcaagtcagc gtaatgctct gccagtgtta   3960
caaccaatta accaattctg attagaaaaa ctcatcgagc atcaaatgaa actgcaattt   4020
attcatatca ggattatcaa taccatattt ttgaaaaagc cgtttctgta atgaaggaga   4080
aaactcaccg aggcagttcc ataggatggc aagatcctgg tatcggtctg cgattccgac   4140
tcgtccaaca tcaatacaac ctattaattt cccctcgtca aaaataaggt tatcaagtga   4200
gaaatcacca tgagtgacga ctgaatccgg tgagaatggc aaaagcttat gcatttcttt   4260
ccagacttgt tcaacaggcc agccattacg ctcgtcatca aaatcactcg catcaaccaa   4320
accgttattc attcgtgatt gcgcctgagc gagacgaaat acgcgatcgc tgttaaaagg   4380
acaattacaa acaggaatcg aatgcaaccg gcgcaggaac actgccagcg catcaacaat   4440
attttcacct gaatcaggat attcttctaa tacctggaat gctgttttcc cggggatcgc   4500
agtggtgagt aaccatgcat catcaggagt acggataaaa tgcttgatgg tcggaagagg   4560
cataaattcc gtcagccagt ttagtctgac catctcatct gtaacatcat tggcaacgct   4620
acctttgcca tgtttcagaa acaactctgg cgcatcgggc ttcccataca atcgatagat   4680
tgtcgcacct gattgcccga cattatcgcg agcccattta tacccatata aatcagcatc   4740
catgttggaa tttaatcgcg gcctcgagca agacgtttcc cgttgaatat ggctcataac   4800
accccttgta ttactgttta tgtaagcaga cagttttatt gttcatgatg atatattttt   4860
atcttgtgca atgtaacatc agagattttg agacacaacg tggctttccc cccccccccca   4920
```

ttattgaagc atttatcagg gttattgtct catgagcgga tacatatttg aatgtattta 4980
gaaaaataaa caaatagggg ttccgcgcac atttccccga aaagtgccac ctgacgtcta 5040
agaaaccatt attatcatga cattaaccta taaaaatagg cgtatcacga ggccctttcg 5100
tc 5102

<210> SEQ ID NO 14
<211> LENGTH: 6684
<212> TYPE: DNA
<213> ORGANISM: Artificial Sequence
<220> FEATURE:
<223> OTHER INFORMATION: Synthetic sequence
<220> FEATURE:
<221> NAME/KEY: repeat_region
<222> LOCATION: (1)..(130)
<223> OTHER INFORMATION: 5' ITR
<220> FEATURE:
<221> NAME/KEY: promoter
<222> LOCATION: (191)..(932)
<223> OTHER INFORMATION: human\CMV\I.E.\enhancer\&\promoter
<220> FEATURE:
<221> NAME/KEY: misc_feature
<222> LOCATION: (897)..(901)
<223> OTHER INFORMATION: TATA\box
<220> FEATURE:
<221> NAME/KEY: Intron
<222> LOCATION: (1047)..(1179)
<223> OTHER INFORMATION: Promega\chimeric\intron
<220> FEATURE:
<221> NAME/KEY: misc_feature
<222> LOCATION: (1236)..(1325)
<223> OTHER INFORMATION: forward\primer\1
<220> FEATURE:
<221> NAME/KEY: misc_feature
<222> LOCATION: (1248)..(1295)
<223> OTHER INFORMATION: c-myc\miniIRES\cloned\into\Nhe\site
<220> FEATURE:
<221> NAME/KEY: misc_feature
<222> LOCATION: (1300)..(1308)
<223> OTHER INFORMATION: KOZAK
<220> FEATURE:
<221> NAME/KEY: misc_feature
<222> LOCATION: (1305)..(1364)
<223> OTHER INFORMATION: IL2\signal\peptide
<220> FEATURE:
<221> NAME/KEY: misc_feature
<222> LOCATION: (1365)..(1750)
<223> OTHER INFORMATION: VH\IgG1
<220> FEATURE:
<221> NAME/KEY: misc_feature
<222> LOCATION: (1752)..(2027)
<223> OTHER INFORMATION: CH1
<220> FEATURE:
<221> NAME/KEY: misc_feature
<222> LOCATION: (2028)..(2716)
<223> OTHER INFORMATION: HCH23
<220> FEATURE:
<221> NAME/KEY: misc_feature
<222> LOCATION: (2699)..(2756)
<223> OTHER INFORMATION: reverse\primer\1
<220> FEATURE:
<221> NAME/KEY: misc_feature
<222> LOCATION: (2724)..(2729)
<223> OTHER INFORMATION: STOP
<220> FEATURE:
<221> NAME/KEY: misc_feature
<222> LOCATION: (2738)..(2797)
<223> OTHER INFORMATION: IL2\signal\peptide
<220> FEATURE:
<221> NAME/KEY: misc_feature
<222> LOCATION: (2745)..(2824)
<223> OTHER INFORMATION: forward\primer\2
<220> FEATURE:
<221> NAME/KEY: misc_feature
<222> LOCATION: (2798)..(3095)

<223> OTHER INFORMATION: 3bnc117\light
<220> FEATURE:
<221> NAME/KEY: misc_feature
<222> LOCATION: (3083)..(3106)
<223> OTHER INFORMATION: reverse\primer\2
<220> FEATURE:
<221> NAME/KEY: misc_feature
<222> LOCATION: (3111)..(3415)
<223> OTHER INFORMATION: CL
<220> FEATURE:
<221> NAME/KEY: polyA_signal
<222> LOCATION: (3438)..(3669)
<223> OTHER INFORMATION: SV40\late\polyadenylation\signal
<220> FEATURE:
<221> NAME/KEY: repeat_region
<222> LOCATION: (3734)..(3863)
<223> OTHER INFORMATION: complement - 3' ITR
<220> FEATURE:
<221> NAME/KEY: rep_origin
<222> LOCATION: (4040)..(4495)
<223> OTHER INFORMATION: f1\ori
<220> FEATURE:
<221> NAME/KEY: misc_feature
<222> LOCATION: (4626)..(5483)
<223> OTHER INFORMATION: Amp-R coding sequence
<220> FEATURE:
<221> NAME/KEY: misc_feature
<222> LOCATION: (5657)..(6245)
<223> OTHER INFORMATION: COL\E1\Origin

<400> SEQUENCE: 14
ctgcgcgctc gctcgctcac tgaggccgcc cgggcaaagc ccgggcgtcg ggcgaccttt 60
ggtcgcccgg cctcagtgag cgagcgagcg cgcagagagg gagtggccaa ctccatcact 120
aggggttcct tgtagttaat gattaacccg ccatgctact tatctacgta gccatgctct 180
aggaagatct tcaatattgg ccattagcca tattattcat tggttatata gcataaatca 240
atattggcta ttggccattg catacgttgt atctatatca taatatgtac atttatattg 300
gctcatgtcc aatatgaccg ccatgttggc attgattatt gactagttat taatagtaat 360
caattacggg gtcattagtt catagcccat atatggagtt ccgcgttaca taacttacgg 420
taaatggccc gcctggctga ccgcccaacg acccccgccc attgacgtca ataatgacgt 480
atgttcccat agtaacgcca atagggactt tccattgacg tcaatgggtg gagtatttac 540
ggtaaactgc ccacttggca gtacatcaag tgtatcatat gccaagtccg ccccctattg 600
acgtcaatga cggtaaatgg cccgcctggc attatgccca gtacatgacc ttacgggact 660
ttcctacttg gcagtacatc tacgtattag tcatcgctat taccatggtg atgcggtttt 720
ggcagtacac caatgggcgt ggatagcggt ttgactcacg gggatttcca agtctccacc 780
ccattgacgt caatgggagt ttgttttggc accaaaatca acgggacttt ccaaaatgtc 840
gtaataaccc cgccccgttg acgcaaatgg gcggtaggcg tgtacggtgg gaggtctata 900
taagcagagc tcgtttagtg aaccgtcaga tcactagaag ctttattgcg gtagtttatc 960
acagttaaat tgctaacgca gtcagtgctt ctgacacaac agtctcgaac ttaagctgca 1020
gaagttggtc gtgaggcact gggcaggtaa gtatcaaggt tacaagacag gtttaaggag 1080
accaatagaa actgggcttg tcgagacaga gaagactctt gcgtttctga taggcaccta 1140
ttggtcttac tgacatccac tttgcctttc tctccacagg tgtccactcc cagttcaatt 1200
acagctctta aggctagagt acttaatacg actcactata ggctagcggg gactttgcac 1260
tggaacttac aacacccgag caaggacgcg actctagacc caccatgtac aggatgcaac 1320
tcctgtcttg cattgcacta agtcttgcac ttgtcacaaa cagtcaggtc caattgttac 1380
agtctggggc agcggtgacg aagcccgggg cctcagtgag agtctcctgc gaggcttctg 1440

-continued

```
gatacaacat tcgtgactac tttattcatt ggtggcgaca ggccccagga cagggccttc   1500
agtgggtggg atggatcaat cctaagacag gtcagccaaa caatcctcgt caatttcagg   1560
gtagagtcag tctgactcga cacgcgtcgt gggactttga cacattttcc ttttacatgg   1620
acctgaaggc actaagatcg gacgacacgg ccgtttattt ctgtgcgcga cagcgcagcg   1680
actattggga tttcgacgtc tggggcagtg gaacccaggt cactgtctcg tcagcgtcga   1740
ccaaggggcc ctcggtcttc cccctggcac cctcctccaa gagcacctct gggggcacag   1800
cggccctggg ctgcctggtc aaggactact tccccgaacc ggtgacggtg tcgtggaact   1860
caggcgccct gaccagcggc gtgcacacct tcccggctgt cctacagtcc tcaggactct   1920
actccctcag cagcgtggtg accgtgccct ccagcagctt gggcacccag acctacatct   1980
gcaacgtgaa tcacaagccc agcaacacca aggtggacaa gaaagttgag cccaaatctt   2040
gtgacaaaac tcacacatgc ccaccgtgcc cagcacctga actcctgggg ggaccgtcag   2100
tcttcctctt ccccccaaaa cccaaggaca ccctcatgat ctcccggacc cctgaggtca   2160
catgcgtggt ggtggacgtg agccacgaag accctgaggt caagttcaac tggtacgtgg   2220
acggcgtgga ggtgcataat gccaagacaa agccgcggga ggagcagtac aacagcacgt   2280
accgtgtggt cagcgtcctc accgtcctgc accaggactg gctgaatggc aaggagtaca   2340
agtgcaaggt ctccaacaaa gccctcccag cccccatcga gaaaaccatc tccaaagcca   2400
aagggcagcc ccgagaacca caggtgtaca ccctgccccc atcccgggat gagctgacca   2460
agaaccaggt cagcctgacc tgcctggtca aaggcttcta tcccagcgac atcgccgtgg   2520
agtgggagag caatgggcag ccggagaaca actacaagac cacgcctccc gtgctggact   2580
ccgacggctc cttcttcctc tacagcaagc tcaccgtgga caagagcagg tggcagcagg   2640
ggaacgtctt ctcatgctcc gtgatgcatg aggctctgca caaccactac acgcagaaga   2700
gcctctccct gtctcccggc aagtgataag gccggccatg taccgcatgc aactcctgtc   2760
ttgcattgca ctaagtcttg cacttgtcac aaacagtgat atccagatga cccagtctcc   2820
atcctccctg tctgcatctg taggagatac cgtcactatc acttgccagg caaacggcta   2880
cttaaattgg tatcaacaga ggcgagggaa agccccaaaa ctcctgatct acgatgggtc   2940
caaattggaa agaggggtcc catcaaggtt cagtggaaga agatgggggc aagaatataa   3000
tctgaccatc aacaatctgc agcccgaaga cattgcaaca tatttttgtc aagtgtatga   3060
gtttgtcgtc cctgggacca gactggattt gaaacgtacg gtggctgcac catctgtctt   3120
catcttcccg ccatctgatg agcagttgaa atctggaact gcctctgttg tgtgcctgct   3180
gaataacttc tatcccagag aagccaaagt gcagtggaag gtggacaacg ccctgcagag   3240
cggaaacagc caggaaagcg tgacagagca ggattccaag gattccacat acagcctgag   3300
cagcacactg acactgtcca aggccgacta cgagaagcac aaggtgtacg cctgcgaagt   3360
gacacaccag ggactgtcct cccctgtgac aaagagcttc aacagaggag aatgctgatg   3420
aaagcttgcg gccgcttcga gcagacatga taagatacat tgatgagttt ggacaaacca   3480
caactagaat gcagtgaaaa aaatgcttta tttgtgaaat ttgtgatgct attgctttat   3540
ttgtaaccat tataagctgc aataaacaag ttaacaacaa caattgcatt cattttatgt   3600
ttcaggttca gggggagatg tgggaggttt tttaaagcaa gtaaaacctc tacaaatgtg   3660
gtaaaatcga taaggatctt cctagagcat ggctacgtag ataagtagca tggcgggtta   3720
atcattaact acaaggaacc cctagtgatg gagttggcca ctccctctct gcgcgctcgc   3780
```

-continued

```
tcgctcactg aggccgggcg accaaaggtc gcccgacgcc cgggctttgc ccgggcggcc   3840
tcagtgagcg agcgagcgcg cagccttaat taacctaatt cactggccgt cgttttacaa   3900
cgtcgtgact gggaaaaccc tggcgttacc caacttaatc gccttgcagc acatccccct   3960
ttcgccagct ggcgtaatag cgaagaggcc cgcaccgatc gcccttccca acagttgcgc   4020
agcctgaatg gcgaatggga cgcgccctgt agcggcgcat taagcgcggc gggtgtggtg   4080
gttacgcgca gcgtgaccgc tacacttgcc agcgccctag cgcccgctcc tttcgctttc   4140
ttcccttcct ttctcgccac gttcgccggc tttccccgtc aagctctaaa tcgggggctc   4200
cctttagggt tccgatttag tgctttacgg cacctcgacc ccaaaaaact tgattagggt   4260
gatggttcac gtagtgggcc atcgccctga tagacggttt ttcgcccttt gacgttggag   4320
tccacgttct ttaatagtgg actcttgttc caaactggaa caacactcaa ccctatctcg   4380
gtctattctt ttgatttata agggattttg ccgatttcgg cctattggtt aaaaaatgag   4440
ctgatttaac aaaaatttaa cgcgaatttt aacaaaatat taacgcttac aatttaggtg   4500
gcacttttcg gggaaatgtg cgcggaaccc ctatttgttt atttttctaa atacattcaa   4560
atatgtatcc gctcatgaga caataaccct gataaatgct tcaataatat tgaaaaagga   4620
agagtatgag tattcaacat ttccgtgtcg cccttattcc cttttttgcg gcattttgcc   4680
ttcctgtttt tgctcaccca gaaacgctgg tgaaagtaaa agatgctgaa gatcagttgg   4740
gtgcacgagt gggttacatc gaactggatc tcaacagcgg taagatcctt gagagttttc   4800
gccccgaaga acgttttcca atgatgagca cttttaaagt tctgctatgt ggcgcggtat   4860
tatcccgtat tgacgccggg caagagcaac tcggtcgccg catacactat tctcagaatg   4920
acttggttga gtactcacca gtcacagaaa agcatcttac ggatggcatg acagtaagag   4980
aattatgcag tgctgccata accatgagtg ataacactgc ggccaactta cttctgacaa   5040
cgatcggagg accgaaggag ctaaccgctt ttttgcacaa catgggggat catgtaactc   5100
gccttgatcg ttgggaaccg gagctgaatg aagccatacc aaacgacgag cgtgacacca   5160
cgatgcctgt agcaatggca acaacgttgc gcaaactatt aactggcgaa ctacttactc   5220
tagcttcccg gcaacaatta atagactgga tggaggcgga taaagttgca ggaccacttc   5280
tgcgctcggc ccttccggct ggctggttta ttgctgataa atctggagcc ggtgagcgtg   5340
ggtctcgcgg tatcattgca gcactggggc cagatggtaa gccctcccgt atcgtagtta   5400
tctacacgac ggggagtcag gcaactatgg atgaacgaaa tagacagatc gctgagatag   5460
gtgcctcact gattaagcat tggtaactgt cagaccaagt ttactcatat atactttaga   5520
ttgatttaaa acttcatttt taatttaaaa ggatctaggt gaagatcctt tttgataatc   5580
tcatgaccaa aatcccttaa cgtgagtttt cgttccactg agcgtcagac cccgtagaaa   5640
agatcaaagg atcttcttga gatccttttt ttctgcgcgt aatctgctgc ttgcaaacaa   5700
aaaaaccacc gctaccagcg gtggtttgtt tgccggatca agagctacca actctttttc   5760
cgaaggtaac tggcttcagc agagcgcaga taccaaatac tgttcttcta gtgtagccgt   5820
agttaggcca ccacttcaag aactctgtag caccgcctac atacctcgct ctgctaatcc   5880
tgttaccagt ggctgctgcc agtggcgata agtcgtgtct taccgggttg gactcaagac   5940
gatagttacc ggataaggcg cagcggtcgg gctgaacggg gggttcgtgc acacagccca   6000
gcttggagcg aacgacctac accgaactga gatacctaca gcgtgagcta tgagaaagcg   6060
ccacgcttcc cgaagggaga aaggcggaca ggtatccggt aagcggcagg gtcggaacag   6120
gagagcgcac gagggagctt ccagggggaa acgcctggta tctttatagt cctgtcgggt   6180
```

```
ttcgccacct ctgacttgag cgtcgatttt tgtgatgctc gtcagggggg cggagcctat   6240

ggaaaaacgc cagcaacgcg gcctttttac ggttcctggc cttttgctgg ccttttgctc   6300

acatgttctt tcctgcgtta tcccctgatt ctgtggataa ccgtattacc gcctttgagt   6360

gagctgatac cgctcgccgc agccgaacga ccgagcgcag cgagtcagtg agcgaggaag   6420

cggaagagcg cccaatacgc aaaccgcctc tccccgcgcg ttggccgatt cattaatgca   6480

gctggcacga caggtttccc gactggaaag cgggcagtga gcgcaacgca attaatgtga   6540

gttagctcac tcattaggca ccccaggctt tacactttat gcttccggct cgtatgttgt   6600

gtggaattgt gagcggataa caatttcaca caggaaacag ctatgaccat gattacgcca   6660

gatttaatta aggccttaat tagg                                          6684
```

<210> SEQ ID NO 15
<211> LENGTH: 6754
<212> TYPE: DNA
<213> ORGANISM: Artificial Sequence
<220> FEATURE:
<223> OTHER INFORMATION: Synthetic sequence
<220> FEATURE:
<221> NAME/KEY: repeat_region
<222> LOCATION: (1)..(130)
<223> OTHER INFORMATION: 5' ITR
<220> FEATURE:
<221> NAME/KEY: promoter
<222> LOCATION: (191)..(932)
<223> OTHER INFORMATION: human\CMV\I.E.\enhancer\&\promoter
<220> FEATURE:
<221> NAME/KEY: misc_feature
<222> LOCATION: (897)..(901)
<223> OTHER INFORMATION: TATA\box
<220> FEATURE:
<221> NAME/KEY: Intron
<222> LOCATION: (1047)..(1179)
<223> OTHER INFORMATION: Promega\chimeric\intron
<220> FEATURE:
<221> NAME/KEY: misc_feature
<222> LOCATION: (1248)..(1295)
<223> OTHER INFORMATION: c-myc\miniIRES\cloned\into\Nhe\site
<220> FEATURE:
<221> NAME/KEY: primer
<222> LOCATION: (1294)..(1322)
<223> OTHER INFORMATION: BG118F
<220> FEATURE:
<221> NAME/KEY: misc_feature
<222> LOCATION: (1311)..(1370)
<223> OTHER INFORMATION: IL2\signal\peptide
<220> FEATURE:
<221> NAME/KEY: misc_feature
<222> LOCATION: (1371)..(1756)
<223> OTHER INFORMATION: VH\IgG1
<220> FEATURE:
<221> NAME/KEY: misc_feature
<222> LOCATION: (1376)..(1394)
<223> OTHER INFORMATION: from\bg102f
<220> FEATURE:
<221> NAME/KEY: misc_feature
<222> LOCATION: (1758)..(2033)
<223> OTHER INFORMATION: CH1
<220> FEATURE:
<221> NAME/KEY: misc_feature
<222> LOCATION: (2034)..(2722)
<223> OTHER INFORMATION: HCH23
<220> FEATURE:
<221> NAME/KEY: primer
<222> LOCATION: (2490)..(2525)
<223> OTHER INFORMATION: complement - BG128R
<220> FEATURE:
<221> NAME/KEY: primer
<222> LOCATION: (2490)..(2525)
<223> OTHER INFORMATION: complement - BG123R
<220> FEATURE:

<221> NAME/KEY: misc_feature
<222> LOCATION: (2700)..(2792)
<223> OTHER INFORMATION: complement - reverse\primer\for\CHCCH23
<220> FEATURE:
<221> NAME/KEY: misc_feature
<222> LOCATION: (2729)..(2738)
<223> OTHER INFORMATION: furin\site
<220> FEATURE:
<221> NAME/KEY: misc_feature
<222> LOCATION: (2739)..(2810)
<223> OTHER INFORMATION: F2A\linker
<220> FEATURE:
<221> NAME/KEY: misc_feature
<222> LOCATION: (2775)..(2834)
<223> OTHER INFORMATION: forward\primer\for\VL\for\MAB
<220> FEATURE:
<221> NAME/KEY: misc_feature
<222> LOCATION: (2854)..(3165)
<223> OTHER INFORMATION: 3bnc117\light
<220> FEATURE:
<221> NAME/KEY: misc_feature
<222> LOCATION: (3174)..(3179)
<223> OTHER INFORMATION: introduce\NarI\here\via\PCR
<220> FEATURE:
<221> NAME/KEY: misc_feature
<222> LOCATION: (3181)..(3485)
<223> OTHER INFORMATION: CL
<220> FEATURE:
<221> NAME/KEY: polyA_signal
<222> LOCATION: (3508)..(3739)
<223> OTHER INFORMATION: SV40\late\polyadenylation\signal
<220> FEATURE:
<221> NAME/KEY: repeat_region
<222> LOCATION: (3804)..(3933)
<223> OTHER INFORMATION: complement -3' ITR
<220> FEATURE:
<221> NAME/KEY: rep_origin
<222> LOCATION: (4110)..(4565)
<223> OTHER INFORMATION: f1\ori
<220> FEATURE:
<221> NAME/KEY: misc_feature
<222> LOCATION: (4696)..(5553)
<223> OTHER INFORMATION: Amp-R coding sequence
<220> FEATURE:
<221> NAME/KEY: misc_feature
<222> LOCATION: (5727)..(6315)
<223> OTHER INFORMATION: COL\E1\Origin

<400> SEQUENCE: 15
ctgcgcgctc gctcgctcac tgaggccgcc cgggcaaagc ccgggcgtcg ggcgaccttt 60
ggtcgcccgg cctcagtgag cgagcgagcg cgcagagagg gagtggccaa ctccatcact 120
aggggttcct tgtagttaat gattaacccg ccatgctact tatctacgta gccatgctct 180
aggaagatct tcaatattgg ccattagcca tattattcat tggttatata gcataaatca 240
atattggcta ttggccattg catacgttgt atctatatca taatatgtac atttatattg 300
gctcatgtcc aatatgaccg ccatgttggc attgattatt gactagttat taatagtaat 360
caattacggg gtcattagtt catagcccat atatggagtt ccgcgttaca taacttacgg 420
taaatggccc gcctggctga ccgcccaacg acccccgccc attgacgtca ataatgacgt 480
atgttcccat agtaacgcca atagggactt tccattgacg tcaatgggtg gagtatttac 540
ggtaaactgc ccacttggca gtacatcaag tgtatcatat gccaagtccg ccccctattg 600
acgtcaatga cggtaaatgg cccgcctggc attatgccca gtacatgacc ttacgggact 660
ttcctacttg gcagtacatc tacgtattag tcatcgctat taccatggtg atgcggtttt 720
ggcagtacac caatgggcgt ggatagcggt ttgactcacg gggatttcca agtctccacc 780
ccattgacgt caatgggagt ttgttttggc accaaaatca acgggacttt ccaaaatgtc 840
gtaataaccc cgccccgttg acgcaaatgg gcggtaggcg tgtacggtgg gaggtctata 900

-continued

```
taagcagagc tcgtttagtg aaccgtcaga tcactagaag ctttattgcg gtagtttatc    960
acagttaaat tgctaacgca gtcagtgctt ctgacacaac agtctcgaac ttaagctgca   1020
gaagttggtc gtgaggcact gggcaggtaa gtatcaaggt tacaagacag gtttaaggag   1080
accaatagaa actgggcttg tcgagacaga gaagactctt gcgtttctga taggcaccta   1140
ttggtcttac tgacatccac tttgcctttc tctccacagg tgtccactcc cagttcaatt   1200
acagctctta aggctagagt acttaatacg actcactata ggctagcggg gactttgcac   1260
tggaacttac aacacccgag caaggacgcg actctagcat cgatgccacc atgtacagga   1320
tgcaactcct gtcttgcatt gcactaagtc ttgcacttgt cacaaacagt caggtccaat   1380
tgttacagtc tggggcagcg gtgacgaagc ccggggcctc agtgagagtc tcctgcgagg   1440
cttctggata caacattcgt gactacttta ttcattggtg gcgacaggcc ccaggacagg   1500
gccttcagtg ggtgggatgg atcaatccta agacaggtca gccaaacaat cctcgtcaat   1560
ttcagggtag agtcagtctg actcgacacg cgtcgtggga ctttgacaca ttttcctttt   1620
acatggacct gaaggcacta agatcggacg acacggccgt ttatttctgt gcgcgacagc   1680
gcagcgacta ttgggatttc gacgtctggg gcagtggaac ccaggtcact gtctcgtcag   1740
cgtcgaccaa ggggccctcg gtcttccccc tggcaccctc ctccaagagc acctctgggg   1800
gcacagcggc cctgggctgc ctggtcaagg actacttccc cgaaccggtg acggtgtcgt   1860
ggaactcagg cgccctgacc agcggcgtgc acaccttccc ggctgtccta cagtcctcag   1920
gactctactc cctcagcagc gtggtgaccg tgccctccag cagcttgggc acccagacct   1980
acatctgcaa cgtgaatcac aagcccagca acaccaaggt ggacaagaaa gttgagccca   2040
aatcttgtga caaaactcac acatgcccac cgtgcccagc acctgaactc ctggggggac   2100
cgtcagtctt cctcttcccc ccaaaaccca aggacaccct catgatctcc cggacccctg   2160
aggtcacatg cgtggtggtg gacgtgagcc acgaagaccc tgaggtcaag ttcaactggt   2220
acgtggacgg cgtggaggtg cataatgcca agacaaagcc gcgggaggag cagtacaaca   2280
gcacgtaccg tgtggtcagc gtcctcaccg tcctgcacca ggactggctg aatggcaagg   2340
agtacaagtg caaggtctcc aacaaagccc tcccagcccc catcgagaaa accatctcca   2400
aagccaaagg gcagccccga gaaccacagg tgtacaccct gcccccatcc cgggatgagc   2460
tgaccaagaa ccaggtcagc ctgacctgcc tggtcaaagg cttctatccc agcgacatcg   2520
ccgtggagtg ggagagcaat gggcagccgg agaacaacta caagaccacg cctcccgtgc   2580
tggactccga cggctccttc ttcctctaca gcaagctcac cgtggacaag agcaggtggc   2640
agcaggggaa cgtcttctca tgctccgtga tgcatgaggc tctgcacaac cactacacgc   2700
agaagagcct ctccctgtct cccggccgaa agcggagagc cccgtgaag cagaccctga   2760
acttcgacct gctgaagctg gccggcgacg tggaaagcaa ccctggccct atgggatggt   2820
catgtatcat cctttttcta gtagcaactg caaccggtgt acattctgac atccagatga   2880
cccagtctcc atcctccctg tctgcatctg taggagatac cgtcactatc acttgccagg   2940
caaacggcta cttaaattgg tatcaacaga ggcgagggaa agccccaaaa ctcctgatct   3000
acgatgggtc caaattggaa agaggggtcc catcaaggtt cagtggaaga agatgggggc   3060
aagaatataa tctgaccatc aacaatctgc agcccgaaga cattgcaaca tatttttgtc   3120
aagtgtatga gtttgtcgtc cctgggacca gactggattt gaaacgtacg gtggctgcac   3180
catctgtctt catcttcccg ccatctgatg agcagttgaa atctggaact gcctctgttg   3240
```

-continued

```
tgtgcctgct gaataacttc taccccagag aagccaaagt gcagtggaag gtggacaacg   3300
ccctgcagag cggaaacagc caggaaagcg tgacagagca ggattccaag gattccacat   3360
acagcctgag cagcacactg acactgtcca aggccgacta cgagaagcac aaggtgtacg   3420
cctgcgaagt gacacaccag ggactgtcct cccctgtgac aaagagcttc aacagaggag   3480
aatgctgatg aaagcttgcg gccgcttcga gcagacatga taagatacat tgatgagttt   3540
ggacaaacca caactagaat gcagtgaaaa aaatgcttta tttgtgaaat ttgtgatgct   3600
attgctttat ttgtaaccat tataagctgc aataaacaag ttaacaacaa caattgcatt   3660
cattttatgt ttcaggttca gggggagatg tgggaggttt tttaaagcaa gtaaaacctc   3720
tacaaatgtg gtaaaatcga taaggatctt cctagagcat ggctacgtag ataagtagca   3780
tggcgggtta atcattaact acaaggaacc cctagtgatg gagttggcca ctccctctct   3840
gcgcgctcgc tcgctcactg aggccgggcg accaaaggtc gcccgacgcc cgggctttgc   3900
ccgggcggcc tcagtgagcg agcgagcgcg cagccttaat taacctaatt cactggccgt   3960
cgttttacaa cgtcgtgact gggaaaaccc tggcgttacc caacttaatc gccttgcagc   4020
acatccccct ttcgccagct ggcgtaatag cgaagaggcc cgcaccgatc gcccttccca   4080
acagttgcgc agcctgaatg gcgaatggga cgcgccctgt agcggcgcat taagcgcggc   4140
gggtgtggtg gttacgcgca gcgtgaccgc tacacttgcc agcgccctag cgcccgctcc   4200
tttcgctttc ttcccttcct ttctcgccac gttcgccggc tttccccgtc aagctctaaa   4260
tcgggggctc cctttagggt tccgatttag tgctttacgg cacctcgacc ccaaaaaact   4320
tgattagggt gatggttcac gtagtgggcc atcgccctga tagacggttt ttcgcccttt   4380
gacgttggag tccacgttct ttaatagtgg actcttgttc caaactggaa caacactcaa   4440
ccctatctcg gtctattctt ttgatttata agggattttg ccgatttcgg cctattggtt   4500
aaaaaatgag ctgatttaac aaaaatttaa cgcgaatttt aacaaaatat taacgcttac   4560
aatttaggtg gcacttttcg gggaaatgtg cgcggaaccc ctatttgttt atttttctaa   4620
atacattcaa atatgtatcc gctcatgaga caataaccct gataaatgct tcaataatat   4680
tgaaaaagga agagtatgag tattcaacat ttccgtgtcg cccttattcc cttttttgcg   4740
gcattttgcc ttcctgtttt tgctcaccca gaaacgctgg tgaaagtaaa agatgctgaa   4800
gatcagttgg gtgcacgagt gggttacatc gaactggatc tcaacagcgg taagatcctt   4860
gagagttttc gccccgaaga acgttttcca atgatgagca cttttaaagt tctgctatgt   4920
ggcgcggtat tatcccgtat tgacgccggg caagagcaac tcggtcgccg catacactat   4980
tctcagaatg acttggttga gtactcacca gtcacagaaa agcatcttac ggatggcatg   5040
acagtaagag aattatgcag tgctgccata accatgagtg ataacactgc ggccaactta   5100
cttctgacaa cgatcggagg accgaaggag ctaaccgctt ttttgcacaa catgggggat   5160
catgtaactc gccttgatcg ttgggaaccg gagctgaatg aagccatacc aaacgacgag   5220
cgtgacacca cgatgcctgt agcaatggca acaacgttgc gcaaactatt aactggcgaa   5280
ctacttactc tagcttcccg gcaacaatta atagactgga tggaggcgga taaagttgca   5340
ggaccacttc tgcgctcggc ccttccggct ggctggttta ttgctgataa atctggagcc   5400
ggtgagcgtg ggtctcgcgg tatcattgca gcactggggc cagatggtaa gccctcccgt   5460
atcgtagtta tctacacgac ggggagtcag gcaactatgg atgaacgaaa tagacagatc   5520
gctgagatag gtgcctcact gattaagcat tggtaactgt cagaccaagt ttactcatat   5580
atactttaga ttgatttaaa acttcatttt taatttaaaa ggatctaggt gaagatcctt   5640
```

-continued

```
tttgataatc tcatgaccaa aatcccttaa cgtgagtttt cgttccactg agcgtcagac   5700

cccgtagaaa agatcaaagg atcttcttga gatccttttt ttctgcgcgt aatctgctgc   5760

ttgcaaacaa aaaaaccacc gctaccagcg gtggtttgtt tgccggatca agagctacca   5820

actctttttc cgaaggtaac tggcttcagc agagcgcaga taccaaatac tgttcttcta   5880

gtgtagccgt agttaggcca ccacttcaag aactctgtag caccgcctac atacctcgct   5940

ctgctaatcc tgttaccagt ggctgctgcc agtggcgata agtcgtgtct taccgggttg   6000

gactcaagac gatagttacc ggataaggcg cagcggtcgg gctgaacggg gggttcgtgc   6060

acacagccca gcttggagcg aacgacctac accgaactga gatacctaca gcgtgagcta   6120

tgagaaagcg ccacgcttcc cgaagggaga aaggcggaca ggtatccggt aagcggcagg   6180

gtcggaacag gagagcgcac gagggagctt ccagggggaa acgcctggta tctttatagt   6240

cctgtcgggt ttcgccacct ctgacttgag cgtcgatttt tgtgatgctc gtcagggggg   6300

cggagcctat ggaaaaacgc cagcaacgcg gcctttttac ggttcctggc cttttgctgg   6360

ccttttgctc acatgttctt tcctgcgtta tcccctgatt ctgtggataa ccgtattacc   6420

gcctttgagt gagctgatac cgctcgccgc agccgaacga ccgagcgcag cgagtcagtg   6480

agcgaggaag cggaagagcg cccaatacgc aaaccgcctc tccccgcgcg ttggccgatt   6540

cattaatgca gctggcacga caggtttccc gactggaaag cgggcagtga gcgcaacgca   6600

attaatgtga gttagctcac tcattaggca ccccaggctt tacactttat gcttccggct   6660

cgtatgttgt gtggaattgt gagcggataa caatttcaca caggaaacag ctatgaccat   6720

gattacgcca gatttaatta aggccttaat tagg                               6754
```

<210> SEQ ID NO 16
<211> LENGTH: 6748
<212> TYPE: DNA
<213> ORGANISM: Artificial Sequence
<220> FEATURE:
<223> OTHER INFORMATION: Synthetic sequence
<220> FEATURE:
<221> NAME/KEY: repeat_region
<222> LOCATION: (1)..(130)
<223> OTHER INFORMATION: 5' ITR
<220> FEATURE:
<221> NAME/KEY: promoter
<222> LOCATION: (191)..(932)
<223> OTHER INFORMATION: human\CMV\I.E.\enhancer\&\promoter
<220> FEATURE:
<221> NAME/KEY: misc_feature
<222> LOCATION: (897)..(901)
<223> OTHER INFORMATION: TATA\box
<220> FEATURE:
<221> NAME/KEY: Intron
<222> LOCATION: (1047)..(1179)
<223> OTHER INFORMATION: Promega\chimeric\intron
<220> FEATURE:
<221> NAME/KEY: misc_feature
<222> LOCATION: (1248)..(1293)
<223> OTHER INFORMATION: c-myc\miniIRES\cloned\into\Nhe\site
<220> FEATURE:
<221> NAME/KEY: misc_feature
<222> LOCATION: (1292)..(1297)
<223> OTHER INFORMATION: 6bp\insertion
<220> FEATURE:
<221> NAME/KEY: misc_feature
<222> LOCATION: (1294)..(3493)
<223> OTHER INFORMATION: 3nbc\ORF\2
<220> FEATURE:
<221> NAME/KEY: polyA_signal
<222> LOCATION: (3502)..(3733)
<223> OTHER INFORMATION: SV40\late\polyadenylation\signal
<220> FEATURE:

-continued

<221> NAME/KEY: repeat_region
<222> LOCATION: (3798)..(3927)
<223> OTHER INFORMATION: complement - 3' ITR
<220> FEATURE:
<221> NAME/KEY: rep_origin
<222> LOCATION: (4104)..(4559)
<223> OTHER INFORMATION: complement - f1\ori
<220> FEATURE:
<221> NAME/KEY: misc_feature
<222> LOCATION: (4690)..(5547)
<223> OTHER INFORMATION: Amp-R coding sequence
<220> FEATURE:
<221> NAME/KEY: misc_feature
<222> LOCATION: (5721)..(6309)
<223> OTHER INFORMATION: COL\E1\Origin

<400> SEQUENCE: 16
ctgcgcgctc gctcgctcac tgaggccgcc cgggcaaagc ccgggcgtcg ggcgaccttt 60
ggtcgcccgg cctcagtgag cgagcgagcg cgcagagagg gagtggccaa ctccatcact 120
aggggttcct tgtagttaat gattaacccg ccatgctact tatctacgta gccatgctct 180
aggaagatct tcaatattgg ccattagcca tattattcat tggttatata gcataaatca 240
atattggcta ttggccattg catacgttgt atctatatca taatatgtac atttatattg 300
gctcatgtcc aatatgaccg ccatgttggc attgattatt gactagttat taatagtaat 360
caattacggg gtcattagtt catagcccat atatggagtt ccgcgttaca taacttacgg 420
taaatggccc gcctggctga ccgcccaacg acccccgccc attgacgtca ataatgacgt 480
atgttcccat agtaacgcca atagggactt tccattgacg tcaatgggtg gagtatttac 540
ggtaaactgc ccacttggca gtacatcaag tgtatcatat gccaagtccg ccccctattg 600
acgtcaatga cggtaaatgg cccgcctggc attatgccca gtacatgacc ttacgggact 660
ttcctacttg gcagtacatc tacgtattag tcatcgctat taccatggtg atgcggtttt 720
ggcagtacac caatgggcgt ggatagcggt ttgactcacg gggatttcca agtctccacc 780
ccattgacgt caatgggagt ttgttttggc accaaaatca acgggacttt ccaaaatgtc 840
gtaataaccc cgccccgttg acgcaaatgg gcggtaggcg tgtacggtgg gaggtctata 900
taagcagagc tcgtttagtg aaccgtcaga tcactagaag ctttattgcg gtagtttatc 960
acagttaaat tgctaacgca gtcagtgctt ctgacacaac agtctcgaac ttaagctgca 1020
gaagttggtc gtgaggcact gggcaggtaa gtatcaaggt tacaagacag gtttaaggag 1080
accaatagaa actgggcttg tcgagacaga gaagactctt gcgtttctga taggcaccta 1140
ttggtcttac tgacatccac tttgcctttc tctccacagg tgtccactcc cagttcaatt 1200
acagctctta aggctagagt acttaatacg actcactata ggctagcggg gactttgcac 1260
tggaacttac aacacccgag caaggacgcg actctagctc tagaaccatg tatcggatgc 1320
agcttctctc ctgcattgcc ttaagtctcg cccttgtaac aaatagtcag gttcagcttt 1380
tacagagtgg cgccgcagtc accaaacccg gagcatccgt gcgagtctcc tgcgaagcca 1440
gtgggtacaa cattagggac tatttcatcc attggtggag gcaggcaccc ggccaaggac 1500
ttcagtgggt tgggtggatc aatcctaaga cgggacagcc caataacccg agacagtttc 1560
aggggcgcgt ctctcttact cgccatgctt cttgggattt tgacaccttt tctttctaca 1620
tggacctcaa agcccttcgc agcgacgata ccgctgtgta tttctgtgcc aggcagcgct 1680
ctgactactg ggactttgat gtttggggat ctggtacgca agtcacagtc tctagtgcaa 1740
gtaccaaagg ccccagtgtg tttcccctcg ctccgtctag caagtctacc tctggcggta 1800
ctgcagccct tggatgtctg gtcaaagact actttccaga gccggtgaca gtgagttgga 1860

-continued

```
attcgggtgc tctaacatct ggcgtgcaca cttttccggc tgtgctgcag tccagtggac   1920
tttactctct gagcagtgtg gttactgtgc cctctagttc tcttgggacg cagacctaca   1980
tctgcaatgt gaatcataag ccatctaata caaaggtgga taagaaggtg gaaccaaagt   2040
catgcgacaa aacccacacg tgcccaccat gtccagctcc ggagttactg ggcggaccct   2100
ctgtctttct gtttccgccc aagccgaagg atacactgat gatatctcgt accccagagg   2160
tgacatgcgt ggttgtcgat gtgtcccatg aggaccccga ggtgaagttt aactggtatg   2220
tggacggcgt ggaagtccat aatgctaaga ctaaaccaag ggaagaacag tacaattcca   2280
cgtaccgcgt cgttagcgtc ttgaccgtgc tccatcagga ctggctcaac ggaaaggagt   2340
ataagtgtaa ggtcagtaac aaggctcttc cggctccaat tgagaaaaca attagtaagg   2400
ctaaggggca gcctcgcgaa cctcaagtct acaccctacc accgtctcgc gacgaactca   2460
ctaagaatca ggtgtcgctc acctgcctcg tcaaaggttt ctatccctct gacatcgcag   2520
tagaatggga atccaatggc cagccggaga acaattacaa gaccaccccg ccagtgctag   2580
actcagacgg gagtttcttc ttatactcta agcttaccgt agataagtcc cggtggcagc   2640
agggcaatgt gttttcctgt tcagtgatgc atgaagcgct gcataatcac tatacacaaa   2700
agtcactttc tctgagtccc ggtcggaaga gaagagctcc tgttaaacag acactgaatt   2760
tcgatttgct caaactcgct ggagacgtag aaagcaatcc tggtcctatg taccgaatgc   2820
agcttttgtc ttgcatcgct ctgagccttg cgcttgttac gaatagcgac atacagatga   2880
cacagtctcc gagttctctt agtgctagtg tgggcgatac agtcactata acatgccagg   2940
ctaatggtta cctgaactgg taccaacaac gccgcggtaa agcccccaaa ctgctcatct   3000
atgatgggtc aaaacttgaa cgcggcgtcc cgagccgctt tagtggccgc cgttgggggc   3060
aggaatacaa tcttaccatc aacaatctac agcccgaaga tattgctact tacttttgcc   3120
aggtttacga atttgtcgtc ccgggaacgc gccttgatct taagcggact gtcgccgctc   3180
cgagtgtgtt tatctttcct ccatcagacg aacagcttaa gtcaggcacc gcttctgtgg   3240
tgtgcttgct gaataacttc tatccccggg aagccaaggt tcagtggaag gtcgacaatg   3300
ctcttcagtc tggtaatagc caggagtcag tgacagaaca ggactccaag gacagtacct   3360
actctctatc cagtacactg accctgagca aagctgacta cgaaaagcac aaagtctatg   3420
cttgtgaagt aacgcatcaa ggccttagct ctcctgttac caagagcttc aataggggtg   3480
aatgctaatg agcggccgct tcgagcagac atgataagat acattgatga gtttggacaa   3540
accacaacta gaatgcagtg aaaaaaatgc tttatttgtg aaatttgtga tgctattgct   3600
ttatttgtaa ccattataag ctgcaataaa caagttaaca acaacaattg cattcatttt   3660
atgtttcagg ttcaggggga gatgtgggag gtttttaaa gcaagtaaaa cctctacaaa   3720
tgtggtaaaa tcgataagga tcttcctaga gcatggctac gtagataagt agcatggcgg   3780
gttaatcatt aactacaagg aacccctagt gatggagttg gccactccct ctctgcgcgc   3840
tcgctcgctc actgaggccg ggcgaccaaa ggtcgcccga cgcccgggct ttgcccgggc   3900
ggcctcagtg agcgagcgag cgcgcagcct taattaacct aattcactgg ccgtcgtttt   3960
acaacgtcgt gactgggaaa accctggcgt tacccaactt aatcgccttg cagcacatcc   4020
ccctttcgcc agctggcgta atagcgaaga ggcccgcacc gatcgccctt cccaacagtt   4080
gcgcagcctg aatggcgaat gggacgcgcc ctgtagcggc gcattaagcg cggcgggtgt   4140
ggtggttacg cgcagcgtga ccgctacact tgccagcgcc ctagcgcccg ctcctttcgc   4200
```

-continued

```
tttcttccct tcctttctcg ccacgttcgc cggctttccc cgtcaagctc taaatcgggg   4260
gctcccttta gggttccgat ttagtgcttt acggcacctc gaccccaaaa aacttgatta   4320
gggtgatggt tcacgtagtg ggccatcgcc ctgatagacg gtttttcgcc ctttgacgtt   4380
ggagtccacg ttctttaata gtggactctt gttccaaact ggaacaacac tcaaccctat   4440
ctcggtctat tcttttgatt tataagggat tttgccgatt tcggcctatt ggttaaaaaa   4500
tgagctgatt taacaaaaat ttaacgcgaa ttttaacaaa atattaacgc ttacaattta   4560
ggtggcactt ttcggggaaa tgtgcgcgga acccctattt gtttattttt ctaaatacat   4620
tcaaatatgt atccgctcat gagacaataa ccctgataaa tgcttcaata atattgaaaa   4680
aggaagagta tgagtattca acatttccgt gtcgccctta ttcccttttt tgcggcattt   4740
tgccttcctg tttttgctca cccagaaacg ctggtgaaag taaaagatgc tgaagatcag   4800
ttgggtgcac gagtgggtta catcgaactg gatctcaaca gcggtaagat ccttgagagt   4860
tttcgccccg aagaacgttt tccaatgatg agcactttta aagttctgct atgtggcgcg   4920
gtattatccc gtattgacgc cgggcaagag caactcggtc gccgcataca ctattctcag   4980
aatgacttgg ttgagtactc accagtcaca gaaaagcatc ttacggatgg catgacagta   5040
agagaattat gcagtgctgc cataaccatg agtgataaca ctgcggccaa cttacttctg   5100
acaacgatcg gaggaccgaa ggagctaacc gcttttttgc acaacatggg ggatcatgta   5160
actcgccttg atcgttggga accggagctg aatgaagcca taccaaacga cgagcgtgac   5220
accacgatgc ctgtagcaat ggcaacaacg ttgcgcaaac tattaactgg cgaactactt   5280
actctagctt cccggcaaca attaatagac tggatggagg cggataaagt tgcaggacca   5340
cttctgcgct cggcccttcc ggctggctgg tttattgctg ataaatctgg agccggtgag   5400
cgtgggtctc gcggtatcat tgcagcactg gggccagatg gtaagccctc ccgtatcgta   5460
gttatctaca cgacggggag tcaggcaact atggatgaac gaaatagaca gatcgctgag   5520
ataggtgcct cactgattaa gcattggtaa ctgtcagacc aagtttactc atatatactt   5580
tagattgatt taaaacttca tttttaattt aaaaggatct aggtgaagat cctttttgat   5640
aatctcatga ccaaaatccc ttaacgtgag ttttcgttcc actgagcgtc agaccccgta   5700
gaaaagatca aaggatcttc ttgagatcct ttttttctgc gcgtaatctg ctgcttgcaa   5760
acaaaaaaac caccgctacc agcggtggtt tgtttgccgg atcaagagct accaactctt   5820
tttccgaagg taactggctt cagcagagcg cagataccaa atactgttct tctagtgtag   5880
ccgtagttag gccaccactt caagaactct gtagcaccgc ctacatacct cgctctgcta   5940
atcctgttac cagtggctgc tgccagtggc gataagtcgt gtcttaccgg gttggactca   6000
agacgatagt taccggataa ggcgcagcgg tcgggctgaa cggggggttc gtgcacacag   6060
cccagcttgg agcgaacgac ctacaccgaa ctgagatacc tacagcgtga gctatgagaa   6120
agcgccacgc ttcccgaagg gagaaaggcg gacaggtatc cggtaagcgg cagggtcgga   6180
acaggagagc gcacgaggga gcttccaggg ggaaacgcct ggtatcttta tagtcctgtc   6240
gggtttcgcc acctctgact tgagcgtcga tttttgtgat gctcgtcagg ggggcggagc   6300
ctatggaaaa acgccagcaa cgcggccttt ttacggttcc tggccttttg ctggcctttt   6360
gctcacatgt tctttcctgc gttatcccct gattctgtgg ataaccgtat taccgccttt   6420
gagtgagctg ataccgctcg ccgcagccga acgaccgagc gcagcgagtc agtgagcgag   6480
gaagcggaag agcgcccaat acgcaaaccg cctctccccg cgcgttggcc gattcattaa   6540
tgcagctggc acgacaggtt tcccgactgg aaagcgggca gtgagcgcaa cgcaattaat   6600
```

gtgagttagc tcactcatta ggcaccccag gctttacact ttatgcttcc ggctcgtatg 6660
ttgtgtggaa ttgtgagcgg ataacaattt cacacaggaa acagctatga ccatgattac 6720
gccagattta attaaggcct taattagg 6748

<210> SEQ ID NO 17
<211> LENGTH: 6748
<212> TYPE: DNA
<213> ORGANISM: Artificial Sequence
<220> FEATURE:
<223> OTHER INFORMATION: Synthetic sequence
<220> FEATURE:
<221> NAME/KEY: repeat_region
<222> LOCATION: (1)..(130)
<223> OTHER INFORMATION: 5' ITR
<220> FEATURE:
<221> NAME/KEY: promoter
<222> LOCATION: (191)..(932)
<223> OTHER INFORMATION: human\CMV\I.E.\enhancer\&\promoter
<220> FEATURE:
<221> NAME/KEY: misc_feature
<222> LOCATION: (897)..(901)
<223> OTHER INFORMATION: TATA\box
<220> FEATURE:
<221> NAME/KEY: Intron
<222> LOCATION: (1047)..(1179)
<223> OTHER INFORMATION: Promega\Chimeric\Intron
<220> FEATURE:
<221> NAME/KEY: misc_feature
<222> LOCATION: (1248)..(1293)
<223> OTHER INFORMATION: c-myc\miniIRES\cloned\into\Nhe\site
<220> FEATURE:
<221> NAME/KEY: misc_feature
<222> LOCATION: (1292)..(1297)
<223> OTHER INFORMATION: 6bp\insertion
<220> FEATURE:
<221> NAME/KEY: misc_feature
<222> LOCATION: (1294)..(3493)
<223> OTHER INFORMATION: 3nbc\ORF\2
<220> FEATURE:
<221> NAME/KEY: polyA_signal
<222> LOCATION: (3502)..(3733)
<223> OTHER INFORMATION: SV40\late\polyadenylation\signal
<220> FEATURE:
<221> NAME/KEY: repeat_region
<222> LOCATION: (3798)..(3927)
<223> OTHER INFORMATION: complement - 3' ITR
<220> FEATURE:
<221> NAME/KEY: rep_origin
<222> LOCATION: (4104)..(4559)
<223> OTHER INFORMATION: complement - f1\ori
<220> FEATURE:
<221> NAME/KEY: misc_feature
<222> LOCATION: (4690)..(5547)
<223> OTHER INFORMATION: Amp-R coding sequence
<220> FEATURE:
<221> NAME/KEY: misc_feature
<222> LOCATION: (5721)..(6309)
<223> OTHER INFORMATION: COL\E1\Origin

<400> SEQUENCE: 17
ctgcgcgctc gctcgctcac tgaggccgcc cgggcaaagc ccgggcgtcg ggcgaccttt 60
ggtcgcccgg cctcagtgag cgagcgagcg cgcagagagg gagtggccaa ctccatcact 120
aggggttcct tgtagttaat gattaacccg ccatgctact tatctacgta gccatgctct 180
aggaagatct tcaatattgg ccattagcca tattattcat tggttatata gcataaatca 240
atattggcta ttggccattg catacgttgt atctatatca taatatgtac atttatattg 300
gctcatgtcc aatatgaccg ccatgttggc attgattatt gactagttat taatagtaat 360
caattacggg gtcattagtt catagcccat atatggagtt ccgcgttaca taacttacgg 420

-continued

```
taaatggccc gcctggctga ccgcccaacg acccccgccc attgacgtca ataatgacgt    480
atgttcccat agtaacgcca atagggactt tccattgacg tcaatgggtg gagtatttac    540
ggtaaactgc ccacttggca gtacatcaag tgtatcatat gccaagtccg ccccctattg    600
acgtcaatga cggtaaatgg cccgcctggc attatgccca gtacatgacc ttacgggact    660
ttcctacttg gcagtacatc tacgtattag tcatcgctat taccatggtg atgcggtttt    720
ggcagtacac caatgggcgt ggatagcggt ttgactcacg gggatttcca agtctccacc    780
ccattgacgt caatgggagt ttgttttggc accaaaatca acgggacttt ccaaaatgtc    840
gtaataaccc cgccccgttg acgcaaatgg gcggtaggcg tgtacggtgg gaggtctata    900
taagcagagc tcgtttagtg aaccgtcaga tcactagaag ctttattgcg gtagtttatc    960
acagttaaat tgctaacgca gtcagtgctt ctgacacaac agtctcgaac ttaagctgca   1020
gaagttggtc gtgaggcact gggcaggtaa gtatcaaggt tacaagacag gtttaaggag   1080
accaatagaa actgggcttg tcgagacaga gaagactctt gcgtttctga taggcaccta   1140
ttggtcttac tgacatccac tttgcctttc tctccacagg tgtccactcc cagttcaatt   1200
acagctctta aggctagagt acttaatacg actcactata ggctagcggg gactttgcac   1260
tggaacttac aacacccgag caaggacgcg actctagctc tagaaccatg taccgtatgc   1320
agctcctatc gtgcattgcc ttgtcgttgg ccttagttac aaacagtcag gtgcagcttt   1380
tgcagtccgg ggctgcagtg accaaacccg gcgcatctgt gagggtgtca tgcgaagcct   1440
cggggtacaa cattcgggac tactttatcc actggtggag gcaggcccca gggcagggat   1500
tacagtgggt ggggtggatc aacccgaaaa cagggcagcc taacaacccc cgacagttcc   1560
aggggcgcgt ctcgttgacg aggcacgcga gttgggattt cgacacattc agcttctaca   1620
tggacctcaa ggcgctgaga agtgacgaca cagccgtcta cttctgcgcg aggcagagat   1680
cggactattg ggacttcgac gtgtggggtt cgggaacgca agtgaccgtg tcctcagcgt   1740
ccacgaaagg gccatcagtg ttccctctgg cgccatcctc gaagtctacg tcaggcggga   1800
cggctgctct gggatgcctg gtgaaagact actttcccga gccggtgact gtctcgtgga   1860
attcaggcgc gttgacatcc ggtgttcaca cgttccccgc tgtgttgcag agcagcggac   1920
tgtactctct gagcagtgtg gtgacagtgc cctcctcatc gctggggacg cagacgtaca   1980
tctgcaacgt gaaccacaag ccgagcaaca cgaaggtgga caagaaggtc gagccgaagt   2040
cttgtgataa gactcacaca tgtcccccat gccccgctcc agagctgctg ggtggcccta   2100
gcgtgtttct gttcccaccg aagccaaagg acaccttgat gatcagcagg accccggaag   2160
tgacctgcgt tgtggtcgac gtgtcacatg aggaccccga agtgaagttt aactggtacg   2220
tggacggggt ggaggtgcat aacgcaaaga ctaagccccg ggaggagcaa tacaattcca   2280
cctaccgggt cgtgtcggtg ctgactgtgc tgcaccagga ctggctgaac gggaaggagt   2340
acaagtgcaa ggtgtcgaat aaggccctgc cagcacctat cgaaaagacg atatctaagg   2400
caaaggggca gccgcgggag ccccaagtat acacactgcc tccgtccagg gatgagttga   2460
ccaagaacca ggtgtctctg acctgcctgg ttaagggctt ctacccatcc gacatagcag   2520
tggagtggga gagcaacggc cagccggaga acaactataa gaccacaccc ccggtgctgg   2580
acagcgacgg ctcgttcttc ctgtacagta agttgaccgt cgacaagagc cggtggcagc   2640
aggggaatgt gttctcatgc agcgtgatgc acgaagccct gcacaatcac tacacccaga   2700
agtcactgtc gctgagccct ggccggaaaa ggagggcccc agtcaaacag actctgaact   2760
tcgacctgct gaagctcgcg ggggacgtgg agagtaatcc cgggccaatg tatcgcatgc   2820
```

agttgctgtc gtgcatcgcc ctgtctctgg cgctggtcac caattctgat attcagatga 2880
cgcagagccc tagcagcctc tctgcaagcg tgggggacac ggtgacgatt acatgccagg 2940
ctaacggata tctgaactgg taccaacagc ggagggggaa ggccccgaag ctgctcatct 3000
acgacgggtc caaattggag cgaggagtac cgtcccggtt ctcggggcgg agatgggggc 3060
aggaatacaa cctaaccata aacaacctac agcccgagga catcgccact tacttctgcc 3120
aggtgtacga gttcgtggtg cccggcacca ggctggacct gaagcggacc gtggccgcac 3180
ctagtgtgtt catcttccca ccgtccgatg agcagttgaa gagcgggaca gcgagcgtgg 3240
tgtgcctgct gaacaacttc tatccgcgcg aggccaaagt acagtggaag gtagataacg 3300
ccctccagtc cggaaacagc caggagtccg tgaccgagca ggactcaaag gattccacat 3360
actccctttc ctcaacactg acgctgagta aggcggatta cgagaagcac aaggtgtatg 3420
cgtgtgaggt gactcaccag ggctgtcct cacccgtgac gaaatcgttt aaccggggcg 3480
agtgttaatg agcggccgct tcgagcagac atgataagat acattgatga gtttggacaa 3540
accacaacta gaatgcagtg aaaaaaatgc tttatttgtg aaatttgtga tgctattgct 3600
ttatttgtaa ccattataag ctgcaataaa caagttaaca acaacaattg cattcatttt 3660
atgtttcagg ttcaggggga gatgtgggag gtttttaaa gcaagtaaaa cctctacaaa 3720
tgtggtaaaa tcgataagga tcttcctaga gcatggctac gtagataagt agcatggcgg 3780
gttaatcatt aactacaagg aacccctagt gatggagttg gccactccct ctctgcgcgc 3840
tcgctcgctc actgaggccg ggcgaccaaa ggtcgcccga cgcccgggct ttgcccgggc 3900
ggcctcagtg agcgagcgag cgcgcagcct taattaacct aattcactgg ccgtcgtttt 3960
acaacgtcgt gactgggaaa accctggcgt tacccaactt aatcgccttg cagcacatcc 4020
ccctttcgcc agctggcgta atagcgaaga ggcccgcacc gatcgccctt cccaacagtt 4080
gcgcagcctg aatggcgaat gggacgcgcc ctgtagcggc gcattaagcg cggcgggtgt 4140
ggtggttacg cgcagcgtga ccgctacact tgccagcgcc ctagcgcccg ctcctttcgc 4200
tttcttccct tcctttctcg ccacgttcgc cggctttccc cgtcaagctc taaatcgggg 4260
gctcccttta gggttccgat ttagtgcttt acggcacctc gaccccaaaa aacttgatta 4320
gggtgatggt tcacgtagtg ggccatcgcc ctgatagacg gtttttcgcc ctttgacgtt 4380
ggagtccacg ttctttaata gtggactctt gttccaaact ggaacaacac tcaaccctat 4440
ctcggtctat tcttttgatt tataagggat tttgccgatt tcggcctatt ggttaaaaaa 4500
tgagctgatt taacaaaaat ttaacgcgaa ttttaacaaa atattaacgc ttacaattta 4560
ggtggcactt ttcggggaaa tgtgcgcgga acccctattt gtttatttt ctaaatacat 4620
tcaaatatgt atccgctcat gagacaataa ccctgataaa tgcttcaata atattgaaaa 4680
aggaagagta tgagtattca acatttccgt gtcgccctta ttcccttttt tgcggcattt 4740
tgccttcctg tttttgctca cccagaaacg ctggtgaaag taaaagatgc tgaagatcag 4800
ttgggtgcac gagtgggtta catcgaactg gatctcaaca gcggtaagat ccttgagagt 4860
tttcgccccg aagaacgttt tccaatgatg agcactttta aagttctgct atgtggcgcg 4920
gtattatccc gtattgacgc cgggcaagag caactcggtc gccgcataca ctattctcag 4980
aatgacttgg ttgagtactc accagtcaca gaaaagcatc ttacggatgg catgacagta 5040
agagaattat gcagtgctgc cataaccatg agtgataaca ctgcggccaa cttacttctg 5100
acaacgatcg gaggaccgaa ggagctaacc gcttttttgc acaacatggg ggatcatgta 5160

-continued

```
actcgccttg atcgttggga accggagctg aatgaagcca taccaaacga cgagcgtgac   5220

accacgatgc ctgtagcaat ggcaacaacg ttgcgcaaac tattaactgg cgaactactt   5280

actctagctt cccggcaaca attaatagac tggatggagg cggataaagt tgcaggacca   5340

cttctgcgct cggcccttcc ggctggctgg tttattgctg ataaatctgg agccggtgag   5400

cgtgggtctc gcggtatcat tgcagcactg gggccagatg gtaagccctc ccgtatcgta   5460

gttatctaca cgacggggag tcaggcaact atggatgaac gaaatagaca gatcgctgag   5520

ataggtgcct cactgattaa gcattggtaa ctgtcagacc aagtttactc atatatactt   5580

tagattgatt taaaacttca tttttaattt aaaaggatct aggtgaagat cctttttgat   5640

aatctcatga ccaaaatccc ttaacgtgag ttttcgttcc actgagcgtc agaccccgta   5700

gaaaagatca aaggatcttc ttgagatcct ttttttctgc gcgtaatctg ctgcttgcaa   5760

acaaaaaaac caccgctacc agcggtggtt tgtttgccgg atcaagagct accaactctt   5820

tttccgaagg taactggctt cagcagagcg cagataccaa atactgttct tctagtgtag   5880

ccgtagttag gccaccactt caagaactct gtagcaccgc ctacatacct cgctctgcta   5940

atcctgttac cagtggctgc tgccagtggc gataagtcgt gtcttaccgg gttggactca   6000

agacgatagt taccggataa ggcgcagcgg tcgggctgaa cggggggttc gtgcacacag   6060

cccagcttgg agcgaacgac ctacaccgaa ctgagatacc tacagcgtga gctatgagaa   6120

agcgccacgc ttcccgaagg gagaaaggcg gacaggtatc cggtaagcgg cagggtcgga   6180

acaggagagc gcacgaggga gcttccaggg ggaaacgcct ggtatcttta tagtcctgtc   6240

gggtttcgcc acctctgact tgagcgtcga tttttgtgat gctcgtcagg ggggcggagc   6300

ctatggaaaa acgccagcaa cgcggccttt ttacggttcc tggccttttg ctggcctttt   6360

gctcacatgt tctttcctgc gttatcccct gattctgtgg ataaccgtat taccgccttt   6420

gagtgagctg ataccgctcg ccgcagccga acgaccgagc gcagcgagtc agtgagcgag   6480

gaagcggaag agcgcccaat acgcaaaccg cctctccccg cgcgttggcc gattcattaa   6540

tgcagctggc acgacaggtt tcccgactgg aaagcgggca gtgagcgcaa cgcaattaat   6600

gtgagttagc tcactcatta ggcaccccag gctttacact ttatgcttcc ggctcgtatg   6660

ttgtgtggaa ttgtgagcgg ataacaattt cacacaggaa acagctatga ccatgattac   6720

gccagattta attaaggcct taattagg                                       6748
```

<210> SEQ ID NO 18
<211> LENGTH: 6703
<212> TYPE: DNA
<213> ORGANISM: Artificial Sequence
<220> FEATURE:
<223> OTHER INFORMATION: Synthetic sequence
<220> FEATURE:
<221> NAME/KEY: repeat_region
<222> LOCATION: (1)..(130)
<223> OTHER INFORMATION: 5' ITR
<220> FEATURE:
<221> NAME/KEY: promoter
<222> LOCATION: (191)..(932)
<223> OTHER INFORMATION: human\CMV\I.E.\enhancer\&\promoter
<220> FEATURE:
<221> NAME/KEY: Intron
<222> LOCATION: (1047)..(1179)
<223> OTHER INFORMATION: Promega\chimeric\intron
<220> FEATURE:
<221> NAME/KEY: primer
<222> LOCATION: (1243)..(1271)
<223> OTHER INFORMATION: BG118F
<220> FEATURE:
<221> NAME/KEY: misc_feature
<222> LOCATION: (1260)..(1319)
<223> OTHER INFORMATION: IL2\signal\peptide
<220> FEATURE:
<221> NAME/KEY: misc_feature
<222> LOCATION: (1320)..(1705)
<223> OTHER INFORMATION: VH\IgG1
<220> FEATURE:
<221> NAME/KEY: misc_feature
<222> LOCATION: (1325)..(1343)
<223> OTHER INFORMATION: from\bg102f
<220> FEATURE:
<221> NAME/KEY: misc_feature
<222> LOCATION: (1707)..(1982)
<223> OTHER INFORMATION: CH1
<220> FEATURE:
<221> NAME/KEY: misc_feature
<222> LOCATION: (1983)..(2671)
<223> OTHER INFORMATION: HCH23
<220> FEATURE:
<221> NAME/KEY: primer
<222> LOCATION: (2439)..(2474)
<223> OTHER INFORMATION: complement - B123R
<220> FEATURE:
<221> NAME/KEY: misc_feature
<222> LOCATION: (2649)..(2741)
<223> OTHER INFORMATION: complement - reverse\primer\for\CHHCH23
<220> FEATURE:
<221> NAME/KEY: misc_feature
<222> LOCATION: (2678)..(2687)
<223> OTHER INFORMATION: furin\site
<220> FEATURE:
<221> NAME/KEY: misc_feature
<222> LOCATION: (2688)..(2759)
<223> OTHER INFORMATION: F2A\linker
<220> FEATURE:
<221> NAME/KEY: misc_feature
<222> LOCATION: (2724)..(2783)
<223> OTHER INFORMATION: forward\primer\for\VL\for\MAB
<220> FEATURE:
<221> NAME/KEY: misc_feature
<222> LOCATION: (2803)..(3114)
<223> OTHER INFORMATION: 3bnc117\light
<220> FEATURE:
<221> NAME/KEY: misc_feature
<222> LOCATION: (3123)..(3128)
<223> OTHER INFORMATION: introduce\NarI\here\via\PCR
<220> FEATURE:
<221> NAME/KEY: misc_feature
<222> LOCATION: (3130)..(3434)
<223> OTHER INFORMATION: CL
<220> FEATURE:
<221> NAME/KEY: polyA_signal
<222> LOCATION: (3457)..(3688)
<223> OTHER INFORMATION: SV40\late\polyadenylation\signal
<220> FEATURE:
<221> NAME/KEY: repeat_region
<222> LOCATION: (3753)..(3882)
<223> OTHER INFORMATION: complement - 3' ITR
<220> FEATURE:
<221> NAME/KEY: rep_origin
<222> LOCATION: (4059)..(4514)
<223> OTHER INFORMATION: complement - f1\ori
<220> FEATURE:
<221> NAME/KEY: misc_feature
<222> LOCATION: (4645)..(5502)
<223> OTHER INFORMATION: Amp-R coding sequence
<220> FEATURE:
<221> NAME/KEY: misc_feature
<222> LOCATION: (5676)..(6264)
<223> OTHER INFORMATION: COL\E1\Origin

<400> SEQUENCE: 18
ctgcgcgctc gctcgctcac tgaggccgcc cgggcaaagc ccgggcgtcg ggcgaccttt 60
ggtcgcccgg cctcagtgag cgagcgagcg cgcagagagg gagtggccaa ctccatcact 120
aggggttcct tgtagttaat gattaacccg ccatgctact tatctacgta gccatgctct 180

-continued

```
aggaagatct tcaatattgg ccattagcca tattattcat tggttatata gcataaatca    240
atattggcta ttggccattg catacgttgt atctatatca taatatgtac atttatattg    300
gctcatgtcc aatatgaccg ccatgttggc attgattatt gactagttat taatagtaat    360
caattacggg gtcattagtt catagcccat atatggagtt ccgcgttaca taacttacgg    420
taaatggccc gcctggctga ccgcccaacg acccccgccc attgacgtca ataatgacgt    480
atgttcccat agtaacgcca atagggactt tccattgacg tcaatgggtg gagtatttac    540
ggtaaactgc ccacttggca gtacatcaag tgtatcatat gccaagtccg ccccctattg    600
acgtcaatga cggtaaatgg cccgcctggc attatgccca gtacatgacc ttacgggact    660
ttcctacttg gcagtacatc tacgtattag tcatcgctat taccatggtg atgcggtttt    720
ggcagtacac caatgggcgt ggatagcggt ttgactcacg gggatttcca agtctccacc    780
ccattgacgt caatgggagt ttgttttggc accaaaatca acgggacttt ccaaaatgtc    840
gtaataaccc cgccccgttg acgcaaatgg gcggtaggcg tgtacggtgg gaggtctata    900
taagcagagc tcgtttagtg aaccgtcaga tcactagaag ctttattgcg gtagtttatc    960
acagttaaat tgctaacgca gtcagtgctt ctgacacaac agtctcgaac ttaagctgca   1020
gaagttggtc gtgaggcact gggcaggtaa gtatcaaggt tacaagacag gtttaaggag   1080
accaatagaa actgggcttg tcgagacaga gaagactctt gcgtttctga taggcaccta   1140
ttggtcttac tgacatccac tttgcctttc tctccacagg tgtccactcc cagttcaatt   1200
acagctctta aggctagagt acttaatacg actcactata ggctagcatc gatgccacca   1260
tgtacaggat gcaactcctg tcttgcattg cactaagtct tgcacttgtc acaaacagtc   1320
aggtccaatt gttacagtct ggggcagcgg tgacgaagcc cggggcctca gtgagagtct   1380
cctgcgaggc ttctggatac aacattcgtg actactttat tcattggtgg cgacaggccc   1440
caggacaggg ccttcagtgg gtgggatgga tcaatcctaa gacaggtcag ccaaacaatc   1500
ctcgtcaatt tcagggtaga gtcagtctga ctcgacacgc gtcgtgggac tttgacacat   1560
tttcctttta catggacctg aaggcactaa gatcggacga cacggccgtt tatttctgtg   1620
cgcgacagcg cagcgactat tgggatttcg acgtctgggg cagtggaacc caggtcactg   1680
tctcgtcagc gtcgaccaag ggccctcgg tcttcccccct ggcaccctcc tccaagagca   1740
cctctggggg cacagcggcc ctgggctgcc tggtcaagga ctacttcccc gaaccggtga   1800
cggtgtcgtg gaactcaggc gccctgacca gcggcgtgca caccttcccg gctgtcctac   1860
agtcctcagg actctactcc ctcagcagcg tggtgaccgt gccctccagc agcttgggca   1920
cccagaccta catctgcaac gtgaatcaca agcccagcaa caccaaggtg gacaagaaag   1980
ttgagcccaa atcttgtgac aaaactcaca catgcccacc gtgcccagca cctgaactcc   2040
tggggggacc gtcagtcttc ctcttccccc caaaacccaa ggacaccctc atgatctccc   2100
ggacccctga ggtcacatgc gtggtggtgg acgtgagcca cgaagaccct gaggtcaagt   2160
tcaactggta cgtggacggc gtggaggtgc ataatgccaa gacaaagccg cgggaggagc   2220
agtacaacag cacgtaccgt gtggtcagcg tcctcaccgt cctgcaccag gactggctga   2280
atggcaagga gtacaagtgc aaggtctcca acaaagccct cccagccccc atcgagaaaa   2340
ccatctccaa agccaaaggg cagccccgag aaccacaggt gtacaccctg cccccatccc   2400
gggatgagct gaccaagaac caggtcagcc tgacctgcct ggtcaaaggc ttctatccca   2460
gcgacatcgc cgtggagtgg gagagcaatg ggcagccgga gaacaactac aagaccacgc   2520
ctcccgtgct ggactccgac ggctccttct tcctctacag caagctcacc gtggacaaga   2580
```

-continued

```
gcaggtggca gcaggggaac gtcttctcat gctccgtgat gcatgaggct ctgcacaacc   2640
actacacgca gaagagcctc tccctgtctc ccggccgaaa gcggagagcc cccgtgaagc   2700
agaccctgaa cttcgacctg ctgaagctgg ccggcgacgt ggaaagcaac cctggcccta   2760
tgggatggtc atgtatcatc ctttttctag tagcaactgc aaccggtgta cattctgaca   2820
tccagatgac ccagtctcca tcctccctgt ctgcatctgt aggagatacc gtcactatca   2880
cttgccaggc aaacggctac ttaaattggt atcaacagag gcgagggaaa gccccaaaac   2940
tcctgatcta cgatgggtcc aaattggaaa gaggggtccc atcaaggttc agtggaagaa   3000
gatgggggca agaatataat ctgaccatca acaatctgca gcccgaagac attgcaacat   3060
atttttgtca agtgtatgag tttgtcgtcc ctgggaccag actggatttg aaacgtacgg   3120
tggctgcacc atctgtcttc atcttcccgc catctgatga gcagttgaaa tctggaactg   3180
cctctgttgt gtgcctgctg aataacttct accccagaga agccaaagtg cagtggaagg   3240
tggacaacgc cctgcagagc ggaaacagcc aggaaagcgt gacagagcag gattccaagg   3300
attccacata cagcctgagc agcacactga cactgtccaa ggccgactac gagaagcaca   3360
aggtgtacgc ctgcgaagtg acacaccagg gactgtcctc ccctgtgaca aagagcttca   3420
acagaggaga atgctgatga aagcttgcgg ccgcttcgag cagacatgat aagatacatt   3480
gatgagtttg gacaaaccac aactagaatg cagtgaaaaa aatgctttat ttgtgaaatt   3540
tgtgatgcta ttgctttatt tgtaaccatt ataagctgca ataaacaagt taacaacaac   3600
aattgcattc attttatgtt tcaggttcag ggggagatgt gggaggtttt ttaaagcaag   3660
taaaacctct acaaatgtgg taaaatcgat aaggatcttc ctagagcatg gctacgtaga   3720
taagtagcat ggcgggttaa tcattaacta caaggaaccc ctagtgatgg agttggccac   3780
tccctctctg cgcgctcgct cgctcactga ggccgggcga ccaaaggtcg cccgacgccc   3840
gggctttgcc cgggcggcct cagtgagcga gcgagcgcgc agccttaatt aacctaattc   3900
actggccgtc gttttacaac gtcgtgactg ggaaaaccct ggcgttaccc aacttaatcg   3960
ccttgcagca catccccctt tcgccagctg gcgtaatagc gaagaggccc gcaccgatcg   4020
cccttcccaa cagttgcgca gcctgaatgg cgaatgggac gcgccctgta gcggcgcatt   4080
aagcgcggcg ggtgtggtgg ttacgcgcag cgtgaccgct acacttgcca gcgccctagc   4140
gcccgctcct ttcgctttct tcccttcctt tctcgccacg ttcgccggct ttccccgtca   4200
agctctaaat cgggggctcc ctttagggtt ccgatttagt gctttacggc acctcgaccc   4260
caaaaaactt gattagggtg atggttcacg tagtgggcca tcgccctgat agacggtttt   4320
tcgccctttg acgttggagt ccacgttctt taatagtgga ctcttgttcc aaactggaac   4380
aacactcaac cctatctcgg tctattcttt tgatttataa gggattttgc cgatttcggc   4440
ctattggtta aaaaatgagc tgatttaaca aaaatttaac gcgaatttta acaaaatatt   4500
aacgcttaca atttaggtgg cacttttcgg ggaaatgtgc gcggaacccc tatttgttta   4560
tttttctaaa tacattcaaa tatgtatccg ctcatgagac aataaccctg ataaatgctt   4620
caataatatt gaaaaaggaa gagtatgagt attcaacatt tccgtgtcgc ccttattccc   4680
ttttttgcgg cattttgcct tcctgttttt gctcacccag aaacgctggt gaaagtaaaa   4740
gatgctgaag atcagttggg tgcacgagtg ggttacatcg aactggatct caacagcggt   4800
aagatccttg agagttttcg ccccgaagaa cgttttccaa tgatgagcac ttttaaagtt   4860
ctgctatgtg gcgcggtatt atcccgtatt gacgccgggc aagagcaact cggtcgccgc   4920
```

-continued

```
atacactatt ctcagaatga cttggttgag tactcaccag tcacagaaaa gcatcttacg   4980

gatggcatga cagtaagaga attatgcagt gctgccataa ccatgagtga taacactgcg   5040

gccaacttac ttctgacaac gatcggagga ccgaaggagc taaccgcttt tttgcacaac   5100

atgggggatc atgtaactcg ccttgatcgt tgggaaccgg agctgaatga agccatacca   5160

aacgacgagc gtgacaccac gatgcctgta gcaatggcaa caacgttgcg caaactatta   5220

actggcgaac tacttactct agcttcccgg caacaattaa tagactggat ggaggcggat   5280

aaagttgcag gaccacttct gcgctcggcc cttccggctg gctggtttat tgctgataaa   5340

tctggagccg gtgagcgtgg gtctcgcggt atcattgcag cactggggcc agatggtaag   5400

ccctcccgta tcgtagttat ctacacgacg gggagtcagg caactatgga tgaacgaaat   5460

agacagatcg ctgagatagg tgcctcactg attaagcatt ggtaactgtc agaccaagtt   5520

tactcatata tactttagat tgatttaaaa cttcattttt aatttaaaag gatctaggtg   5580

aagatccttt ttgataatct catgaccaaa atcccttaac gtgagttttc gttccactga   5640

gcgtcagacc ccgtagaaaa gatcaaagga tcttcttgag atcctttttt tctgcgcgta   5700

atctgctgct tgcaaacaaa aaaaccaccg ctaccagcgg tggtttgttt gccggatcaa   5760

gagctaccaa ctctttttcc gaaggtaact ggcttcagca gagcgcagat accaaatact   5820

gttcttctag tgtagccgta gttaggccac cacttcaaga actctgtagc accgcctaca   5880

tacctcgctc tgctaatcct gttaccagtg gctgctgcca gtggcgataa gtcgtgtctt   5940

accgggttgg actcaagacg atagttaccg gataaggcgc agcggtcggg ctgaacgggg   6000

ggttcgtgca cacagcccag cttggagcga acgacctaca ccgaactgag atacctacag   6060

cgtgagctat gagaaagcgc cacgcttccc gaagggagaa aggcggacag gtatccggta   6120

agcggcaggg tcggaacagg agagcgcacg agggagcttc cagggggaaa cgcctggtat   6180

ctttatagtc ctgtcgggtt tcgccacctc tgacttgagc gtcgattttt gtgatgctcg   6240

tcaggggggc ggagcctatg gaaaaacgcc agcaacgcgg cctttttacg gttcctggcc   6300

ttttgctggc cttttgctca catgttcttt cctgcgttat cccctgattc tgtggataac   6360

cgtattaccg cctttgagtg agctgatacc gctcgccgca gccgaacgac cgagcgcagc   6420

gagtcagtga gcgaggaagc ggaagagcgc ccaatacgca aaccgcctct ccccgcgcgt   6480

tggccgattc attaatgcag ctggcacgac aggtttcccg actggaaagc gggcagtgag   6540

cgcaacgcaa ttaatgtgag ttagctcact cattaggcac cccaggcttt acactttatg   6600

cttccggctc gtatgttgtg tggaattgtg agcggataac aatttcacac aggaaacagc   6660

tatgaccatg attacgccag atttaattaa ggccttaatt agg                     6703
```

```
<210> SEQ ID NO 19
<211> LENGTH: 6748
<212> TYPE: DNA
<213> ORGANISM: Artificial Sequence
<220> FEATURE:
<223> OTHER INFORMATION: Synthetic sequence
<220> FEATURE:
<221> NAME/KEY: repeat_region
<222> LOCATION: (1)..(130)
<223> OTHER INFORMATION: 5' ITR
<220> FEATURE:
<221> NAME/KEY: promoter
<222> LOCATION: (191)..(932)
<223> OTHER INFORMATION: human\CMV\I.E.\enhancer\&\promoter
<220> FEATURE:
<221> NAME/KEY: misc_feature
<222> LOCATION: (897)..(901)
<223> OTHER INFORMATION: TATA\box
```

<220> FEATURE:
<221> NAME/KEY: Intron
<222> LOCATION: (1047)..(1179)
<223> OTHER INFORMATION: Promega\chimeric\intron
<220> FEATURE:
<221> NAME/KEY: misc_feature
<222> LOCATION: (1248)..(1293)
<223> OTHER INFORMATION: c-myc\miniIRES\cloned\into\Nhe\site
<220> FEATURE:
<221> NAME/KEY: misc_feature
<222> LOCATION: (1292)..(1297)
<223> OTHER INFORMATION: 6\bp\insertion
<220> FEATURE:
<221> NAME/KEY: misc_feature
<222> LOCATION: (1294)..(3493)
<223> OTHER INFORMATION: 3bnc\ORF\11
<220> FEATURE:
<221> NAME/KEY: polyA_signal
<222> LOCATION: (3502)..(3733)
<223> OTHER INFORMATION: SV40\late\polyadenylation\signal
<220> FEATURE:
<221> NAME/KEY: repeat_region
<222> LOCATION: (3897)..(3927)
<223> OTHER INFORMATION: complement -3' ITR
<220> FEATURE:
<221> NAME/KEY: rep_origin
<222> LOCATION: (4104)..(4559)
<223> OTHER INFORMATION: complement - f1\ori
<220> FEATURE:
<221> NAME/KEY: misc_feature
<222> LOCATION: (4690)..(5547)
<223> OTHER INFORMATION: Amp-R coding sequence
<220> FEATURE:
<221> NAME/KEY: misc_feature
<222> LOCATION: (5721)..(6309)
<223> OTHER INFORMATION: COL\E1\Origin

<400> SEQUENCE: 19
ctgcgcgctc gctcgctcac tgaggccgcc cgggcaaagc ccgggcgtcg ggcgaccttt 60
ggtcgcccgg cctcagtgag cgagcgagcg cgcagagagg gagtggccaa ctccatcact 120
aggggttcct tgtagttaat gattaacccg ccatgctact tatctacgta gccatgctct 180
aggaagatct tcaatattgg ccattagcca tattattcat tggttatata gcataaatca 240
atattggcta ttggccattg catacgttgt atctatatca taatatgtac atttatattg 300
gctcatgtcc aatatgaccg ccatgttggc attgattatt gactagttat taatagtaat 360
caattacggg gtcattagtt catagcccat atatggagtt ccgcgttaca taacttacgg 420
taaatggccc gcctggctga ccgcccaacg acccccgccc attgacgtca ataatgacgt 480
atgttcccat agtaacgcca atagggactt tccattgacg tcaatgggtg gagtatttac 540
ggtaaactgc ccacttggca gtacatcaag tgtatcatat gccaagtccg cccccctattg 600 acgtcaatga cggtaaatgg cccgcctggc attatgccca gtacatgacc ttacgggact 660
ttcctacttg gcagtacatc tacgtattag tcatcgctat taccatggtg atgcggtttt 720
ggcagtacac caatgggcgt ggatagcggt ttgactcacg gggatttcca agtctccacc 780
ccattgacgt caatgggagt ttgttttggc accaaaatca acgggacttt ccaaaatgtc 840
gtaataaccc cgccccgttg acgcaaatgg gcggtaggcg tgtacggtgg gaggtctata 900
taagcagagc tcgtttagtg aaccgtcaga tcactagaag ctttattgcg gtagtttatc 960
acagttaaat tgctaacgca gtcagtgctt ctgacacaac agtctcgaac ttaagctgca 1020
gaagttggtc gtgaggcact gggcaggtaa gtatcaaggt tacaagacag gtttaaggag 1080
accaatagaa actgggcttg tcgagacaga gaagactctt gcgtttctga taggcaccta 1140
ttggtcttac tgacatccac tttgcctttc tctccacagg tgtccactcc cagttcaatt 1200

-continued

```
acagctctta aggctagagt acttaatacg actcactata ggctagcggg gactttgcac   1260
tggaacttac aacacccgag caaggacgcg actctagctc tagaaccatg taccgcatgc   1320
aattactctc ctgtatcgct ctgtctctgg ctctggtgac aaacagccag gtccagctgc   1380
tgcagagtgg cgccgcagtg actaagcctg gcgctagtgt gagagtcagt tgcgaagcaa   1440
gcggctacaa cattcgcgat tactttatcc attggtggag gcaggctccc ggtcagggct   1500
tgcaatgggt cggctggatt aaccccaaaa ccgggcagcc caataaccct cgacaatttc   1560
agggacgcgt tagtttaacg aggcatgcgt catgggattt tgacacattt tcgttctata   1620
tggatctgaa ggctctgcgg tctgatgaca ccgctgtgta cttttgtgcc aggcaacggt   1680
ccgactattg ggactttgat gtgtgggggt cgggtacgca agtaacggtg tccagcgctt   1740
ccacaaaagg cccaagcgtg tttcccctcg ctccatcttc taagtctaca agcggcggca   1800
ccgctgctct gggctgtctg gtgaaagatt actttccaga gccggtcact gtgtcctgga   1860
atagcggcgc tctgacttct ggtgttcata cctttcccgc tgtcctgcaa agcagcggcc   1920
tgtacagcct gagctccgtg gtgaccgtac cctcctccag cttgggcaca cagacataca   1980
tatgcaatgt gaaccacaag cctagtaata ccaaggttga taagaaggta gaacctaaga   2040
gttgtgacaa gacccatact tgtccaccgt gtcctgcacc agaactgctc gggggaccca   2100
gcgtctttct gtttccgcca aaacctaagg atactctaat gatttcccgt acccccgaag   2160
tcacttgcgt ggtcgtggac gtgtcacatg aggaccccga ggtaaagttt aactggtatg   2220
tggacggcgt ggaggttcat aacgccaaga ctaagccccg ggaggaacag tataacagta   2280
cgtatcgagt cgtaagcgtg ctgactgttc tgcaccaaga ctggttgaat gggaaggagt   2340
ataagtgtaa ggtcagcaac aaggctcttc ccgctcctat cgaaaagacc atttcaaaag   2400
ccaagggaca gccgcgggag cctcaagtgt ataccctgcc gccaagtaga gacgagctca   2460
ccaagaacca ggtttcactg acatgtctgg taaagggctt ctatccatcc gacattgccg   2520
tagaatggga gagtaacggc cagccagaga ataactataa gaccacgccc cctgtgttgg   2580
actccgacgg gtcattcttt ctgtatagca agctgacagt tgacaagtca cggtggcaac   2640
agggcaacgt gttttcatgt tccgtgatgc acgaagctct gcataaccac tatacccaga   2700
agtccctgtc tctgagccca gggaggaaga ggcgcgcacc agtgaaacag accttgaatt   2760
tcgacctgct gaagctggct ggcgatgttg aatccaaccc aggccccatg tatagaatgc   2820
agctgctgtc ttgtatcgcc ttgagcctgg ccttggtcac aaattcggat atccagatga   2880
cgcaatcccc ctcctccctc agcgcttcag taggtgacac agtaacaatt acatgtcagg   2940
ccaatgggta cctcaattgg tatcagcagc gaaggggcaa agctcctaag ttgctgatct   3000
atgacggctc taagttggaa cgcggcgttc cgagtaggtt tagtggccgg agatggggac   3060
aagagtataa cctgacgatc aacaacttgc aacccgagga cattgctacc tatttctgtc   3120
aggtgtatga atttgtagta ccaggcaccc ggctagatct gaaacggaca gtagctgccc   3180
ccagcgtgtt catattccct ccatctgacg aacagcttaa gtcgggcacc gcaagcgtgg   3240
tgtgcctgtt gaataacttc tatccgagag aggctaaggt gcagtggaag gtcgacaacg   3300
ccctacagtc tggcaattct caagaaagcg ttaccgaaca ggatagcaag gacagcacgt   3360
atagcttgtc ctccacactg acgctttcca aggcagacta tgaaaaacat aaggtgtacg   3420
cgtgtgaggt gactcatcag ggcctgtcca gcccggttac aaagtccttt aacaggggcg   3480
aatgctaatg agcggccgct tcgagcagac atgataagat acattgatga gtttggacaa   3540
accacaacta gaatgcagtg aaaaaaatgc tttatttgtg aaatttgtga tgctattgct   3600
```

-continued

```
ttatttgtaa ccattataag ctgcaataaa caagttaaca acaacaattg cattcatttt   3660
atgtttcagg ttcaggggga gatgtgggag gtttttttaaa gcaagtaaaa cctctacaaa   3720
tgtggtaaaa tcgataagga tcttcctaga gcatggctac gtagataagt agcatggcgg   3780
gttaatcatt aactacaagg aacccctagt gatggagttg gccactccct ctctgcgcgc   3840
tcgctcgctc actgaggccg ggcgaccaaa ggtcgcccga cgcccgggct ttgcccgggc   3900
ggcctcagtg agcgagcgag cgcgcagcct taattaacct aattcactgg ccgtcgtttt   3960
acaacgtcgt gactgggaaa accctggcgt tacccaactt aatcgccttg cagcacatcc   4020
ccctttcgcc agctggcgta atagcgaaga ggcccgcacc gatcgccctt cccaacagtt   4080
gcgcagcctg aatggcgaat gggacgcgcc ctgtagcggc gcattaagcg cggcgggtgt   4140
ggtggttacg cgcagcgtga ccgctacact tgccagcgcc ctagcgcccg ctcctttcgc   4200
tttcttccct tcctttctcg ccacgttcgc cggctttccc cgtcaagctc taaatcgggg   4260
gctcccttta gggttccgat ttagtgcttt acggcacctc gaccccaaaa aacttgatta   4320
gggtgatggt tcacgtagtg ggccatcgcc ctgatagacg gtttttcgcc ctttgacgtt   4380
ggagtccacg ttctttaata gtggactctt gttccaaact ggaacaacac tcaaccctat   4440
ctcggtctat tcttttgatt tataagggat tttgccgatt tcggcctatt ggttaaaaaa   4500
tgagctgatt taacaaaaat ttaacgcgaa ttttaacaaa atattaacgc ttacaattta   4560
ggtggcactt ttcggggaaa tgtgcgcgga acccctattt gtttattttt ctaaatacat   4620
tcaaatatgt atccgctcat gagacaataa ccctgataaa tgcttcaata atattgaaaa   4680
aggaagagta tgagtattca acatttccgt gtcgccctta ttcccttttt tgcggcattt   4740
tgccttcctg tttttgctca cccagaaacg ctggtgaaag taaaagatgc tgaagatcag   4800
ttgggtgcac gagtgggtta catcgaactg gatctcaaca gcggtaagat ccttgagagt   4860
tttcgccccg aagaacgttt tccaatgatg agcactttta aagttctgct atgtggcgcg   4920
gtattatccc gtattgacgc cgggcaagag caactcggtc gccgcataca ctattctcag   4980
aatgacttgg ttgagtactc accagtcaca gaaaagcatc ttacggatgg catgacagta   5040
agagaattat gcagtgctgc cataaccatg agtgataaca ctgcggccaa cttacttctg   5100
acaacgatcg gaggaccgaa ggagctaacc gcttttttgc acaacatggg ggatcatgta   5160
actcgccttg atcgttggga accggagctg aatgaagcca taccaaacga cgagcgtgac   5220
accacgatgc ctgtagcaat ggcaacaacg ttgcgcaaac tattaactgg cgaactactt   5280
actctagctt cccggcaaca attaatagac tggatggagg cggataaagt tgcaggacca   5340
cttctgcgct cggcccttcc ggctggctgg tttattgctg ataaatctgg agccggtgag   5400
cgtgggtctc gcggtatcat tgcagcactg gggccagatg gtaagccctc ccgtatcgta   5460
gttatctaca cgacggggag tcaggcaact atggatgaac gaaatagaca gatcgctgag   5520
ataggtgcct cactgattaa gcattggtaa ctgtcagacc aagtttactc atatatactt   5580
tagattgatt taaaacttca tttttaattt aaaaggatct aggtgaagat cctttttgat   5640
aatctcatga ccaaaatccc ttaacgtgag ttttcgttcc actgagcgtc agaccccgta   5700
gaaaagatca aaggatcttc ttgagatcct ttttttctgc gcgtaatctg ctgcttgcaa   5760
acaaaaaaac caccgctacc agcggtggtt tgtttgccgg atcaagagct accaactctt   5820
tttccgaagg taactggctt cagcagagcg cagataccaa atactgttct tctagtgtag   5880
ccgtagttag gccaccactt caagaactct gtagcaccgc ctacatacct cgctctgcta   5940
```

```
atcctgttac cagtggctgc tgccagtggc gataagtcgt gtcttaccgg gttggactca   6000

agacgatagt taccggataa ggcgcagcgg tcgggctgaa cggggggttc gtgcacacag   6060

cccagcttgg agcgaacgac ctacaccgaa ctgagatacc tacagcgtga gctatgagaa   6120

agcgccacgc ttcccgaagg gagaaaggcg gacaggtatc cggtaagcgg cagggtcgga   6180

acaggagagc gcacgaggga gcttccaggg ggaaacgcct ggtatcttta tagtcctgtc   6240

gggtttcgcc acctctgact tgagcgtcga tttttgtgat gctcgtcagg ggggcggagc   6300

ctatggaaaa acgccagcaa cgcggccttt ttacggttcc tggccttttg ctggcctttt   6360

gctcacatgt tctttcctgc gttatcccct gattctgtgg ataaccgtat taccgccttt   6420

gagtgagctg ataccgctcg ccgcagccga acgaccgagc gcagcgagtc agtgagcgag   6480

gaagcggaag agcgcccaat acgcaaaccg cctctccccg cgcgttggcc gattcattaa   6540

tgcagctggc acgacaggtt tcccgactgg aaagcgggca gtgagcgcaa cgcaattaat   6600

gtgagttagc tcactcatta ggcaccccag gctttacact ttatgcttcc ggctcgtatg   6660

ttgtgtggaa ttgtgagcgg ataacaattt cacacaggaa acagctatga ccatgattac   6720

gccagattta attaaggcct taattagg                                      6748
```

```
<210> SEQ ID NO 20
<211> LENGTH: 6748
<212> TYPE: DNA
<213> ORGANISM: Artificial Sequence
<220> FEATURE:
<223> OTHER INFORMATION: Synthetic sequence
<220> FEATURE:
<221> NAME/KEY: repeat_region
<222> LOCATION: (1)..(130)
<223> OTHER INFORMATION: 5' ITR
<220> FEATURE:
<221> NAME/KEY: promoter
<222> LOCATION: (191)..(932)
<223> OTHER INFORMATION: human\CMV\I.E.\enhancer\&\promoter
<220> FEATURE:
<221> NAME/KEY: misc_feature
<222> LOCATION: (897)..(901)
<223> OTHER INFORMATION: TATA\box
<220> FEATURE:
<221> NAME/KEY: Intron
<222> LOCATION: (1047)..(1179)
<223> OTHER INFORMATION: Promega\chimeric\intron
<220> FEATURE:
<221> NAME/KEY: misc_feature
<222> LOCATION: (1248)..(1293)
<223> OTHER INFORMATION: c-myc\miniIRES\cloned\into\Nhe\site
<220> FEATURE:
<221> NAME/KEY: misc_feature
<222> LOCATION: (1292)..(1297)
<223> OTHER INFORMATION: 6\bp\insertion
<220> FEATURE:
<221> NAME/KEY: misc_feature
<222> LOCATION: (1294)..(3493)
<223> OTHER INFORMATION: 3bnc\ORF\26
<220> FEATURE:
<221> NAME/KEY: polyA_signal
<222> LOCATION: (3502)..(3733)
<223> OTHER INFORMATION: SV40\late\polyadenylation\signal
<220> FEATURE:
<221> NAME/KEY: repeat_region
<222> LOCATION: (3798)..(3927)
<223> OTHER INFORMATION: complement - 3' ITR
<220> FEATURE:
<221> NAME/KEY: rep_origin
<222> LOCATION: (4104)..(4559)
<223> OTHER INFORMATION: complement - f1\ori
<220> FEATURE:
<221> NAME/KEY: misc_feature
<222> LOCATION: (4690)..(5547)
<223> OTHER INFORMATION: Amp-R coding sequence
```

```
<220> FEATURE:
<221> NAME/KEY: misc_feature
<222> LOCATION: (5721)..(6309)
<223> OTHER INFORMATION: COL\E1\Origin

<400> SEQUENCE: 20

ctgcgcgctc gctcgctcac tgaggccgcc cgggcaaagc ccgggcgtcg ggcgaccttt     60

ggtcgcccgg cctcagtgag cgagcgagcg cgcagagagg gagtggccaa ctccatcact    120

aggggttcct tgtagttaat gattaacccg ccatgctact tatctacgta gccatgctct    180

aggaagatct tcaatattgg ccattagcca tattattcat tggttatata gcataaatca    240

atattggcta ttggccattg catacgttgt atctatatca taatatgtac atttatattg    300

gctcatgtcc aatatgaccg ccatgttggc attgattatt gactagttat taatagtaat    360

caattacggg gtcattagtt catagcccat atatggagtt ccgcgttaca taacttacgg    420

taaatggccc gcctggctga ccgcccaacg acccccgccc attgacgtca ataatgacgt    480

atgttcccat agtaacgcca atagggactt tccattgacg tcaatgggtg gagtatttac    540

ggtaaactgc ccacttggca gtacatcaag tgtatcatat gccaagtccg ccccctattg    600

acgtcaatga cggtaaatgg cccgcctggc attatgccca gtacatgacc ttacgggact    660

ttcctacttg gcagtacatc tacgtattag tcatcgctat taccatggtg atgcggtttt    720

ggcagtacac caatgggcgt ggatagcggt ttgactcacg gggatttcca agtctccacc    780

ccattgacgt caatgggagt ttgttttggc accaaaatca acgggacttt ccaaaatgtc    840

gtaataaccc cgccccgttg acgcaaatgg gcggtaggcg tgtacggtgg gaggtctata    900

taagcagagc tcgtttagtg aaccgtcaga tcactagaag ctttattgcg gtagtttatc    960

acagttaaat tgctaacgca gtcagtgctt ctgacacaac agtctcgaac ttaagctgca   1020

gaagttggtc gtgaggcact gggcaggtaa gtatcaaggt tacaagacag gtttaaggag   1080

accaatagaa actgggcttg tcgagacaga gaagactctt gcgtttctga taggcaccta   1140

ttggtcttac tgacatccac tttgcctttc tctccacagg tgtccactcc cagttcaatt   1200

acagctctta aggctagagt acttaatacg actcactata ggctagcggg gactttgcac   1260

tggaacttac aacacccgag caaggacgcg actctagctc tagaaccatg taccggatgc   1320

agttactttc gtgcatcgcc ctgtcactcg cccttgtgac taatagccag gtacagctac   1380

tgcagagcgg tgctgctgtg actaagccag gggcctctgt gcgggtgtct tgcgaggcgt   1440

cgggatacaa tatccgggac tactttatcc actggtggag acaggcaccg ggtcagggac   1500

ttcagtgggt gggctggatc aatcccaaaa caggccagcc caacaatccc cggcagttcc   1560

agggtcgcgt ctctctgact aggcacgcct cctgggattt cgacaccttc tcgttctata   1620

tggacctcaa ggctcttcgg tccgacgaca ccgccgtgta cttttgcgca cgccagagat   1680

ccgactactg ggactttgac gtttgggggt ccggaactca agtgacagtt agttctgcgt   1740

ctaccaaggg tccctcagtg ttccctctgg ccccctctag taagtcaacc tctggtggta   1800

ccgcggcctt aggctgtctg gtgaaagatt actttcccga acccgtgacc gtgtcttgga   1860

atagcggtgc tctcacgagt ggggtgcata cgtttcctgc cgtcctgcaa tcaagtggac   1920

tttacagctt gtcaagtgtc gtgacggtgc cgtccagctc actaggtacc cagacctaca   1980

tctgcaatgt gaatcataag ccttcgaata ccaaggtgga taagaaggtg gagcccaagt   2040

catgcgacaa gacccatacc tgtcctccct gccccgcacc tgagctgttg ggcggtccat   2100

ccgtgtttct gtttcccccct aagcccaagg acaccctgat gatatctcgc accccagagg   2160
```

-continued

```
tgacctgcgt agtggtcgac gtcagtcacg aggacccaga agtgaagttt aactggtacg   2220

tggacggcgt agaagtgcat aatgccaaaa ccaagccccg ggaagaacag tacaattcca   2280

cctaccgtgt ggtgtctgtt ttgaccgtgc tccaccagga ttggctgaat gggaaggaat   2340

acaagtgcaa ggtgtctaac aaggctctcc ctgcacccat tgagaaaacc atttccaagg   2400

ccaagggtca gccccgagaa ccccaagtgt acaccttacc gccctcccgc gacgaactga   2460

ccaaaaacca ggtgtccctt acctgcctgg tgaagggatt ctacccgagt gacatcgctg   2520

tggaatggga aagcaacggc cagcctgaaa acaattacaa gactacccca ccagtactcg   2580

attcagacgg aagctttttc ctttacagca agctcactgt ggacaagtct cgatggcagc   2640

agggcaatgt gttctcatgc tctgtgatgc atgaggcatt gcataaccac tatacacaga   2700

agtcattatc actctccccc ggcagaaaac gcagggctcc tgtgaagcag actcttaact   2760

ttgacctgct gaaacttgct ggtgacgtgg aatcaaaccc cggtccaatg tacagaatgc   2820

agcttttgtc atgcattgct ctcagcctag ctctagtgac caattcagat attcagatga   2880

ctcagagtcc aagtagtcta agcgcctcag tcggcgatac agtgacgatc acctgtcagg   2940

caaacggata cttgaattgg taccagcaga ggagggggaa ggctccgaag cttctgatct   3000

atgacggcag taagcttgaa cgcggtgtgc ctagccgctt ctccggtcgc cgctggggtc   3060

aggagtacaa cttaaccata aacaacctcc agcctgagga catagcaacc tatttctgtc   3120

aggtgtatga gtttgttgtg cccggtacaa ggctagacct caagcgaacc gtggccgctc   3180

catccgtctt tatctttcct cctagcgacg agcagctgaa gtccggcacc gcttcagtgg   3240

tctgcctcct caacaatttc taccccaggg aagccaaggt gcagtggaaa gtggacaatg   3300

cactgcagag tggaaattct caagagtctg tgaccgagca ggactcaaaa gactctacct   3360

acagcctgag ttcaaccctt accctgtcaa aggccgatta cgaaaagcat aaggtgtatg   3420

cttgcgaggt gacccaccag ggcctgtcga gccccgtgac caagagcttt aaccgtggag   3480

aatgctaatg agcggccgct tcgagcagac atgataagat acattgatga gtttggacaa   3540

accacaacta gaatgcagtg aaaaaaatgc tttatttgtg aaatttgtga tgctattgct   3600

ttatttgtaa ccattataag ctgcaataaa caagttaaca acaacaattg cattcatttt   3660

atgtttcagg ttcaggggga gatgtgggag gtttttttaaa gcaagtaaaa cctctacaaa   3720

tgtggtaaaa tcgataagga tcttcctaga gcatggctac gtagataagt agcatggcgg   3780

gttaatcatt aactacaagg aacccctagt gatggagttg gccactccct ctctgcgcgc   3840

tcgctcgctc actgaggccg ggcgaccaaa ggtcgcccga cgcccgggct ttgcccgggc   3900

ggcctcagtg agcgagcgag cgcgcagcct taattaacct aattcactgg ccgtcgtttt   3960

acaacgtcgt gactgggaaa accctggcgt tacccaactt aatcgccttg cagcacatcc   4020

ccctttcgcc agctggcgta atagcgaaga ggcccgcacc gatcgccctt cccaacagtt   4080

gcgcagcctg aatggcgaat gggacgcgcc ctgtagcggc gcattaagcg cggcgggtgt   4140

ggtggttacg cgcagcgtga ccgctacact tgccagcgcc ctagcgcccg ctcctttcgc   4200

tttcttccct tcctttctcg ccacgttcgc cggctttccc cgtcaagctc taaatcgggg   4260

gctcccttta gggttccgat ttagtgcttt acggcacctc gaccccaaaa aacttgatta   4320

gggtgatggt tcacgtagtg ggccatcgcc ctgatagacg gtttttcgcc ctttgacgtt   4380

ggagtccacg ttctttaata gtggactctt gttccaaact ggaacaacac tcaaccctat   4440

ctcggtctat tcttttgatt tataagggat tttgccgatt tcggcctatt ggttaaaaaa   4500

tgagctgatt taacaaaaat ttaacgcgaa ttttaacaaa atattaacgc ttacaattta   4560
```

-continued

```
ggtggcactt ttcggggaaa tgtgcgcgga acccctattt gtttattttt ctaaatacat   4620

tcaaatatgt atccgctcat gagacaataa ccctgataaa tgcttcaata atattgaaaa   4680

aggaagagta tgagtattca acatttccgt gtcgccctta ttcccttttt tgcggcattt   4740

tgccttcctg tttttgctca cccagaaacg ctggtgaaag taaaagatgc tgaagatcag   4800

ttgggtgcac gagtgggtta catcgaactg gatctcaaca gcggtaagat ccttgagagt   4860

tttcgccccg aagaacgttt tccaatgatg agcactttta aagttctgct atgtggcgcg   4920

gtattatccc gtattgacgc cgggcaagag caactcggtc gccgcataca ctattctcag   4980

aatgacttgg ttgagtactc accagtcaca gaaaagcatc ttacggatgg catgacagta   5040

agagaattat gcagtgctgc cataaccatg agtgataaca ctgcggccaa cttacttctg   5100

acaacgatcg gaggaccgaa ggagctaacc gcttttttgc acaacatggg ggatcatgta   5160

actcgccttg atcgttggga accggagctg aatgaagcca taccaaacga cgagcgtgac   5220

accacgatgc ctgtagcaat ggcaacaacg ttgcgcaaac tattaactgg cgaactactt   5280

actctagctt cccggcaaca attaatagac tggatggagg cggataaagt tgcaggacca   5340

cttctgcgct cggcccttcc ggctggctgg tttattgctg ataaatctgg agccggtgag   5400

cgtgggtctc gcggtatcat tgcagcactg gggccagatg gtaagccctc ccgtatcgta   5460

gttatctaca cgacggggag tcaggcaact atggatgaac gaaatagaca gatcgctgag   5520

ataggtgcct cactgattaa gcattggtaa ctgtcagacc aagtttactc atatatactt   5580

tagattgatt taaaacttca tttttaattt aaaaggatct aggtgaagat cctttttgat   5640

aatctcatga ccaaaatccc ttaacgtgag ttttcgttcc actgagcgtc agaccccgta   5700

gaaaagatca aaggatcttc ttgagatcct ttttttctgc gcgtaatctg ctgcttgcaa   5760

acaaaaaaac caccgctacc agcggtggtt tgtttgccgg atcaagagct accaactctt   5820

tttccgaagg taactggctt cagcagagcg cagataccaa atactgttct tctagtgtag   5880

ccgtagttag gccaccactt caagaactct gtagcaccgc ctacatacct cgctctgcta   5940

atcctgttac cagtggctgc tgccagtggc gataagtcgt gtcttaccgg gttggactca   6000

agacgatagt taccggataa ggcgcagcgg tcgggctgaa cggggggttc gtgcacacag   6060

cccagcttgg agcgaacgac ctacaccgaa ctgagatacc tacagcgtga gctatgagaa   6120

agcgccacgc ttcccgaagg gagaaaggcg gacaggtatc cggtaagcgg cagggtcgga   6180

acaggagagc gcacgaggga gcttccaggg ggaaacgcct ggtatcttta tagtcctgtc   6240

gggtttcgcc acctctgact tgagcgtcga tttttgtgat gctcgtcagg ggggcggagc   6300

ctatggaaaa acgccagcaa cgcggccttt ttacggttcc tggccttttg ctggcctttt   6360

gctcacatgt tctttcctgc gttatcccct gattctgtgg ataaccgtat taccgccttt   6420

gagtgagctg ataccgctcg ccgcagccga acgaccgagc gcagcgagtc agtgagcgag   6480

gaagcggaag agcgcccaat acgcaaaccg cctctccccg cgcgttggcc gattcattaa   6540

tgcagctggc acgacaggtt tcccgactgg aaagcgggca gtgagcgcaa cgcaattaat   6600

gtgagttagc tcactcatta ggcaccccag gctttacact ttatgcttcc ggctcgtatg   6660

ttgtgtggaa ttgtgagcgg ataacaattt cacacaggaa acagctatga ccatgattac   6720

gccagattta attaaggcct taattagg                                      6748
```

<210> SEQ ID NO 21
<211> LENGTH: 6748
<212> TYPE: DNA

<213> ORGANISM: Artificial Sequence
<220> FEATURE:
<223> OTHER INFORMATION: Synthetic sequence
<220> FEATURE:
<221> NAME/KEY: repeat_region
<222> LOCATION: (1)..(130)
<223> OTHER INFORMATION: 5' ITR
<220> FEATURE:
<221> NAME/KEY: promoter
<222> LOCATION: (191)..(932)
<223> OTHER INFORMATION: human\CMV\I.E.\enhancer\&\promoter
<220> FEATURE:
<221> NAME/KEY: misc_feature
<222> LOCATION: (897)..(901)
<223> OTHER INFORMATION: TATA\box
<220> FEATURE:
<221> NAME/KEY: Intron
<222> LOCATION: (1047)..(1179)
<223> OTHER INFORMATION: Promega\chimeric\intron
<220> FEATURE:
<221> NAME/KEY: misc_feature
<222> LOCATION: (1248)..(1293)
<223> OTHER INFORMATION: c-myc\miniIRES\cloned\into\Nhe\site
<220> FEATURE:
<221> NAME/KEY: misc_feature
<222> LOCATION: (1292)..(1297)
<223> OTHER INFORMATION: 6\bp\insertion
<220> FEATURE:
<221> NAME/KEY: misc_feature
<222> LOCATION: (1294)..(3493)
<223> OTHER INFORMATION: 3bnc\ORF\42
<220> FEATURE:
<221> NAME/KEY: polyA_signal
<222> LOCATION: (3502)..(3733)
<223> OTHER INFORMATION: SV40\late\polyadenylation\signal
<220> FEATURE:
<221> NAME/KEY: repeat_region
<222> LOCATION: (3798)..(3927)
<223> OTHER INFORMATION: complement - 3' ITR
<220> FEATURE:
<221> NAME/KEY: rep_origin
<222> LOCATION: (4104)..(4559)
<223> OTHER INFORMATION: complement - f1\ori
<220> FEATURE:
<221> NAME/KEY: misc_feature
<222> LOCATION: (4690)..(5547)
<223> OTHER INFORMATION: Amp-R coding sequence
<220> FEATURE:
<221> NAME/KEY: misc_feature
<222> LOCATION: (5721)..(6309)
<223> OTHER INFORMATION: COL\E1\Origin

<400> SEQUENCE: 21
ctgcgcgctc gctcgctcac tgaggccgcc cgggcaaagc ccgggcgtcg ggcgaccttt 60
ggtcgcccgg cctcagtgag cgagcgagcg cgcagagagg gagtggccaa ctccatcact 120
aggggttcct tgtagttaat gattaacccg ccatgctact tatctacgta gccatgctct 180
aggaagatct tcaatattgg ccattagcca tattattcat tggttatata gcataaatca 240
atattggcta ttggccattg catacgttgt atctatatca taatatgtac atttatattg 300
gctcatgtcc aatatgaccg ccatgttggc attgattatt gactagttat taatagtaat 360
caattacggg gtcattagtt catagcccat atatggagtt ccgcgttaca taacttacgg 420
taaatggccc gcctggctga ccgcccaacg acccccgccc attgacgtca ataatgacgt 480
atgttcccat agtaacgcca atagggactt tccattgacg tcaatgggtg gagtatttac 540
ggtaaactgc ccacttggca gtacatcaag tgtatcatat gccaagtccg ccccctattg 600
acgtcaatga cggtaaatgg cccgcctggc attatgccca gtacatgacc ttacgggact 660
ttcctacttg gcagtacatc tacgtattag tcatcgctat taccatggtg atgcggtttt 720
ggcagtacac caatgggcgt ggatagcggt ttgactcacg gggatttcca agtctccacc 780

-continued

```
ccattgacgt caatgggagt ttgttttggc accaaaatca acgggacttt ccaaaatgtc    840
gtaataaccc cgccccgttg acgcaaatgg gcggtaggcg tgtacggtgg gaggtctata    900
taagcagagc tcgtttagtg aaccgtcaga tcactagaag ctttattgcg gtagtttatc    960
acagttaaat tgctaacgca gtcagtgctt ctgacacaac agtctcgaac ttaagctgca   1020
gaagttggtc gtgaggcact gggcaggtaa gtatcaaggt tacaagacag gtttaaggag   1080
accaatagaa actgggcttg tcgagacaga gaagactctt gcgtttctga taggcaccta   1140
ttggtcttac tgacatccac tttgcctttc tctccacagg tgtccactcc cagttcaatt   1200
acagctctta aggctagagt acttaatacg actcactata ggctagcggg gactttgcac   1260
tggaacttac aacacccgag caaggacgcg actctagctc tagaaccatg taccggatgc   1320
agctactgtc gtgtatcgct ctttcgttag cattagtcac aaactcgcaa gtccagctgc   1380
tgcagtcagg ggctgcagtg acaaagcccg gagcatcagt tcgcgtttca tgtgaggcca   1440
gtggctacaa catacgggac tatttcatcc actggtggag acaggcacca ggccagggat   1500
tacagtgggt tggctggatc aacccgaaaa caggccagcc caataacccg cgacagtttc   1560
agggccgtgt cagtctcacc cgccacgcat cttgggattt cgatacgttt tccttctaca   1620
tggatctgaa ggcactgcgc agcgacgata ccgcagttta cttctgcgca aggcagcgta   1680
gcgattactg ggacttcgat gtctgggggt caggcacaca agtaacggtt tcatccgctt   1740
ccacaaaagg gccatcagtg tttcccctgg caccctcctc aaaatctacc agcggaggca   1800
ccgcagctct cggctgtctg gttaaagact actttcccga acccgtcacc gtttcttgga   1860
attctggggc tctaacctca ggcgtgcaca cgttccccgc cgttctgcag agcagcggcc   1920
tgtactcctt atcaagtgta gtaactgttc catcatcaag cttgggcacc cagacctaca   1980
tctgcaatgt taatcacaaa ccttccaaca ctaaggtgga caagaaggtt gagccaaaaa   2040
gttgtgataa gacccacaca tgtcctccgt gtcccgctcc tgagctgcta ggtggcccca   2100
gtgtgttcct ctttccccct aaacccaaag acacactgat gatctcaagg acccctgaag   2160
ttacatgcgt tgttgttgat gtttcccacg aagatccaga agttaagttc aactggtatg   2220
ttgatggcgt tgaagttcac aacgcaaaaa ctaaaccgcg tgaagaacag tataactcta   2280
cataccgtgt ggtttcagtt cttacagtcc tgcatcagga ttggcttaac gggaaagaat   2340
acaaatgtaa agtatccaac aaagcacttc ccgcacccat tgagaaaacg atttcaaaag   2400
caaagggaca gcccagggaa ccccaagttt acacgctgcc gccatctcgt gatgagctga   2460
ccaagaatca ggtatctttg acgtgcctgg tcaaaggttt ctacccttcg gacatcgcgg   2520
ttgagtggga gtcaaacggc cagccagaaa acaattacaa aaccactcct cctgtcttgg   2580
acagcgatgg gtcattcttt ctttactcaa aactcactgt tgacaagtct cgatggcagc   2640
aaggcaacgt ctttagttgc tctgtgatgc atgaagccct ccacaatcac tatacacaga   2700
aaagtctatc actctcacct ggcagaaaac ggagggcacc cgtgaagcag acactcaatt   2760
tcgacttact gaaactggct ggggatgtcg aatctaatcc aggccctatg taccgcatgc   2820
aactactgtc atgtattgcc ctttcattag ctctcgtaac aaattctgat atccagatga   2880
cccagtcccc ctcatctctg tcagcatcgg ttggcgatac cgttactatt acgtgccagg   2940
caaatggcta cttgaactgg taccaacaac ggcgcggtaa agcacccaaa ctattgatat   3000
acgatggctc aaagttggaa agaggcgtgc cttcaagatt ctccggcaga cgctggggcc   3060
aggagtacaa cctaactatc aacaaccttc agccagagga tattgcaacc tacttctgtc   3120
```

-continued

```
aggtgtatga gtttgtggtg cccggcacgc gtctggattt gaagagaaca gtcgcggcac   3180
cctcagtgtt tatcttccct cccagtgatg agcagctgaa atcaggcacc gcctcagtgg   3240
tatgcctgtt gaacaacttc tacccccgtg aggcaaaagt tcagtggaag gtggataatg   3300
ccttacagtc aggcaactca caagagagcg tcactgagca ggattcaaaa gattcaacat   3360
acagtcttag ctcaaccctg accctctcta aagcggatta cgaaaaacac aaagtttatg   3420
cctgcgaagt cacgcaccag ggtctgagta gccctgttac taaaagtttc aaccgaggcg   3480
aatgttaatg agcggccgct tcgagcagac atgataagat acattgatga gtttggacaa   3540
accacaacta gaatgcagtg aaaaaaatgc tttatttgtg aaatttgtga tgctattgct   3600
ttatttgtaa ccattataag ctgcaataaa caagttaaca acaacaattg cattcatttt   3660
atgtttcagg ttcaggggga gatgtgggag gtttttttaaa gcaagtaaaa cctctacaaa   3720
tgtggtaaaa tcgataagga tcttcctaga gcatggctac gtagataagt agcatggcgg   3780
gttaatcatt aactacaagg aacccctagt gatggagttg gccactccct ctctgcgcgc   3840
tcgctcgctc actgaggccg ggcgaccaaa ggtcgcccga cgcccgggct ttgcccgggc   3900
ggcctcagtg agcgagcgag cgcgcagcct taattaacct aattcactgg ccgtcgtttt   3960
acaacgtcgt gactgggaaa accctggcgt tacccaactt aatcgccttg cagcacatcc   4020
ccctttcgcc agctggcgta atagcgaaga ggcccgcacc gatcgccctt cccaacagtt   4080
gcgcagcctg aatggcgaat gggacgcgcc ctgtagcggc gcattaagcg cggcgggtgt   4140
ggtggttacg cgcagcgtga ccgctacact tgccagcgcc ctagcgcccg ctcctttcgc   4200
tttcttccct tcctttctcg ccacgttcgc cggctttccc cgtcaagctc taaatcgggg   4260
gctcccttta gggttccgat ttagtgcttt acggcacctc gaccccaaaa aacttgatta   4320
gggtgatggt tcacgtagtg ggccatcgcc ctgatagacg gtttttcgcc ctttgacgtt   4380
ggagtccacg ttctttaata gtggactctt gttccaaact ggaacaacac tcaaccctat   4440
ctcggtctat tcttttgatt tataagggat tttgccgatt tcggcctatt ggttaaaaaa   4500
tgagctgatt taacaaaaat ttaacgcgaa ttttaacaaa atattaacgc ttacaattta   4560
ggtggcactt ttcggggaaa tgtgcgcgga acccctattt gtttattttt ctaaatacat   4620
tcaaatatgt atccgctcat gagacaataa ccctgataaa tgcttcaata atattgaaaa   4680
aggaagagta tgagtattca acatttccgt gtcgccctta ttcccttttt tgcggcattt   4740
tgccttcctg tttttgctca cccagaaacg ctggtgaaag taaaagatgc tgaagatcag   4800
ttgggtgcac gagtgggtta catcgaactg gatctcaaca gcggtaagat ccttgagagt   4860
tttcgccccg aagaacgttt tccaatgatg agcactttta aagttctgct atgtggcgcg   4920
gtattatccc gtattgacgc cgggcaagag caactcggtc gccgcataca ctattctcag   4980
aatgacttgg ttgagtactc accagtcaca gaaaagcatc ttacggatgg catgacagta   5040
agagaattat gcagtgctgc cataaccatg agtgataaca ctgcggccaa cttacttctg   5100
acaacgatcg gaggaccgaa ggagctaacc gcttttttgc acaacatggg ggatcatgta   5160
actcgccttg atcgttggga accggagctg aatgaagcca taccaaacga cgagcgtgac   5220
accacgatgc ctgtagcaat ggcaacaacg ttgcgcaaac tattaactgg cgaactactt   5280
actctagctt cccggcaaca attaatagac tggatggagg cggataaagt tgcaggacca   5340
cttctgcgct cggcccttcc ggctggctgg tttattgctg ataaatctgg agccggtgag   5400
cgtgggtctc gcggtatcat tgcagcactg gggccagatg gtaagccctc ccgtatcgta   5460
gttatctaca cgacggggag tcaggcaact atggatgaac gaaatagaca gatcgctgag   5520
```

```
ataggtgcct cactgattaa gcattggtaa ctgtcagacc aagtttactc atatatactt   5580

tagattgatt taaaacttca tttttaattt aaaaggatct aggtgaagat cctttttgat   5640

aatctcatga ccaaaatccc ttaacgtgag ttttcgttcc actgagcgtc agaccccgta   5700

gaaaagatca aaggatcttc ttgagatcct ttttttctgc gcgtaatctg ctgcttgcaa   5760

acaaaaaaac caccgctacc agcggtggtt tgtttgccgg atcaagagct accaactctt   5820

tttccgaagg taactggctt cagcagagcg cagataccaa atactgttct tctagtgtag   5880

ccgtagttag gccaccactt caagaactct gtagcaccgc ctacatacct cgctctgcta   5940

atcctgttac cagtggctgc tgccagtggc gataagtcgt gtcttaccgg gttggactca   6000

agacgatagt taccggataa ggcgcagcgg tcgggctgaa cggggggttc gtgcacacag   6060

cccagcttgg agcgaacgac ctacaccgaa ctgagatacc tacagcgtga gctatgagaa   6120

agcgccacgc ttcccgaagg gagaaaggcg gacaggtatc cggtaagcgg cagggtcgga   6180

acaggagagc gcacgaggga gcttccaggg ggaaacgcct ggtatcttta tagtcctgtc   6240

gggtttcgcc acctctgact tgagcgtcga tttttgtgat gctcgtcagg ggggcggagc   6300

ctatggaaaa acgccagcaa cgcggccttt ttacggttcc tggccttttg ctggcctttt   6360

gctcacatgt tctttcctgc gttatcccct gattctgtgg ataaccgtat taccgccttt   6420

gagtgagctg ataccgctcg ccgcagccga acgaccgagc gcagcgagtc agtgagcgag   6480

gaagcggaag agcgcccaat acgcaaaccg cctctccccg cgcgttggcc gattcattaa   6540

tgcagctggc acgacaggtt tcccgactgg aaagcgggca gtgagcgcaa cgcaattaat   6600

gtgagttagc tcactcatta ggcaccccag gctttacact ttatgcttcc ggctcgtatg   6660

ttgtgtggaa ttgtgagcgg ataacaattt cacacaggaa acagctatga ccatgattac   6720

gccagattta attaaggcct taattagg                                      6748
```

```
<210> SEQ ID NO 22
<211> LENGTH: 6748
<212> TYPE: DNA
<213> ORGANISM: Artificial Sequence
<220> FEATURE:
<223> OTHER INFORMATION: Synthetic sequence
<220> FEATURE:
<221> NAME/KEY: repeat_region
<222> LOCATION: (1)..(130)
<223> OTHER INFORMATION: 5' ITR
<220> FEATURE:
<221> NAME/KEY: promoter
<222> LOCATION: (191)..(932)
<223> OTHER INFORMATION: human\CMV\I.E.\enhancer\&\promoter
<220> FEATURE:
<221> NAME/KEY: misc_feature
<222> LOCATION: (897)..(901)
<223> OTHER INFORMATION: TATA\box
<220> FEATURE:
<221> NAME/KEY: Intron
<222> LOCATION: (1047)..(1179)
<223> OTHER INFORMATION: Promega\chimeric\intron
<220> FEATURE:
<221> NAME/KEY: misc_feature
<222> LOCATION: (1248)..(1295)
<223> OTHER INFORMATION: "mini  c-myc"
<220> FEATURE:
<221> NAME/KEY: misc_feature
<222> LOCATION: (1294)..(3493)
<223> OTHER INFORMATION: AnnaT_TestRef\28
<220> FEATURE:
<221> NAME/KEY: misc_feature
<222> LOCATION: (1294)..(3493)
<223> OTHER INFORMATION: 3bnc\ORF\28
<220> FEATURE:
```

<221> NAME/KEY: polyA_signal
<222> LOCATION: (3502)..(3733)
<223> OTHER INFORMATION: SV40\late\polyadenylation\signal
<220> FEATURE:
<221> NAME/KEY: repeat_region
<222> LOCATION: (3798)..(3927)
<223> OTHER INFORMATION: complement - 3' ITR
<220> FEATURE:
<221> NAME/KEY: rep_origin
<222> LOCATION: (4104)..(4559)
<223> OTHER INFORMATION: complement - f1\ori
<220> FEATURE:
<221> NAME/KEY: misc_feature
<222> LOCATION: (4690)..(5547)
<223> OTHER INFORMATION: Amp-R coding sequence
<220> FEATURE:
<221> NAME/KEY: misc_feature
<222> LOCATION: (5721)..(6309)
<223> OTHER INFORMATION: COL\E1\Origin

<400> SEQUENCE: 22
ctgcgcgctc gctcgctcac tgaggccgcc cgggcaaagc ccgggcgtcg ggcgaccttt 60
ggtcgcccgg cctcagtgag cgagcgagcg cgcagagagg gagtggccaa ctccatcact 120
aggggttcct tgtagttaat gattaacccg ccatgctact tatctacgta gccatgctct 180
aggaagatct tcaatattgg ccattagcca tattattcat tggttatata gcataaatca 240
atattggcta ttggccattg catacgttgt atctatatca taatatgtac atttatattg 300
gctcatgtcc aatatgaccg ccatgttggc attgattatt gactagttat taatagtaat 360
caattacggg gtcattagtt catagcccat atatggagtt ccgcgttaca taacttacgg 420
taaatggccc gcctggctga ccgcccaacg acccccgccc attgacgtca ataatgacgt 480
atgttcccat agtaacgcca atagggactt tccattgacg tcaatgggtg gagtatttac 540
ggtaaactgc ccacttggca gtacatcaag tgtatcatat gccaagtccg ccccctattg 600
acgtcaatga cggtaaatgg cccgcctggc attatgccca gtacatgacc ttacgggact 660
ttcctacttg gcagtacatc tacgtattag tcatcgctat taccatggtg atgcggtttt 720
ggcagtacac caatgggcgt ggatagcggt ttgactcacg gggatttcca agtctccacc 780
ccattgacgt caatgggagt ttgttttggc accaaaatca acgggacttt ccaaaatgtc 840
gtaataaccc cgccccgttg acgcaaatgg gcggtaggcg tgtacggtgg gaggtctata 900
taagcagagc tcgtttagtg aaccgtcaga tcactagaag ctttattgcg gtagtttatc 960
acagttaaat tgctaacgca gtcagtgctt ctgacacaac agtctcgaac ttaagctgca 1020
gaagttggtc gtgaggcact gggcaggtaa gtatcaaggt tacaagacag gtttaaggag 1080
accaatagaa actgggcttg tcgagacaga gaagactctt gcgtttctga taggcaccta 1140
ttggtcttac tgacatccac tttgcctttc tctccacagg tgtccactcc cagttcaatt 1200
acagctctta aggctagagt acttaatacg actcactata ggctagcggg gactttgcac 1260
tggaacttac aacacccgag caaggacgcg actctagctc tagaaccatg tacagaatgc 1320
agcttctgtc ttgcattgca ctttctctgg ccttagtgac taactctcaa gtgcagctcc 1380
ttcagagcgg cgcagctgtg acaaagcctg ggccagcgt tagagtgtcg tgtgaggcat 1440
ccggctataa catcagagac tatttcattc attggtggcg ccaagcgccc ggtcagggac 1500
ttcagtgggt gggctggatc aatccaaaga cagggcagcc taacaatcca agacagtttc 1560
agggccgggt gtccttgact cggcatgcga gctgggattt tgatacgttc tccttttaca 1620
tggacctgaa ggccctaagg tctgacgaca ccgctgtgta tttctgcgcc aggcagagat 1680
cagactattg ggactttgat gtgtggggct ctggtactca agtgacagtg agcagtgcgt 1740

-continued

```
ctacaaaggg cccatcagtc tttcctctgg ccccttccag caagtctacg tccggcggga   1800
ctgccgccct cggatgctta gtgaaggact atttccctga gcccgtgacc gtgagctgga   1860
atagcggcgc tctgacgtct ggcgtgcaca cattccctgc tgtgctgcag agcagtggcc   1920
tttactccct tagtagcgtg gtgacagtgc cctctagttc tctaggcacc cagacataca   1980
tttgtaatgt aaatcacaaa cctagcaaca caaaggtgga caagaaggtg gaacctaaga   2040
gttgtgataa gacccataca tgtcccccat gcccagcccc agagcttctt ggcggtccat   2100
cagttttctt gtttcctcca aaacctaagg acactctgat gatttcgaga acaccggaag   2160
tcacttgtgt ggtcgtggat gtgtcacacg aggaccctga ggtcaagttc aattggtatg   2220
tggacggcgt ggaggtacat aacgccaaaa cgaagcctcg tgaggagcag tacaactcca   2280
cctatcgagt ggtcagcgtc cttaccgtgt tacaccagga ctggcttaac ggaaaggagt   2340
ataagtgtaa ggtatccaac aaagccctgc ctgcacctat tgagaaaact atatctaaag   2400
ccaagggcca gccgcgagag cctcaagttt acacacttcc tccttcgaga gacgagctca   2460
ccaagaatca ggtgtcactt acctgccttg tgaaaggctt ttaccctagt gatatcgcgg   2520
tggaatggga gagcaatggg cagcctgaga acaactataa gacaacccct cccgtactgg   2580
acagcgatgg cagcttcttt ctctattcta agctgaccgt cgataagagt cggtggcagc   2640
agggtaacgt gttctcttgt tctgtgatgc atgaggcatt gcacaatcat tacacgcaga   2700
agagtctgtc cctttctcct ggccgtaaaa ggcgagctcc tgtgaagcag actcttaact   2760
ttgacttgct caagctcgct ggcgatgtgg agtccaatcc tgggcccatg taccgaatgc   2820
aacttcttag ctgcatagca ctttccctg cacttgtgac gaattctgac atccagatga   2880
cccagagtcc ctcctctttg agtgcaagtg tgggcgacac cgtgaccatc acttgtcagg   2940
ccaatggcta tctcaactgg tatcagcagc ggagagggaa ggcacctaag ctactcatct   3000
atgacggcag taaactggag agaggcgttc caagcagatt ctccggtcgc cgatggggcc   3060
aggaatacaa tcttaccatc aataacctgc agcccgagga cattgccacc tatttctgtc   3120
aggtgtatga gttcgtggtg cccggaacga gactcgatct caagagaact gtggctgccc   3180
ccagcgtgtt cattttccct ccttccgacg agcagcttaa gagtggcacc gcttcagtgg   3240
tgtgtttact aaacaatttc taccctcgag aggcgaaggt gcagtggaag gtggataatg   3300
cccttcagtc aggcaattct caagaaagtg tgaccgagca ggatagtaag gactctacat   3360
actcactctc ctcaaccctg acactcagta aggccgacta tgagaagcac aaggtgtacg   3420
cgtgcgaagt cacgcatcag ggcctatcta gccccgtcac aaagtcattc aataggggcg   3480
agtgctaatg agcggccgct tcgagcagac atgataagat acattgatga gtttggacaa   3540
accacaacta gaatgcagtg aaaaaaatgc tttatttgtg aaatttgtga tgctattgct   3600
ttatttgtaa ccattataag ctgcaataaa caagttaaca acaacaattg cattcatttt   3660
atgtttcagg ttcaggggga gatgtgggag gtttttaaa gcaagtaaaa cctctacaaa   3720
tgtggtaaaa tcgataagga tcttcctaga gcatggctac gtagataagt agcatggcgg   3780
gttaatcatt aactacaagg aacccctagt gatggagttg gccactccct ctctgcgcgc   3840
tcgctcgctc actgaggccg ggcgaccaaa ggtcgcccga cgcccgggct ttgcccgggc   3900
ggcctcagtg agcgagcgag cgcgcagcct taattaacct aattcactgg ccgtcgtttt   3960
acaacgtcgt gactgggaaa accctggcgt tacccaactt aatcgccttg cagcacatcc   4020
ccctttcgcc agctggcgta atagcgaaga ggcccgcacc gatcgccctt cccaacagtt   4080
```

-continued

```
gcgcagcctg aatggcgaat gggacgcgcc ctgtagcggc gcattaagcg cggcgggtgt   4140
ggtggttacg cgcagcgtga ccgctacact tgccagcgcc ctagcgcccg ctcctttcgc   4200
tttcttccct tcctttctcg ccacgttcgc cggctttccc cgtcaagctc taaatcgggg   4260
gctcccttta gggttccgat ttagtgcttt acggcacctc gaccccaaaa aacttgatta   4320
gggtgatggt tcacgtagtg ggccatcgcc ctgatagacg gtttttcgcc ctttgacgtt   4380
ggagtccacg ttctttaata gtggactctt gttccaaact ggaacaacac tcaaccctat   4440
ctcggtctat tcttttgatt tataagggat tttgccgatt tcggcctatt ggttaaaaaa   4500
tgagctgatt taacaaaaat ttaacgcgaa ttttaacaaa atattaacgc ttacaattta   4560
ggtggcactt ttcggggaaa tgtgcgcgga acccctattt gtttattttt ctaaatacat   4620
tcaaatatgt atccgctcat gagacaataa ccctgataaa tgcttcaata atattgaaaa   4680
aggaagagta tgagtattca acatttccgt gtcgccctta ttcccttttt tgcggcattt   4740
tgccttcctg tttttgctca cccagaaacg ctggtgaaag taaaagatgc tgaagatcag   4800
ttgggtgcac gagtgggtta catcgaactg gatctcaaca gcggtaagat ccttgagagt   4860
tttcgccccg aagaacgttt tccaatgatg agcactttta aagttctgct atgtggcgcg   4920
gtattatccc gtattgacgc cgggcaagag caactcggtc gccgcataca ctattctcag   4980
aatgacttgg ttgagtactc accagtcaca gaaaagcatc ttacggatgg catgacagta   5040
agagaattat gcagtgctgc cataaccatg agtgataaca ctgcggccaa cttacttctg   5100
acaacgatcg gaggaccgaa ggagctaacc gcttttttgc acaacatggg ggatcatgta   5160
actcgccttg atcgttggga accggagctg aatgaagcca taccaaacga cgagcgtgac   5220
accacgatgc ctgtagcaat ggcaacaacg ttgcgcaaac tattaactgg cgaactactt   5280
actctagctt cccggcaaca attaatagac tggatggagg cggataaagt tgcaggacca   5340
cttctgcgct cggcccttcc ggctggctgg tttattgctg ataaatctgg agccggtgag   5400
cgtgggtctc gcggtatcat tgcagcactg gggccagatg gtaagccctc ccgtatcgta   5460
gttatctaca cgacggggag tcaggcaact atggatgaac gaaatagaca gatcgctgag   5520
ataggtgcct cactgattaa gcattggtaa ctgtcagacc aagtttactc atatatactt   5580
tagattgatt taaaacttca tttttaattt aaaaggatct aggtgaagat cctttttgat   5640
aatctcatga ccaaaatccc ttaacgtgag ttttcgttcc actgagcgtc agaccccgta   5700
gaaaagatca aaggatcttc ttgagatcct ttttttctgc gcgtaatctg ctgcttgcaa   5760
acaaaaaaac caccgctacc agcggtggtt tgtttgccgg atcaagagct accaactctt   5820
tttccgaagg taactggctt cagcagagcg cagataccaa atactgttct tctagtgtag   5880
ccgtagttag gccaccactt caagaactct gtagcaccgc ctacatacct cgctctgcta   5940
atcctgttac cagtggctgc tgccagtggc gataagtcgt gtcttaccgg gttggactca   6000
agacgatagt taccggataa ggcgcagcgg tcgggctgaa cggggggttc gtgcacacag   6060
cccagcttgg agcgaacgac ctacaccgaa ctgagatacc tacagcgtga gctatgagaa   6120
agcgccacgc ttcccgaagg gagaaaggcg gacaggtatc cggtaagcgg cagggtcgga   6180
acaggagagc gcacgaggga gcttccaggg ggaaacgcct ggtatcttta tagtcctgtc   6240
gggtttcgcc acctctgact tgagcgtcga tttttgtgat gctcgtcagg ggggcggagc   6300
ctatggaaaa acgccagcaa cgcggccttt ttacggttcc tggccttttg ctggcctttt   6360
gctcacatgt tctttcctgc gttatcccct gattctgtgg ataaccgtat taccgccttt   6420
gagtgagctg ataccgctcg ccgcagccga acgaccgagc gcagcgagtc agtgagcgag   6480
```

```
gaagcggaag agcgcccaat acgcaaaccg cctctccccg cgcgttggcc gattcattaa   6540

tgcagctggc acgacaggtt tcccgactgg aaagcgggca gtgagcgcaa cgcaattaat   6600

gtgagttagc tcactcatta ggcaccccag gctttacact ttatgcttcc ggctcgtatg   6660

ttgtgtggaa ttgtgagcgg ataacaattt cacacaggaa acagctatga ccatgattac   6720

gccagattta attaaggcct taattagg                                      6748


<210> SEQ ID NO 23
<211> LENGTH: 6748
<212> TYPE: DNA
<213> ORGANISM: Artificial Sequence
<220> FEATURE:
<223> OTHER INFORMATION: Synthetic sequence
<220> FEATURE:
<221> NAME/KEY: repeat_region
<222> LOCATION: (1)..(130)
<223> OTHER INFORMATION: 5' ITR
<220> FEATURE:
<221> NAME/KEY: promoter
<222> LOCATION: (191)..(932)
<223> OTHER INFORMATION: human\CMV\I.E.\enhancer\&\promoter
<220> FEATURE:
<221> NAME/KEY: misc_feature
<222> LOCATION: (897)..(901)
<223> OTHER INFORMATION: TATA\box
<220> FEATURE:
<221> NAME/KEY: Intron
<222> LOCATION: (1047)..(1179)
<223> OTHER INFORMATION: Promega\chimeric\intron
<220> FEATURE:
<221> NAME/KEY: misc_feature
<222> LOCATION: (1248)..(1293)
<223> OTHER INFORMATION: c-myc\miniIRES\cloned\into\Nhe\site
<220> FEATURE:
<221> NAME/KEY: misc_feature
<222> LOCATION: (1294)..(3493)
<223> OTHER INFORMATION: AnnaT_TestRef\30
<220> FEATURE:
<221> NAME/KEY: misc_feature
<222> LOCATION: (1294)..(3493)
<223> OTHER INFORMATION: 3bnc\ORF\30
<220> FEATURE:
<221> NAME/KEY: polyA_signal
<222> LOCATION: (3502)..(3733)
<223> OTHER INFORMATION: SV40\late\polyadenylation\signal
<220> FEATURE:
<221> NAME/KEY: repeat_region
<222> LOCATION: (3798)..(3927)
<223> OTHER INFORMATION: complement -3'  ITR
<220> FEATURE:
<221> NAME/KEY: rep_origin
<222> LOCATION: (4104)..(4559)
<223> OTHER INFORMATION: complement - f1\ori
<220> FEATURE:
<221> NAME/KEY: misc_feature
<222> LOCATION: (4690)..(5547)
<223> OTHER INFORMATION: Amp-R coding sequence
<220> FEATURE:
<221> NAME/KEY: misc_feature
<222> LOCATION: (5721)..(6309)
<223> OTHER INFORMATION: COL\E1\Origin

<400> SEQUENCE: 23

ctgcgcgctc gctcgctcac tgaggccgcc cgggcaaagc ccgggcgtcg ggcgaccttt     60

ggtcgcccgg cctcagtgag cgagcgagcg cgcagagagg gagtggccaa ctccatcact    120

aggggttcct tgtagttaat gattaacccg ccatgctact tatctacgta gccatgctct    180

aggaagatct tcaatattgg ccattagcca tattattcat tggttatata gcataaatca    240

atattggcta ttggccattg catacgttgt atctatatca taatatgtac atttatattg    300
```

-continued

```
gctcatgtcc aatatgaccg ccatgttggc attgattatt gactagttat taatagtaat    360
caattacggg gtcattagtt catagcccat atatggagtt ccgcgttaca taacttacgg    420
taaatggccc gcctggctga ccgcccaacg acccccgccc attgacgtca ataatgacgt    480
atgttcccat agtaacgcca atagggactt tccattgacg tcaatgggtg gagtatttac    540
ggtaaactgc ccacttggca gtacatcaag tgtatcatat gccaagtccg ccccctattg    600
acgtcaatga cggtaaatgg cccgcctggc attatgccca gtacatgacc ttacgggact    660
ttcctacttg gcagtacatc tacgtattag tcatcgctat taccatggtg atgcggtttt    720
ggcagtacac caatgggcgt ggatagcggt ttgactcacg gggatttcca agtctccacc    780
ccattgacgt caatgggagt ttgttttggc accaaaatca acgggacttt ccaaaatgtc    840
gtaataaccc cgccccgttg acgcaaatgg gcggtaggcg tgtacggtgg gaggtctata    900
taagcagagc tcgtttagtg aaccgtcaga tcactagaag ctttattgcg gtagtttatc    960
acagttaaat tgctaacgca gtcagtgctt ctgacacaac agtctcgaac ttaagctgca   1020
gaagttggtc gtgaggcact gggcaggtaa gtatcaaggt tacaagacag gtttaaggag   1080
accaatagaa actgggcttg tcgagacaga gaagactctt gcgtttctga taggcaccta   1140
ttggtcttac tgacatccac tttgcctttc tctccacagg tgtccactcc cagttcaatt   1200
acagctctta aggctagagt acttaatacg actcactata ggctagcggg gactttgcac   1260
tggaacttac aacacccgag caaggacgcg actctagctc tagaaccatg tatcgtatgc   1320
aacttctcag ctgcattgca cttagtctcg ctctggttac aaacagtcaa gttcagctgc   1380
ttcagtccgg cgctgccgtg accaagcctg gagcttcggt cagagtgtca tgtgaagcca   1440
gcgggtataa cattagagac tatttcattc actggtggag acaggcccct ggacaggggc   1500
ttcagtgggt cggctggatt aaccctaaaa ccggccagcc caacaatcca agacagtttc   1560
agggccgggt gtcccttacc cgacatgcca gctgggattt cgatacattt tcgttctata   1620
tggaccttaa ggctttgaga tctgatgata cagctgtgta tttctgtgca cgacagcggt   1680
ctgattactg ggattttgac gtgtgggggt ccggcacaca agtcacagtg tccagtgcat   1740
ccacaaaagg accttcagtc tttcctctcg ccccgtccag caagtcaacc agcgggggta   1800
cagcggcttt ggggtgcctt gtcaaggact actttcctga acccgtgact gtgtcatgga   1860
actcgggtgc cctgacatcg gggtccaca cttttcccgc tgtgctccag tcctcggggc   1920
tatactccct tagctcggtg gttacagtcc catcctcatc attagggaca cagacataca   1980
tctgtaatgt gaaccacaag ccttcaaata ctaaggttga taagaaagtt gaacccaagt   2040
cttgcgataa gacacacaca tgtccccctt gtcctgcacc agagctgctt ggcgggcctt   2100
cagtttttct tttcctccca aaacctaagg atacacttat gatctcaagg acaccagaag   2160
tcacatgcgt cgtggtggat gtgtcccatg aggaccccga ggtcaagttt aactggtatg   2220
tggatggggt cgaagtgcac aacgccaaaa caaagccacg cgaagagcaa tacaattcga   2280
cttacagagt cgtgagtgta ctgaccgtgc tgcaccagga ttggctgaac ggcaaagagt   2340
acaaatgcaa agtgagcaac aaagctctac cagctcccat agaaaagaca atctctaaag   2400
ctaaggggca gccgcgggag ccccaagtct ataccctacc tccttcccgc gacgaactca   2460
caaagaacca ggttagcctt acatgtctcg taaaggggtt ctatccttcg gatatcgctg   2520
tcgaatggga gtctaacggg cagcctgaaa acaactacaa aacaactccc cctgtgcttg   2580
atagcgacgg tagtttcttt ctgtacagca aacttacagt cgataagagt agatggcaac   2640
aggggaatgt gttttcttgt tccgtgatgc acgaggcact gcacaatcac tacacacaga   2700
```

-continued

```
agagtctcag cttatctcct ggaaggaaga gacgagctcc cgtcaaacag acgctaaact   2760
ttgacctgtt aaagcttgcc ggcgatgtcg aatccaatcc agggcctatg taccggatgc   2820
agctacttag ttgcatagct cttagccttg ctctcgtgac taacagcgac atccagatga   2880
cgcagtcacc ttcctccctg tcagcctcag tcggcgatac cgtaactata acatgtcagg   2940
cgaatgggta tctgaattgg tatcagcagc gacgtgggaa agctcctaag ttgcttatct   3000
atgatgggtc taagcttgag agaggggtgc caagtagatt ttctggacga aggtgggggc   3060
aggagtataa cttgaccatc aataaccttc agcctgaaga tatcgccaca tacttttgcc   3120
aggtatatga gtttgttgtg cccgggacga gacttgatct caaacgaacg gtggctgctc   3180
cttctgtgtt tatctttcct ccttctgatg agcagctcaa gagcggaaca gcatccgttg   3240
tctgtctgct caacaacttt taccctaggg aagctaaggt gcagtggaag gttgacaatg   3300
ctttacagag cggaaatagc caggagtccg tcacagaaca ggatagcaag gatagcacat   3360
atagcttgag ctccactctg acactcagta aggctgatta tgagaagcat aaggtatatg   3420
cctgtgaagt cacacatcaa ggcctttcat cccctgttac taagtctttc aacagagggg   3480
aatgctaatg agcggccgct tcgagcagac atgataagat acattgatga gtttggacaa   3540
accacaacta gaatgcagtg aaaaaaatgc tttatttgtg aaatttgtga tgctattgct   3600
ttatttgtaa ccattataag ctgcaataaa caagttaaca acaacaattg cattcatttt   3660
atgtttcagg ttcaggggga gatgtgggag gtttttttaaa gcaagtaaaa cctctacaaa   3720
tgtggtaaaa tcgataagga tcttcctaga gcatggctac gtagataagt agcatggcgg   3780
gttaatcatt aactacaagg aacccctagt gatggagttg gccactccct ctctgcgcgc   3840
tcgctcgctc actgaggccg ggcgaccaaa ggtcgcccga cgcccgggct ttgcccgggc   3900
ggcctcagtg agcgagcgag cgcgcagcct taattaacct aattcactgg ccgtcgtttt   3960
acaacgtcgt gactgggaaa accctggcgt tacccaactt aatcgccttg cagcacatcc   4020
ccctttcgcc agctggcgta atagcgaaga ggcccgcacc gatcgccctt cccaacagtt   4080
gcgcagcctg aatggcgaat gggacgcgcc ctgtagcggc gcattaagcg cggcgggtgt   4140
ggtggttacg cgcagcgtga ccgctacact tgccagcgcc ctagcgcccg ctcctttcgc   4200
tttcttccct tcctttctcg ccacgttcgc cggctttccc cgtcaagctc taaatcgggg   4260
gctcccttta gggttccgat ttagtgcttt acggcacctc gaccccaaaa aacttgatta   4320
gggtgatggt tcacgtagtg ggccatcgcc ctgatagacg gtttttcgcc ctttgacgtt   4380
ggagtccacg ttctttaata gtggactctt gttccaaact ggaacaacac tcaaccctat   4440
ctcggtctat tcttttgatt tataagggat tttgccgatt tcggcctatt ggttaaaaaa   4500
tgagctgatt taacaaaaat ttaacgcgaa ttttaacaaa atattaacgc ttacaattta   4560
ggtggcactt ttcggggaaa tgtgcgcgga acccctattt gtttattttt ctaaatacat   4620
tcaaatatgt atccgctcat gagacaataa ccctgataaa tgcttcaata atattgaaaa   4680
aggaagagta tgagtattca acatttccgt gtcgccctta ttcccttttt tgcggcattt   4740
tgccttcctg tttttgctca cccagaaacg ctggtgaaag taaaagatgc tgaagatcag   4800
ttgggtgcac gagtgggtta catcgaactg gatctcaaca gcggtaagat ccttgagagt   4860
tttcgccccg aagaacgttt tccaatgatg agcactttta aagttctgct atgtggcgcg   4920
gtattatccc gtattgacgc cgggcaagag caactcggtc gccgcataca ctattctcag   4980
aatgacttgg ttgagtactc accagtcaca gaaaagcatc ttacggatgg catgacagta   5040
```

-continued

```
agagaattat gcagtgctgc cataaccatg agtgataaca ctgcggccaa cttacttctg   5100

acaacgatcg gaggaccgaa ggagctaacc gcttttttgc acaacatggg ggatcatgta   5160

actcgccttg atcgttggga accggagctg aatgaagcca taccaaacga cgagcgtgac   5220

accacgatgc ctgtagcaat ggcaacaacg ttgcgcaaac tattaactgg cgaactactt   5280

actctagctt cccggcaaca attaatagac tggatggagg cggataaagt tgcaggacca   5340

cttctgcgct cggcccttcc ggctggctgg tttattgctg ataaatctgg agccggtgag   5400

cgtgggtctc gcggtatcat tgcagcactg gggccagatg gtaagccctc ccgtatcgta   5460

gttatctaca cgacggggag tcaggcaact atggatgaac gaaatagaca gatcgctgag   5520

ataggtgcct cactgattaa gcattggtaa ctgtcagacc aagtttactc atatatactt   5580

tagattgatt taaaacttca tttttaattt aaaaggatct aggtgaagat cctttttgat   5640

aatctcatga ccaaaatccc ttaacgtgag ttttcgttcc actgagcgtc agaccccgta   5700

gaaaagatca aaggatcttc ttgagatcct ttttttctgc gcgtaatctg ctgcttgcaa   5760

acaaaaaaac caccgctacc agcggtggtt tgtttgccgg atcaagagct accaactctt   5820

tttccgaagg taactggctt cagcagagcg cagataccaa atactgttct tctagtgtag   5880

ccgtagttag gccaccactt caagaactct gtagcaccgc ctacatacct cgctctgcta   5940

atcctgttac cagtggctgc tgccagtggc gataagtcgt gtcttaccgg gttggactca   6000

agacgatagt taccggataa ggcgcagcgg tcgggctgaa cggggggttc gtgcacacag   6060

cccagcttgg agcgaacgac ctacaccgaa ctgagatacc tacagcgtga gctatgagaa   6120

agcgccacgc ttcccgaagg gagaaaggcg gacaggtatc cggtaagcgg cagggtcgga   6180

acaggagagc gcacgaggga gcttccaggg ggaaacgcct ggtatcttta tagtcctgtc   6240

gggtttcgcc acctctgact tgagcgtcga tttttgtgat gctcgtcagg ggggcggagc   6300

ctatggaaaa acgccagcaa cgcggccttt ttacggttcc tggccttttg ctggcctttt   6360

gctcacatgt tctttcctgc gttatcccct gattctgtgg ataaccgtat taccgccttt   6420

gagtgagctg ataccgctcg ccgcagccga acgaccgagc gcagcgagtc agtgagcgag   6480

gaagcggaag agcgcccaat acgcaaaccg cctctccccg cgcgttggcc gattcattaa   6540

tgcagctggc acgacaggtt tcccgactgg aaagcgggca gtgagcgcaa cgcaattaat   6600

gtgagttagc tcactcatta ggcaccccag gctttacact ttatgcttcc ggctcgtatg   6660

ttgtgtggaa ttgtgagcgg ataacaattt cacacaggaa acagctatga ccatgattac   6720

gccagattta attaaggcct taattagg                                       6748
```

<210> SEQ ID NO 24
<211> LENGTH: 6748
<212> TYPE: DNA
<213> ORGANISM: Artificial Sequence
<220> FEATURE:
<223> OTHER INFORMATION: Synthetic sequence
<220> FEATURE:
<221> NAME/KEY: repeat_region
<222> LOCATION: (1)..(130)
<223> OTHER INFORMATION: 5' ITR
<220> FEATURE:
<221> NAME/KEY: promoter
<222> LOCATION: (191)..(932)
<223> OTHER INFORMATION: human\CMV\I.E.\enhancer\&\promoter
<220> FEATURE:
<221> NAME/KEY: misc_feature
<222> LOCATION: (897)..(901)
<223> OTHER INFORMATION: TATA\box
<220> FEATURE:
<221> NAME/KEY: Intron
<222> LOCATION: (1047)..(1179)
<223> OTHER INFORMATION: Promega\chimeric\intron
<220> FEATURE:
<221> NAME/KEY: misc_feature
<222> LOCATION: (1248)..(1293)
<223> OTHER INFORMATION: c-myc\miniIRES\cloned\into\Nhe\site
<220> FEATURE:
<221> NAME/KEY: misc_feature
<222> LOCATION: (1294)..(3493)
<223> OTHER INFORMATION: AnnaT_TestRef\35
<220> FEATURE:
<221> NAME/KEY: misc_feature
<222> LOCATION: (1294)..(3493)
<223> OTHER INFORMATION: 3bnc\ORF\35
<220> FEATURE:
<221> NAME/KEY: polyA_signal
<222> LOCATION: (3502)..(3733)
<223> OTHER INFORMATION: SV40\late\polyadenylation\signal
<220> FEATURE:
<221> NAME/KEY: repeat_region
<222> LOCATION: (3798)..(3927)
<223> OTHER INFORMATION: complement - 3' ITR
<220> FEATURE:
<221> NAME/KEY: rep_origin
<222> LOCATION: (4104)..(4559)
<223> OTHER INFORMATION: complement - F1\ori
<220> FEATURE:
<221> NAME/KEY: misc_feature
<222> LOCATION: (4690)..(5547)
<223> OTHER INFORMATION: Amp-R coding sequence
<220> FEATURE:
<221> NAME/KEY: misc_feature
<222> LOCATION: (5721)..(6309)
<223> OTHER INFORMATION: COL\E1\Origin

<400> SEQUENCE: 24
ctgcgcgctc gctcgctcac tgaggccgcc cgggcaaagc ccgggcgtcg ggcgaccttt 60
ggtcgcccgg cctcagtgag cgagcgagcg cgcagagagg gagtggccaa ctccatcact 120
aggggttcct tgtagttaat gattaacccg ccatgctact tatctacgta gccatgctct 180
aggaagatct tcaatattgg ccattagcca tattattcat tggttatata gcataaatca 240
atattggcta ttggccattg catacgttgt atctatatca taatatgtac atttatattg 300
gctcatgtcc aatatgaccg ccatgttggc attgattatt gactagttat taatagtaat 360
caattacggg gtcattagtt catagcccat atatggagtt ccgcgttaca taacttacgg 420
taaatggccc gcctggctga ccgcccaacg acccccgccc attgacgtca ataatgacgt 480
atgttcccat agtaacgcca atagggactt tccattgacg tcaatgggtg gagtatttac 540
ggtaaactgc ccacttggca gtacatcaag tgtatcatat gccaagtccg ccccctattg 600
acgtcaatga cggtaaatgg cccgcctggc attatgccca gtacatgacc ttacgggact 660
ttcctacttg gcagtacatc tacgtattag tcatcgctat taccatggtg atgcggtttt 720
ggcagtacac caatgggcgt ggatagcggt ttgactcacg gggatttcca agtctccacc 780
ccattgacgt caatgggagt ttgttttggc accaaaatca acgggacttt ccaaaatgtc 840
gtaataaccc cgccccgttg acgcaaatgg gcggtaggcg tgtacggtgg gaggtctata 900
taagcagagc tcgtttagtg aaccgtcaga tcactagaag ctttattgcg gtagtttatc 960
acagttaaat tgctaacgca gtcagtgctt ctgacacaac agtctcgaac ttaagctgca 1020
gaagttggtc gtgaggcact gggcaggtaa gtatcaaggt tacaagacag gtttaaggag 1080
accaatagaa actgggcttg tcgagacaga gaagactctt gcgtttctga taggcaccta 1140
ttggtcttac tgacatccac tttgcctttc tctccacagg tgtccactcc cagttcaatt 1200
acagctctta aggctagagt acttaatacg actcactata ggctagcggg gactttgcac 1260

-continued

```
tggaacttac aacacccgag caaggacgcg actctagctc tagaaccatg tataggatgc   1320
aactgttgtc gtgcattgct ctgagcctcg ccttagtgac caatagccaa gtacaactcc   1380
tccagtctgg agcagctgtt accaagccag gcgcttcggt tagggtttca tgcgaagcaa   1440
gtggctataa catccgggac tatttcatcc attggtggag acaagccccc ggacaagggc   1500
tgcaatgggt cggctggatt aacccaaaga ccggccaacc caacaacccc cggcagtttc   1560
aagggagggt gagcctgacc cgccatgcaa gctgggactt cgacactttt tccttctaca   1620
tggatctgaa agctctgagg tccgacgaca ccgccgtgta cttctgtgct cggcagagga   1680
gcgactattg ggactttgac gtttggggct ctggcaccca agttacagtt tcctcggctt   1740
ccacaaaggg cccctcggta tttcccttgg ccccctcgtc taagtccacc agcggaggaa   1800
ctgctgcttt aggctgcctt gttaaggact acttccccga gcccgtgact gtctcgtgga   1860
actcaggcgc gctcactagc ggggttcata cctttcccgc tgtgttgcag agcagtggct   1920
tgtatagcct gtctagcgtc gtgaccgttc ccagcagcag cctcgggacc cagacgtaca   1980
tttgtaacgt taatcataag ccttcaaaca ccaaagtcga taagaaggtg gaacccaaga   2040
gttgtgacaa aacccacacc tgcccgccct gtcccgcacc cgagctgtta ggtggtcctt   2100
ctgtctttct gtttcctccc aagccaaagg acacccttat gatatcgagg acccctgaag   2160
taacctgcgt cgtagttgac gtttcccacg aagatcccga ggtcaagttc aactggtatg   2220
tcgacggggt tgaagtgcac aacgcaaaaa caaagcctcg tgaggaacaa tacaactcaa   2280
cgtatagggt tgtctccgtt cttaccgttc tgcaccaaga ctggttgaac gggaaggagt   2340
acaaatgcaa agtatcgaac aaagccctgc ccgcacccat tgagaaaacc atttcgaagg   2400
ccaaaggcca accccgggaa ccccaagtgt ataccctccc accttccaga gatgaactga   2460
ccaagaatca ggtgtcgctg acctgcctgg tgaagggctt ctacccctct gatattgccg   2520
tggaatggga aagcaatggc caacccgaaa acaattacaa gaccactccc ccggttttag   2580
actcagacgg ctcattcttt ctgtattcaa agttgactgt tgacaagtcc agatggcagc   2640
aagggaacgt tttctcctgt agtgttatgc atgaagccct gcataatcat tacacccaga   2700
agtcgttgag cctatctccc ggtaggaaaa ggcgggctcc tgtgaagcaa actctgaact   2760
ttgacttgct gaagctcgcc ggtgacgtag aatcaaaccc tggacccatg tacagaatgc   2820
agctgttgtc ctgtattgca ctgagtctgg ctctcgtgac caattcagac atccagatga   2880
cccaatcacc ctccagcctt tccgcctcgg ttggagacac cgtaacaatt acttgtcagg   2940
ctaacggtta ccttaactgg tatcagcagc gccgagggaa agctcccaag ctactcatat   3000
acgacggctc taagctggaa cgcggcgttc cttcacggtt tagtggccgg aggtggggcc   3060
aggaatacaa cctgaccatt aacaacctgc agcccgaaga tattgccacc tatttctgtc   3120
aggtgtatga atttgttgtt cccgggaccc gactggactt gaagcggacc gttgcggcac   3180
ccagcgtctt tatctttccc ccatcggatg aacaactgaa atccggcacc gcctcagttg   3240
tttgcctgct gaacaacttc tatccgcggg aagcgaaggt ccagtggaaa gttgacaacg   3300
ccctgcagtc aggtaactcg caagaatctg tcaccgaaca ggacagcaag gactcgacct   3360
atagtctcag ctccacccta acgctgtcca aagccgatta tgagaagcac aaagtctatg   3420
cttgtgaggt tacgcaccaa gggctaagca gtcccgttac aaagtccttt aaccggggag   3480
agtgttaatg agcggccgct tcgagcagac atgataagat acattgatga gtttggacaa   3540
accacaacta gaatgcagtg aaaaaaatgc tttatttgtg aaatttgtga tgctattgct   3600
ttatttgtaa ccattataag ctgcaataaa caagttaaca acaacaattg cattcatttt   3660
```

-continued

```
atgtttcagg ttcaggggga gatgtgggag gttttttaaa gcaagtaaaa cctctacaaa   3720
tgtggtaaaa tcgataagga tcttcctaga gcatggctac gtagataagt agcatggcgg   3780
gttaatcatt aactacaagg aacccctagt gatggagttg gccactccct ctctgcgcgc   3840
tcgctcgctc actgaggccg ggcgaccaaa ggtcgcccga cgcccgggct ttgcccgggc   3900
ggcctcagtg agcgagcgag cgcgcagcct taattaacct aattcactgg ccgtcgtttt   3960
acaacgtcgt gactgggaaa accctggcgt tacccaactt aatcgccttg cagcacatcc   4020
ccctttcgcc agctggcgta atagcgaaga ggcccgcacc gatcgccctt cccaacagtt   4080
gcgcagcctg aatggcgaat gggacgcgcc ctgtagcggc gcattaagcg cggcgggtgt   4140
ggtggttacg cgcagcgtga ccgctacact tgccagcgcc ctagcgcccg ctcctttcgc   4200
tttcttccct tcctttctcg ccacgttcgc cggctttccc cgtcaagctc taaatcgggg   4260
gctcccttta gggttccgat ttagtgcttt acggcacctc gaccccaaaa aacttgatta   4320
gggtgatggt tcacgtagtg ggccatcgcc ctgatagacg gtttttcgcc ctttgacgtt   4380
ggagtccacg ttctttaata gtggactctt gttccaaact ggaacaacac tcaaccctat   4440
ctcggtctat tcttttgatt tataagggat tttgccgatt tcggcctatt ggttaaaaaa   4500
tgagctgatt taacaaaaat ttaacgcgaa ttttaacaaa atattaacgc ttacaattta   4560
ggtggcactt ttcggggaaa tgtgcgcgga acccctattt gtttattttt ctaaatacat   4620
tcaaatatgt atccgctcat gagacaataa ccctgataaa tgcttcaata atattgaaaa   4680
aggaagagta tgagtattca acatttccgt gtcgccctta ttcccttttt tgcggcattt   4740
tgccttcctg tttttgctca cccagaaacg ctggtgaaag taaaagatgc tgaagatcag   4800
ttgggtgcac gagtgggtta catcgaactg gatctcaaca gcggtaagat ccttgagagt   4860
tttcgccccg aagaacgttt tccaatgatg agcactttta aagttctgct atgtggcgcg   4920
gtattatccc gtattgacgc cgggcaagag caactcggtc gccgcataca ctattctcag   4980
aatgacttgg ttgagtactc accagtcaca gaaaagcatc ttacggatgg catgacagta   5040
agagaattat gcagtgctgc cataaccatg agtgataaca ctgcggccaa cttacttctg   5100
acaacgatcg gaggaccgaa ggagctaacc gcttttttgc acaacatggg ggatcatgta   5160
actcgccttg atcgttggga accggagctg aatgaagcca taccaaacga cgagcgtgac   5220
accacgatgc ctgtagcaat ggcaacaacg ttgcgcaaac tattaactgg cgaactactt   5280
actctagctt cccggcaaca attaatagac tggatggagg cggataaagt tgcaggacca   5340
cttctgcgct cggcccttcc ggctggctgg tttattgctg ataaatctgg agccggtgag   5400
cgtgggtctc gcggtatcat tgcagcactg gggccagatg gtaagccctc ccgtatcgta   5460
gttatctaca cgacggggag tcaggcaact atggatgaac gaaatagaca gatcgctgag   5520
ataggtgcct cactgattaa gcattggtaa ctgtcagacc aagtttactc atatatactt   5580
tagattgatt taaaacttca tttttaattt aaaaggatct aggtgaagat cctttttgat   5640
aatctcatga ccaaaatccc ttaacgtgag ttttcgttcc actgagcgtc agaccccgta   5700
gaaaagatca aaggatcttc ttgagatcct ttttttctgc gcgtaatctg ctgcttgcaa   5760
acaaaaaaac caccgctacc agcggtggtt tgtttgccgg atcaagagct accaactctt   5820
tttccgaagg taactggctt cagcagagcg cagataccaa atactgttct tctagtgtag   5880
ccgtagttag gccaccactt caagaactct gtagcaccgc ctacatacct cgctctgcta   5940
atcctgttac cagtggctgc tgccagtggc gataagtcgt gtcttaccgg gttggactca   6000
```

```
agacgatagt taccggataa ggcgcagcgg tcgggctgaa cggggggttc gtgcacacag   6060

cccagcttgg agcgaacgac ctacaccgaa ctgagatacc tacagcgtga gctatgagaa   6120

agcgccacgc ttcccgaagg gagaaaggcg gacaggtatc cggtaagcgg cagggtcgga   6180

acaggagagc gcacgaggga gcttccaggg ggaaacgcct ggtatcttta tagtcctgtc   6240

gggtttcgcc acctctgact tgagcgtcga tttttgtgat gctcgtcagg ggggcggagc   6300

ctatggaaaa acgccagcaa cgcggccttt ttacggttcc tggccttttg ctggcctttt   6360

gctcacatgt tctttcctgc gttatcccct gattctgtgg ataaccgtat taccgccttt   6420

gagtgagctg ataccgctcg ccgcagccga acgaccgagc gcagcgagtc agtgagcgag   6480

gaagcggaag agcgcccaat acgcaaaccg cctctccccg cgcgttggcc gattcattaa   6540

tgcagctggc acgacaggtt tcccgactgg aaagcgggca gtgagcgcaa cgcaattaat   6600

gtgagttagc tcactcatta ggcaccccag gctttacact ttatgcttcc ggctcgtatg   6660

ttgtgtggaa ttgtgagcgg ataacaattt cacacaggaa acagctatga ccatgattac   6720

gccagattta attaaggcct taattagg                                      6748
```

```
<210> SEQ ID NO 25
<211> LENGTH: 6748
<212> TYPE: DNA
<213> ORGANISM: Artificial Sequence
<220> FEATURE:
<223> OTHER INFORMATION: Synthetic sequence
<220> FEATURE:
<221> NAME/KEY: repeat_region
<222> LOCATION: (1)..(130)
<223> OTHER INFORMATION: 5' ITR
<220> FEATURE:
<221> NAME/KEY: promoter
<222> LOCATION: (191)..(932)
<223> OTHER INFORMATION: human\CMV\I.E.\enhancer\&\promoter
<220> FEATURE:
<221> NAME/KEY: misc_feature
<222> LOCATION: (897)..(901)
<223> OTHER INFORMATION: TATA\box
<220> FEATURE:
<221> NAME/KEY: Intron
<222> LOCATION: (1047)..(1179)
<223> OTHER INFORMATION: Promega\chimeric\intron
<220> FEATURE:
<221> NAME/KEY: misc_feature
<222> LOCATION: (1248)..(1293)
<223> OTHER INFORMATION: c-myc\miniIRES\cloned\into\Nhe\site
<220> FEATURE:
<221> NAME/KEY: misc_feature
<222> LOCATION: (1294)..(3493)
<223> OTHER INFORMATION: AnnaT_TestRef\39
<220> FEATURE:
<221> NAME/KEY: misc_feature
<222> LOCATION: (1294)..(3493)
<223> OTHER INFORMATION: 3bnc\ORF\39
<220> FEATURE:
<221> NAME/KEY: polyA_signal
<222> LOCATION: (3502)..(3733)
<223> OTHER INFORMATION: SV40\late\polyadenylation\signal
<220> FEATURE:
<221> NAME/KEY: repeat_region
<222> LOCATION: (3798)..(3927)
<223> OTHER INFORMATION: complement - 3' ITR
<220> FEATURE:
<221> NAME/KEY: rep_origin
<222> LOCATION: (4104)..(4559)
<223> OTHER INFORMATION: complement - f1\ori
<220> FEATURE:
<221> NAME/KEY: misc_feature
<222> LOCATION: (4690)..(5547)
<223> OTHER INFORMATION: Amp-R coding sequence
<220> FEATURE:
<221> NAME/KEY: misc_feature
```

<222> LOCATION: (5721)..(6309)
<223> OTHER INFORMATION: COL\E1\Origin

<400> SEQUENCE: 25
ctgcgcgctc gctcgctcac tgaggccgcc cgggcaaagc ccgggcgtcg ggcgaccttt 60
ggtcgcccgg cctcagtgag cgagcgagcg cgcagagagg gagtggccaa ctccatcact 120
aggggttcct tgtagttaat gattaacccg ccatgctact tatctacgta gccatgctct 180
aggaagatct tcaatattgg ccattagcca tattattcat tggttatata gcataaatca 240
atattggcta ttggccattg catacgttgt atctatatca taatatgtac atttatattg 300
gctcatgtcc aatatgaccg ccatgttggc attgattatt gactagttat taatagtaat 360
caattacggg gtcattagtt catagcccat atatggagtt ccgcgttaca taacttacgg 420
taaatggccc gcctggctga ccgcccaacg acccccgccc attgacgtca ataatgacgt 480
atgttcccat agtaacgcca atagggactt tccattgacg tcaatgggtg gagtatttac 540
ggtaaactgc ccacttggca gtacatcaag tgtatcatat gccaagtccg ccccctattg 600
acgtcaatga cggtaaatgg cccgcctggc attatgccca gtacatgacc ttacgggact 660
ttcctacttg gcagtacatc tacgtattag tcatcgctat taccatggtg atgcggtttt 720
ggcagtacac caatgggcgt ggatagcggt ttgactcacg gggatttcca agtctccacc 780
ccattgacgt caatgggagt ttgttttggc accaaaatca acgggacttt ccaaaatgtc 840
gtaataaccc cgccccgttg acgcaaatgg gcggtaggcg tgtacggtgg gaggtctata 900
taagcagagc tcgtttagtg aaccgtcaga tcactagaag ctttattgcg gtagtttatc 960
acagttaaat tgctaacgca gtcagtgctt ctgacacaac agtctcgaac ttaagctgca 1020
gaagttggtc gtgaggcact gggcaggtaa gtatcaaggt tacaagacag gtttaaggag 1080
accaatagaa actgggcttg tcgagacaga gaagactctt gcgtttctga taggcaccta 1140
ttggtcttac tgacatccac tttgcctttc tctccacagg tgtccactcc cagttcaatt 1200
acagctctta aggctagagt acttaatacg actcactata ggctagcggg gactttgcac 1260
tggaacttac aacacccgag caaggacgcg actctagctc tagaaccatg tataggatgc 1320
agttactctc atgcattgct ctctcactgg cacttgtaac caattctcaa gtgcagcttc 1380
tccagtctgg cgctgccgtc accaagccag gagccagcgt tcgagtttca tgcgaagctt 1440
ctgggtacaa tatcagagat tacttcattc actggtggcg ccaggctccc gggcaggggc 1500
tccagtgggt gggatggatt aaccccaaga cgggacagcc caacaatccc aggcagttcc 1560
aggggcgtgt tagcctgaca agacatgcct catgggactt tgatacattc agtttctata 1620
tggacttgaa agctctgaga agtgatgata ccgctgttta cttttgcgct cggcagcgat 1680
cagactattg ggatttcgat gtgtggggat caggcaccca agtgacggtg tcaagcgctt 1740
caacaaaagg accctcagtg ttccctctcg ccccttcatc taaatcaaca agcggtggca 1800
ccgctgcctt gggatgtctc gttaaggact actttcccga gcccgtcaca gtgagttgga 1860
attctggcgc tcttactagc ggggtgcata ctttccccgc tgtactgcag tccagcggcc 1920
tgtattcatt gtcatcagtg gttacagtac cctcatcgag tctgggcacg cagacctaca 1980
tctgcaacgt caaccataaa ccctctaaca ccaaagtcga taagaaagta gaacccaaat 2040
cttgcgacaa aacacataca tgcccaccat gtcccgctcc agagttgttg ggtggaccct 2100
ccgtgtttct gttccctccc aaacccaaag atacactcat gatttcgcgg acccccgagg 2160
tgacttgcgt cgtcgtggat gtgtcccacg aggaccccga ggtcaaattc aactggtatg 2220

-continued

```
ttgatggagt ggaggttcat aacgccaaga ccaaacccag agaggagcag tacaacagta   2280

cgtacagagt tgtgtctgtt ctcactgttc tacaccagga ctggcttaac ggaaaggagt   2340

ataagtgtaa agtgtccaac aaggcactcc ctgctcccat tgaaaagaca atctcaaaag   2400

ctaagggcca gcccagagaa ccgcaagtgt acacgctacc gcctagtcga gatgagctga   2460

ccaagaacca ggtgtccttg acttgcctcg ttaaagggtt ctatccctcg gatatagctg   2520

tcgagtggga gtcaaatggg caacccgaga ataactacaa gaccacaccc cctgtgctgg   2580

attcagacgg tagcttcttt ctatactcca aactgacggt tgacaaatcc cgttggcagc   2640

aggggaacgt tttctcatgc tcagttatgc atgaagcact gcataaccac tatacgcaga   2700

aatcattatc acttagtccc ggacggaaaa ggcgcgctcc cgtgaaacag accctcaact   2760

ttgacttact gaagctcgcc ggagacgtcg agtcaaatcc tggtccgatg tatagaatgc   2820

agctgctttc ttgcattgca ttgagtctcg ccctggtcac caacagtgat atccagatga   2880

cccagagtcc ttcatctctc tcagcttcag tgggagacac ggtcacgata acctgccagg   2940

ctaacggcta tctcaattgg taccagcagc gcaggggtaa agctcccaaa ctgctgatct   3000

atgatggttc aaaactggag cgcggcgtac cctcacggtt ttccggacga cgatggggcc   3060

aggagtacaa tctgactatc aacaacctgc agcccgagga catagcgacg tatttctgcc   3120

aggtatatga gtttgtcgtc cctgggaccc ggctggacct gaaaaggacg gtcgctgcac   3180

cctcagtatt catattccca ccctccgatg agcagttgaa aagcggaaca gcgtcagtcg   3240

tgtgcctcct caataacttc tacccccggg aagccaaagt tcagtggaaa gttgacaatg   3300

cacttcagtc tggaaatagt caggagagcg tgactgagca ggattcaaaa gattctacgt   3360

attccctgag ctcaacgctc acactgtcta aagctgatta tgagaaacat aaggtttatg   3420

cctgcgaggt aacgcatcag ggtctatcat cgcccgtcac gaaaagcttt aacagagggg   3480

agtgttaatg agcggccgct tcgagcagac atgataagat acattgatga gtttggacaa   3540

accacaacta gaatgcagtg aaaaaaatgc tttatttgtg aaatttgtga tgctattgct   3600

ttatttgtaa ccattataag ctgcaataaa caagttaaca acaacaattg cattcatttt   3660

atgtttcagg ttcaggggga gatgtgggag gtttttttaaa gcaagtaaaa cctctacaaa   3720

tgtggtaaaa tcgataagga tcttcctaga gcatggctac gtagataagt agcatggcgg   3780

gttaatcatt aactacaagg aacccctagt gatggagttg gccactccct ctctgcgcgc   3840

tcgctcgctc actgaggccg ggcgaccaaa ggtcgcccga cgcccgggct ttgcccgggc   3900

ggcctcagtg agcgagcgag cgcgcagcct taattaacct aattcactgg ccgtcgtttt   3960

acaacgtcgt gactgggaaa accctggcgt tacccaactt aatcgccttg cagcacatcc   4020

ccctttcgcc agctggcgta atagcgaaga ggcccgcacc gatcgccctt cccaacagtt   4080

gcgcagcctg aatggcgaat gggacgcgcc ctgtagcggc gcattaagcg cggcgggtgt   4140

ggtggttacg cgcagcgtga ccgctacact tgccagcgcc ctagcgcccg ctcctttcgc   4200

tttcttccct tcctttctcg ccacgttcgc cggctttccc cgtcaagctc taaatcgggg   4260

gctcccttta gggttccgat ttagtgcttt acggcacctc gaccccaaaa aacttgatta   4320

gggtgatggt tcacgtagtg ggccatcgcc ctgatagacg gtttttcgcc ctttgacgtt   4380

ggagtccacg ttctttaata gtggactctt gttccaaact ggaacaacac tcaaccctat   4440

ctcggtctat tcttttgatt tataagggat tttgccgatt tcggcctatt ggttaaaaaa   4500

tgagctgatt taacaaaaat ttaacgcgaa ttttaacaaa atattaacgc ttacaattta   4560

ggtggcactt ttcggggaaa tgtgcgcgga acccctattt gtttattttt ctaaatacat   4620
```

tcaaatatgt atccgctcat gagacaataa ccctgataaa tgcttcaata atattgaaaa 4680
aggaagagta tgagtattca acatttccgt gtcgccctta ttcccttttt tgcggcattt 4740
tgccttcctg tttttgctca cccagaaacg ctggtgaaag taaaagatgc tgaagatcag 4800
ttgggtgcac gagtgggtta catcgaactg gatctcaaca gcggtaagat ccttgagagt 4860
tttcgccccg aagaacgttt tccaatgatg agcactttta aagttctgct atgtggcgcg 4920
gtattatccc gtattgacgc cgggcaagag caactcggtc gccgcataca ctattctcag 4980
aatgacttgg ttgagtactc accagtcaca gaaaagcatc ttacggatgg catgacagta 5040
agagaattat gcagtgctgc cataaccatg agtgataaca ctgcggccaa cttacttctg 5100
acaacgatcg gaggaccgaa ggagctaacc gcttttttgc acaacatggg ggatcatgta 5160
actcgccttg atcgttggga accggagctg aatgaagcca taccaaacga cgagcgtgac 5220
accacgatgc ctgtagcaat ggcaacaacg ttgcgcaaac tattaactgg cgaactactt 5280
actctagctt cccggcaaca attaatagac tggatggagg cggataaagt tgcaggacca 5340
cttctgcgct cggcccttcc ggctggctgg tttattgctg ataaatctgg agccggtgag 5400
cgtgggtctc gcggtatcat tgcagcactg gggccagatg gtaagccctc ccgtatcgta 5460
gttatctaca cgacggggag tcaggcaact atggatgaac gaaatagaca gatcgctgag 5520
ataggtgcct cactgattaa gcattggtaa ctgtcagacc aagtttactc atatatactt 5580
tagattgatt taaaacttca tttttaattt aaaaggatct aggtgaagat cctttttgat 5640
aatctcatga ccaaaatccc ttaacgtgag ttttcgttcc actgagcgtc agaccccgta 5700
gaaaagatca aaggatcttc ttgagatcct ttttttctgc gcgtaatctg ctgcttgcaa 5760
acaaaaaaac caccgctacc agcggtggtt tgtttgccgg atcaagagct accaactctt 5820
tttccgaagg taactggctt cagcagagcg cagataccaa atactgttct tctagtgtag 5880
ccgtagttag gccaccactt caagaactct gtagcaccgc ctacatacct cgctctgcta 5940
atcctgttac cagtggctgc tgccagtggc gataagtcgt gtcttaccgg gttggactca 6000
agacgatagt taccggataa ggcgcagcgg tcgggctgaa cggggggttc gtgcacacag 6060
cccagcttgg agcgaacgac ctacaccgaa ctgagatacc tacagcgtga gctatgagaa 6120
agcgccacgc ttcccgaagg gagaaaggcg gacaggtatc cggtaagcgg cagggtcgga 6180
acaggagagc gcacgaggga gcttccaggg ggaaacgcct ggtatcttta tagtcctgtc 6240
gggtttcgcc acctctgact tgagcgtcga tttttgtgat gctcgtcagg ggggcggagc 6300
ctatggaaaa acgccagcaa cgcggccttt ttacggttcc tggccttttg ctggcctttt 6360
gctcacatgt tctttcctgc gttatcccct gattctgtgg ataaccgtat taccgccttt 6420
gagtgagctg ataccgctcg ccgcagccga acgaccgagc gcagcgagtc agtgagcgag 6480
gaagcggaag agcgcccaat acgcaaaccg cctctccccg cgcgttggcc gattcattaa 6540
tgcagctggc acgacaggtt tcccgactgg aaagcgggca gtgagcgcaa cgcaattaat 6600
gtgagttagc tcactcatta ggcaccccag gctttacact ttatgcttcc ggctcgtatg 6660
ttgtgtggaa ttgtgagcgg ataacaattt cacacaggaa acagctatga ccatgattac 6720
gccagattta attaaggcct taattagg 6748

<210> SEQ ID NO 26
<211> LENGTH: 6748
<212> TYPE: DNA
<213> ORGANISM: Artificial Sequence
<220> FEATURE:

<223> OTHER INFORMATION: Synthetic sequence
<220> FEATURE:
<221> NAME/KEY: repeat_region
<222> LOCATION: (1)..(130)
<223> OTHER INFORMATION: 5' ITR
<220> FEATURE:
<221> NAME/KEY: promoter
<222> LOCATION: (191)..(932)
<223> OTHER INFORMATION: human\CMV\I.E.\enhancer\&\promoter
<220> FEATURE:
<221> NAME/KEY: misc_feature
<222> LOCATION: (897)..(901)
<223> OTHER INFORMATION: TATA\box
<220> FEATURE:
<221> NAME/KEY: Intron
<222> LOCATION: (1047)..(1179)
<223> OTHER INFORMATION: Promega\chimeric\intron
<220> FEATURE:
<221> NAME/KEY: misc_feature
<222> LOCATION: (1248)..(1293)
<223> OTHER INFORMATION: c-myc\miniIRES\cloned\into\Nhe\site
<220> FEATURE:
<221> NAME/KEY: misc_feature
<222> LOCATION: (1294)..(3493)
<223> OTHER INFORMATION: AnnaT_TestRef\40
<220> FEATURE:
<221> NAME/KEY: misc_feature
<222> LOCATION: (1294)..(3493)
<223> OTHER INFORMATION: 3bnc\ORF\40
<220> FEATURE:
<221> NAME/KEY: polyA_signal
<222> LOCATION: (3502)..(3733)
<223> OTHER INFORMATION: SV40\late\polyadenylation\signal
<220> FEATURE:
<221> NAME/KEY: repeat_region
<222> LOCATION: (3798)..(3927)
<223> OTHER INFORMATION: complement - 3' ITR
<220> FEATURE:
<221> NAME/KEY: rep_origin
<222> LOCATION: (4104)..(4559)
<223> OTHER INFORMATION: complement - f1\ori
<220> FEATURE:
<221> NAME/KEY: misc_feature
<222> LOCATION: (4690)..(5547)
<223> OTHER INFORMATION: Amp-R coding sequence
<220> FEATURE:
<221> NAME/KEY: misc_feature
<222> LOCATION: (5721)..(6309)
<223> OTHER INFORMATION: COL\E1\Origin

<400> SEQUENCE: 26
ctgcgcgctc gctcgctcac tgaggccgcc cgggcaaagc ccgggcgtcg ggcgaccttt 60
ggtcgcccgg cctcagtgag cgagcgagcg cgcagagagg gagtggccaa ctccatcact 120
aggggttcct tgtagttaat gattaacccg ccatgctact tatctacgta gccatgctct 180
aggaagatct tcaatattgg ccattagcca tattattcat tggttatata gcataaatca 240
atattggcta ttggccattg catacgttgt atctatatca taatatgtac atttatattg 300
gctcatgtcc aatatgaccg ccatgttggc attgattatt gactagttat taatagtaat 360
caattacggg gtcattagtt catagcccat atatggagtt ccgcgttaca taacttacgg 420
taaatggccc gcctggctga ccgcccaacg acccccgccc attgacgtca ataatgacgt 480
atgttcccat agtaacgcca atagggactt tccattgacg tcaatgggtg gagtatttac 540
ggtaaactgc ccacttggca gtacatcaag tgtatcatat gccaagtccg ccccctattg 600
acgtcaatga cggtaaatgg cccgcctggc attatgccca gtacatgacc ttacgggact 660
ttcctacttg gcagtacatc tacgtattag tcatcgctat taccatggtg atgcggtttt 720
ggcagtacac caatgggcgt ggatagcggt ttgactcacg gggatttcca agtctccacc 780
ccattgacgt caatgggagt ttgttttggc accaaaatca acgggacttt ccaaaatgtc 840

-continued

```
gtaataaccc cgccccgttg acgcaaatgg gcggtaggcg tgtacggtgg gaggtctata    900
taagcagagc tcgtttagtg aaccgtcaga tcactagaag ctttattgcg gtagtttatc    960
acagttaaat tgctaacgca gtcagtgctt ctgacacaac agtctcgaac ttaagctgca   1020
gaagttggtc gtgaggcact gggcaggtaa gtatcaaggt tacaagacag gtttaaggag   1080
accaatagaa actgggcttg tcgagacaga gaagactctt gcgtttctga taggcaccta   1140
ttggtcttac tgacatccac tttgcctttc tctccacagg tgtccactcc cagttcaatt   1200
acagctctta aggctagagt acttaatacg actcactata ggctagcggg gactttgcac   1260
tggaacttac aacacccgag caaggacgcg actctagctc tagaaccatg taccgtatgc   1320
agcttctctc atgtatagcc ctgagtttag ccctagttac aaatagccag gtgcagctgc   1380
tacagagcgg ggctgcggtc acaaagcctg ggccagcgt tcgcgtgtcc tgtgaggctt    1440
ccgggtacaa tatccgcgat tactttatcc actggtggcg tcaagctccg ggtcaggggt   1500
tacagtgggt cggttggatc aatccaaaaa caggacagcc caacaatcct cgccagtttc   1560
aggggcgtgt cagccttaca cgtcacgcca gttgggattt tgacacattc agcttttaca   1620
tggacctgaa ggccctgcga agcgacgaca cagccgtgta cttttgcgcc agacagcgga   1680
gcgactactg ggactttgat gtgtggggga gcggtacaca agtgacagtc tccagcgcgt   1740
ccaccaaagg acccagcgtg tttcctctgg ccccatcttc caagtcaaca tccggcggaa   1800
ctgcggccct agggtgcctg gtgaaagact actttcctga gcccgtaact gtgagctgga   1860
actccggggc tctgacatcc ggggttcata cattccctgc agtacttcag tcctccggcc   1920
tgtatagctt atctagcgta gtaacagtgc cctcctcttc cttggggaca cagacctaca   1980
tttgcaatgt gaatcataag ccctccaaca caaaggtgga taagaaggtg gagccgaaat   2040
cctgcgacaa aacgcacact tgccctcctt gtccagcccc cgagctgcta gggggaccct   2100
ccgtttttct gtttccacca aaacccaagg acacccttat gatttcacgc acaccggagg   2160
taacctgtgt tgtggtagac gtgtcgcatg aagatccaga ggtcaagttt aactggtatg   2220
ttgatggagt ggaggtccat aacgcaaaga caaaacccag agaggagcag tacaatagta   2280
cttaccgtgt ggtttctgta ctgacagtat tacatcagga ctggttgaac gggaaagagt   2340
acaaatgtaa agttagtaac aaagcccttc ctgcacctat agaaaagacc atatccaaag   2400
ccaaaggcca gcccagagag ccccaagttt acacgctacc gccaagccga gacgagctga   2460
ctaagaatca ggtgtccctg acttgtctag tcaagggctt ttaccccagc gatattgctg   2520
tggagtggga gagcaatggc cagcccgaga ataactacaa aacaacaccc ccggtccttg   2580
actccgatgg gagtttcttt ctgtacagca aattgacagt agacaagagc agatggcagc   2640
aggggaatgt gtttagctgc agcgtgatgc atgaggctct ccataatcat tacacgcaga   2700
aatccctgag cttgtctccc gggcgtaaac gacgcgcacc cgtgaaacag acattgaatt   2760
tcgacttgct gaagttagcc ggggacgtcg agagtaatcc aggccctatg tacagaatgc   2820
agctcctgtc ctgcatagct ctcagcctgg cccttgtgac aaattctgat atacagatga   2880
cgcagtcgcc ctcaagcctc agtgcctccg tgggggatac tgttacaatc acatgtcagg   2940
ccaatggcta tctaaactgg tatcagcagc ggaggggaaa ggcacccaag ttactgatat   3000
acgacggctc caagttggag cgcggggtcc ccagcaggtt ttccggcagg agatgggggc   3060
aggagtacaa cctgaccata aacaatctcc agcctgagga tattgccaca tacttttgcc   3120
aggtatacga gtttgttgtg cctggcacac ggctcgatct gaaaaggacc gtggctgccc   3180
```

```
caagcgtgtt cattttccct cccagcgacg aacagcttaa gtctgggact gcgtccgtcg   3240
tatgtttgct gaacaacttc tatccccgtg aagccaaagt gcagtggaaa gtggacaatg   3300
cactgcagtc cgggaactcc caagagagcg tcacagagca ggactccaaa gactcgacct   3360
actctctaag ctccacactg acactcagca aggctgacta tgagaagcac aaagtttacg   3420
cctgtgaagt gactcatcag ggctcagct cccccgtgac aaaaagcttt aaccggggag    3480
aatgttaatg agcggccgct tcgagcagac atgataagat acattgatga gtttggacaa   3540
accacaacta gaatgcagtg aaaaaaatgc tttatttgtg aaatttgtga tgctattgct   3600
ttatttgtaa ccattataag ctgcaataaa caagttaaca acaacaattg cattcatttt   3660
atgtttcagg ttcaggggga gatgtgggag gtttttaaa gcaagtaaaa cctctacaaa    3720
tgtggtaaaa tcgataagga tcttcctaga gcatggctac gtagataagt agcatggcgg   3780
gttaatcatt aactacaagg aacccctagt gatggagttg gccactccct ctctgcgcgc   3840
tcgctcgctc actgaggccg ggcgaccaaa ggtcgcccga cgcccgggct ttgcccgggc   3900
ggcctcagtg agcgagcgag cgcgcagcct taattaacct aattcactgg ccgtcgtttt   3960
acaacgtcgt gactgggaaa accctggcgt tacccaactt aatcgccttg cagcacatcc   4020
ccctttcgcc agctggcgta atagcgaaga ggcccgcacc gatcgccctt cccaacagtt   4080
gcgcagcctg aatggcgaat gggacgcgcc ctgtagcggc gcattaagcg cggcgggtgt   4140
ggtggttacg cgcagcgtga ccgctacact tgccagcgcc ctagcgcccg ctcctttcgc   4200
tttcttccct tcctttctcg ccacgttcgc cggctttccc cgtcaagctc taaatcgggg   4260
gctcccttta gggttccgat ttagtgcttt acggcacctc gaccccaaaa aacttgatta   4320
gggtgatggt tcacgtagtg ggccatcgcc ctgatagacg gtttttcgcc ctttgacgtt   4380
ggagtccacg ttctttaata gtggactctt gttccaaact ggaacaacac tcaaccctat   4440
ctcggtctat tcttttgatt tataagggat tttgccgatt tcggcctatt ggttaaaaaa   4500
tgagctgatt taacaaaaat ttaacgcgaa ttttaacaaa atattaacgc ttacaattta   4560
ggtggcactt ttcggggaaa tgtgcgcgga acccctattt gtttattttt ctaaatacat   4620
tcaaatatgt atccgctcat gagacaataa ccctgataaa tgcttcaata atattgaaaa   4680
aggaagagta tgagtattca acatttccgt gtcgccctta ttcccttttt tgcggcattt   4740
tgccttcctg tttttgctca cccagaaacg ctggtgaaag taaaagatgc tgaagatcag   4800
ttgggtgcac gagtgggtta catcgaactg gatctcaaca gcggtaagat ccttgagagt   4860
tttcgccccg aagaacgttt tccaatgatg agcactttta aagttctgct atgtggcgcg   4920
gtattatccc gtattgacgc cgggcaagag caactcggtc gccgcataca ctattctcag   4980
aatgacttgg ttgagtactc accagtcaca gaaaagcatc ttacggatgg catgacagta   5040
agagaattat gcagtgctgc cataaccatg agtgataaca ctgcggccaa cttacttctg   5100
acaacgatcg gaggaccgaa ggagctaacc gcttttttgc acaacatggg ggatcatgta   5160
actcgccttg atcgttggga accggagctg aatgaagcca taccaaacga cgagcgtgac   5220
accacgatgc ctgtagcaat ggcaacaacg ttgcgcaaac tattaactgg cgaactactt   5280
actctagctt cccggcaaca attaatagac tggatggagg cggataaagt tgcaggacca   5340
cttctgcgct cggcccttcc ggctggctgg tttattgctg ataaatctgg agccggtgag   5400
cgtgggtctc gcggtatcat tgcagcactg gggccagatg gtaagccctc ccgtatcgta   5460
gttatctaca cgacggggag tcaggcaact atggatgaac gaaatagaca gatcgctgag   5520
ataggtgcct cactgattaa gcattggtaa ctgtcagacc aagtttactc atatatactt   5580
```

```
tagattgatt taaaacttca tttttaattt aaaaggatct aggtgaagat cctttttgat   5640

aatctcatga ccaaaatccc ttaacgtgag ttttcgttcc actgagcgtc agaccccgta   5700

gaaaagatca aaggatcttc ttgagatcct ttttttctgc gcgtaatctg ctgcttgcaa   5760

acaaaaaaac caccgctacc agcggtggtt tgtttgccgg atcaagagct accaactctt   5820

tttccgaagg taactggctt cagcagagcg cagataccaa atactgttct tctagtgtag   5880

ccgtagttag gccaccactt caagaactct gtagcaccgc ctacatacct cgctctgcta   5940

atcctgttac cagtggctgc tgccagtggc gataagtcgt gtcttaccgg gttggactca   6000

agacgatagt taccggataa ggcgcagcgg tcgggctgaa cggggggttc gtgcacacag   6060

cccagcttgg agcgaacgac ctacaccgaa ctgagatacc tacagcgtga gctatgagaa   6120

agcgccacgc ttcccgaagg gagaaaggcg gacaggtatc cggtaagcgg cagggtcgga   6180

acaggagagc gcacgaggga gcttccaggg ggaaacgcct ggtatcttta tagtcctgtc   6240

gggtttcgcc acctctgact tgagcgtcga tttttgtgat gctcgtcagg ggggcggagc   6300

ctatggaaaa acgccagcaa cgcggccttt ttacggttcc tggccttttg ctggcctttt   6360

gctcacatgt tctttcctgc gttatcccct gattctgtgg ataaccgtat taccgccttt   6420

gagtgagctg ataccgctcg ccgcagccga acgaccgagc gcagcgagtc agtgagcgag   6480

gaagcggaag agcgcccaat acgcaaaccg cctctccccg cgcgttggcc gattcattaa   6540

tgcagctggc acgacaggtt tcccgactgg aaagcgggca gtgagcgcaa cgcaattaat   6600

gtgagttagc tcactcatta ggcaccccag gctttacact ttatgcttcc ggctcgtatg   6660

ttgtgtggaa ttgtgagcgg ataacaattt cacacaggaa acagctatga ccatgattac   6720

gccagattta attaaggcct taattagg                                      6748
```

<210> SEQ ID NO 27
<211> LENGTH: 6748
<212> TYPE: DNA
<213> ORGANISM: Artificial Sequence
<220> FEATURE:
<223> OTHER INFORMATION: Synthetic sequence
<220> FEATURE:
<221> NAME/KEY: repeat_region
<222> LOCATION: (1)..(130)
<223> OTHER INFORMATION: 5' ITR
<220> FEATURE:
<221> NAME/KEY: promoter
<222> LOCATION: (191)..(932)
<223> OTHER INFORMATION: human\CMV\I.E.\enhancer\&\promoter
<220> FEATURE:
<221> NAME/KEY: misc_feature
<222> LOCATION: (897)..(901)
<223> OTHER INFORMATION: TATA\box
<220> FEATURE:
<221> NAME/KEY: Intron
<222> LOCATION: (1047)..(1179)
<223> OTHER INFORMATION: Promega\chimeric\intron
<220> FEATURE:
<221> NAME/KEY: misc_feature
<222> LOCATION: (1248)..(1293)
<223> OTHER INFORMATION: c-myc\miniIRES\cloned\into\Nhe\site
<220> FEATURE:
<221> NAME/KEY: misc_feature
<222> LOCATION: (1294)..(3493)
<223> OTHER INFORMATION: AnnaT_Test3bnIA_Usage
<220> FEATURE:
<221> NAME/KEY: misc_feature
<222> LOCATION: (1294)..(3493)
<223> OTHER INFORMATION: 3bnc\ORFIA_Usage
<220> FEATURE:
<221> NAME/KEY: misc_feature
<222> LOCATION: (3500)..(3500)

<223> OTHER INFORMATION: DELETION:\73bp - Position: 3493:
-AAAATCAGCCTCGACTGTGCCTTCTAGTTGCCAGCCATCTGTTGTTTGCCCCTCCCCCGTGCCT
TCCGGCCGC
<220> FEATURE:
<221> NAME/KEY: polyA_signal
<222> LOCATION: (3502)..(3733)
<223> OTHER INFORMATION: SV40\late\polyadenylation\signal
<220> FEATURE:
<221> NAME/KEY: repeat_region
<222> LOCATION: (3798)..(3927)
<223> OTHER INFORMATION: complement - 3' ITR
<220> FEATURE:
<221> NAME/KEY: rep_origin
<222> LOCATION: (4104)..(4559)
<223> OTHER INFORMATION: complement - f1\ori
<220> FEATURE:
<221> NAME/KEY: misc_feature
<222> LOCATION: (4690)..(5547)
<223> OTHER INFORMATION: Amp-R coding sequence
<220> FEATURE:
<221> NAME/KEY: misc_feature
<222> LOCATION: (5721)..(6309)
<223> OTHER INFORMATION: COL\E1\Origin

<400> SEQUENCE: 27

```
ctgcgcgctc gctcgctcac tgaggccgcc cgggcaaagc ccgggcgtcg ggcgaccttt     60

ggtcgcccgg cctcagtgag cgagcgagcg cgcagagagg gagtggccaa ctccatcact    120

aggggttcct tgtagttaat gattaacccg ccatgctact tatctacgta gccatgctct    180

aggaagatct tcaatattgg ccattagcca tattattcat tggttatata gcataaatca    240

atattggcta ttggccattg catacgttgt atctatatca taatatgtac atttatattg    300

gctcatgtcc aatatgaccg ccatgttggc attgattatt gactagttat taatagtaat    360

caattacggg gtcattagtt catagcccat atatggagtt ccgcgttaca taacttacgg    420

taaatggccc gcctggctga ccgcccaacg acccccgccc attgacgtca ataatgacgt    480

atgttcccat agtaacgcca atagggactt tccattgacg tcaatgggtg gagtatttac    540

ggtaaactgc ccacttggca gtacatcaag tgtatcatat gccaagtccg ccccctattg    600

acgtcaatga cggtaaatgg cccgcctggc attatgccca gtacatgacc ttacgggact    660

ttcctacttg gcagtacatc tacgtattag tcatcgctat taccatggtg atgcggtttt    720

ggcagtacac caatgggcgt ggatagcggt ttgactcacg gggatttcca agtctccacc    780

ccattgacgt caatgggagt ttgttttggc accaaaatca acgggacttt ccaaaatgtc    840

gtaataaccc cgccccgttg acgcaaatgg gcggtaggcg tgtacggtgg gaggtctata    900

taagcagagc tcgtttagtg aaccgtcaga tcactagaag ctttattgcg gtagtttatc    960

acagttaaat tgctaacgca gtcagtgctt ctgacacaac agtctcgaac ttaagctgca   1020

gaagttggtc gtgaggcact gggcaggtaa gtatcaaggt tacaagacag gtttaaggag   1080

accaatagaa actgggcttg tcgagacaga gaagactctt gcgtttctga taggcaccta   1140

ttggtcttac tgacatccac tttgcctttc tctccacagg tgtccactcc cagttcaatt   1200

acagctctta aggctagagt acttaatacg actcactata ggctagcggg gactttgcac   1260

tggaacttac aacacccgag caaggacgcg actctagctc tagaaccatg taccgaatgc   1320

aactgctgtc ctgcatcgcc ctgtccctgg cactggtcac caacagccag gtccagctgc   1380

tgcagagcgg agcagcagtc acaaaaccag gagccagcgt cagagtcagc tgcgaggcca   1440

gcgggtacaa cattcgggac tacttcatcc actggtggcg gcaggcacca gggcaggggc   1500

tgcagtgggt gggctggatc aaccctaaaa ccggacaacc caacaaccca cgacagtttc   1560

agggcagagt gagcctgacc agacacgcca gctgggactt tgacaccttt tccttctata   1620
```

-continued

```
tggatctgaa agcactgcga tccgacgata ccgccgtgta cttttgcgca cgacagcggt   1680
ccgattactg ggacttcgac gtctggggca gcgggacaca agtcacagtg tccagcgcct   1740
ccaccaaggg accaagcgtg tttccactgg caccatccag caagagcaca tccggaggca   1800
ccgcagcact gggctgcctg gtcaaggatt acttccctga accagtcacc gtcagctgga   1860
actccggagc cctgacaagc ggcgtgcaca ccttccctgc cgtgctgcag tccagcggcc   1920
tgtattccct gagctccgtg gtgaccgtgc ccagctccag cctgggcacc cagacctaca   1980
tttgcaatgt caaccataaa ccaagcaata ccaaagtcga caagaaagtc gagcccaaaa   2040
gctgcgacaa aacccacaca tgccctccat gccctgcccc agagctgctg gggggaccct   2100
ccgtctttct gtttcccccct aaaccaaaag acaccctgat gatcagcaga acccccgaag   2160
tcacatgcgt ggtggtcgac gtcagccacg aggaccctga ggtcaagttc aattggtacg   2220
tcgacggggt cgaggtccac aatgccaaga ccaagcccag agaggaacag tataacagca   2280
cctaccgggt cgtgtccgtg ctgacagtgc tgcatcagga ctggctgaac ggaaaggagt   2340
acaagtgcaa ggtgtccaac aaggccctgc ccgcaccaat tgaaaagaca atcagcaagg   2400
ccaaggggca gccccgagag ccccaagtct ataccctgcc cccttcccga gatgaactga   2460
ccaagaacca agtcagcctg acatgcctgg tgaagggatt ctacccttcc gatatcgccg   2520
tcgagtggga atccaacggc caacccgaga ataactacaa aacaacccca cccgtgctgg   2580
acagcgacgg gtccttcttt ctgtatagca agctgaccgt ggacaaatcc cgatggcagc   2640
aaggaaacgt gttcagctgc agcgtgatgc atgaggccct gcacaaccac tatacccaga   2700
aaagcctgag cctgagccca ggccggaagc ggagagcccc agtcaaacag accctgaact   2760
tcgatctgct gaaactggca ggcgacgtgg agtccaaccc agggccaatg tatagaatgc   2820
agctgctgag ctgcattgcc ctgagcctgg ccctggtgac caattccgat atccagatga   2880
cccagagccc ctcctccctg agcgcatccg tcggagacac cgtgacaatc acatgccagg   2940
caaacggcta tctgaactgg tatcagcagc ggagagggaa ggcacctaag ctgctgatct   3000
acgacggaag caagctggaa cgaggcgtcc ccagccggtt cagcgggaga agatgggggc   3060
aggaatacaa cctgacaatc aacaatctgc agcccgagga cattgcaacc tacttctgcc   3120
aggtgtacga gtttgtcgtc ccagggacac gactggatct gaagcggaca gtggccgcac   3180
ccagcgtgtt tatcttccct ccctccgacg aacagctgaa gtccggcacc gcatccgtgg   3240
tgtgcctgct gaacaatttc tatcccagag aggccaaagt ccagtggaag gtggacaatg   3300
cactgcagtc cggaaatagc caagaaagcg tcaccgagca ggactccaag gactccacat   3360
actccctgag cagcacactg accctgagca aggcagacta cgagaagcac aaggtctacg   3420
cctgcgaagt cacccaccag ggactgtcct cccctgtgac caaatccttc aatagaggag   3480
agtgctaatg agcggccgct tcgagcagac atgataagat acattgatga gtttggacaa   3540
accacaacta gaatgcagtg aaaaaaatgc tttatttgtg aaatttgtga tgctattgct   3600
ttatttgtaa ccattataag ctgcaataaa caagttaaca acaacaattg cattcatttt   3660
atgtttcagg ttcaggggga gatgtgggag gtttttttaaa gcaagtaaaa cctctacaaa   3720
tgtggtaaaa tcgataagga tcttcctaga gcatggctac gtagataagt agcatggcgg   3780
gttaatcatt aactacaagg aacccctagt gatggagttg gccactccct ctctgcgcgc   3840
tcgctcgctc actgaggccg ggcgaccaaa ggtcgcccga cgcccgggct ttgcccgggc   3900
ggcctcagtg agcgagcgag cgcgcagcct taattaacct aattcactgg ccgtcgtttt   3960
```

-continued

```
acaacgtcgt gactgggaaa accctggcgt tacccaactt aatcgccttg cagcacatcc   4020
ccctttcgcc agctggcgta atagcgaaga ggcccgcacc gatcgccctt cccaacagtt   4080
gcgcagcctg aatggcgaat gggacgcgcc ctgtagcggc gcattaagcg cggcgggtgt   4140
ggtggttacg cgcagcgtga ccgctacact tgccagcgcc ctagcgcccg ctcctttcgc   4200
tttcttccct tcctttctcg ccacgttcgc cggctttccc cgtcaagctc taaatcgggg   4260
gctcccttta gggttccgat ttagtgcttt acggcacctc gaccccaaaa aacttgatta   4320
gggtgatggt tcacgtagtg ggccatcgcc ctgatagacg gtttttcgcc ctttgacgtt   4380
ggagtccacg ttctttaata gtggactctt gttccaaact ggaacaacac tcaaccctat   4440
ctcggtctat tcttttgatt tataagggat tttgccgatt tcggcctatt ggttaaaaaa   4500
tgagctgatt taacaaaaat ttaacgcgaa ttttaacaaa atattaacgc ttacaattta   4560
ggtggcactt ttcggggaaa tgtgcgcgga acccctattt gtttattttt ctaaatacat   4620
tcaaatatgt atccgctcat gagacaataa ccctgataaa tgcttcaata atattgaaaa   4680
aggaagagta tgagtattca acatttccgt gtcgccctta ttcccttttt tgcggcattt   4740
tgccttcctg tttttgctca cccagaaacg ctggtgaaag taaaagatgc tgaagatcag   4800
ttgggtgcac gagtgggtta catcgaactg gatctcaaca gcggtaagat ccttgagagt   4860
tttcgccccg aagaacgttt tccaatgatg agcactttta aagttctgct atgtggcgcg   4920
gtattatccc gtattgacgc cgggcaagag caactcggtc gccgcataca ctattctcag   4980
aatgacttgg ttgagtactc accagtcaca gaaaagcatc ttacggatgg catgacagta   5040
agagaattat gcagtgctgc cataaccatg agtgataaca ctgcggccaa cttacttctg   5100
acaacgatcg gaggaccgaa ggagctaacc gcttttttgc acaacatggg ggatcatgta   5160
actcgccttg atcgttggga accggagctg aatgaagcca taccaaacga cgagcgtgac   5220
accacgatgc ctgtagcaat ggcaacaacg ttgcgcaaac tattaactgg cgaactactt   5280
actctagctt cccggcaaca attaatagac tggatggagg cggataaagt tgcaggacca   5340
cttctgcgct cggcccttcc ggctggctgg tttattgctg ataaatctgg agccggtgag   5400
cgtgggtctc gcggtatcat tgcagcactg gggccagatg gtaagccctc ccgtatcgta   5460
gttatctaca cgacggggag tcaggcaact atggatgaac gaaatagaca gatcgctgag   5520
ataggtgcct cactgattaa gcattggtaa ctgtcagacc aagtttactc atatatactt   5580
tagattgatt taaaacttca tttttaattt aaaaggatct aggtgaagat cctttttgat   5640
aatctcatga ccaaaatccc ttaacgtgag ttttcgttcc actgagcgtc agaccccgta   5700
gaaaagatca aaggatcttc ttgagatcct ttttttctgc gcgtaatctg ctgcttgcaa   5760
acaaaaaaac caccgctacc agcggtggtt tgtttgccgg atcaagagct accaactctt   5820
tttccgaagg taactggctt cagcagagcg cagataccaa atactgttct tctagtgtag   5880
ccgtagttag gccaccactt caagaactct gtagcaccgc ctacatacct cgctctgcta   5940
atcctgttac cagtggctgc tgccagtggc gataagtcgt gtcttaccgg gttggactca   6000
agacgatagt taccggataa ggcgcagcgg tcgggctgaa cggggggttc gtgcacacag   6060
cccagcttgg agcgaacgac ctacaccgaa ctgagatacc tacagcgtga gctatgagaa   6120
agcgccacgc ttcccgaagg gagaaaggcg gacaggtatc cggtaagcgg cagggtcgga   6180
acaggagagc gcacgaggga gcttccaggg ggaaacgcct ggtatcttta tagtcctgtc   6240
gggtttcgcc acctctgact tgagcgtcga tttttgtgat gctcgtcagg ggggcggagc   6300
ctatggaaaa acgccagcaa cgcggccttt ttacggttcc tggccttttg ctggcctttt   6360
```

gctcacatgt tctttcctgc gttatcccct gattctgtgg ataaccgtat taccgccttt 6420
gagtgagctg ataccgctcg ccgcagccga acgaccgagc gcagcgagtc agtgagcgag 6480
gaagcggaag agcgcccaat acgcaaaccg cctctccccg cgcgttggcc gattcattaa 6540
tgcagctggc acgacaggtt tcccgactgg aaagcgggca gtgagcgcaa cgcaattaat 6600
gtgagttagc tcactcatta ggcaccccag gctttacact ttatgcttcc ggctcgtatg 6660
ttgtgtggaa ttgtgagcgg ataacaattt cacacaggaa acagctatga ccatgattac 6720
gccagattta attaaggcct taattagg 6748

<210> SEQ ID NO 28
<211> LENGTH: 6748
<212> TYPE: DNA
<213> ORGANISM: Artificial Sequence
<220> FEATURE:
<223> OTHER INFORMATION: Synthetic sequence
<220> FEATURE:
<221> NAME/KEY: repeat_region
<222> LOCATION: (1)..(130)
<223> OTHER INFORMATION: 5' ITR
<220> FEATURE:
<221> NAME/KEY: promoter
<222> LOCATION: (191)..(932)
<223> OTHER INFORMATION: human\CMV\I.E.\enhancer\&\promoter
<220> FEATURE:
<221> NAME/KEY: misc_feature
<222> LOCATION: (897)..(901)
<223> OTHER INFORMATION: TATA\box
<220> FEATURE:
<221> NAME/KEY: Intron
<222> LOCATION: (1047)..(1179)
<223> OTHER INFORMATION: Promega\chimeric\intron
<220> FEATURE:
<221> NAME/KEY: misc_feature
<222> LOCATION: (1248)..(1293)
<223> OTHER INFORMATION: c-myc\miniIRES\cloned\into\Nhe\site
<220> FEATURE:
<221> NAME/KEY: misc_feature
<222> LOCATION: (1294)..(3493)
<223> OTHER INFORMATION: AnnaT_Test3bnIAM_Usage
<220> FEATURE:
<221> NAME/KEY: polyA_signal
<222> LOCATION: (3502)..(3733)
<223> OTHER INFORMATION: SV40\late\polyadenylation\signal
<220> FEATURE:
<221> NAME/KEY: repeat_region
<222> LOCATION: (3798)..(3927)
<223> OTHER INFORMATION: complement -3' ITR
<220> FEATURE:
<221> NAME/KEY: rep_origin
<222> LOCATION: (4104)..(4559)
<223> OTHER INFORMATION: complement - f1\ori
<220> FEATURE:
<221> NAME/KEY: misc_feature
<222> LOCATION: (4690)..(5547)
<223> OTHER INFORMATION: Amp-R coding sequence
<220> FEATURE:
<221> NAME/KEY: misc_feature
<222> LOCATION: (5721)..(6309)
<223> OTHER INFORMATION: COL\E1\Origin

<400> SEQUENCE: 28
ctgcgcgctc gctcgctcac tgaggccgcc cgggcaaagc ccgggcgtcg ggcgaccttt 60
ggtcgcccgg cctcagtgag cgagcgagcg cgcagagagg gagtggccaa ctccatcact 120
aggggttcct tgtagttaat gattaacccg ccatgctact tatctacgta gccatgctct 180
aggaagatct tcaatattgg ccattagcca tattattcat tggttatata gcataaatca 240
atattggcta ttggccattg catacgttgt atctatatca taatatgtac atttatattg 300

-continued

```
gctcatgtcc aatatgaccg ccatgttggc attgattatt gactagttat taatagtaat    360
caattacggg gtcattagtt catagcccat atatggagtt ccgcgttaca taacttacgg    420
taaatggccc gcctggctga ccgcccaacg acccccgccc attgacgtca ataatgacgt    480
atgttcccat agtaacgcca atagggactt tccattgacg tcaatgggtg gagtatttac    540
ggtaaactgc ccacttggca gtacatcaag tgtatcatat gccaagtccg ccccctattg    600
acgtcaatga cggtaaatgg cccgcctggc attatgccca gtacatgacc ttacgggact    660
ttcctacttg gcagtacatc tacgtattag tcatcgctat taccatggtg atgcggtttt    720
ggcagtacac caatgggcgt ggatagcggt ttgactcacg gggatttcca agtctccacc    780
ccattgacgt caatgggagt ttgttttggc accaaaatca acgggacttt ccaaaatgtc    840
gtaataaccc cgccccgttg acgcaaatgg gcggtaggcg tgtacggtgg gaggtctata    900
taagcagagc tcgtttagtg aaccgtcaga tcactagaag ctttattgcg gtagtttatc    960
acagttaaat tgctaacgca gtcagtgctt ctgacacaac agtctcgaac ttaagctgca   1020
gaagttggtc gtgaggcact gggcaggtaa gtatcaaggt tacaagacag gtttaaggag   1080
accaatagaa actgggcttg tcgagacaga gaagactctt gcgtttctga taggcaccta   1140
ttggtcttac tgacatccac tttgcctttc tctccacagg tgtccactcc cagttcaatt   1200
acagctctta aggctagagt acttaatacg actcactata ggctagcggg gactttgcac   1260
tggaacttac aacacccgag caaggacgcg actctagctc tagaaccatg taccgaatgc   1320
aactgctgtc ctgcatcgcc ctgtccctgg cactggtcac caacagccag gtccagctgc   1380
tgcagagcgg cgccgccgtg acaaagccag gagccagcgt gcgggtcagc tgcgaggcct   1440
ccggctacaa cattcgggat tacttcatcc actggtggcg gcaggcccca ggccagggac   1500
tgcagtgggt gggctggatc aacccaaaga caggccagcc aaacaaccct cggcagttcc   1560
agggacgggt gagcctgacc cggcacgcca gctgggattt cgatacattc tccttctaca   1620
tggatctgaa agccctgcgg tccgacgata cagccgtgta cttctgcgcc cggcagcggt   1680
ccgattactg ggacttcgat gtgtggggaa gcggcacaca agtcaccgtc agcagcgcca   1740
gcaccaaggg ccccttccgtg ttcccactgg ccccttccag caagtccacc tccggaggca   1800
cagccgccct gggctgcctg gtgaaagatt acttccctga gcccgtgacc gtgagctgga   1860
actccggagc cctgaccagc ggagtgcaca ccttccctgc cgtgctgcag tccagcggac   1920
tgtacagcct gtcctccgtg gtgacagtgc ccagctccag cctgggcacc cagacctaca   1980
tttgcaacgt caaccataag ccaagcaaca caaaggtgga taagaaagtg gagccaaaaa   2040
gctgtgacaa gacacacacc tgtcctccct gccccgcccc cgagctgctg ggcggaccaa   2100
gcgtgttcct gttccctcct aagcccaagg acacactgat gatcagccgg accccagagg   2160
tcacatgtgt ggtggtggat gtgagccacg aggaccctga ggtgaagttc aactggtacg   2220
tggatggagt cgaagtgcac aacgccaaaa ccaagcctcg ggaggagcag tacaacagca   2280
cctaccgggt ggtgagcgtg ctgaccgtgc tgcatcagga ctggctgaat ggaaaggaat   2340
acaagtgtaa agtgtccaac aaagccctgc cagcccccat cgaaaagaca atttccaaag   2400
ccaagggaca gccacgggag ccacaagtgt acaccctgcc cccaagccgg gatgagctga   2460
caaagaatca ggtcagcctg acatgtctgg tcaagggctt ctacccaagc gatatcgccg   2520
tggagtggga gtccaatggc cagcccgaaa acaactacaa gaccaccccca ccagtgctgg   2580
actccgatgg ctccttcttc ctgtactcca agctgaccgt ggacaaaagc cggtggcagc   2640
agggaaacgt gttcagctgt agcgtgatgc acgaagccct gcacaaccac tacacccaga   2700
```

-continued

```
aaagcctgag cctgagccca ggccggaagc ggcgggcccc agtgaaacag accctgaatt   2760
tcgatctgct gaagctggcc ggagatgtgg aaagcaaccc cggacccatg taccggatgc   2820
agctgctgag ctgtatcgcc ctgagcctgg ccctggtgac caattccgat attcagatga   2880
cacagagccc cagctccctg agcgccagcg tgggcgatac cgtcaccatc acatgccagg   2940
ccaacggata cctgaactgg taccagcagc ggcggggaaa ggccccaaag ctgctgatct   3000
acgatggaag caagctggag cggggagtgc ccagccggtt cagcggacgg cggtggggcc   3060
aggaatacaa cctgaccatc aacaatctgc agccagagga catcgccacc tacttctgcc   3120
aggtctacga gttcgtggtg cctggaaccc ggctggatct gaagcggaca gtggccgccc   3180
cctccgtgtt catcttcccc cctagcgacg agcagctgaa atccggaaca gccagcgtgg   3240
tctgtctgct gaacaacttc taccctcggg aggccaaagt gcagtggaag gtcgataacg   3300
ccctgcagtc cggaaacagc caggagtccg tgaccgagca ggattccaag gatagcacct   3360
acagcctgag ctccaccctg acactgtcca aggccgatta cgagaaacac aaggtgtacg   3420
cctgcgaagt gacccatcag ggactgagca gcccagtgac caagagcttc aatcggggag   3480
aatgctaatg agcggccgct tcgagcagac atgataagat acattgatga gtttggacaa   3540
accacaacta gaatgcagtg aaaaaaatgc tttatttgtg aaatttgtga tgctattgct   3600
ttatttgtaa ccattataag ctgcaataaa caagttaaca acaacaattg cattcatttt   3660
atgtttcagg ttcaggggga gatgtgggag gtttttttaaa gcaagtaaaa cctctacaaa   3720
tgtggtaaaa tcgataagga tcttcctaga gcatggctac gtagataagt agcatggcgg   3780
gttaatcatt aactacaagg aacccctagt gatggagttg gccactccct ctctgcgcgc   3840
tcgctcgctc actgaggccg ggcgaccaaa ggtcgcccga cgcccgggct ttgcccgggc   3900
ggcctcagtg agcgagcgag cgcgcagcct taattaacct aattcactgg ccgtcgtttt   3960
acaacgtcgt gactgggaaa accctggcgt tacccaactt aatcgccttg cagcacatcc   4020
ccctttcgcc agctggcgta atagcgaaga ggcccgcacc gatcgccctt cccaacagtt   4080
gcgcagcctg aatggcgaat gggacgcgcc ctgtagcggc gcattaagcg cggcgggtgt   4140
ggtggttacg cgcagcgtga ccgctacact tgccagcgcc ctagcgcccg ctcctttcgc   4200
tttcttccct tcctttctcg ccacgttcgc cggctttccc cgtcaagctc taaatcgggg   4260
gctcccttta gggttccgat ttagtgcttt acggcacctc gaccccaaaa aacttgatta   4320
gggtgatggt tcacgtagtg ggccatcgcc ctgatagacg gtttttcgcc ctttgacgtt   4380
ggagtccacg ttctttaata gtggactctt gttccaaact ggaacaacac tcaaccctat   4440
ctcggtctat tcttttgatt tataagggat tttgccgatt tcggcctatt ggttaaaaaa   4500
tgagctgatt taacaaaaat ttaacgcgaa ttttaacaaa atattaacgc ttacaattta   4560
ggtggcactt ttcggggaaa tgtgcgcgga acccctattt gtttattttt ctaaatacat   4620
tcaaatatgt atccgctcat gagacaataa ccctgataaa tgcttcaata atattgaaaa   4680
aggaagagta tgagtattca acatttccgt gtcgccctta ttcccttttt tgcggcattt   4740
tgccttcctg tttttgctca cccagaaacg ctggtgaaag taaaagatgc tgaagatcag   4800
ttgggtgcac gagtgggtta catcgaactg gatctcaaca gcggtaagat ccttgagagt   4860
tttcgccccg aagaacgttt tccaatgatg agcactttta aagttctgct atgtggcgcg   4920
gtattatccc gtattgacgc cgggcaagag caactcggtc gccgcataca ctattctcag   4980
aatgacttgg ttgagtactc accagtcaca gaaaagcatc ttacggatgg catgacagta   5040
```

agagaattat gcagtgctgc cataaccatg agtgataaca ctgcggccaa cttacttctg 5100
acaacgatcg gaggaccgaa ggagctaacc gcttttttgc acaacatggg ggatcatgta 5160
actcgccttg atcgttggga accggagctg aatgaagcca taccaaacga cgagcgtgac 5220
accacgatgc ctgtagcaat ggcaacaacg ttgcgcaaac tattaactgg cgaactactt 5280
actctagctt cccggcaaca attaatagac tggatggagg cggataaagt tgcaggacca 5340
cttctgcgct cggcccttcc ggctggctgg tttattgctg ataaatctgg agccggtgag 5400
cgtgggtctc gcggtatcat tgcagcactg gggccagatg gtaagccctc ccgtatcgta 5460
gttatctaca cgacggggag tcaggcaact atggatgaac gaaatagaca gatcgctgag 5520
ataggtgcct cactgattaa gcattggtaa ctgtcagacc aagtttactc atatatactt 5580
tagattgatt taaaacttca tttttaattt aaaaggatct aggtgaagat cctttttgat 5640
aatctcatga ccaaaatccc ttaacgtgag ttttcgttcc actgagcgtc agaccccgta 5700
gaaaagatca aaggatcttc ttgagatcct ttttttctgc gcgtaatctg ctgcttgcaa 5760
acaaaaaaac caccgctacc agcggtggtt tgtttgccgg atcaagagct accaactctt 5820
tttccgaagg taactggctt cagcagagcg cagataccaa atactgttct tctagtgtag 5880
ccgtagttag gccaccactt caagaactct gtagcaccgc ctacatacct cgctctgcta 5940
atcctgttac cagtggctgc tgccagtggc gataagtcgt gtcttaccgg gttggactca 6000
agacgatagt taccggataa ggcgcagcgg tcgggctgaa cggggggttc gtgcacacag 6060
cccagcttgg agcgaacgac ctacaccgaa ctgagatacc tacagcgtga gctatgagaa 6120
agcgccacgc ttcccgaagg gagaaaggcg gacaggtatc cggtaagcgg cagggtcgga 6180
acaggagagc gcacgaggga gcttccaggg ggaaacgcct ggtatcttta tagtcctgtc 6240
gggtttcgcc acctctgact tgagcgtcga tttttgtgat gctcgtcagg ggggcggagc 6300
ctatggaaaa acgccagcaa cgcggccttt ttacggttcc tggccttttg ctggcctttt 6360
gctcacatgt tctttcctgc gttatcccct gattctgtgg ataaccgtat taccgccttt 6420
gagtgagctg ataccgctcg ccgcagccga acgaccgagc gcagcgagtc agtgagcgag 6480
gaagcggaag agcgcccaat acgcaaaccg cctctccccg cgcgttggcc gattcattaa 6540
tgcagctggc acgacaggtt tcccgactgg aaagcgggca gtgagcgcaa cgcaattaat 6600
gtgagttagc tcactcatta ggcaccccag gctttacact ttatgcttcc ggctcgtatg 6660
ttgtgtggaa ttgtgagcgg ataacaattt cacacaggaa acagctatga ccatgattac 6720
gccagattta attaaggcct taattagg 6748

<210> SEQ ID NO 29
<211> LENGTH: 5826
<212> TYPE: DNA
<213> ORGANISM: Artificial Sequence
<220> FEATURE:
<223> OTHER INFORMATION: Synthetic sequence
<220> FEATURE:
<221> NAME/KEY: misc_feature
<222> LOCATION: (1380)..(1384)
<223> OTHER INFORMATION: KOZAK
<220> FEATURE:
<221> NAME/KEY: misc_feature
<222> LOCATION: (1385)..(2800)
<223> OTHER INFORMATION: VRC01H\[VRC01VH-B12CH)

<400> SEQUENCE: 29
tcgcgcgttt cggtgatgac ggtgaaaacc tctgacacat gcagctcccg gagacggtca 60
cagcttgtct gtaagcggat gccgggagca gacaagcccg tcagggcgcg tcagcgggtg 120

-continued ttggcgggtg tcggggctgg cttaactatg cggcatcaga gcagattgta ctgagagtgc 180
accatatgcg gtgtgaaata ccgcacagat gcgtaaggag aaaataccgc atcagattgg 240
ctattggcca ttgcatacgt tgtatccata tcataatatg tacatttata ttggctcatg 300
tccaacatta ccgccatgtt gacattgatt attgactagt tattaatagt aatcaattac 360
ggggtcatta gttcatagcc catatatgga gttccgcgtt acataactta cggtaaatgg 420
cccgcctggc tgaccgccca acgacccccg cccattgacg tcaataatga cgtatgttcc 480
catagtaacg ccaataggga ctttccattg acgtcaatgg gtggagtatt tacggtaaac 540
tgcccacttg gcagtacatc aagtgtatca tatgccaagt acgcccccta ttgacgtcaa 600
tgacggtaaa tggcccgcct ggcattatgc ccagtacatg accttatggg actttcctac 660
ttggcagtac atctacgtat tagtcatcgc tattaccatg gtgatgcggt tttggcagta 720
catcaatggg cgtggatagc ggtttgactc acggggattt ccaagtctcc accccattga 780
cgtcaatggg agtttgtttt ggcaccaaaa tcaacgggac tttccaaaat gtcgtaacaa 840
ctccgcccca ttgacgcaaa tgggcggtag gcgtgtacgg tgggaggtct atataagcag 900
agctcgttta gtgaaccgtc agatcgcctg gagacgccat ccacgctgtt ttgacctcca 960
tagaagacac cgggaccgat ccagcctcca tcggctcgca tctctccttc acgcgcccgc 1020
cgccctacct gaggccgcca tccacgccgg ttgagtcgcg ttctgccgcc tcccgcctgt 1080
ggtgcctcct gaactgcgtc cgccgtctag gtaagtttaa agctcaggtc gagaccgggc 1140
ctttgtccgg cgctcccttg gagcctacct agactcagcc ggctctccac gctttgcctg 1200
accctgcttg ctcaactcta gttaacggtg gagggcagtg tagtctgagc agtactcgtt 1260
gctgccgcgc gcgccaccag acataatagc tgacagacta acagactgtt cctttccatg 1320
ggtcttttct gcagtcaccg tcgtcgacac gtgtgatcag atatcgcggc cgctctagac 1380
caccatggga tggtcatgta tcatcctttt tctagtagca actgcaaccg gtgtacattc 1440
ccaggtgcag ctggtgcagt ctggaggtca gatgaagaag cctggcgagt cgatgagaat 1500
ttcttgtcgg gcttctggat atgaatttat tgattgtacg ctaaattgga ttcgtctggc 1560
ccccggaaaa aggcctgagt ggatgggatg gctgaagcct cggggggggg ccgtcaacta 1620
cgcacgtcca cttcagggca gagtgaccat gactcgagac gtttattccg acacagcctt 1680
tttggagctg cgctcgttga cagtagacga cacggccgtc tacttttgta ctaggggaaa 1740
aaactgtgat tacaattggg acttcgaaca ctggggccgg ggcaccccgg tcatcgtctc 1800
atcaccgtcg accaagggcc catcggtctt cccccctggca ccctcctcca agagcacctc 1860
tgggggcaca gcggccctgg gctgcctggt caaggactac ttccccgaac cggtgacggt 1920
gtcgtggaac tcaggcgccc tgaccagcgg cgtgcacacc ttcccggctg tcctacagtc 1980
ctcaggactc tactccctca gcagcgtggt gaccgtgccc tccagcagct tgggcaccca 2040
gacctacatc tgcaacgtga atcacaagcc cagcaacacc aaggtggaca agaaagttga 2100
gcccaaatct tgtgacaaaa ctcacacatg cccaccgtgc ccagcacctg aactcctggg 2160
gggaccgtca gtcttcctct tcccccccaaa acccaaggac accctcatga tctcccggac 2220
ccctgaggtc acatgcgtgg tggtggacgt gagccacgaa gaccctgagg tcaagttcaa 2280
ctggtacgtg gacggcgtgg aggtgcataa tgccaagaca aagccgcggg aggagcagta 2340
caacagcacg taccgtgtgg tcagcgtcct caccgtcctg caccaggact ggctgaatgg 2400
caaggagtac aagtgcaagg tctccaacaa agccctccca gcccccatcg agaaaaccat 2460

-continued

```
ctccaaagcc aaagggcagc cccgagaacc acaggtgtac accctgcccc catcccggga   2520
tgagctgacc aagaaccagg tcagcctgac ctgcctggtc aaaggcttct atcccagcga   2580
catcgccgtg gagtgggaga gcaatgggca gccggagaac aactacaaga ccacgcctcc   2640
cgtgctggac tccgacggct ccttcttcct ctacagcaag ctcaccgtgg acaagagcag   2700
gtggcagcag gggaacgtct tctcatgctc cgtgatgcat gaggctctgc acaaccacta   2760
cacgcagaag agcctctccc tgtctccggg taaatgatga ggatccagat ctgctgtgcc   2820
ttctagttgc cagccatctg ttgtttgccc ctcccccgtg ccttccttga ccctggaagg   2880
tgccactccc actgtccttt cctaataaaa tgaggaaatt gcatcgcatt gtctgagtag   2940
gtgtcattct attctggggg gtggggtggg gcaggacagc aagggggagg attgggaaga   3000
caatagcagg catgctgggg atgcggtggg ctctatgggt acccaggtgc tgaagaattg   3060
acccggttcc tcctgggcca gaaagaagca ggcacatccc cttctctgtg acacaccctg   3120
tccacgcccc tggttcttag ttccagcccc actcatagga cactcatagc tcaggagggc   3180
tccgccttca atcccacccg ctaaagtact tggagcggtc tctccctccc tcatcagccc   3240
accaaaccaa acctagcctc caagagtggg aagaaattaa agcaagatag gctattaagt   3300
gcagagggag agaaaatgcc tccaacatgt gaggaagtaa tgagagaaat catagaattt   3360
taaggccatg atttaaggcc atcatggcct taatcttccg cttcctcgct cactgactcg   3420
ctgcgctcgg tcgttcggct gcggcgagcg gtatcagctc actcaaaggc ggtaatacgg   3480
ttatccacag aatcagggga taacgcagga aagaacatgt gagcaaaagg ccagcaaaag   3540
gccaggaacc gtaaaaaggc cgcgttgctg gcgtttttcc ataggctccg cccccctgac   3600
gagcatcaca aaaatcgacg ctcaagtcag aggtggcgaa acccgacagg actataaaga   3660
taccaggcgt ttccccctgg aagctccctc gtgcgctctc ctgttccgac cctgccgctt   3720
accggatacc tgtccgcctt tctcccttcg ggaagcgtgg cgctttctca tagctcacgc   3780
tgtaggtatc tcagttcggt gtaggtcgtt cgctccaagc tgggctgtgt gcacgaaccc   3840
cccgttcagc ccgaccgctg cgccttatcc ggtaactatc gtcttgagtc caacccggta   3900
agacacgact tatcgccact ggcagcagcc actggtaaca ggattagcag agcgaggtat   3960
gtaggcggtg ctacagagtt cttgaagtgg tggcctaact acggctacac tagaagaaca   4020
gtatttggta tctgcgctct gctgaagcca gttaccttcg gaaaaagagt tggtagctct   4080
tgatccggca aacaaaccac cgctggtagc ggtggttttt ttgtttgcaa gcagcagatt   4140
acgcgcagaa aaaaaggatc tcaagaagat cctttgatct tttctacggg gtctgacgct   4200
cagtggaacg aaaactcacg ttaagggatt ttggtcatga gattatcaaa aaggatcttc   4260
acctagatcc ttttaaatta aaaatgaagt tttaaatcaa tctaaagtat atatgagtaa   4320
acttggtctg acagttacca atgcttaatc agtgaggcac ctatctcagc gatctgtcta   4380
tttcgttcat ccatagttgc ctgactcggg gggggggggc gctgaggtct gcctcgtgaa   4440
gaaggtgttg ctgactcata ccaggcctga atcgccccat catccagcca gaaagtgagg   4500
gagccacggt tgatgagagc tttgttgtag gtggaccagt tggtgatttt gaacttttgc   4560
tttgccacgg aacggtctgc gttgtcggga agatgcgtga tctgatcctt caactcagca   4620
aaagttcgat ttattcaaca aagccgccgt cccgtcaagt cagcgtaatg ctctgccagt   4680
gttacaacca attaaccaat tctgattaga aaaactcatc gagcatcaaa tgaaactgca   4740
atttattcat atcaggatta tcaataccat atttttgaaa aagccgtttc tgtaatgaag   4800
gagaaaactc accgaggcag ttccatagga tggcaagatc ctggtatcgg tctgcgattc   4860
```

cgactcgtcc aacatcaata caacctatta atttcccctc gtcaaaaata aggttatcaa 4920
gtgagaaatc accatgagtg acgactgaat ccggtgagaa tggcaaaagc ttatgcattt 4980
ctttccagac ttgttcaaca ggccagccat tacgctcgtc atcaaaatca ctcgcatcaa 5040
ccaaaccgtt attcattcgt gattgcgcct gagcgagacg aaatacgcga tcgctgttaa 5100
aaggacaatt acaaacagga atcgaatgca accggcgcag gaacactgcc agcgcatcaa 5160
caatattttc acctgaatca ggatattctt ctaatacctg gaatgctgtt ttcccgggga 5220
tcgcagtggt gagtaaccat gcatcatcag gagtacggat aaaatgcttg atggtcggaa 5280
gaggcataaa ttccgtcagc cagtttagtc tgaccatctc atctgtaaca tcattggcaa 5340
cgctaccttt gccatgtttc agaaacaact ctggcgcatc gggcttccca tacaatcgat 5400
agattgtcgc acctgattgc ccgacattat cgcgagccca tttataccca tataaatcag 5460
catccatgtt ggaatttaat cgcggcctcg agcaagacgt ttcccgttga atatggctca 5520
taacacccct tgtattactg tttatgtaag cagacagttt tattgttcat gatgatatat 5580
ttttatcttg tgcaatgtaa catcagagat tttgagacac aacgtggctt tccccccccc 5640
cccattattg aagcatttat cagggttatt gtctcatgag cggatacata tttgaatgta 5700
tttagaaaaa taaacaaata ggggttccgc gcacatttcc ccgaaaagtg ccacctgacg 5760
tctaagaaac cattattatc atgacattaa cctataaaaa taggcgtatc acgaggccct 5820
ttcgtc 5826

<210> SEQ ID NO 30
<211> LENGTH: 2178
<212> TYPE: DNA
<213> ORGANISM: Artificial Sequence
<220> FEATURE:
<223> OTHER INFORMATION: Synthetic sequence

<400> SEQUENCE: 30
atgtaccgga tgcagctact gtcgtgtatc gctctttcgt tagcattagt cacaaactcg 60
caagtccagc tgctgcagtc aggggctgca gtgacaaagc ccggagcatc agttcgcgtt 120
tcatgtgagg ccagtggcta caacatacgg gactatttca tccactggtg gagacaggca 180
ccaggccagg gattacagtg ggttggctgg atcaacccga aaacaggcca gcccaataac 240
ccgcgacagt ttcagggccg tgtcagtctc acccgccacg catcttggga tttcgatacg 300
ttttccttct acatggatct gaaggcactg cgcagcgacg ataccgcagt ttacttctgc 360
gcaaggcagc gtagcgatta ctgggacttc gatgtctggg ggtcaggcac acaagtaacg 420
gtttcatccg cttccacaaa agggccatca gtgtttcccc tggcaccctc ctcaaaatct 480
accagcggag gcaccgcagc tctcggctgt ctggttaaag actactttcc cgaacccgtc 540
accgtttctt ggaattctgg ggctctaacc tcaggcgtgc acacgttccc cgcccgttctg 600 cagagcagcg gcctgtactc cttatcaagt gtagtaactg ttccatcatc aagcttgggc 660
acccagacct acatctgcaa tgttaatcac aaaccttcca acactaaggt ggacaagaag 720
gttgagccaa aaagttgtga taagacccac acatgtcctc cgtgtcccgc tcctgagctg 780
ctaggtggcc ccagtgtgtt cctctttccc cctaaaccca aagacacact gatgatctca 840
aggacccctg aagttacatg cgttgttgtt gatgtttccc acgaagatcc agaagttaag 900
ttcaactggt atgttgatgg cgttgaagtt cacaacgcaa aaactaaacc gcgtgaagaa 960
cagtataact ctacataccg tgtggtttca gttcttacag tcctgcatca ggattggctt 1020

-continued aacgggaaag aatacaaatg taaagtatcc aacaaagcac ttcccgcacc cattgagaaa 1080
acgatttcaa aagcaaaggg acagcccagg gaaccccaag tttacacgct gccgccatct 1140
cgtgatgagc tgaccaagaa tcaggtatct ttgacgtgcc tggtcaaagg tttctaccct 1200
tcggacatcg cggttgagtg ggagtcaaac ggccagccag aaaacaatta caaaaccact 1260
cctcctgtct tggacagcga tgggtcattc tttctttact caaaactcac tgttgacaag 1320
tctcgatggc agcaaggcaa cgtctttagt tgctctgtga tgcatgaagc cctccacaat 1380
cactatacac agaaaagtct atcactctca cctggcagaa aacggagggc acccgtgaag 1440
cagacactca atttcgactt actgaaactg gctggggatg tcgaatctaa tccaggccct 1500
atgtaccgca tgcaactact gtcatgtatt gccctttcat tagctctcgt aacaaattct 1560
gatatccaga tgacccagtc cccctcatct ctgtcagcat cggttggcga taccgttact 1620
attacgtgcc aggcaaatgg ctacttgaac tggtaccaac aacggcgcgg taaagcaccc 1680
aaactattga tatacgatgg ctcaaagttg gaaagaggcg tgccttcaag attctccggc 1740
agacgctggg gccaggagta caacctaact atcaacaacc ttcagccaga ggatattgca 1800
acctacttct gtcaggtgta tgagtttgtg gtgcccggca cgcgtctgga tttgaagaga 1860
acagtcgcgg caccctcagt gtttatcttc cctcccagtg atgagcagct gaaatcaggc 1920
accgcctcag tggtatgcct gttgaacaac ttctaccccc gtgaggcaaa agttcagtgg 1980
aaggtggata atgccttaca gtcaggcaac tcacaagaga gcgtcactga gcaggattca 2040
aaagattcaa catacagtct tagctcaacc ctgaccctct ctaaagcgga ttacgaaaaa 2100
cacaaagttt atgcctgcga agtcacgcac cagggtctga gtagccctgt tactaaaagt 2160
ttcaaccgag gcgaatgt 2178

<210> SEQ ID NO 31
<211> LENGTH: 1530
<212> TYPE: DNA
<213> ORGANISM: Artificial Sequence
<220> FEATURE:
<223> OTHER INFORMATION: Synthetic Sequence

<400> SEQUENCE: 31
atggagttcg ggctgagctg ggtctttctg gtggccctgc tgaagggagt ccagtgcgag 60
gtgcagctgc tggaatccgg acctggcctg gtgaaaccat ctgagacact gagtctgact 120
tgtgctgtct ccggcctgtc tatcagctcc gatttctcct gggcatggat taggcagacc 180
cccggcaagg ccctggaata tgtggggtac atccgcggga acaccggaga tacatactat 240
aatcctagtc tgaagtcaag gctgactatc tcaaaggaca ccagcaaaaa ccaaatctac 300
ctgaatctgt ctagtgtcac cgctggcgat gccgccgtgt actattgcgc aagggaccgg 360
gtgtgcgacg atgactacgg atactattac accgaggtgt gcttcggcct ggattcttgg 420
gggcagggaa tcgtggtcac agtgtcaagc ggcggaggag gcagcggagg aggagggtcc 480
ggaggcgggg gatctgcaga actggtcatg acacagtccc cactgagcct gtccgtcgct 540
ccaggacaga ctgcatctat tagttgtcga tcctctcagt ccctggacta tgctaacggc 600
aatacctacc tgtcttggtt tcaccagcga ccaggacagc cacctcggag actgatctat 660
cagatttcca acagagattc tggagtgccc gacaggttct caggcagcgg agcaggaact 720
gagtttaccc tgcgaatcag tcggatggaa tcagatgacg tggggatcta ctactgcgga 780
caggggacca cattcccacg gacatttgga cagggcacta aggtggagat caaaacctgt 840
ggaggaggaa gcaagccacc aacctgccct ccatgtacat ctcccgaact gctgggcggg 900
cctagcgtgt tcctgtttcc ccctaagcct aaagatacac tgatgattag tagaacccca 960
gaggtcacat gcgtggtcgt ggacgtgtcc caggaagatc ctgacgtgaa gttcaactgg 1020
tacgtgaatg gcgccgaggt gcaccatgct cagactaaac cacgcgaaac ccagtataat 1080
agtacatacc gagtcgtgtc agtcctgaca gtgactcacc aggattggct gaacggcaag 1140
gagtatacct gcaaggtgtc taacaaggcc ctgcccgccc ctatccagaa aacaattagc 1200
aaggacaaag ggcagccacg ggaaccccag gtgtacactc tgccaccctc aagagaggaa 1260
ctgactaaga accaggtcag cctgacctgt ctggtgaaag gcttctaccc cagcgatatc 1320
gtcgtggagt gggaaagttc aggccagcct gagaatactt acaagactac ccctccagtg 1380
ctggatagcg acgggtccta tttcctgtac agcaagctga cagtggacaa atcccgctgg 1440
cagcagggaa acgtcttttc ctgttctgtg atgcatgagg ccctgcacaa tcattacacc 1500
cagaagagtc tgtcactgag ccccggcaaa 1530

<210> SEQ ID NO 32
<211> LENGTH: 1539
<212> TYPE: DNA
<213> ORGANISM: Artificial Sequence
<220> FEATURE:
<223> OTHER INFORMATION: Synthetic Sequence

<400> SEQUENCE: 32
atgggcagca ccgccatcct ggctctgctg ctggcagtgc tgcagggcgt ctgggcagag 60
gtgcagctgg tccagagcgg agcagagatg aagcgaccag gagaatcact gagaatcagc 120
tgcaaaactt ctggctacag tttcaccaac gactggatta catgggtgcg acagatgcct 180
ggcaaggggc tggagtggat gggcatgatc taccctgccg attctgaaac aagatattct 240
ccaagtgtgc aggggcaggt cactctgagc gtggacaaat caattagcac cgcctacctg 300
cagtggagct ccctgaaggc cagcgatacc gctacatact attgcgctaa actgggccct 360
tgcacttccg tcacctgtta tttcgctctg gacttttggg gacagggcgc agtggtcacc 420
gtgtctagtg gaggaggagg cagtggagga ggagggtcag gaggaggagg cagccagtct 480
gtcctgacac agccacctag tgcatcagga gcaccaggac agagcgtgac tatcagctgt 540
tccggctcaa gctccaacat tgaggggaat tacgtgcact ggtatcagca tctgtctggg 600
aaggccccca aactgctgat ctacaacgac aatgaaaggc caagcggagt gcccgatcgc 660
ttctctggaa gtaaatcagg caccagcgcc agcctggcaa tctccggact gcagtctaaa 720
gacgaagcag attactattg tagcacatgg gacctgtccc tgaatgatta tatttttggg 780
tctggaacac ggctgactgt gctgggccag cccaaggcta gtaaacgggt cgagatcaag 840
acttgtggag gcgggtctaa accccctact tgcccaccct gtaccagccc tgaactgctg 900
ggaggcccat ccgtgttcct gtttcctcca aagcctaaag acaccctgat gatttccaga 960
accccagagg tgacatgcgt cgtggtcgat gtctctcagg aagaccctga tgtgaagttt 1020
aactggtacg tgaatggcgc agaggtccac catgcccaga caaaaccacg agaaactcag 1080
tataactcta cctaccgggt ggtcagtgtg ctgaccgtca cacaccagga ctggctgaac 1140
gggaaggagt atacctgcaa ggtgagtaac aaggccctgc cagctcccat ccagaaaaca 1200
attagcaagg ataaaggaca gccaagagaa ccccaggtgt acactctgcc cccttctagg 1260
gaggaactga ctaagaacca ggtgagtctg acctgtctgg tcaaaggctt ctatcccagc 1320
gacatcgtgg tcgagtggga aagctccggg cagcctgaga atacatacaa gaccacacca 1380
cccgtgctgg acagtgatgg ctcatatttc ctgtactcca agctgaccgt ggataaatct 1440
cgatggcagc aggggaacgt gtttagttgt tcagtcatgc atgaggcact gcacaatcat 1500
tatacacaga agagcctgtc cctgtctcca ggaaagtga 1539

<210> SEQ ID NO 33
<211> LENGTH: 1470
<212> TYPE: DNA
<213> ORGANISM: Artificial Sequence
<220> FEATURE:
<223> OTHER INFORMATION: Synthetic Sequence

<400> SEQUENCE: 33
atggagttcg ggctgagctg ggtctttctg gtggccctgc tgaagggagt ccagtgccag 60
gtgcagctgc tgcagtccgg agccgccgtg accaaaccag gaggaagcgt gcgggtgagc 120
tgtgaggcct ccggctacaa catccgggat tacttcatcc actggtggag gcaggccccc 180
ggccagggac tgcagtgggt ggggtggatc aacccaaaga ccggacagcc aaacaaccca 240
cggcagttcc agggaagggt gagcctgacc cggcacgcca gctgggattt cgataccttc 300
agcttctaca tggatctgaa ggccctgcgg agcgatgata ccgccgtgta cttctgcgca 360
aggcagcgga gcgattactg ggacttcgat gtgtggggaa gcggaaccca ggtcacagtg 420
tcaagcgcgt cgaccaaggg gccctcaagc ggcggaggag gcagcggagg aggagggtcc 480
ggaggcgggg gatctgcaga tatccagatg acacagtccc caagcagcct gtccgccagc 540
gtgggagata ctgtgaccat tacctgtcag gctaacggct acctgaactg gtaccagcag 600
cgacggggaa aggcccctaa gctgctgatc tatgatggat ccaagctgga gcggggagtg 660
cccagcaggt tctcaggccg gcggtgggga caggagtaca acctgaccat caacaacctg 720
cagccagagg acatcgccac ctacttctgc caggtgtacg agttcgtggt gccaggcact 780
cggctggatc tgaaacgtac gacctgccct ccatgtccag cccccgaact gctgggcggg 840
cctagcgtgt tcctgtttcc ccctaagcct aaagatacac tgatgattag tagaacccca 900
gaggtcacat gcgtggtcgt ggacgtgtcc cacgaagagc ctgacgtgaa gttcaactgg 960
tacgtggatg gcgtggaggt gcacaatgct aagactaaac cacgcgaaga gcagtataat 1020
agtacatacc gagtcgtgtc agtcctgaca gtgctgcacc aggattggct gaacggcaag 1080
gagtataagt gcaaggtgtc taacaaggcc ctgcccgccc ctatcgagaa aacaattagc 1140
aaggccaaag ggcagccacg ggaaccccag gtgtacactc tgccaccctc aagagatgaa 1200
ctgactaaga accaggtcag cctgacctgt ctggtgaaag gcttctaccc cagcgacatc 1260
gccgtggagt gggaaagtaa cggccagcct gagaataact acaagactac ccctccagtg 1320
ctggatagcg acgggtcctt cttcctgtac agcaagctga cagtggacaa atcccgctgg 1380
cagcagggaa acgtcttttc ctgttctgtg atgcatgagg ccctgcacaa tcattacacc 1440
cagaagagtc tgtcactgag ccccggcaaa 1470

<210> SEQ ID NO 34
<211> LENGTH: 1473
<212> TYPE: DNA
<213> ORGANISM: Artificial Sequence
<220> FEATURE:
<223> OTHER INFORMATION: Synthetic Sequence

<400> SEQUENCE: 34
atgtaccgga tgcaactcct gtcttgcatt gcactaagtc ttgcacttgt cacaaacagt 60
caggtccaat tgttacagtc tggggcagcg gtgacgaagc ccggggcctc agtgagagtc 120

-continued

```
tcctgcgagg cttctggata caacattcgt gactacttta ttcattggtg gcgacaggcc    180
ccaggacagg gccttcagtg ggtgggatgg atcaatccta agacaggtca gccaaacaat    240
cctcgtcaat ttcagggtag agtcagtctg actcgacacg cgtcgtggga ctttgacaca    300
ttttcctttt acatggacct gaaggcacta agatcggacg acacggccgt ttatttctgt    360
gcgcgacagc gcagcgacta ttgggatttc gacgtctggg gcagtggaac ccaggtcact    420
gtctcgtcag cgtcgaccaa ggggccctca agcggcggag gaggcagcgg aggaggaggg    480
tccggaggcg ggggatctgc agacatccag atgacccagt ctccatcctc cctgtctgca    540
tctgtaggag ataccgtcac tatcacttgc caggcaaacg gctacttaaa ttggtatcaa    600
cagaggcgag ggaaagcccc aaaactcctg atctacgatg ggtccaaatt ggaaagaggg    660
gtcccatcaa ggttcagtgg aagaagatgg gggcaagaat ataatctgac catcaacaat    720
ctgcagcccg aagacattgc aacatatttt tgtcaagtgt atgagtttgt cgtccctggg    780
accagactgg atttgaaacg tacgacatgc ccaccgtgcc cagcacctga actcctgggg    840
ggaccgtcag tcttcctctt ccccccaaaa cccaaggaca ccctcatgat ctcccggacc    900
cctgaggtca catgcgtggt ggtggacgtg agccacgaag accctgaggt caagttcaac    960
tggtacgtgg acggcgtgga ggtgcataat gccaagacaa agccgcggga ggagcagtac   1020
aacagcacgt accgtgtggt cagcgtcctc accgtcctgc accaggactg gctgaatggc   1080
aaggagtaca agtgcaaggt ctccaacaaa gccctcccag cccccatcga gaaaaccatc   1140
tccaaagcca aagggcagcc ccgagaacca caggtgtaca ccctgccccc atcccgggat   1200
gagctgacca agaaccaggt cagcctgacc tgcctggtca aaggcttcta tcccagcgat   1260
atcgccgtgg aatgggagag caacggccag cccgagaaca actacaagac caccccccct   1320
gtgctggaca gcgacggctc attcttcctg tacagcaagc tgaccgtgga caagagccgg   1380
tggcagcagg gcaacgtgtt cagctgcagc gtgatgcacg aggccctgca caaccactac   1440
acccagaagt ccctgagcct gagccccggc aag                                1473
```